(12) United States Patent
Dolente et al.

(10) Patent No.: US 8,513,238 B2
(45) Date of Patent: Aug. 20, 2013

(54) HETEROARYL-CYCLOHEXYL-TETRAAZABENZO[E]AZULENES

(75) Inventors: Cosimo Dolente, Allschwil (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 193 days.

(21) Appl. No.: 13/101,173

(22) Filed: May 5, 2011

(65) Prior Publication Data

US 2011/0275801 A1    Nov. 10, 2011

(30) Foreign Application Priority Data

May 10, 2010   (EP) ..................... 10162451

(51) Int. Cl.
*A61P 25/00* (2006.01)
*A61K 31/55* (2006.01)
*C07D 487/12* (2006.01)

(52) U.S. Cl.
USPC .......................... 514/220; 540/563

(58) Field of Classification Search
USPC .......................... 514/220; 540/563
See application file for complete search history.

(56) References Cited

U.S. PATENT DOCUMENTS

| | | | |
|---|---|---|---|
| 7,265,104 | B2 | 9/2007 | Elliott et al. |
| 2002/0103373 | A1 | 8/2002 | Hockstra et al. |
| 2007/0167430 | A1 | 7/2007 | Ryckmans |
| 2007/0249585 | A1 | 10/2007 | Johnson |
| 2011/0245237 | A1 | 10/2011 | Dolente et al. |
| 2011/0251183 | A1 | 10/2011 | Dolente et al. |
| 2011/0263573 | A1 | 10/2011 | Dolente et al. |
| 2011/0263578 | A1 | 10/2011 | Dolente et al. |
| 2011/0275801 | A1 | 11/2011 | Dolente et al. |

FOREIGN PATENT DOCUMENTS

| | | |
|---|---|---|
| EP | 2292621 | 9/2011 |
| KR | 2007/0020462 | 2/2007 |
| WO | 95/14676 | 6/1995 |
| WO | 96/2292 | 7/1996 |
| WO | 02/083678 | 10/2002 |
| WO | 02/083681 | 10/2002 |
| WO | 03/066634 | 8/2003 |
| WO | 2004/074291 | 2/2004 |
| WO | 2005/068466 | 7/2005 |
| WO | 2006/114706 | 2/2006 |
| WO | 2006/021882 | 3/2006 |
| WO | 2006/123242 | 11/2006 |
| WO | 2008/084005 | 7/2008 |
| WO | 2010/057795 | 5/2010 |

OTHER PUBLICATIONS (Opposition in Costa Rican Appl. No. 2011-0220 Sep. 20, 2011).
Gal et al., Progress in Brain Research, Elsevier 139:197-210 XP001205440 ( 2002).
(International Search Report for PCT/EP2011/057368 Jul. 14, 2011).
Altemus et al., Arch. Gen. Psychiatry 49:9-20 ( 1992).
(International Search Report for PCT/EP2009/064804 Jan. 14, 2010).
Regier et al., Br. J. Psychiatry Suppl.:24-28 ( 1998).
(International Search Report PCT/EP2011/056391 Jun. 27, 2011).
Aughton et al., Br. J. Pharmacol.:253 ( 2008).
Robben et al., Am. J. Physiol. Renal. Physiol. 291:F257-270 ( 2006).
Vankerckhoven et al., Eur. J. Pharmacol. 449(1-2):135-141 ( 2002).
(International Search Report PCT/EP2011/056071 May 12, 2011).
Gupta et al., Br. J. Pharmacol. 155:118-126 ( 2008).
Raskind et al., Biol. Psychiatry 22:453-462 ( 1987).
Neumann, J. Neuroendocrinol. 20:858-865 ( 2008).
Bielsky et al., Neuropsychopharmacology 29:483-493 ( 2004).
Brouard et al., Bjog. 107:614-619 ( 2000).
(International Search Report for PCT/EP2011/054582 Mar. 25, 2011).
Michelini et al., Ann. NY Academy Science 897:198-211 ( 1999).
(International Search Report PCT/EP2009/065354 Feb. 8, 2010).
Ebner et al., Eur. J. Neuroscience 15:384-388 ( 2002).
Liebsch et al., Regulatory Peptides 59(2):229-239 ( 1995).
Yirmiya et al., 11:488-494 ( 2006).
(International Search Report PCT/EP2011/055516 May 23, 2011).
Kendler et al., Arch. Gen. Psychiatry 60:789-796 ( 2003).
Thompson et al., Psychoneuroendocrinology 29:35-48 ( 2004).
The Taiwanese Search Report, issued on Mar. 28, 2013, in the corresponding Taiwanese application No. 100116207., p. 1.
Cheng and Prusoff, "*Relationship between the inhibition constant (K1)and the concentration of inhibitor which causes 50 per cent inhibition (I50) of an enzymatic reaction*" Biochem. Pharmacol. 22:3099-3108 (1973).
The letter of opposition in the corresponding Costa Rican Application No. 2012-0542, notified by the Costa Rican Patent Office on Apr. 19, 2013., pp. 8.

*Primary Examiner* — Brenda Coleman

(57) ABSTRACT

The present invention provides heteroaryl-cyclohexyl-tetraazabenzo[e]azulenes of formula I

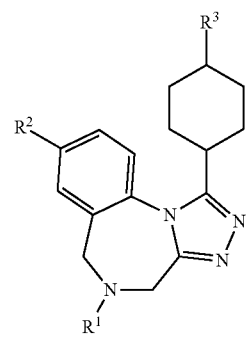

wherein $R^1$, $R^2$ and $R^3$ are as described herein.

The compounds according to the invention act as V1a receptor modulators, and in particular as V1a receptor antagonists, their manufacture, pharmaceutical compositions containing them and their use as medicaments. The active compounds of the present invention are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

27 Claims, No Drawings

HETEROARYL-CYCLOHEXYL-TETRAAZABENZO[E]AZULENES

PRIORITY TO RELATED APPLICATION(S)

This application claims the benefit of European Patent Application No. 10162451.8 filed May 10, 2010, which is hereby incorporated by reference in its entirety.

BACKGROUND OF THE INVENTION

Vasopressin is a 9 amino acid peptide mainly produced by the paraventricular nucleus of the hypothalamus. In the periphery vasopressin acts as a neurohormone and stimulates vasoconstriction, glycogenolysis and antidiuresis.

Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water reabsorption and mediates the antidiuretic effects of vasopressin (Robben, et al. (2006). Am J Physiol Renal Physiol. 291, F257-70, "Cell biological aspects of the vasopressin type-2 receptor and aquaporin 2 water channel in nephrogenic diabetes insipidus"). Compounds with activity at the V2 receptor can therefore cause side-effects on blood homeostasis.

The oxytocin receptor is related to the Vasopressin receptor family and mediates the effects of the neurohormone oxytocin in the brain and the periphery. Oxytocin is believed to have central anxiolytic effects (Neumann (2008). J Neuroendocrinol. 20, 858-65, "Brain oxytocin: a key regulator of emotional and social behaviors in both females and males"). Central oxytocin receptor antagonism might therefore lead to anxiogenic effects, which are regarded as undesired side-effects.

In the brain vasopressin acts as a neuromodulator and is elevated in the amygdala during stress (Ebner, et al. (2002). Eur J Neurosci. 15, 384-8, "Forced swimming triggers vasopressin release within the amygdala to modulate stress-coping strategies in rats"). It is known that stressful life events can trigger major depression and anxiety (Kendler, et al. (2003). Arch Gen Psychiatry. 60, 789-96, "Life Event Dimensions of Loss, Humiliation, Entrapment, and Danger in the Prediction of Onsets of Major Depression and Generalized Anxiety") and that both have very high comorbidity, with anxiety often preceding major depression (Regier, et al. (1998). Br J Psychiatry Suppl. 24-8, "Prevalence of anxiety disorders and their comorbidity with mood and addictive disorders"). The V1a receptor is extensively expressed in the brain and particularly in limbic areas like the amygdala, lateral septum and hippocampus which are playing an important role in the regulation of anxiety. Indeed V1a knock-out mice show a reduction in anxious behavior in the plus-maze, open field and light-dark box (Bielsky, et al. (2004). Neuropsychopharmacology. 29, 483-93, "Profound impairment in social recognition and reduction in anxiety-like behavior in vasopressin V1a receptor knockout mice"). The downregulation of the V1a receptor using antisense oligonucleotide injection in the septum also causes a reduction in anxious behavior (Landgraf, et al. (1995). Regul Pept. 59, 229-39, "V1 vasopressin receptor antisense oligodeoxynucleotide into septum reduces vasopressin binding, social discrimination abilities, and anxiety-related behavior in rats"). Vasopressin or the V1a receptor are also implicated in other neuropsychological disorders: genetic studies recently linked sequence polymorphism in the promoter of the human V1a receptor to autistic spectrum disorders (Yirmiya, et al. (2006). 11, 488-94, "Association between the arginine vasopressin 1a receptor (AVPR1a) gene and autism in a family-based study: mediation by socialization skills"), intranasal administration of vasopressin was shown to influence aggression in human males (Thompson, et al. (2004). Psychoneuroendocrinology. 29, 35-48, "The effects of vasopressin on human facial responses related to social communication") and vasopressin levels were found to be elevated in schizophrenic patients (Raskind, et al. (1987). Biol Psychiatry. 22, 453-62, "Antipsychotic drugs and plasma vasopressin in normals and acute schizophrenic patients") and patients with obsessive-compulsive disorder (Altemus, et al. (1992). Arch Gen Psychiatry. 49, 9-20, "Abnormalities in the regulation of vasopressin and corticotropin releasing factor secretion in obsessive-compulsive disorder").

The V1a receptor is also mediating the cardiovascular effects of vasopressin in the brain by centrally regulating blood pressure and heart rate in the solitary tract nucleus (Michelini and Morris (1999). Ann N Y Acad Sci. 897, 198-211, "Endogenous vasopressin modulates the cardiovascular responses to exercise"). In the periphery it induces the contraction of vascular smooth muscles and chronic inhibition of the V1a receptor improves hemodynamic parameters in myocardial infarcted rats (Van Kerckhoven, et al. (2002). Eur J Pharmacol. 449, 135-41, "Chronic vasopressin V(1A) but not V(2) receptor antagonism prevents heart failure in chronically infarcted rats"). Hence, V1a antagonists with improved penetration through the blood-brain barrier are expected to be of advantage.

A vasopressin V1a receptor antagonist was shown to be effective in reducing dysmenorrhea in the clinic (Brouard, et al. (2000). Bjog. 107, 614-9, "Effect of SR49059, an orally active V1a vasopressin receptor antagonist, in the prevention of dysmenorrhea"). V1a receptor antagonism has also been implicated in the treatment of female sexual dysfunction (Aughton, et al. (2008). Br J Pharmacol. doi:10.1038/bjp.2008.253, "Pharmacological profiling of neuropeptides on rabbit vaginal wall and vaginal artery smooth muscle in vitro"). In a recent study V1a receptor antagonists were suggested to have a therapeutic role in both erectile dysfunction and premature ejaculation (Gupta, et al. (2008). Br J Pharmacol. 155, 118-26, "Oxytocin-induced contractions within rat and rabbit ejaculatory tissues are mediated by vasopressin V(1A) receptors and not oxytocin receptors").

FIELD OF THE INVENTION

The present invention is concerned with heteroaryl-cyclohexyl-tetraazabenzo[e]azulenes, which act as V1a receptor modulators, and in particular as V1a receptor antagonists, their manufacture, pharmaceutical compositions containing them and their use as medicaments.

SUMMARY OF THE INVENTION

The present invention provides compounds of formula I useful for acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

In particular, the present invention provides compounds of formula I

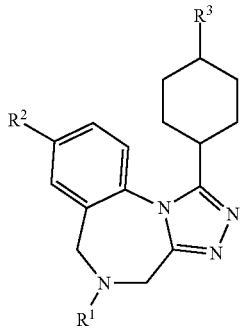

wherein $R^1$, $R^2$ and $R^3$ are as described in herein.

DETAILED DESCRIPTION OF THE INVENTION

The present invention provides compounds which act as V1a receptor modulators, and in particular as V1a receptor antagonists. The invention also provides selective inhibitors of the V1a receptor. It is expected that selectivity affords a low potential to cause unwanted off-target related side effects such as discussed above.

Such V1a antagonists are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior. Particular indications with regard to the present invention are the treatment of anxiety, depressive disorders, obsessive compulsive disorder, autistic spectrum disorders, schizophrenia, and aggressive behavior.

The V1a activity can be detected as described in the experimental section.

The following definitions of the general terms used in the present description apply irrespective of whether the terms in question appear alone or in combination.

As used herein, the terms "$C_{1-6}$alkyl", alone or in combination with other groups, stands for a hydrocarbon radical that is linear or branched, with single or multiple branching, whereby the alkyl group contains 1 to 6 carbon atoms, for example, methyl (Me), ethyl (Et), propyl, isopropyl (i-propyl), n-butyl, i-butyl (iso-butyl), 2-butyl (sec-butyl), t-butyl (tert-butyl) and the like. Particular alkyl groups are groups with 1 to 4 carbon atoms. More particular are methyl, ethyl and isopropyl.

The term "$C_{1-6}$alkoxy", alone or in combination with other groups, denotes a group —O—R' wherein R' is alkyl as defined above, for example methoxy, ethoxy, propoxy, tert-butoxy and the like. Particular alkoxy groups are groups with 1 to 4 carbon atoms. More particular is methoxy.

The term "aryl", alone or in combination with other groups, refers to an aromatic carbocyclic group containing 6 to 14, particularly 6 to 10, carbon atoms and having at least one aromatic ring or multiple condensed rings in which at least one ring is aromatic. Examples include phenyl (Ph), benzyl, naphthyl, biphenyl, anthryl, azalenyl or indanyl. Particular is phenyl.

The term "heteroaryl", alone or in combination with other groups, refers to a cyclic aromatic group having a 5 to 6 membered ring, containing 1, 2 or 3 heteroatoms, in which group at least one heterocyclic ring is aromatic. The term "5-membered heteroaryl" refers to an aromatic group having a single 5 membered ring, and comprising 1, 2 or 3 heteroatoms independently selected from O, S and N. Particular single 5 membered rings have 2N and 1O, 2N and 1S, 2N, 1S and 1N, or 1O and 1N. Examples of "5-membered heteroaryl" include thiazolyl, isoxazolyl, isothiazolyl, oxadiazolyl, thiadiazolyl, 1H-pyrazol-1-yl and the like. Particular are thiazol-4-yl, [1,2,4]oxadiazol-5-yl, 1,2,4]thiadiazol-5-yl, isoxazol-3-yl, oxazol-2-yl, thiazol-2-yl, [1,2,4]oxadiazol-3-yl, [1,2,4]thiadiazol-3-yl and [1,3,4]oxadiazol-2-yl. Specific "5-membered heteroaryl" are attached via a carbon atom to the cyclohexyl moiety.

The "5-membered heteroaryl", alone or in combination with other groups, substituted by two adjacent R* which form together a "ring comprising 4, 5, 6 or 7 C" refers to an aromatic group having a 5 membered aromatic ring, and comprising 1, 2 or 3 heteroatoms independently selected from O, S and N, particularly selected from O and N, and a fused non-aromatic ring having 4, 5, 6 or 7 C atoms, particularly 6 C atoms. Examples include 4,5,6,7-tetrahydro-benzo[d]isoxazolyl, 4,5,6,7-tetrahydro-benzo[c]isoxazolyl, 5,6-dihydro-4H-cyclopenta[d]isoxazol and the like. Particular are 4,5,6,7-tetrahydro-benzo[d]isoxazol-3-yl and 4,5,6,7-tetrahydro-benzo[c]isoxazol-3-yl.

The term "heterocyclyl" refers to a monovalent 3 to 7 membered saturated or partly unsaturated monocyclic ring containing one, two or three ring heteroatoms selected from N, O and S. In particular such rings will contain one or two ring heteroatoms. Heterocyclyl includes 4 to 6 membered heterocyclyl groups comprising one or two ring heteroatoms selected from N, O and S. S can optionally be substituted by two oxo groups. Examples for heterocyclyl moieties are pyrrolidinyl, tetrahydro-furanyl, tetrahydro-pyranyl, tetrahydro-thienyl, tetrahydro-pyridinyl, tetrahydro-pyryl, azetidinyl, thiazolidinyl, oxazolidinyl, piperidinyl, morpholinyl, thiomorpholinyl, 1,1-dioxo-thiomorpholin-4-yl, piperazinyl, azepanyl, diazepanyl, oxazepanyl and dihydro-oxazolyl. In particular, heterocyclyl is azetidin-1-yl, pyrrolidin-1-yl, tetrahydro-furan-3-yl, tetrahydro-pyran-4-yl and 1,1-dioxo-1,6-thiomorpholin-4-yl; more particularly pyrrolidin-1-yl, tetrahydro-furan-3-yl and tetrahydro-pyran-4-yl.

The term "cycloalkyl" refers to a 3 to 8 membered carbon ring, for example cyclopropyl, cyclobutyl, cyclopentyl, cyclohexyl, cycloheptyl or cyclooctyl. Particular are cycloalkyl groups having a 3, 4, 5 or 6 membered carbon ring. Examples include cyclobutyl and cyclopentyl.

The term "cyano", alone or in combination with other groups, denotes the group —CN.

The term "hydroxy", alone or in combination with other groups, denotes the group —OH.

The term "Boc" ("BOC", "boc"), alone or in combination with other groups, denotes the group —C(=O)O(CH$_3$)$_3$.

The term "halogen", alone or in combination with other groups, denotes chloro (Cl), iodo (I), fluoro (F) and bromo (Br). Specific halogens are F and Cl, particular is Cl.

The term "halogen-$C_{1-6}$alkyl", alone or in combination with other groups, refers to a $C_{1-6}$alkyl group substituted by one or multiple halogen, particular is "fluoro-$C_{1-6}$alkyl", for example the following groups: CF$_3$, CHF$_2$, CH$_2$F, CH$_2$CF$_3$, CH$_2$CH$_2$CF$_3$, CF$_2$CHF$_2$, and the like.

The term "hydroxy-$C_{1-6}$alkyl", alone or in combination with other groups, refers to a $C_{1-6}$alkyl group substituted by one or multiple hydroxy, for example the following groups:

hydroxymethyl-, 2-hydroxyethyl-, 2-hydroxy-1-methyl-ethyl- or 2-hydroxypropyl- and the like.

The term "cyano-$C_{1-6}$alkyl", alone or in combination with other groups, refers to a $C_{1-6}$alkyl group substituted by one or multiple cyano, for example the following groups: cyanomethyl-, 2-cyanoethyl-, 2-cyano-1-methyl-ethyl- or 2-cyanopropyl- and the like.

The term "halogen-$C_{1-6}$alkoxy", alone or in combination with other groups, refers to a $C_{1-6}$alkoxy group substituted by one or multiple halogen, particular is fluoro-$C_{1-6}$alkoxy", for example the following group: F—$CH_2$—O—.

When indicating the number of substituents, the term "one or multiple" means from one substituent to the highest possible number of substitution, i.e. replacement of one hydrogen up to replacement of all hydrogens by substituents. Thereby, one, two or three substituents are particular. Even more particular are one or two substituents or one substituent.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log$ Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The term "pharmaceutically acceptable salts" refers to salts that are suitable for use in contact with the tissues of humans and animals without undue toxicity, irritation, allergic response, and the like. Examples of suitable salts with inorganic and organic acids are, but are not limited to, hydrochloric acid, nitric acid, sulphuric acid, phosphoric acid, sulphuric acid, citric acid, formic acid, fumaric acid, maleic acid, lactic acid, malic acid, acetic acid, succinic acid, tartaric acid, methane-sulfonic acid, p-toluenesulphonic acid, trifluoroacetic acid and the like. Particular are hydrochloric acid and formic acid. Specific is hydrochloric acid.

The term "leaving group" denotes the group with the meaning conventionally associated with it in synthetic organic chemistry, i.e., an atom or group displaceable under substitution reaction conditions. Examples of leaving groups include halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, and acyloxy. The following table lists abbreviations used within the present document.

TABLE 1

| abbreviations | |
|---|---|
| $(BOC)_2O$ | di-tert-butyl pyrocarbonate |
| $(COCl)_2$ | oxalyl (di)chloride |
| AcOH | acetic acid |
| $CH_2Cl_2$ | dichloromethane |
| $((CH_3)_3CCO)_2O$ | trimethylacetic anhydride |
| CuCl | copper(I) chloride |
| Dess-Martin periodinane | 1,1,1-triacetoxy-1,1-dihydro-1,2-benziodoxol-3(1H)-one |
| DMF | dimethylformamide |
| DMAP | 4-(dimethylamino)-pyridine |
| DMSO | dimethylsulfoxide |
| $(dppf)/PdCl_2$ | [1,1'-Bis(diphenylphosphino)ferrocene]dichloropalladium(II). |
| EDTA | ethylendiamin tetraacetate |
| $EtN_3$ | triethylamine |
| EtOAc | ethyl acetate |
| EtOH | ethanol |
| HATU | 2-(7-aza-1H-benzotriazole-1-yl)-1,1,3,3-tetramethyluronium hexafluorophosphate |
| HEPES | 2-(4-(2-hydroxyethyl)-1-piperazinyl)-ethanesulfonic acid |
| HF-pyridine | pyridine hydrofluoride |
| $H_2O$ | water |

TABLE 1-continued

| abbreviations | |
|---|---|
| H$_2$SO$_4$ | sulphuric acid |
| HPLC | high performance liquid crystallography |
| KHF$_2$ | potassium bifluoride |
| K$_3$PO$_4$ | potassium phosphate |
| Lawesson's reagent | 2,4-bis-(4-methoxyphenyl)-1,3,2,4-dithiadiphosphetane-2,4-disulfide |
| MeOH | methanol |
| MS | mass spectroscopy |
| Na$_2$CO$_3$ | sodium carbonate |
| NaNO$_2$ | sodium nitrite |
| NaOEt | sodium ethoxide |
| NaOH | sodium hydroxide |
| n-BuOH | n-butanol |
| NCS | N-chlorosuccinimide |
| NMR | nuclear magnetic resonance |
| PdCl$_2$ | palladium dichloride |
| Pd(OAc)$_2$ | palladium acetate |
| Pd(PPh)$_3$ | tetrakis(triphenylphosphine)palladium(0) |
| POCl$_3$ | phosphorus oxychloride |
| PtO$_2$ | platinum oxide |
| p-TsOH | p-toluenesulfonic acid |
| (PPh)$_3$ | triphenylphosphine |
| RNA | ribonucleic acid |
| RP-HPLC | reversed phase high performance liquid chromatography |
| RT | room temperature |
| RT-PCR | reverse transcription-polymerase chain reaction |
| Selectfluor | 1-chloromethyl-4-fluro-1,4-diazoniabicyclo[2.2.2]octane bis(tetrafluoroborate) |
| SOCl$_2$ | thionyl chloride |
| t-BuOK | potassium-tert-butoxide |
| THF | tetrahydrofuran |
| Tris | Tris(hydroxymethyl)-aminomethane |
| ZnBr$_2$ | zinc bromide |

The invention also provides pharmaceutical compositions, methods of using, and methods of preparing the aforementioned compounds.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective spirit and scope of the present invention. All such modifications are intended to be within the scope of the claims appended hereto. All separate embodiments can be combined.

The compounds of formula I can contain asymmetric carbon atoms. Accordingly, the present invention includes all stereoisomeric forms of the compounds of formula I, including each of the individual stereoisomers and mixtures thereof, i.e. their individual optical isomers and mixtures thereof. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to comprehend all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

This applies in particular to the aryl-head group (HG) of the compounds of formula I, namely

wherein at least the carbon atoms 1 and 4 are asymmetric carbon atoms and R$^3$ could further comprise asymmetric carbon atoms. It is to be understood that present invention includes all individual stereoisomers of head groups and mixtures thereof.

In particular, these head groups HG are

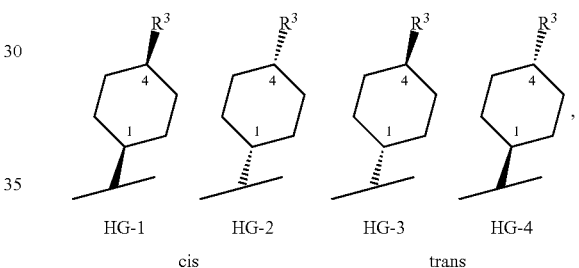

more particular HG are trans.

It is further understood that all embodiments of the invention as described herein can be combined with each other.

In detail, the present invention provides compounds of formula I

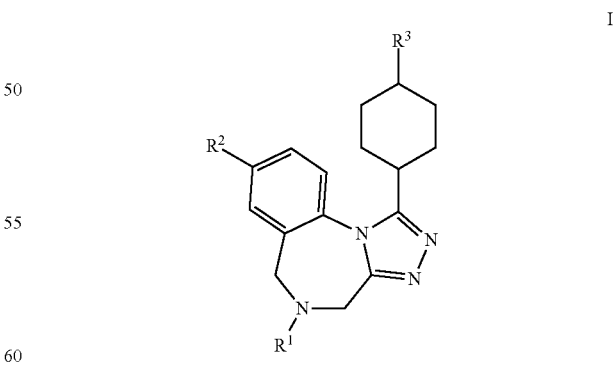

wherein
R$^1$ is selected from the group consisting of
i) H,
ii) —C$_{1-6}$-alkyl, unsubstituted or substituted by 1 to 5 substituents individually selected from the group consisting of OH, halogen, cyano and C$_{1-6}$-alkoxy, iii) —S(O)$_2$—C$_{1-6}$-alkyl, whereby the C$_{1-6}$-alkyl is unsubstituted or substituted by 1 to 5 substituents individually selected from the group consisting of OH, halogen, cyano and C$_{1-6}$-alkoxy,
iv) —C(O)—C$_{1-6}$-alkyl, whereby the C$_{1-6}$-alkyl is unsubstituted or substituted by 1 to 5 substituents individually selected from the group consisting of OH, halogen, cyano and C$_{1-6}$-alkoxy,
v) —C(O)O—C$_{1-6}$-alkyl, whereby the C$_{1-6}$-alkyl is unsubstituted or substituted by 1 to 5 substituents individually selected from the group consisting of OH, halogen, cyano and C$_{1-6}$-alkoxy;
vi) cycloalkyl, unsubstituted or substituted by 1 to 5 substituents individually selected from the group consisting of OH, halogen, cyano, C$_{1-6}$-alkyl and C$_{1-6}$-alkoxy,
vii) —S(O)$_2$—(CH$_2$)$_q$—NR$^i$R$^{ii}$, wherein
q is 0 or 1,
R$^i$ and R$^{ii}$ is each individually selected from the group consisting of H and C$_{1-6}$-alkyl, or R$^i$ and R$^{ii}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, C$_{1-6}$-alkyl and C$_{1-6}$-alkoxy,
viii) —(CH$_2$)$_r$—NR$^{iii}$R$^{iv}$, wherein
r is 1, 2 or 3,
R$^{iii}$ and R$^{iv}$ is each individually selected from the group consisting of H and C$_{1-6}$-alkyl, or R$^{iii}$ and R$^{iv}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, C$_{1-6}$-alkyl and C$_{1-6}$-alkoxy, and
ix) —C(O)(CH$_2$)$_s$—NR$^v$R$^{vi}$, wherein
s is 1, 2 or 3,
R$^v$ and R$^{vi}$ is each individually selected from the group consisting of H and C$_{1-6}$-alkyl, or R$^v$ and R$^{vi}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, C$_{1-6}$-alkyl and C$_{1-6}$-alkoxy;
R$^2$ is halogen;
R$^3$ is a 5-membered heteroaryl, unsubstituted or substituted by (R*)$_n$, each R* is individually selected from the group consisting of halogen, C$_{1-6}$-alkyl, halogen-C$_{1-6}$-alkyl and hydroxy-C$_{1-6}$-alkyl, wherein
n is 1, 2 or 3;
and two R* adjacent to each other can form a ring comprising 4, 5, 6 or 7 C;
or a pharmaceutically acceptable salt thereof.

A certain embodiment of the invention is a compound of formula I as described herein, wherein R$^1$ is methyl and R$^2$ is chloro.

A certain embodiment of the invention is a compound of formula I as described herein, wherein R$^1$ is H and R$^2$ is chloro.

A certain embodiment of the invention is a compound of formula I as described herein, wherein R$^1$ is Boc and R$^2$ is chloro.

A certain embodiment of the invention is a compound of formula I,

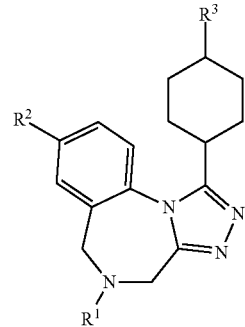

wherein
R$^1$ is selected from the group consisting of
i) H,
ii) —C$_{1-6}$-alkyl, unsubstituted or substituted by 1 to 5 substituents individually selected from the group consisting of OH, halogen, cyano and C$_{1-6}$-alkoxy,
iii) —S(O)$_2$—C$_{1-6}$-alkyl, whereby the C$_{1-6}$-alkyl is unsubstituted or substituted by 1 to 5 substituents individually selected from the group consisting of OH, halogen, cyano and C$_{1-6}$-alkoxy,
iv) —C(O)—C$_{1-6}$-alkyl, whereby the C$_{1-6}$-alkyl is unsubstituted or substituted by 1 to 5 substituents individually selected from the group consisting of OH, halogen, cyano and C$_{1-6}$-alkoxy,
v) —C(O)O—C$_{1-6}$-alkyl, whereby the C$_{1-6}$-alkyl is unsubstituted or substituted by 1 to 5 substituents individually selected from the group consisting of OH, halogen, cyano and C$_{1-6}$-alkoxy;
vi) cycloalkyl, unsubstituted or substituted by 1 to 5 substituents individually selected from the group consisting of OH, halogen, cyano, C$_{1-6}$-alkyl and C$_{1-6}$-alkoxy,
vii) —S(O)$_2$—(CH$_2$)$_q$—NR$^i$R$^{ii}$, wherein
q is 0 or 1,
R$^i$ and R$^{ii}$ is each individually selected from the group consisting of H and C$_{1-6}$-alkyl, or R$^i$ and R$^{ii}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, C$_{1-6}$-alkyl and C$_{1-6}$-alkoxy,
viii) —(CH$_2$)$_r$—NR$^{iii}$R$^{iv}$, wherein
r is 1, 2 or 3,
R$^{iii}$ and R$^{iv}$ is each individually selected from the group consisting of H and C$_{1-6}$-alkyl, or R$^{iii}$ and R$^{iv}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, C$_{1-6}$-alkyl and C$_{1-6}$-alkoxy, and
ix) —C(O)(CH$_2$)$_s$—NR$^v$R$^{vi}$, wherein
s is 1, 2 or 3,
R$^v$ and R$^{vi}$ is each individually selected from the group consisting of H and C$_{1-6}$-alkyl, or R$^v$ and R$^{vi}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy;

$R^2$ is halogen;

$R^3$ is a 5-membered heteroaryl, unsubstituted or substituted by $(R^*)_n$, each $R^*$ is individually selected from the group consisting of halogen, $C_{1-6}$-alkyl and halogen-$C_{1-6}$-alkyl, wherein n is 1-2;

and two $R^*$ adjacent to each other can form with the groups to which they are attached a ring comprising 4, 5, 6 or 7 C;

or a pharmaceutically acceptable salt thereof.

A certain embodiment of the invention is a compound of formula I as described herein, wherein $R^1$ is selected from the group consisting of i) H, ii) —$C_{1-6}$-alkyl, unsubstituted or substituted by 1 to 2 substituents individually selected from the group consisting of halogen and $C_{1-6}$-alkoxy, iii) —$S(O)_2$—$C_{1-6}$-alkyl, whereby the $C_{1-6}$-alkyl is unsubstituted, iv) —$C(O)$—$C_{1-6}$-alkyl, whereby the $C_{1-6}$-alkyl is unsubstituted or substituted by 1 to 2 OH, v) —$C(O)O$—$C_{1-6}$-alkyl, whereby the $C_{1-6}$-alkyl is unsubstituted;

vi) unsubstituted cycloalkyl, vii) —$S(O)_2$—$(CH_2)_q$—$NR^iR^{ii}$, wherein q is 0 and $R^i$ and $R^{ii}$ is each individually selected from the group consisting of H and $C_{1-6}$-alkyl, viii) —$(CH_2)_r$—$NR^{iii}R^{iv}$, wherein r is 2, and $R^{iii}$ and $R^{iv}$ is each individually selected from the group consisting of H and $C_{1-6}$-alkyl, and ix) —$C(O)(CH_2)_s$—$NR^vR^{vi}$, wherein s is 1, and $R^v$ and $R^{vi}$ is each individually selected from the group consisting of H and $C_{1-6}$-alkyl.

A certain embodiment of the invention is a compound of formula I as described herein, wherein $R^1$ is selected from the group consisting of H, methyl, ethyl, isopropyl, 2,2-difluoro-ethyl, 2-methoxy-ethyl, 2-methylamino-ethyl, acetyl, 2-dimethylamino-acetyl, 2-hydroxy-acetyl, Boc, cyclobutyl, cyclopentyl, dimethylsulfonamidyl and methanesulfonyl.

A certain embodiment of the invention is a compound of formula I as described herein, wherein $R^1$ is selected from the group consisting of i) H, ii) —$C_{1-6}$-alkyl, unsubstituted or substituted by 1 to 2 halogen, iii) —$S(O)_2$—$C_{1-6}$-alkyl, iv) —$C(O)$—$C_{1-6}$-alkyl, whereby the $C_{1-6}$-alkyl is unsubstituted or substituted by 1 to 2 OH, and v) unsubstituted cycloalkyl.

A certain embodiment of the invention is a compound of formula I as described herein, wherein $R^1$ is selected from the group consisting of H, methyl, 2,2-difluoro-ethyl, cyclobutyl, acetyl and methanesulfonyl.

A certain embodiment of the invention is a compound of formula I as described herein, wherein $R^1$ is H.

A certain embodiment of the invention is a compound of formula I as described herein, wherein $R^1$ is —$C_{1-6}$-alkyl.

A certain embodiment of the invention is a compound of formula I as described herein, wherein $R^1$ is methyl.

A certain embodiment of the invention is a compound of formula I as described herein, wherein $R^1$ is ethyl.

A certain embodiment of the invention is a compound of formula I as described herein, wherein $R^1$ is isopropyl.

A certain embodiment of the invention is a compound of formula I as described herein, wherein $R^1$ is —$C_{1-6}$-alkyl substituted by 1 to 2 halogen.

A certain embodiment of the invention is a compound of formula I as described herein, wherein $R^1$ is 2,2-difluoro-ethyl.

A certain embodiment of the invention is a compound of formula I as described herein, wherein $R^1$ is $C_{1-6}$-alkyl substituted by 1 to 2 $C_{1-6}$-alkoxy.

A certain embodiment of the invention is a compound of formula I as described herein, wherein $R^1$ is 2-methoxy-ethyl.

A certain embodiment of the invention is a compound of formula I as described herein, wherein $R^1$ is —$S(O)_2$—$C_{1-6}$-alkyl.

A certain embodiment of the invention is a compound of formula I as described herein, wherein $R^1$ is methanesulfonyl.

A certain embodiment of the invention is a compound of formula I as described herein, wherein $R^1$ is —$C(O)$—$C_{1-6}$-alkyl.

A certain embodiment of the invention is a compound of formula I as described herein, wherein $R^1$ is acetyl.

A certain embodiment of the invention is a compound of formula I as described herein, wherein $R^1$ is —$C(O)$—$C_{1-6}$-alkyl substituted by 1 to 2 OH.

A certain embodiment of the invention is a compound of formula I as described herein, wherein $R^1$ is 2-hydroxy-acetyl.

A certain embodiment of the invention is a compound of formula I as described herein, wherein $R^1$ is —$C(O)O$—$C_{1-6}$-alkyl.

A certain embodiment of the invention is a compound of formula I as described herein, wherein $R^1$ is Boc.

A certain embodiment of the invention is a compound of formula I as described herein, wherein $R^1$ is unsubstituted cycloalkyl.

A certain embodiment of the invention is a compound of formula I as described herein, wherein $R^1$ is cyclobutyl.

A certain embodiment of the invention is a compound of formula I as described herein, wherein $R^1$ is cyclopentyl.

A certain embodiment of the invention is a compound of formula I as described herein, wherein $R^1$ is —$S(O)_2$—$(CH_2)_q$—$NR^iR^{ii}$, wherein q is 0 and $R^i$ and $R^{ii}$ is each individually selected from the group consisting of H and $C_{1-6}$-alkyl.

A certain embodiment of the invention is a compound of formula I as described herein, wherein $R^1$ is dimethylsulfonamidyl.

A certain embodiment of the invention is a compound of formula I as described herein, wherein $R^1$ is —$(CH_2)_r$—$NR^{iii}R^{iv}$, wherein r is 2, and $R^{iii}$ and $R^{iv}$ is each individually selected from the group consisting of H and $C_{1-6}$-alkyl.

A certain embodiment of the invention is a compound of formula I as described herein, wherein $R^1$ is 2-methylamino-ethyl.

A certain embodiment of the invention is a compound of formula I as described herein, wherein $R^1$ is —$C(O)(CH_2)_s$—$NR^vR^{vi}$, wherein s is 1, and $R^v$ and $R^{vi}$ is each individually selected from the group consisting of H and $C_{1-6}$-alkyl.

A certain embodiment of the invention is a compound of formula I as described herein, wherein $R^1$ is 2-dimethylamino-acetyl.

A certain embodiment of the invention is a compound of formula I as described herein, wherein $R^2$ is chloro or fluoro.

A certain embodiment of the invention is a compound of formula I as described herein, wherein $R^2$ is chloro.

A certain embodiment of the invention is a compound of formula I as described herein, wherein $R^2$ is fluoro.

A certain embodiment of the invention is a compound of formula I as described herein, wherein $R^3$ is selected from the group consisting of
i) [1,2,4]oxadiazolyl,
ii) [1,3,4]oxadiazolyl,
iii) oxazolyl,
iv) thiazolyl,
v) [1,2,4]thiadiazolyl,
vi) isoxazolyl, and
vii) 1H-pyrazolyl;
each unsubstituted or substituted by $(R^*)_n$, each $R^*$ is individually selected from the group consisting halogen and $C_{1-6}$-alkyl, wherein n=1, 2 or 3, or two $R^*$ adjacent to each other form with the atoms to which they are attached a ring comprising 6 C.

A certain embodiment of the invention is a compound of formula I as described herein, wherein $R^3$ is selected from the group consisting of
i) [1,2,4]oxadiazolyl,
ii) [1,3,4]oxadiazolyl,
iii) oxazolyl,
iv) thiazolyl,
v) [1,2,4]thiadiazolyl, and
vi) isoxazolyl,
each unsubstituted or substituted by $(R^*)_n$, each $R^*$ is individually selected from the group consisting halogen and $C_{1-6}$-alkyl, wherein n=1-2 and two $R^*$ adjacent to each other can form with the atoms to which they are attached a ring comprising 6 C.

A certain embodiment of the invention is a compound of formula I as described herein, wherein $R^3$ is selected from the group consisting of oxazol-2-yl, 1H-pyrazol-1-yl, 2-methyl-thiazol-4-yl, 3,4,5-trimethyl-1H-pyrazol-1-yl, 3,5-dimethyl-1H-pyrazol-1-yl, 3-methyl-[1,2,4]thiadiazol-5-yl, 4,5,6,7-tetrahydro-benzo[c]isoxazol-3-yl, 4,5,6,7-tetrahydro-benzo[d]isoxazol-3-yl, 4,5-bis(hydroxymethyl)isoxazol-3-yl, 4,5-dimethyl-isoxazol-3-yl, 4,5-dimethyl-oxazol-2-yl, 4,5-dimethylthiazol-2-yl, 4-chloro-5-methyl-isoxazol-3-yl, 4-fluoro-5-methyl-isoxazol-3-yl, 4-methyl-oxazol-2-yl, 4-methyl-thiazol-2-yl, 5,6-dihydro-4H-cyclopenta[d]isoxazol, 5-chloro-4-methylthiazol-2-yl, 5-ethyl-[1,2,4]oxadiazol-3-yl, 5-ethyl-isoxazol-3-yl, 5-isopropyl-[1,2,4]oxadiazol-3-yl, 5-methyl-[1,2,4]oxadiazol-3-yl, 5-methyl-[1,2,4]thiadiazol-3-yl, 5-methyl-[1,3,4]oxadiazol-2-yl, 5-methyl-isoxazol-3-yl, 5-methyl-oxazol-2-yl, oxazol-2-yl and thiazol-2-yl.

A certain embodiment of the invention is a compound of formula I as described herein, wherein $R^3$ is selected from the group consisting of 2-methyl-thiazol-4-yl, 3-methyl-[1,2,4] oxadiazol-5-yl, 3-methyl-[1,2,4]thiadiazol-5-yl, 4,5,6,7-tetrahydro-benzo[c]isoxazol-3-yl, 4,5,6,7-tetrahydro-benzo[d] isoxazol-3-yl, 4,5-dimethyl-isoxazol-3-yl, 4,5-dimethyl-oxazol-2-yl, 4-chloro-5-methyl-isoxazol-3-yl, 4-fluoro-5-methyl-isoxazol-3-yl, 4-methyl-oxazol-2-yl, 4-methyl-thiazol-2-yl, oxazol-2-yl, thiazol-2-yl, 5-ethyl-[1,2,4]oxadiazol-3-yl, 5-ethyl-isoxazol-3-yl, 5-isopropyl-[1,2,4]oxadiazol-3-yl, 5-methyl-[1,2,4]oxadiazol-3-yl, 5-methyl-[1,2,4]thiadiazol-3-yl, 5-methyl-[1,3,4]oxadiazol-2-yl, 5-methyl-isoxazol-3-yl and 5-methyl-oxazol-2-yl.

A certain embodiment of the invention is a compound of formula I as described herein, wherein $R^3$ is selected from the group consisting of [1,2,4]oxadiazolyl, isoxazolyl, [1,2,4]thiadiazolyl, oxazolyl and thiazolyl, each unsubstituted or substituted by $(R^*)_n$, wherein n=1-2 and each $R^*$ is individually selected from the group consisting halogen and $C_{1-6}$-alkyl.

A certain embodiment of the invention is a compound of formula I as described herein, wherein $R^3$ is [1,2,4]oxadiazolyl, [1,3,4]oxadiazolyl, [1,2,4]thiadiazolyl, oxazolyl or thiazolyl, each unsubstituted or substituted by 1-2 $C_{1-6}$-alkyl.

A certain embodiment of the invention is a compound of formula I as described herein, wherein $R^3$ is isoxazolyl, each unsubstituted or substituted by $(R^*)_n$, wherein n=1-2 and each $R^*$ is individually selected from the group consisting halogen and $C_{1-6}$-alkyl.

A certain embodiment of the invention is a compound of formula I as described herein, wherein $R^3$ is selected from the group consisting of 5-ethyl-isoxazol-3-yl, 5-methyl-[1,2,4]oxadiazol-3-yl, 5-methyl-isoxazol-3-yl, 5-methyl-[1,2,4]thiadiazol-3-yl, 5-methyl-[1,2,4]oxadiazol-3-yl, 5-methyl-oxazol-2-yl, 4-methyl-thiazol-2-yl, 4-chloro-5-methyl-isoxazol-3-yl, 4,5-dimethyl-isoxazol-3-yl, 4,5-dimethyl-oxazol-2-yl and 4-fluoro-5-methyl-isoxazol-3-yl.

A certain embodiment of the invention is a compound of formula I as described herein, wherein $R^3$ is [1,2,4]oxadiazolyl, unsubstituted or substituted by $(R^*)_n$, wherein n=1-2 and each $R^*$ is individually selected from the group consisting halogen and $C_{1-6}$-alkyl.

A certain embodiment of the invention is a compound of formula I as described herein, wherein $R^3$ is [1,2,4]oxadiazolyl, unsubstituted or substituted by $C_{1-6}$-alkyl.

A certain embodiment of the invention is a compound of formula I as described herein, wherein $R^3$ is 3-methyl-[1,2,4]oxadiazol-5-yl.

A certain embodiment of the invention is a compound of formula I as described herein, wherein $R^3$ is 5-isopropyl-[1,2,4]oxadiazol-3-yl.

A certain embodiment of the invention is a compound of formula I as described herein, wherein $R^3$ is 5-methyl-[1,2,4]oxadiazol-3-yl.

A certain embodiment of the invention is a compound of formula I as described herein, wherein $R^3$ is 5-ethyl-[1,2,4]oxadiazol-3-yl.

A certain embodiment of the invention is a compound of formula I as described herein, wherein $R^3$ is [1,3,4]oxadiazolyl, unsubstituted or substituted by $(R^*)_n$, wherein n=1-2 and each $R^*$ is individually selected from the group consisting halogen and $C_{1-6}$-alkyl.

A certain embodiment of the invention is a compound of formula I as described herein, wherein $R^3$ is [1,3,4]oxadiazolyl, unsubstituted or substituted by $C_{1-6}$-alkyl.

A certain embodiment of the invention is a compound of formula I as described herein, wherein $R^3$ is 5-methyl-[1,3,4]oxadiazol-2-yl.

A certain embodiment of the invention is a compound of formula I as described herein, wherein $R^3$ is oxazolyl, unsubstituted or substituted by $(R^*)_n$, wherein n=1-2 and each $R^*$ is individually selected from the group consisting halogen and $C_{1-6}$-alkyl.

A certain embodiment of the invention is a compound of formula I as described herein, wherein $R^3$ is oxazolyl, unsubstituted or substituted by $(R^*)_n$, wherein n=1-2 and each $R^*$ is individually selected from halogen and $C_{1-6}$-alkyl.

A certain embodiment of the invention is a compound of formula I as described herein, wherein $R^3$ is 5-chloro-4-methyloxazol-2-yl.

A certain embodiment of the invention is a compound of formula I as described herein, wherein $R^3$ is oxazolyl, unsubstituted or substituted by $(R^*)_n$, wherein n=1-2 and each $R^*$ is individually $C_{1-6}$-alkyl.

A certain embodiment of the invention is a compound of formula I as described herein, wherein $R^3$ is 4,5-dimethyl-oxazol-2-yl.

A certain embodiment of the invention is a compound of formula I as described herein, wherein $R^3$ is 4-methyl-oxazol-2-yl.

A certain embodiment of the invention is a compound of formula I as described herein, wherein $R^3$ is oxazol-2-yl.

A certain embodiment of the invention is a compound of formula I as described herein, wherein $R^3$ is 5-methyl-oxazol-2-yl.

A certain embodiment of the invention is a compound of formula I as described herein, wherein $R^3$ is thiazolyl, unsubstituted or substituted by $(R^*)_n$, wherein n=1-2 and each $R^*$ is individually selected from the group consisting halogen and $C_{1-6}$-alkyl.

A certain embodiment of the invention is a compound of formula I as described herein, wherein $R^3$ is 5-chloro-4-methylthiazol-2-yl.

A certain embodiment of the invention is a compound of formula I as described herein, wherein $R^3$ is thiazolyl, unsubstituted or substituted by $C_{1-6}$-alkyl.

A certain embodiment of the invention is a compound of formula I as described herein, wherein $R^3$ is 4-methyl-thiazol-2-yl.

A certain embodiment of the invention is a compound of formula I as described herein, wherein $R^3$ is 2-methyl-thiazol-4-yl.

A certain embodiment of the invention is a compound of formula I as described herein, wherein $R^3$ is 4,5-dimethylthiazol-2-yl.

A certain embodiment of the invention is a compound of formula I as described herein, wherein $R^3$ is thiazol-2-yl.

A certain embodiment of the invention is a compound of formula I as described herein, wherein $R^3$ is [1,2,4]thiadiazolyl, unsubstituted or substituted by $(R^*)_n$, wherein n=1-2 and each $R^*$ is individually selected from the group consisting halogen and $C_{1-6}$-alkyl.

A certain embodiment of the invention is a compound of formula I as described herein, wherein $R^3$ is [1,2,4]thiadiazolyl, unsubstituted or substituted by $C_{1-6}$-alkyl.

A certain embodiment of the invention is a compound of formula I as described herein, wherein $R^3$ is 3-methyl-[1,2,4]thiadiazol-5-yl.

A certain embodiment of the invention is a compound of formula I as described herein, wherein $R^3$ is 5-methyl-[1,2,4]thiadiazol-3-yl.

A certain embodiment of the invention is a compound of formula I as described herein, wherein $R^3$ is isoxazolyl, unsubstituted or substituted by $(R^*)_n$, wherein n=1-2 and each $R^*$ is individually selected from the group consisting halogen and $C_{1-6}$-alkyl, and two $R^*$ adjacent to each other can form a ring comprising 6 C.

A certain embodiment of the invention is a compound of formula I as described herein, wherein $R^3$ is isoxazolyl, substituted by $(R^*)_n$, wherein n=2 and each $R^*$ is individually $C_{1-6}$-alkyl, and two $R^*$ adjacent to each other form a ring comprising 6 C.

A certain embodiment of the invention is a compound of formula I as described herein, wherein $R^3$ is 4,5,6,7-tetrahydro-benzo[c]isoxazol-3-yl.

A certain embodiment of the invention is a compound of formula I as described herein, wherein $R^3$ is 4,5,6,7-tetrahydro-benzo[d]isoxazol-3-yl.

A certain embodiment of the invention is a compound of formula I as described herein, wherein $R^3$ is isoxazolyl, and each $R^*$ is individually $C_{1-6}$-alkyl, and two $R^*$ adjacent to each other form a ring comprising 5 C.

A certain embodiment of the invention is a compound of formula I as described herein, wherein $R^3$ is 5,6-dihydro-4H-cyclopenta[d]isoxazol.

A certain embodiment of the invention is a compound of formula I as described herein, wherein $R^3$ is 4,5-dimethyl-isoxazol-3-yl.

A certain embodiment of the invention is a compound of formula I as described herein, wherein $R^3$ is isoxazolyl, substituted by $(R^*)_n$, wherein n=1-2 and each $R^*$ is individually selected from the group consisting halogen and hydroxy-$C_{1-6}$-alkyl.

A certain embodiment of the invention is a compound of formula I as described herein, wherein $R^3$ is 4,5-bis(hydroxymethyl)isoxazol-3-yl.

A certain embodiment of the invention is a compound of formula I as described herein, wherein $R^3$ is isoxazolyl, substituted by $(R^*)_n$, wherein n=1-2 and each $R^*$ is individually selected from the group consisting halogen and $C_{1-6}$-alkyl.

A certain embodiment of the invention is a compound of formula I as described herein, wherein $R^3$ is 4-chloro-5-methyl-isoxazol-3-yl.

A certain embodiment of the invention is a compound of formula I as described herein, wherein $R^3$ is 4-fluoro-5-methyl-isoxazol-3-yl.

A certain embodiment of the invention is a compound of formula I as described herein, wherein $R^3$ is 5-ethyl-isoxazol-3-yl.

A certain embodiment of the invention is a compound of formula I as described herein, wherein $R^3$ is 5-methyl-isoxazol-3-yl.

A certain embodiment of the invention is a compound of formula I as described herein, wherein $R^3$ is 1H-pyrazol-1-yl.

A certain embodiment of the invention is a compound of formula I as described herein, wherein $R^3$ is 1H-pyrazol-1-yl substituted by $(R^*)_n$, wherein n=1, 2 or 3 and each $R^*$ is individually selected from the group consisting of $C_{1-6}$-alkyl.

A certain embodiment of the invention is a compound of formula I as described herein, wherein $R^3$ is 3,5-dimethyl-1H-pyrazol-1-yl.

A certain embodiment of the invention is a compound of formula I as described herein, wherein $R^3$ is 3,4,5-trimethyl-1H-pyrazol-1-yl.

Examples for the compound according to the invention are shown in the experimental part and the table below.

TABLE 2

| | structures of selected examples |
|---|---|
| Ex | Structure |
| 1 | 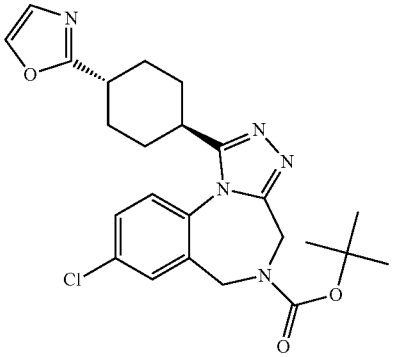 [SMILES: CC(C)(C)OC(=O)N1Cc2cc(Cl)ccc2-n2c(nnc2[C@H]2CC[C@H](c3ncco3)CC2)C1] |

TABLE 2-continued
structures of selected examples
| Ex | Structure |
|----|-----------|
| 2 | 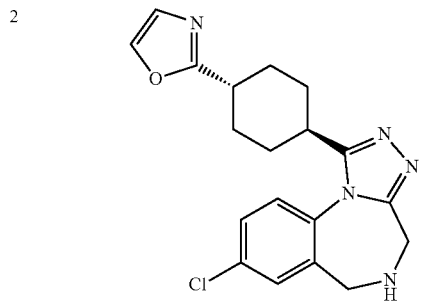 |
| 3 | 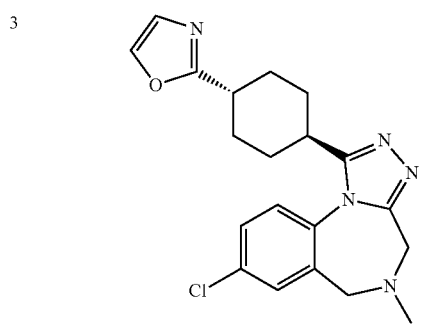 |
| 4 | 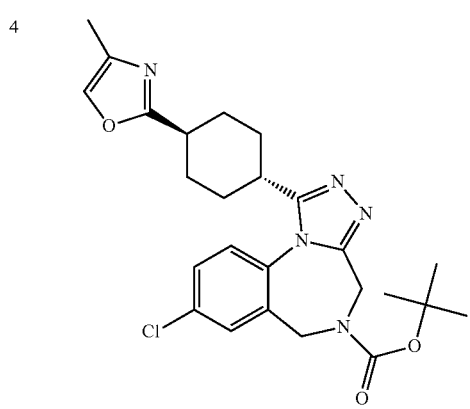 |
| 5 | 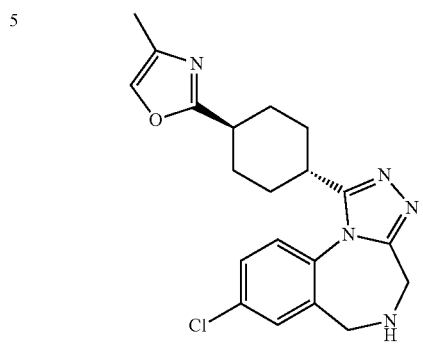 |
| 6 | 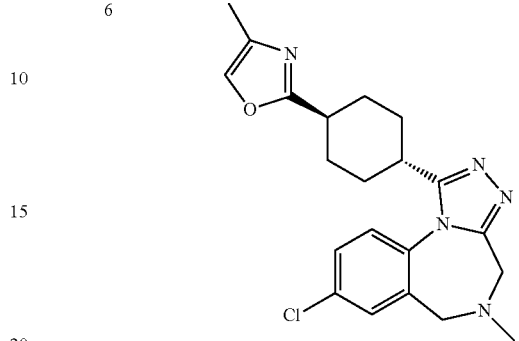 |
| 7 | 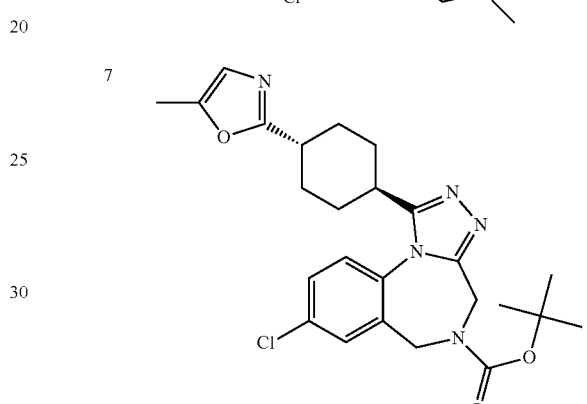 |
| 8 | 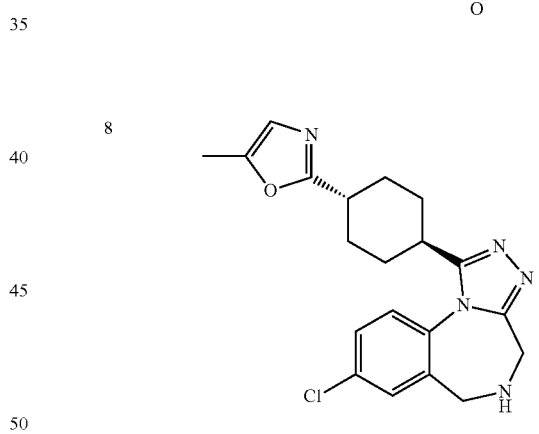 |
| 9 | 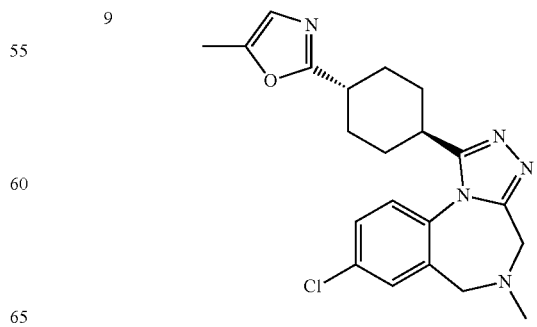 |

TABLE 2-continued
structures of selected examples
| Ex | Structure |
|---|---|
| 10 | 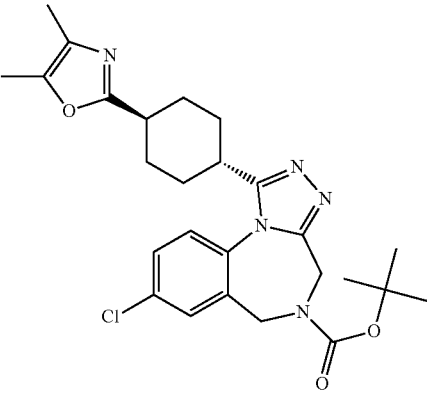 [SMILES: Cc1nc([C@H]2CC[C@H](c3nnc4n3-c3ccc(Cl)cc3CN(C(=O)OC(C)(C)C)C4)CC2)oc1C] |
| 11 | 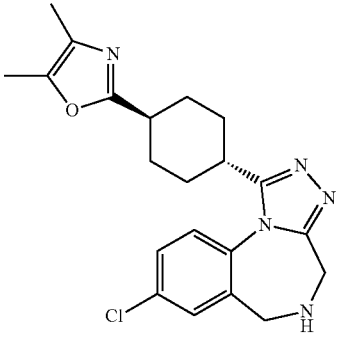 [SMILES: Cc1nc([C@H]2CC[C@H](c3nnc4n3-c3ccc(Cl)cc3CNC4)CC2)oc1C] |
| 12 | 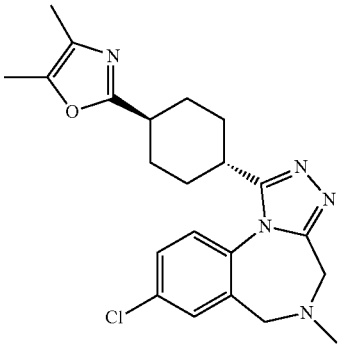 |
| 13 | 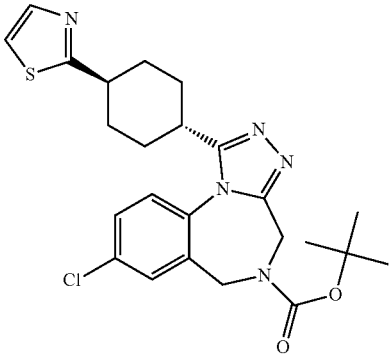 [SMILES: CC(C)(C)OC(=O)N1Cc2cc(Cl)ccc2-n2c(nnc2[C@H]2CC[C@H](c3nccs3)CC2)C1] |
| 14 | 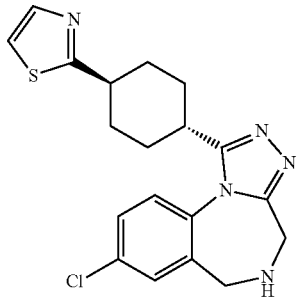 [SMILES: Clc1ccc2c(c1)CNCc1nnc([C@H]3CC[C@H](c4nccs4)CC3)n1-2] |
| 15 | 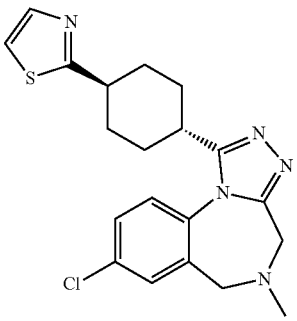 [SMILES: CN1Cc2cc(Cl)ccc2-n2c(nnc2[C@H]2CC[C@H](c3nccs3)CC2)C1] |
| 16 |  |
| 17 | 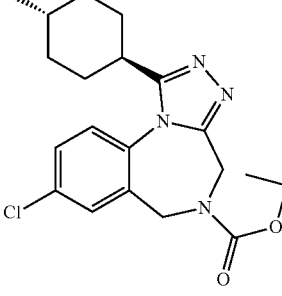 |

TABLE 2-continued
structures of selected examples
| Ex | Structure |
|----|-----------|
| 18 | 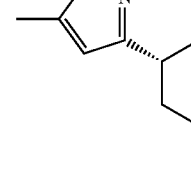 |
| 19 | 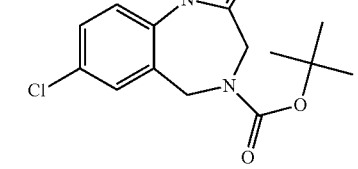 |
| 20 | 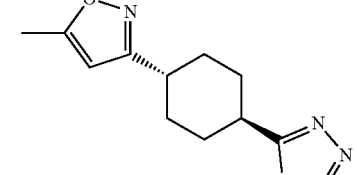 |
| 21 | 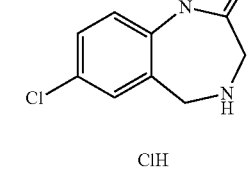 |
| 22 | 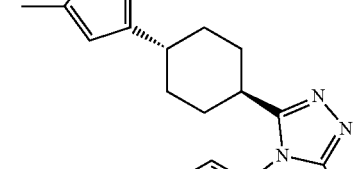 |
| 23 | 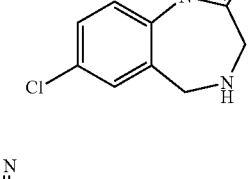 ClH |
| 24 | 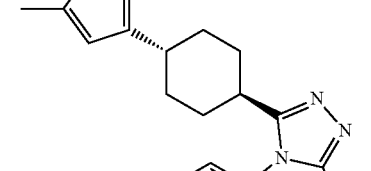 |
| 25 | 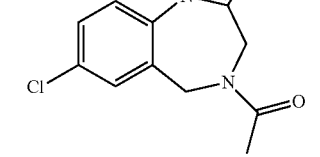 |

TABLE 2-continued structures of selected examples

| Ex | Structure |
|---|---|
| 26 | 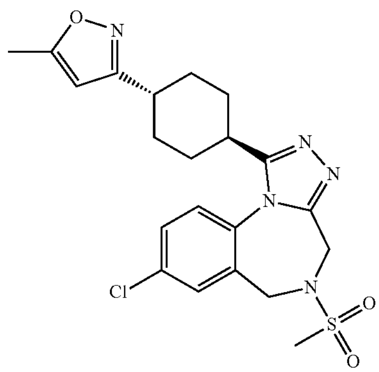 [SMILES: Cc1cc([C@H]2CC[C@H](c3nnc4n3-c3ccc(Cl)cc3CN(S(C)(=O)=O)C4)CC2)no1] |
| 27 | 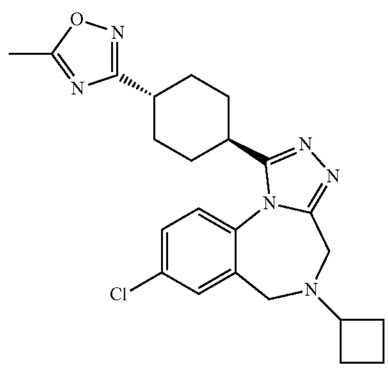 [SMILES: Cc1nc([C@H]2CC[C@H](c3nnc4n3-c3ccc(Cl)cc3CN(C3CCC3)C4)CC2)no1] |
| 28 | 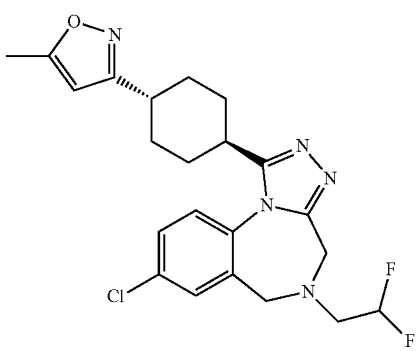 [SMILES: Cc1cc([C@H]2CC[C@H](c3nnc4n3-c3ccc(Cl)cc3CN(CC(F)F)C4)CC2)no1] |
| 29 | 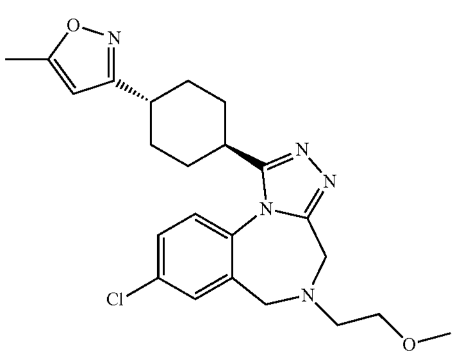 |
| 30 | |
| 31 | |
| 32 | |
| 33 | |

TABLE 2-continued
structures of selected examples
| Ex | Structure |
|---|---|
| 34 | 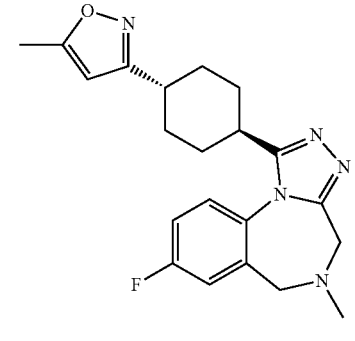 |
| 35 | 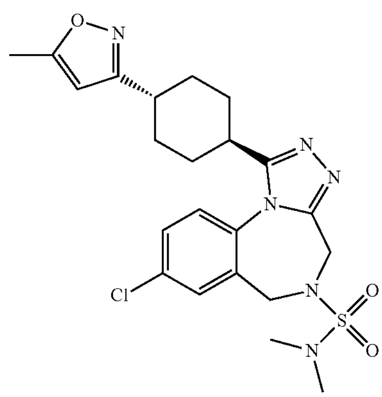 [SMILES: Cc1cc([C@H]2CC[C@H](c3nnc4n3-c3ccc(Cl)cc3CN(S(=O)(=O)N(C)C)C4)CC2)no1] |
| 36 | 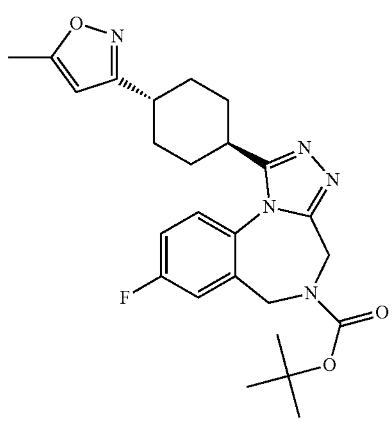 [SMILES: Cc1cc([C@H]2CC[C@H](c3nnc4n3-c3ccc(F)cc3CN(C(=O)OC(C)(C)C)C4)CC2)no1] |
| 37 | 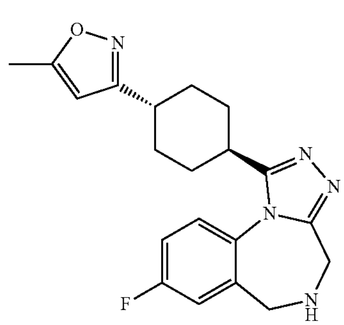 [SMILES: Cc1cc([C@H]2CC[C@H](c3nnc4n3-c3ccc(F)cc3CNC4)CC2)no1] |
| 38 | 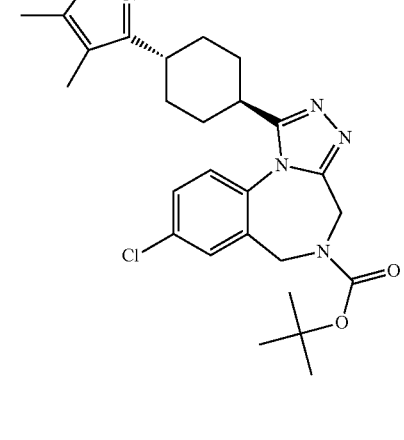 |
| 39 | |
| 40 | |
| 41 | |

TABLE 2-continued
structures of selected examples
| Ex | Structure |
|----|-----------|
| 42 | 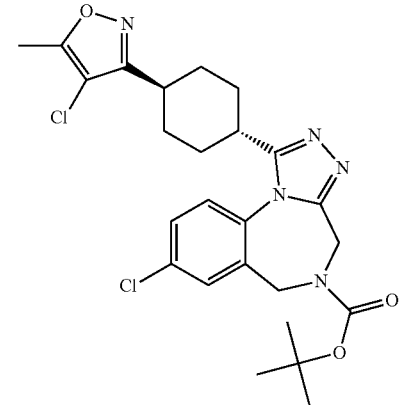 [SMILES: Cc1onc([C@H]2CC[C@H](c3nnc4n3-c3ccc(Cl)cc3CN(C(=O)OC(C)(C)C)C4)CC2)c1Cl] |
| 43 | 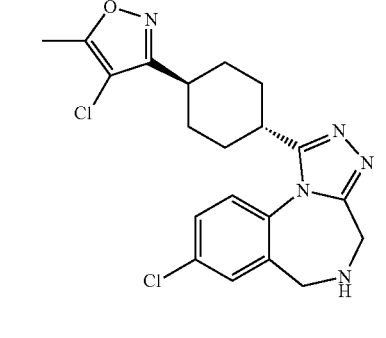 [SMILES: Cc1onc([C@H]2CC[C@H](c3nnc4n3-c3ccc(Cl)cc3CNC4)CC2)c1Cl] |
| 44 | 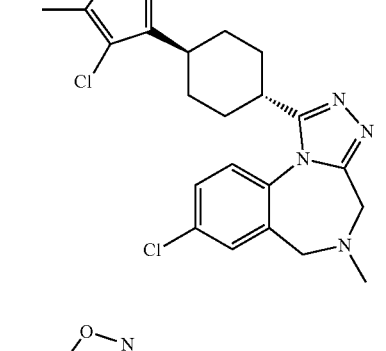 |
| 45 | 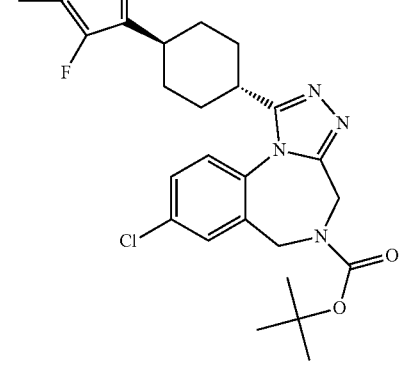 |
| 46 | 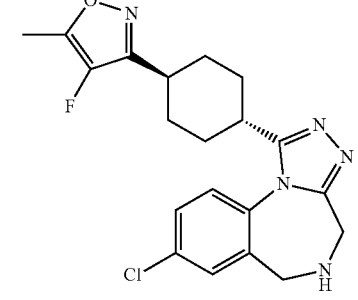 |
| 47 | 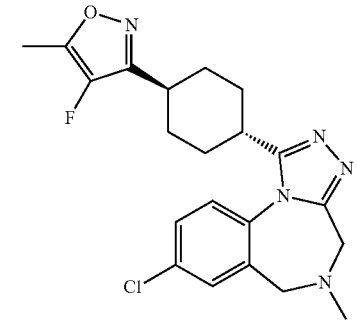 [SMILES: Cc1onc([C@H]2CC[C@H](c3nnc4n3-c3ccc(Cl)cc3CN(C)C4)CC2)c1F] |
| 48 | 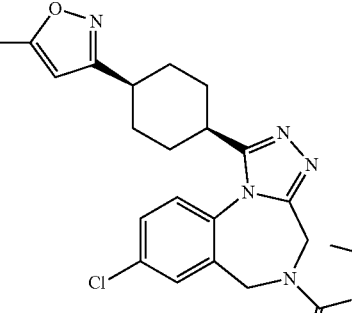 |
| 49 | 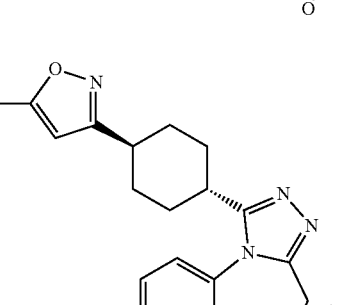 |

TABLE 2-continued structures of selected examples

| Ex | Structure |
|---|---|
| 50 | (structure with ethyl-isoxazole, cyclohexyl, triazole, chloro-benzodiazepine; ClH salt) |
| 51 | (structure with ethyl-isoxazole, cyclohexyl, triazole, chloro-N-methyl-benzodiazepine) |
| 52 | (structure with ethyl-isoxazole, cyclohexyl, triazole, chloro-benzodiazepine; ClH salt) |
| 53 | (structure with ethyl-isoxazole, cyclohexyl, triazole, chloro-N-methyl-benzodiazepine) |
| 54 | (structure with tetrahydrobenzisoxazole, cyclohexyl, triazole, chloro-benzodiazepine N-Boc) |
| 55 | (structure with tetrahydrobenzisoxazole, cyclohexyl, triazole, chloro-benzodiazepine NH) |
| 56 | (structure with tetrahydrobenzisoxazole, cyclohexyl, triazole, chloro-N-methyl-benzodiazepine) |
| 57 | (structure with tetrahydrobenzisoxazole, cyclohexyl, triazole, chloro-benzodiazepine N-Boc) |
| 58 | (structure with tetrahydrobenzisoxazole, cyclohexyl, triazole, chloro-benzodiazepine NH) |

TABLE 2-continued
structures of selected examples
| Ex | Structure |
|---|---|
| 59 | 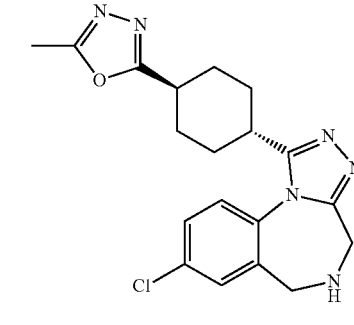 |
| 60 | 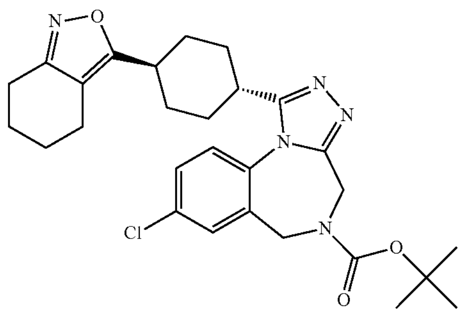 [SMILES: CC(C)(C)OC(=O)N1Cc2cc(Cl)ccc2-n2c(nnc2[C@H]2CC[C@H](c3onc4c3CCCC4)CC2)C1] |
| 61 | 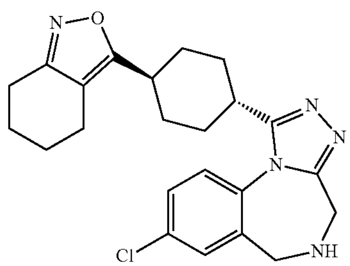 [SMILES: Clc1ccc2c(c1)CNCc1nnc([C@H]3CC[C@H](c4onc5c4CCCC5)CC3)n1-2] |
| 62 | 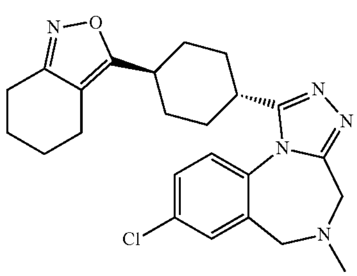 [SMILES: CN1Cc2cc(Cl)ccc2-n2c(nnc2[C@H]2CC[C@H](c3onc4c3CCCC4)CC2)C1] |
| 63 | 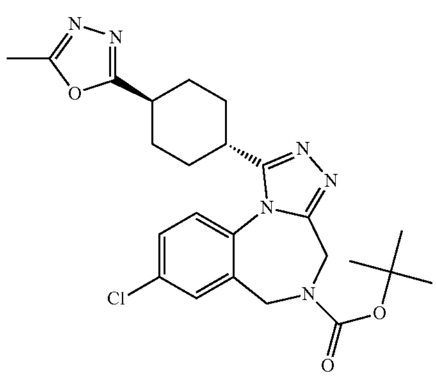 [SMILES: Cc1nnc([C@H]2CC[C@H](c3nnc4n3-c3ccc(Cl)cc3CN(C(=O)OC(C)(C)C)C4)CC2)o1] |
TABLE 2-continued
structures of selected examples
| Ex | Structure |
|---|---|
| 64 | 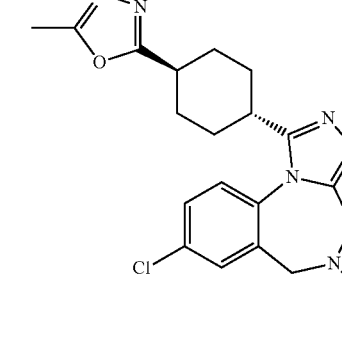 |
| 65 | 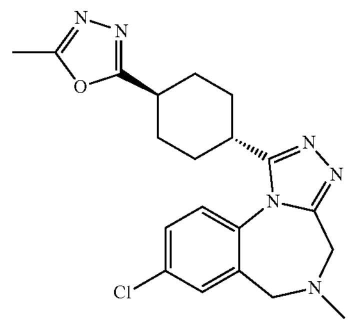 |
| 66 | 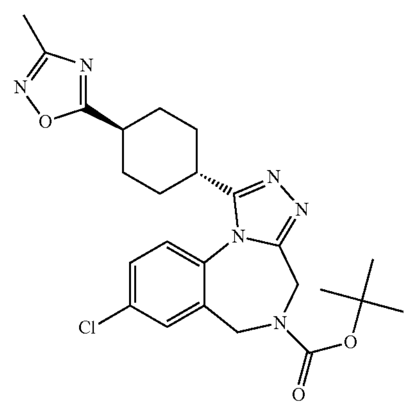 [SMILES: Cc1noc([C@H]2CC[C@H](c3nnc4n3-c3ccc(Cl)cc3CN(C(=O)OC(C)(C)C)C4)CC2)n1] |
| 67 | 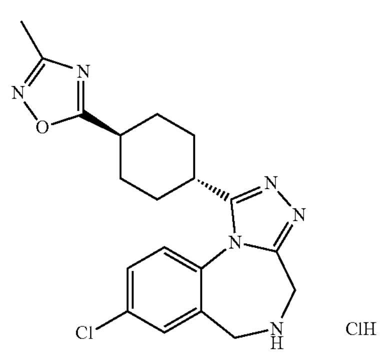 [SMILES: Cc1noc([C@H]2CC[C@H](c3nnc4n3-c3ccc(Cl)cc3CNC4)CC2)n1 ; Cl] |

TABLE 2-continued structures of selected examples

| Ex | Structure |
|---|---|
| 68 | 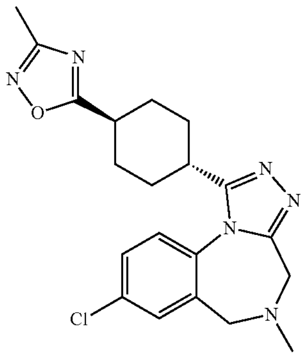 [SMILES: Cc1noc([C@H]2CC[C@H](c3nnc4n3-c3ccc(Cl)cc3CN(C)C4)CC2)n1] |
| 69 | 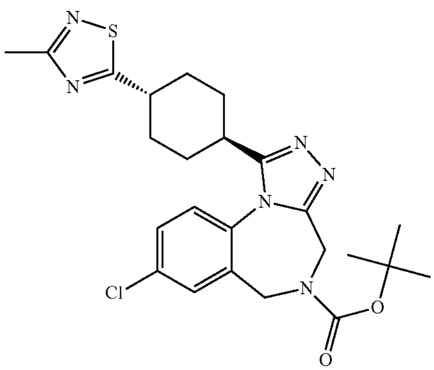 [SMILES: Cc1nsc([C@H]2CC[C@H](c3nnc4n3-c3ccc(Cl)cc3CN(C(=O)OC(C)(C)C)C4)CC2)n1] |
| 70 | 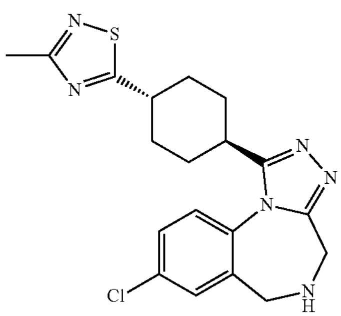 [SMILES: Cc1nsc([C@H]2CC[C@H](c3nnc4n3-c3ccc(Cl)cc3CNC4)CC2)n1] |
| 71 | 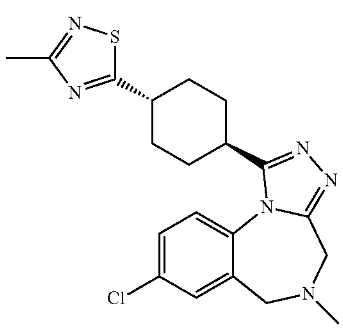 |
| 72 | |
| 73 | |
| 74 | |
| 75 | |

TABLE 2-continued structures of selected examples

| Ex | Structure |
|---|---|
| 76 | (5-methyl-1,2,4-oxadiazol-3-yl)cyclohexyl-triazolo-benzodiazepine with Cl and N-isopropyl) |
| 77 | (same core, N-cyclobutyl) |
| 78 | (same core, N-cyclopentyl) |
| 79 | (same core, N-CH2CHF2) |
| 80 | (same core, N-acetyl) |
| 81 | (same core, N-SO2Me) |
| 82 | (same core, N-Boc) |
| 83 | (same core, NH, HCl salt) |

TABLE 2-continued
structures of selected examples
| Ex | Structure |
|---|---|
| 84 | 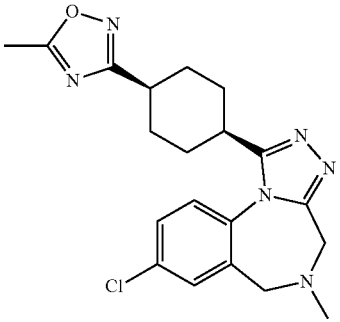 [SMILES: Cc1nc([C@H]2CC[C@@H](c3nnc4n3-c3ccc(Cl)cc3CN(C)C4)CC2)no1] |
| 85 | 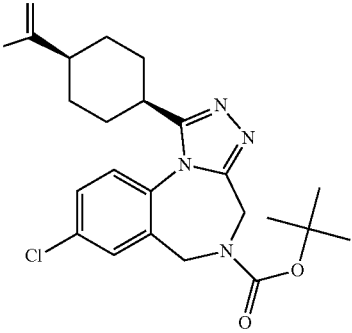 |
| 86 | 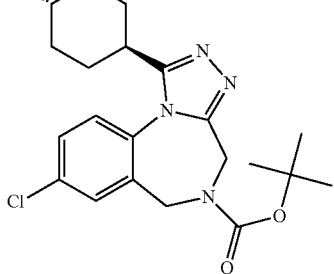 |
| 87 | 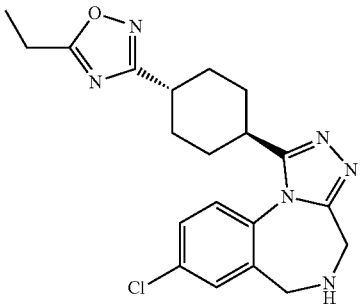<br>ClH |
| 88 | 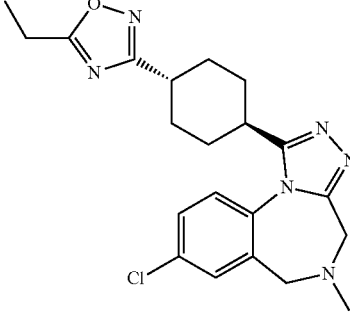 |
| 89 | 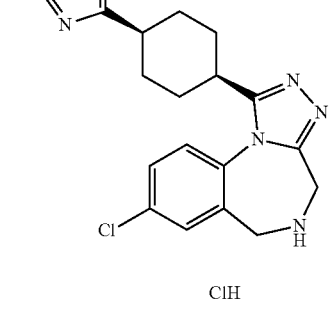<br>ClH |
| 90 | 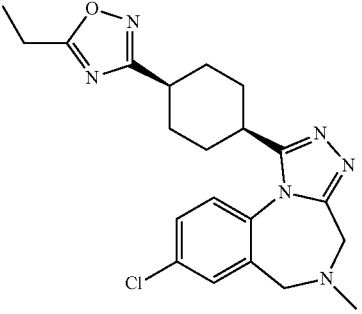 [SMILES: CCc1nc([C@H]2CC[C@@H](c3nnc4n3-c3ccc(Cl)cc3CN(C)C4)CC2)no1] |
| 91 | 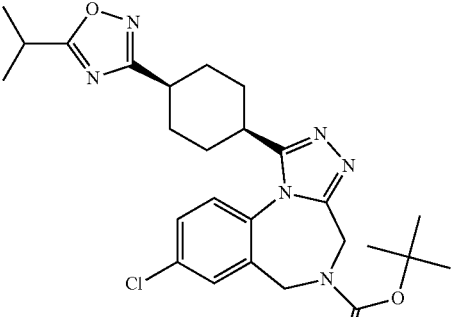 |

TABLE 2-continued
structures of selected examples
| Ex | Structure |
|---|---|
| 92 | 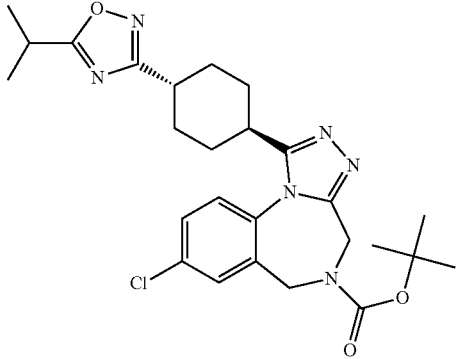 [SMILES: CC(C)c1nc([C@H]2CC[C@H](c3nnc4n3-c3ccc(Cl)cc3CN(C(=O)OC(C)(C)C)C4)CC2)no1] |
| 93 | 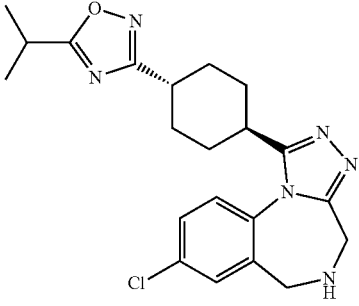<br>ClH |
| 94 | 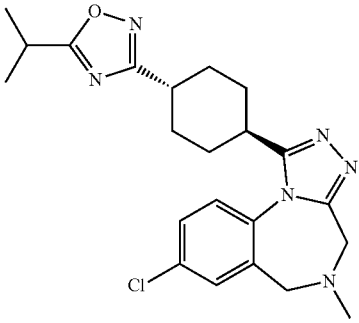 [SMILES: CC(C)c1nc([C@H]2CC[C@H](c3nnc4n3-c3ccc(Cl)cc3CN(C)C4)CC2)no1] |
| 95 | 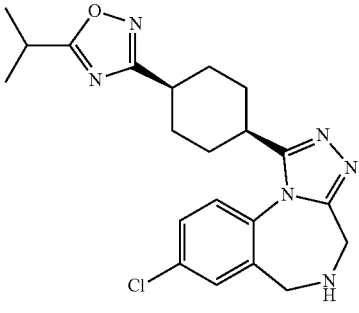<br>ClH |
| 96 | 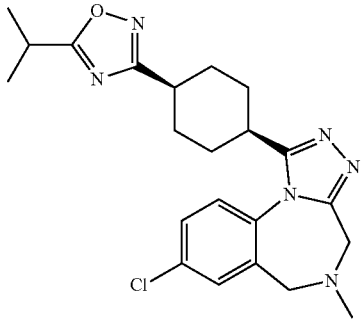 [SMILES: CC(C)c1nc([C@H]2CC[C@@H](c3nnc4n3-c3ccc(Cl)cc3CN(C)C4)CC2)no1] |
| 97 | 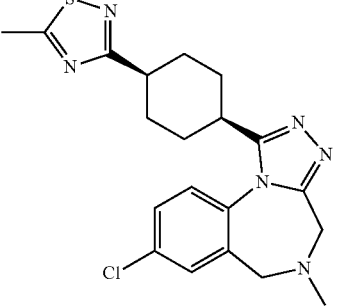 |
| 98 | 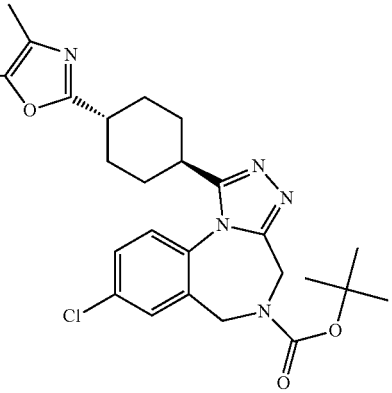 |
| 99 | 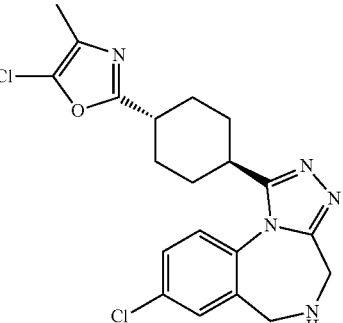 |

TABLE 2-continued
structures of selected examples
| Ex | Structure |
|---|---|
| 100 | 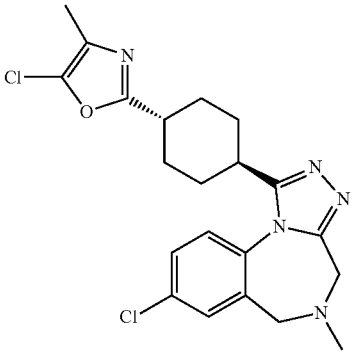 [SMILES: Cc1nc([C@H]2CC[C@H](c3nnc4n3-c3ccc(Cl)cc3CN(C)C4)CC2)oc1Cl] |
| 101 | 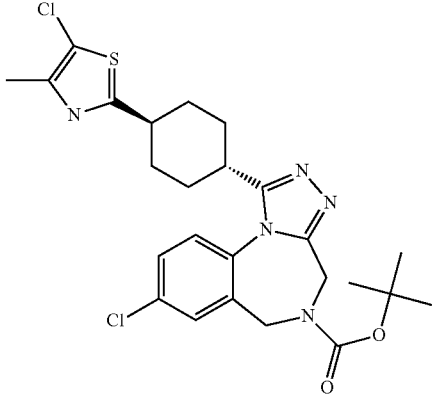 |
| 102 | 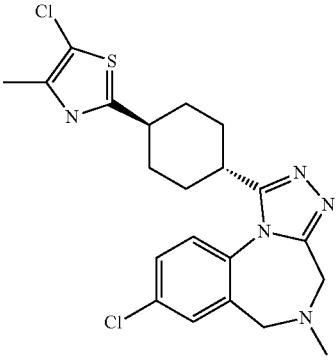 |
| 103 | 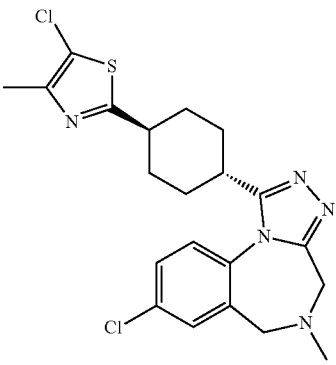 [SMILES: Cc1nc([C@H]2CC[C@H](c3nnc4n3-c3ccc(Cl)cc3CN(C)C4)CC2)sc1Cl] |
| 104 | 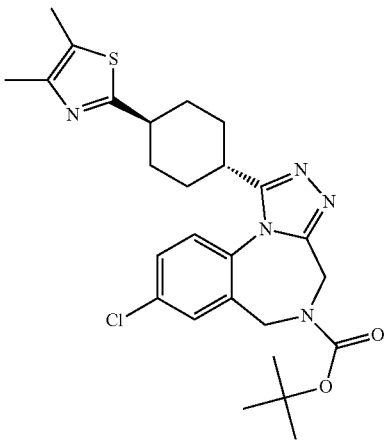 [SMILES: Cc1nc([C@H]2CC[C@H](c3nnc4n3-c3ccc(Cl)cc3CN(C(=O)OC(C)(C)C)C4)CC2)sc1C] |
| 105 | 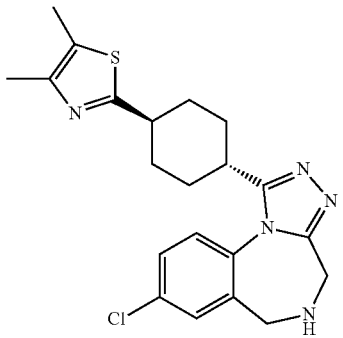 [SMILES: Cc1nc([C@H]2CC[C@H](c3nnc4n3-c3ccc(Cl)cc3CNC4)CC2)sc1C] |
| 106 | 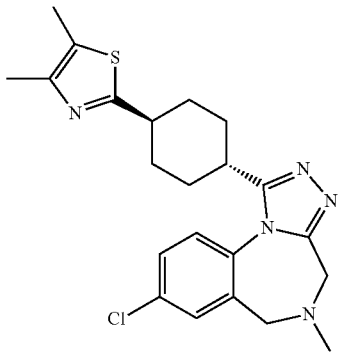 [SMILES: Cc1nc([C@H]2CC[C@H](c3nnc4n3-c3ccc(Cl)cc3CN(C)C4)CC2)sc1C] |
| 107 | 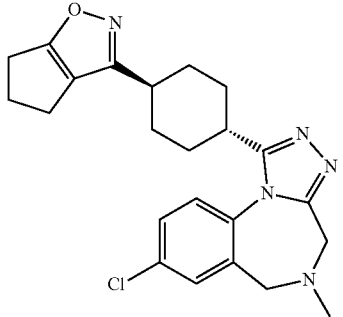 [SMILES: CN1Cc2cc(Cl)ccc2-n2c(nnc2[C@H]2CC[C@H](c3noc4c3CCC4)CC2)C1] |

TABLE 2-continued structures of selected examples

| Ex | Structure |
|---|---|
| 108 | 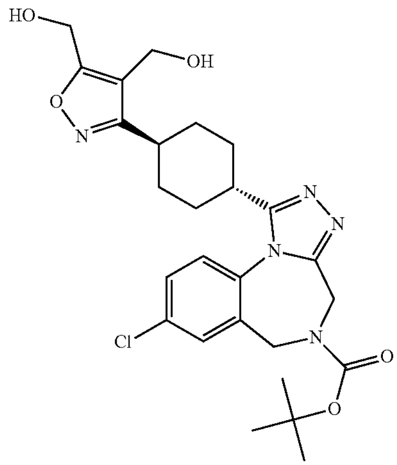 [SMILES: CC(C)(C)OC(=O)N1Cc2cc(Cl)ccc2-n2c(nnc2[C@H]2CC[C@H](c3noc(CO)c3CO)CC2)C1] |
| 109 | 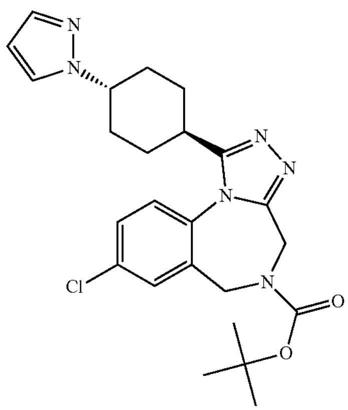 [SMILES: CC(C)(C)OC(=O)N1Cc2cc(Cl)ccc2-n2c(nnc2[C@H]2CC[C@H](n3cccn3)CC2)C1] |
| 110 | 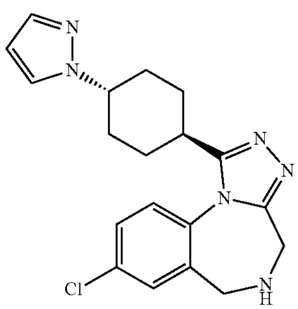 [SMILES: Clc1ccc2c(c1)CNCc1nnc([C@H]3CC[C@H](n4cccn4)CC3)n1-2] |
| 111 | 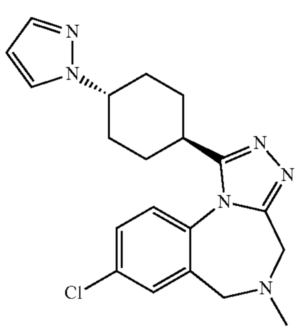 [SMILES: CN1Cc2cc(Cl)ccc2-n2c(nnc2[C@H]2CC[C@H](n3cccn3)CC2)C1] |
| 112 | |
| 113 | |
| 114 | |
| 115 | |

TABLE 2-continued structures of selected examples

| Ex | Structure |
|---|---|
| 116 | 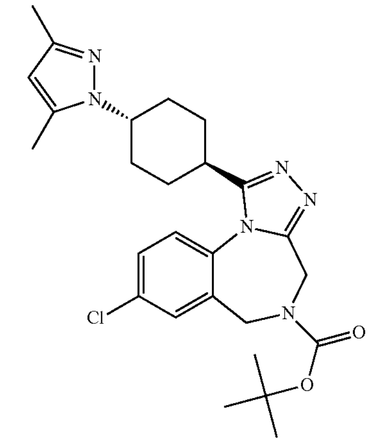 [SMILES: Cc1cc(C)n([C@H]2CC[C@H](c3nnc4n3-c3ccc(Cl)cc3CN(C(=O)OC(C)(C)C)C4)CC2)n1] |
| 117 | 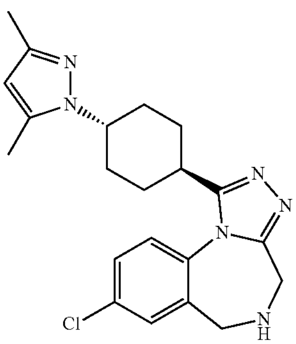 [SMILES: Cc1cc(C)n([C@H]2CC[C@H](c3nnc4n3-c3ccc(Cl)cc3CNC4)CC2)n1] |
| 118 | 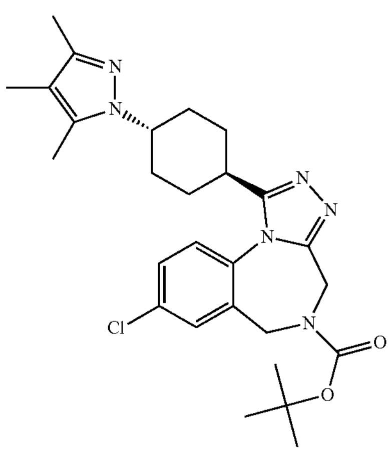 [SMILES: Cc1nn([C@H]2CC[C@H](c3nnc4n3-c3ccc(Cl)cc3CN(C(=O)OC(C)(C)C)C4)CC2)c(C)c1C] |
| 119 | 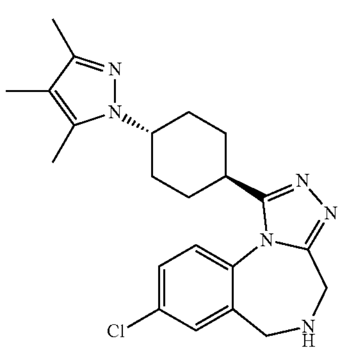 [SMILES: Cc1nn([C@H]2CC[C@H](c3nnc4n3-c3ccc(Cl)cc3CNC4)CC2)c(C)c1C] |

TABLE 2-continued structures of selected examples

| Ex | Structure |
|---|---|
| 120 | |

Specific compounds of the invention are shown in the examples. More particular are
trans-8-Chloro-1-(4-oxazol-2-yl-cyclohexyl)-4H,6H-2,3,5,10b-tetraaza-benzo[e]azulene-5-carboxylic acid tert-butyl ester,
cis-8-Chloro-1-(4-pyrazol-1-yl-cyclohexyl)-5,6-dihydro-4H-2,3,5,10b-tetraaza-benzo[e]azulene,
cis-8-Chloro-1-[4-(4,5,6,7-tetrahydro-benzo[d]isoxazol-3-yl)-cyclohexyl]-4H,6H-2,3,5,10b-tetraaza-benzo[e]azulene-5-carboxylic acid tert-butyl ester,
cis-8-Chloro-1-[4-(4,5,6,7-tetrahydro-benzo[d]isoxazol-3-yl)-cyclohexyl]-5,6-dihydro-4H-2,3,5,10b-tetraaza-benzo[e]azulene,
cis-8-Chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester,
cis-8-Chloro-1-[4-(5-ethyl-[1,2,4]oxadiazol-3-yl)-cyclohexyl]-5,6-dihydro-4H-2,3,5,10b-tetraaza-benzo[e]azulene,
cis-8-Chloro-1-[4-(5-ethyl-[1,2,4]oxadiazol-3-yl)-cyclohexyl]-5-methyl-5,6-dihydro-4H-2,3,5,10b-tetraaza-benzo[e]azulene,
cis-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester,
cis-8-Chloro-1-[4-(5-ethyl-isoxazol-3-yl)-cyclohexyl]-5,6-dihydro-4H-2,3,5,10b-tetraaza-benzo[e]azulene,
cis-8-Chloro-1-[4-(5-ethyl-isoxazol-3-yl)-cyclohexyl]-5-methyl-5,6-dihydro-4H-2,3,5,10b-tetraaza-benzo[e]azulene,
cis-8-Chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester,
cis-8-Chloro-1-[4-(5-isopropyl-[1,2,4]oxadiazol-3-yl)-cyclohexyl]-5,6-dihydro-4H-2,3,5,10b-tetraaza-benzo[e]azulene,
cis-8-Chloro-1-[4-(5-isopropyl-[1,2,4]oxadiazol-3-yl)-cyclohexyl]-5-methyl-5,6-dihydro-4H-2,3,5,10b-tetraaza-benzo[e]azulene,
cis-8-Chloro-1-[4-(5-methyl-[1,2,4]oxadiazol-3-yl)-cyclohexyl]-4H,6H-2,3,5,10b-tetraaza-benzo[e]azulene-5-carboxylic acid tert-butyl ester,
cis-8-Chloro-1-[4-(5-methyl-[1,2,4]oxadiazol-3-yl)-cyclohexyl]-5,6-dihydro-4H-2,3,5,10b-tetraaza-benzo[e]azulene, cis-8-Chloro-5-methyl-1-(4-pyrazol-1-yl-cyclohexyl)-5,6-dihydro-4H-2,3,5,10b-tetraaza-benzo[e]azulene, cis-8-Chloro-5-methyl-1-(4-pyrazol-1-yl-cyclohexyl)-5,6-dihydro-4H-2,3,5,10b-tetraaza-benzo[e]azulene, cis-8-Chloro-5-methyl-1-[4-(4,5,6,7-tetrahydro-benzo[d]isoxazol-3-yl)-cyclohexyl]-5,6-dihydro-4H-2,3,5,10b-tetraaza-benzo[e]azulene, cis-8-Chloro-5-methyl-1-[4-(5-methyl-[1,2,4]oxadiazol-3-yl)-cyclohexyl]-5,6-dihydro-4H-2,3,5,10b-tetraaza-benzo[e]azulene, trans-(2-{8-Chloro-1-[4-(5-methyl-isoxazol-3-yl)-cyclohexyl]-4H,6H-2,3,5,10b-tetraaza-benzo[e]azulen-5-yl}-ethyl)-methyl-amine, trans-1-[4-(4,5-Bis-hydroxymethyl-isoxazol-3-yl)-cyclohexyl]-8-chloro-4H,6H-2,3,5,10b-tetraaza-benzo[e]azulene-5-carboxylic acid tert-butyl ester, trans-1-{8-Chloro-1-[4-(5-methyl-[1,2,4]oxadiazol-3-yl)-cyclohexyl]-4H,6H-2,3,5,10b-tetraaza-benzo[e]azulen-5-yl}-ethanone, trans-1-{8-Chloro-1-[4-(5-methyl-isoxazol-3-yl)-cyclohexyl]-4H,6H-2,3,5,10b-tetraaza-benzo[e]azulen-5-yl}-ethanone, trans-1-{8-Chloro-1-[4-(5-methyl-isoxazol-3-yl)-cyclohexyl]-4H,6H-2,3,5,10b-tetraaza-benzo[e]azulen-5-yl}-2-hydroxy-ethanone, trans-1-{8-Chloro-1-[4-(5-methyl-isoxazol-3-yl)-cyclohexyl]-4H,6H-2,3,5,10b-tetraaza-benzo[e]azulen-5-yl}-2-dimethylamino-ethanone, trans-8-Chloro-1-(4-oxazol-2-yl-cyclohexyl)-5,6-dihydro-4H-2,3,5,10b-tetraaza-benzo[e]azulene, trans-8-Chloro-1-(4-pyrazol-1-yl-cyclohexyl)-4H,6H-2,3,5,10b-tetraaza-benzo[e]azulene-5-carboxylic acid tert-butyl ester, trans-8-Chloro-1-(4-pyrazol-1-yl-cyclohexyl)-5,6-dihydro-4H-2,3,5,10b-tetraaza-benzo[e]azulene, trans-8-Chloro-1-(4-thiazol-2-yl-cyclohexyl)-4H,6H-2,3,5,10b-tetraaza-benzo[e]azulene-5-carboxylic acid tert-butyl ester, trans-8-Chloro-1-(4-thiazol-2-yl-cyclohexyl)-5,6-dihydro-4H-2,3,5,10b-tetraaza-benzo[e]azulene, trans-8-Chloro-1-[4-(2-methyl-thiazol-4-yl)-cyclohexyl]-4H,6H-2,3,5,10b-tetraaza-benzo[e]azulene-5-carboxylic acid tert-butyl ester, trans-8-Chloro-1-[4-(3,4,5-trimethyl-pyrazol-1-yl)-cyclohexyl]-4H,6H-2,3,5,10b-tetraaza-benzo[e]azulene-5-carboxylic acid tert-butyl ester, trans-8-Chloro-1-[4-(3,4,5-trimethyl-pyrazol-1-yl)-cyclohexyl]-5-methyl-5,6-dihydro-4H-2,3,5,10b-tetraaza-benzo[e]azulene, trans-8-Chloro-1-[4-(3,4,5-trimethyl-pyrazol-1-yl)-cyclohexyl]-5,6-dihydro-4H-2,3,5,10b-tetraaza-benzo[e]azulene, trans-8-Chloro-1-[4-(3,5-dimethyl-pyrazol-1-yl)-cyclohexyl]-4H,6H-2,3,5,10b-tetraaza-benzo[e]azulene-5-carboxylic acid tert-butyl ester, trans-8-Chloro-1-[4-(3,5-dimethyl-pyrazol-1-yl)-cyclohexyl]-5,6-dihydro-4H-2,3,5,10b-tetraaza-benzo[e]azulene, trans-8-Chloro-1-[4-(3,5-dimethyl-pyrazol-1-yl)-cyclohexyl]-5-methyl-5,6-dihydro-4H-2,3,5,10b-tetraaza-benzo[e]azulene, trans-8-Chloro-1-[4-(3-methyl-[1,2,4]oxadiazol-5-yl)-cyclohexyl]-4H,6H-2,3,5,10b-tetraaza-benzo[e]azulene-5-carboxylic acid tert-butyl ester, trans-8-Chloro-1-[4-(3-methyl-[1,2,4]oxadiazol-5-yl)-cyclohexyl]-5,6-dihydro-4H-2,3,5,10b-tetraaza-benzo[e]azulene, trans-8-Chloro-1-[4-(3-methyl-[1,2,4]thiadiazol-5-yl)-cyclohexyl]-4H,6H-2,3,5,10b-tetraaza-benzo[e]azulene-5-carboxylic acid tert-butyl ester, trans-8-Chloro-1-[4-(3-methyl-[1,2,4]thiadiazol-5-yl)-cyclohexyl]-5,6-dihydro-4H-2,3,5,10b-tetraaza-benzo[e]azulene, trans-8-Chloro-1-[4-(4,5,6,7-tetrahydro-benzo[c]isoxazol-3-yl)-cyclohexyl]-4H,6H-2,3,5,10b-tetraaza-benzo[e]azulene-5-carboxylic acid tert-butyl ester, trans-8-Chloro-1-[4-(4,5,6,7-tetrahydro-benzo[c]isoxazol-3-yl)-cyclohexyl]-5,6-dihydro-4H-2,3,5,10b-tetraaza-benzo[e]azulene, trans-8-Chloro-1-[4-(4,5,6,7-tetrahydro-benzo[d]isoxazol-3-yl)-cyclohexyl]-4H,6H-2,3,5,10b-tetraaza-benzo[e]azulene-5-carboxylic acid tert-butyl ester, trans-8-Chloro-1-[4-(4,5,6,7-tetrahydro-benzo[d]isoxazol-3-yl)-cyclohexyl]-5,6-dihydro-4H-2,3,5,10b-tetraaza-benzo[e]azulene, trans-8-Chloro-1-[4-(4,5-dimethyl-isoxazol-3-yl)-cyclohexyl]-4H,6H-2,3,5,10b-tetraaza-benzo[e]azulene-5-carboxylic acid tert-butyl ester, trans-8-Chloro-1-[4-(4,5-dimethyl-isoxazol-3-yl)-cyclohexyl]-5,6-dihydro-4H-2,3,5,10b-tetraaza-benzo[e]azulene, trans-8-Chloro-1-[4-(4,5-dimethyl-isoxazol-3-yl)-cyclohexyl]-5-methyl-5,6-dihydro-4H-2,3,5,10b-tetraaza-benzo[e]azulene, trans-8-Chloro-1-[4-(4,5-dimethyl-oxazol-2-yl)-cyclohexyl]-4H,6H-2,3,5,10b-tetraaza-benzo[e]azulene-5-carboxylic acid tert-butyl ester, trans-8-Chloro-1-[4-(4,5-dimethyl-oxazol-2-yl)-cyclohexyl]-5,6-dihydro-4H-2,3,5,10b-tetraaza-benzo[e]azulene, trans-8-Chloro-1-[4-(4,5-dimethyl-oxazol-2-yl)-cyclohexyl]-5-methyl-5,6-dihydro-4H-2,3,5,10b-tetraaza-benzo[e]azulene, trans-8-Chloro-1-[4-(4,5-dimethyl-thiazol-2-yl)-cyclohexyl]-4H,6H-2,3,5,10b-tetraaza-benzo[e]azulene-5-carboxylic acid tert-butyl ester, trans-8-Chloro-1-[4-(4,5-dimethyl-thiazol-2-yl)-cyclohexyl]-5,6-dihydro-4H-2,3,5,10b-tetraaza-benzo[e]azulene, trans-8-Chloro-1-[4-(4,5-dimethyl-thiazol-2-yl)-cyclohexyl]-5-methyl-5,6-dihydro-4H-2,3,5,10b-tetraaza-benzo[e]azulene, trans-8-Chloro-1-[4-(4-chloro-5-methyl-isoxazol-3-yl)-cyclohexyl]-4H,6H-2,3,5,10b-tetraaza-benzo[e]azulene-5-carboxylic acid tert-butyl ester, trans-8-Chloro-1-[4-(4-chloro-5-methyl-isoxazol-3-yl)-cyclohexyl]-5,6-dihydro-4H-2,3,5,10b-tetraaza-benzo[e]azulene, trans-8-Chloro-1-[4-(4-chloro-5-methyl-isoxazol-3-yl)-cyclohexyl]-5-methyl-5,6-dihydro-4H-2,3,5,10b-tetraaza-benzo[e]azulene, trans-8-Chloro-1-[4-(4-fluoro-5-methyl-isoxazol-3-yl)-cyclohexyl]-4H,6H-2,3,5,10b-tetraaza-benzo[e]azulene-5-carboxylic acid tert-butyl ester, trans-8-Chloro-1-[4-(4-fluoro-5-methyl-isoxazol-3-yl)-cyclohexyl]-5,6-dihydro-4H-2,3,5,10b-tetraaza-benzo[e]azulene, trans-8-Chloro-1-[4-(4-fluoro-5-methyl-isoxazol-3-yl)-cyclohexyl]-5-methyl-5,6-dihydro-4H-2,3,5,10b-tetraaza-benzo[e]azulene, trans-8-Chloro-1-[4-(4-methyl-oxazol-2-yl)-cyclohexyl]-4H,6H-2,3,5,10b-tetraaza-benzo[e]azulene-5-carboxylic acid tert-butyl ester, trans-8-Chloro-1-[4-(4-methyl-oxazol-2-yl)-cyclohexyl]-5,6-dihydro-4H-2,3,5,10b-tetraaza-benzo[e]azulene,
trans-8-Chloro-1-[4-(4-methyl-thiazol-2-yl)-cyclohexyl]-4H,6H-2,3,5,10b-tetraaza-benzo[e]azulene-5-carboxylic acid tert-butyl ester,
trans-8-Chloro-1-[4-(4-methyl-thiazol-2-yl)-cyclohexyl]-5,6-dihydro-4H-2,3,5,10b-tetraaza-benzo[e]azulene,
trans-8-Chloro-1-[4-(5,6-dihydro-4H-cyclopenta[d]isoxazol-3-yl)-cyclohexyl]-5-methyl-5,6-dihydro-4H-2,3,5,10b-tetraaza-benzo[e]azulene,
trans-8-Chloro-1-[4-(5-chloro-4-methyl-oxazol-2-yl)-cyclohexyl]-4H,6H-2,3,5,10b-tetraaza-benzo[e]azulene-5-carboxylic acid tert-butyl ester,
trans-8-Chloro-1-[4-(5-chloro-4-methyl-oxazol-2-yl)-cyclohexyl]-5,6-dihydro-4H-2,3,5,10b-tetraaza-benzo[e]azulene,
trans-8-Chloro-1-[4-(5-chloro-4-methyl-oxazol-2-yl)-cyclohexyl]-5-methyl-5,6-dihydro-4H-2,3,5,10b-tetraaza-benzo[e]azulene,
trans-8-Chloro-1-[4-(5-chloro-4-methyl-thiazol-2-yl)-cyclohexyl]-4H,6H-2,3,5,10b-tetraaza-benzo[e]azulene-5-carboxylic acid tert-butyl ester,
trans-8-Chloro-1-[4-(5-chloro-4-methyl-thiazol-2-yl)-cyclohexyl]-5,6-dihydro-4H-2,3,5,10b-tetraaza-benzo[e]azulene,
trans-8-Chloro-1-[4-(5-chloro-4-methyl-thiazol-2-yl)-cyclohexyl]-5-methyl-5,6-dihydro-4H-2,3,5,10b-tetraaza-benzo[e]azulene,
trans-8-Chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester,
trans-8-Chloro-1-[4-(5-ethyl-[1,2,4]oxadiazol-3-yl)-cyclohexyl]-5,6-dihydro-4H-2,3,5,10b-tetraaza-benzo[e]azulene,
trans-8-Chloro-1-[4-(5-ethyl-[1,2,4]oxadiazol-3-yl)-cyclohexyl]-5-methyl-5,6-dihydro-4H-2,3,5,10b-tetraaza-benzo[e]azulene,
trans-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester,
trans-8-Chloro-1-[4-(5-ethyl-isoxazol-3-yl)-cyclohexyl]-5,6-dihydro-4H-2,3,5,10b-tetraaza-benzo[e]azulene,
trans-8-Chloro-1-[4-(5-ethyl-isoxazol-3-yl)-cyclohexyl]-5-methyl-5,6-dihydro-4H-2,3,5,10b-tetraaza-benzo[e]azulene,
trans-8-Chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester,
trans-8-Chloro-1-[4-(5-isopropyl-[1,2,4]oxadiazol-3-yl)-cyclohexyl]-5,6-dihydro-4H-2,3,5,10b-tetraaza-benzo[e]azulene,
trans-8-Chloro-1-[4-(5-isopropyl-[1,2,4]oxadiazol-3-yl)-cyclohexyl]-5-methyl-5,6-dihydro-4H-2,3,5,10b-tetraaza-benzo[e]azulene,
trans-8-Chloro-1-[4-(5-methyl-[1,2,4]oxadiazol-3-yl)-cyclohexyl]-4H,6H-2,3,5,10b-tetraaza-benzo[e]azulene-5-carboxylic acid tert-butyl ester,
trans-8-Chloro-1-[4-(5-methyl-[1,2,4]oxadiazol-3-yl)-cyclohexyl]-5,6-dihydro-4H-2,3,5,10b-tetraaza-benzo[e]azulene,
trans-8-Chloro-1-[4-(5-methyl-[1,3,4]oxadiazol-2-yl)-cyclohexyl]-4H,6H-2,3,5,10b-tetraaza-benzo[e]azulene-5-carboxylic acid tert-butyl ester,
trans-8-Chloro-1-[4-(5-methyl-[1,3,4]oxadiazol-2-yl)-cyclohexyl]-5,6-dihydro-4H-2,3,5,10b-tetraaza-benzo[e]azulene,
trans-8-Chloro-1-[4-(5-methyl-isoxazol-3-yl)-cyclohexyl]-4H,6H-2,3,5,10b-tetraaza-benzo[e]azulene-5-carboxylic acid tert-butyl ester,
trans-8-Chloro-1-[4-(5-methyl-isoxazol-3-yl)-cyclohexyl]-4H,6H-2,3,5,10b-tetraaza-benzo[e]azulene-5-sulfonic acid dimethylamide,
trans-8-Chloro-1-[4-(5-methyl-isoxazol-3-yl)-cyclohexyl]-5,6-dihydro-4H-2,3,5,10b-tetraaza-benzo[e]azulene,
trans-8-Chloro-1-[4-(5-methyl-oxazol-2-yl)-cyclohexyl]-4H,6H-2,3,5,10b-tetraaza-benzo[e]azulene-5-carboxylic acid tert-butyl ester,
trans-8-Chloro-1-[4-(5-methyl-oxazol-2-yl)-cyclohexyl]-5,6-dihydro-4H-2,3,5,10b-tetraaza-benzo[e]azulene,
trans-8-Chloro-5-(2,2-difluoro-ethyl)-1-[4-(5-methyl-[1,2,4]oxadiazol-3-yl)-cyclohexyl]-5,6-dihydro-4H-2,3,5,10b-tetraaza-benzo[e]azulene,
trans-8-Chloro-5-(2,2-difluoro-ethyl)-1-[4-(5-methyl-isoxazol-3-yl)-cyclohexyl]-5,6-dihydro-4H-2,3,5,10b-tetraaza-benzo[e]azulene,
trans-8-Chloro-5-(2-methoxy-ethyl)-1-[4-(5-methyl-isoxazol-3-yl)-cyclohexyl]-5,6-dihydro-4H-2,3,5,10b-tetraaza-benzo[e]azulene,
trans-8-Chloro-5-cyclobutyl-1-[4-(5-methyl-[1,2,4]oxadiazol-3-yl)-cyclohexyl]-5,6-dihydro-4H-2,3,5,10b-tetraaza-benzo[e]azulene,
trans-8-Chloro-5-cyclobutyl-1-[4-(5-methyl-isoxazol-3-yl)-cyclohexyl]-5,6-dihydro-4H-2,3,5,10b-tetraaza-benzo[e]azulene,
trans-8-Chloro-5-cyclopentyl-1-[4-(5-methyl-[1,2,4]oxadiazol-3-yl)-cyclohexyl]-5,6-dihydro-4H-2,3,5,10b-tetraaza-benzo[e]azulene,
trans-8-Chloro-5-ethyl-1-[4-(5-methyl-[1,2,4]oxadiazol-3-yl)-cyclohexyl]-5,6-dihydro-4H-2,3,5,10b-tetraaza-benzo[e]azulene,
trans-8-Chloro-5-ethyl-1-[4-(5-methyl-isoxazol-3-yl)-cyclohexyl]-5,6-dihydro-4H-2,3,5,10b-tetraaza-benzo[e]azulene,
trans-8-Chloro-5-isopropyl-1-[4-(5-methyl-[1,2,4]oxadiazol-3-yl)-cyclohexyl]-5,6-dihydro-4H-2,3,5,10b-tetraaza-benzo[e]azulene,
trans-8-Chloro-5-isopropyl-1-[4-(5-methyl-isoxazol-3-yl)-cyclohexyl]-5,6-dihydro-4H-2,3,5,10b-tetraaza-benzo[e]azulene,
trans-8-Chloro-5-methanesulfonyl-1-[4-(5-methyl-[1,2,4]oxadiazol-3-yl)-cyclohexyl]-5,6-dihydro-4H-2,3,5,10b-tetraaza-benzo[e]azulene,
trans-8-Chloro-5-methanesulfonyl-1-[4-(5-methyl-isoxazol-3-yl)-cyclohexyl]-5,6-dihydro-4H-2,3,5,10b-tetraaza-benzo[e]azulene,
trans-8-Chloro-5-methyl-1-(4-oxazol-2-yl-cyclohexyl)-5,6-dihydro-4H-2,3,5,10b-tetraaza-benzo[e]azulene,
trans-8-Chloro-5-methyl-1-(4-pyrazol-1-yl-cyclohexyl)-5,6-dihydro-4H-2,3,5,10b-tetraaza-benzo[e]azulene,
trans-8-Chloro-5-methyl-1-(4-thiazol-2-yl-cyclohexyl)-5,6-dihydro-4H-2,3,5,10b-tetraaza-benzo[e]azulene,
trans-8-Chloro-5-methyl-1-[4-(2-methyl-thiazol-4-yl)-cyclohexyl]-5,6-dihydro-4H-2,3,5,10b-tetraaza-benzo[e]azulene,
trans-8-Chloro-5-methyl-1-[4-(3-methyl-[1,2,4]oxadiazol-5-yl)-cyclohexyl]-5,6-dihydro-4H-2,3,5,10b-tetraaza-benzo[e]azulene,
trans-8-Chloro-5-methyl-1-[4-(3-methyl-[1,2,4]thiadiazol-5-yl)-cyclohexyl]-5,6-dihydro-4H-2,3,5,10b-tetraaza-benzo[e]azulene,
trans-8-Chloro-5-methyl-1-[4-(4,5,6,7-tetrahydro-benzo[c]isoxazol-3-yl)-cyclohexyl]-5,6-dihydro-4H-2,3,5,10b-tetraaza-benzo[e]azulene, trans-8-Chloro-5-methyl-1-[4-(4,5,6,7-tetrahydro-benzo[d]isoxazol-3-yl)-cyclohexyl]-5,6-dihydro-4H-2,3,5,10b-tetraaza-benzo[e]azulene, trans-8-Chloro-5-methyl-1-[4-(4-methyl-oxazol-2-yl)-cyclohexyl]-5,6-dihydro-4H-2,3,5,10b-tetraaza-benzo[e]azulene, trans-8-Chloro-5-methyl-1-[4-(4-methyl-thiazol-2-yl)-cyclohexyl]-5,6-dihydro-4H-2,3,5,10b-tetraaza-benzo[e]azulene, trans-8-Chloro-5-methyl-1-[4-(5-methyl-[1,2,4]oxadiazol-3-yl)-cyclohexyl]-5,6-dihydro-4H-2,3,5,10b-tetraaza-benzo[e]azulene, trans-8-Chloro-5-methyl-1-[4-(5-methyl-[1,2,4]thiadiazol-3-yl)-cyclohexyl]-5,6-dihydro-4H-2,3,5,10b-tetraaza-benzo[e]azulene, trans-8-Chloro-5-methyl-1-[4-(5-methyl-[1,3,4]oxadiazol-2-yl)-cyclohexyl]-5,6-dihydro-4H-2,3,5,10b-tetraaza-benzo[e]azulene, trans-8-Chloro-5-methyl-1-[4-(5-methyl-isoxazol-3-yl)-cyclohexyl]-5,6-dihydro-4H-2,3,5,10b-tetraaza-benzo[e]azulene, trans-8-Chloro-5-methyl-1-[4-(5-methyl-oxazol-2-yl)-cyclohexyl]-5,6-dihydro-4H-2,3,5,10b-tetraaza-benzo[e]azulene, trans-8-Fluoro-1-[4-(5-methyl-isoxazol-3-yl)-cyclohexyl]-4H,6H-2,3,5,10b-tetraaza-benzo[e]azulene-5-carboxylic acid tert-butyl ester, trans-8-Fluoro-1-[4-(5-methyl-isoxazol-3-yl)-cyclohexyl]-5,6-dihydro-4H-2,3,5,10b-tetraaza-benzo[e]azulene, trans-8-Fluoro-5-methyl-1-[4-(5-methyl-isoxazol-3-yl)-cyclohexyl]-5,6-dihydro-4H-2,3,5,10b-tetraaza-benzo[e]azulene, and trans-Chloro-1-[4-(2-methyl-thiazol-4-yl)-cyclohexyl]-5,6-dihydro-4H-2,3,5,10b-tetraaza-benzo[e]azulene, or a pharmaceutically acceptable salt thereof.

Specific compounds of the invention are shown in the examples. More particular are trans-8-Chloro-1-(4-oxazol-2-yl-cyclohexyl)-4H,6H-2,3,5,10b-tetraaza-benzo[e]azulene-5-carboxylic acid tert-butyl ester, trans-8-Chloro-1-(4-oxazol-2-yl-cyclohexyl)-5,6-dihydro-4H-2,3,5,10b-tetraaza-benzo[e]azulene, trans-8-Chloro-5-methyl-1-(4-oxazol-2-yl-cyclohexyl)-5,6-dihydro-4H-2,3,5,10b-tetraaza-benzo[e]azulene, trans-8-Chloro-1-[4-(4-methyl-oxazol-2-yl)-cyclohexyl]-4H,6H-2,3,5,10b-tetraaza-benzo[e]azulene-5-carboxylic acid tert-butyl ester, trans-8-Chloro-1-[4-(4-methyl-oxazol-2-yl)-cyclohexyl]-5,6-dihydro-4H-2,3,5,10b-tetraaza-benzo[e]azulene, trans-8-Chloro-5-methyl-1-[4-(4-methyl-oxazol-2-yl)-cyclohexyl]-5,6-dihydro-4H-2,3,5,10b-tetraaza-benzo[e]azulene, trans-8-Chloro-1-[4-(5-methyl-oxazol-2-yl)-cyclohexyl]-4H,6H-2,3,5,10b-tetraaza-benzo[e]azulene-5-carboxylic acid tert-butyl ester, trans-8-Chloro-1-[4-(5-methyl-oxazol-2-yl)-cyclohexyl]-5,6-dihydro-4H-2,3,5,10b-tetraaza-benzo[e]azulene, trans-8-Chloro-5-methyl-1-[4-(5-methyl-oxazol-2-yl)-cyclohexyl]-5,6-dihydro-4H-2,3,5,10b-tetraaza-benzo[e]azulene, trans-8-Chloro-1-[4-(4,5-dimethyl-oxazol-2-yl)-cyclohexyl]-4H,6H-2,3,5,10b-tetraaza-benzo[e]azulene-5-carboxylic acid tert-butyl ester, trans-8-Chloro-1-[4-(4,5-dimethyl-oxazol-2-yl)-cyclohexyl]-5,6-dihydro-4H-2,3,5,10b-tetraaza-benzo[e]azulene, trans-8-Chloro-1-[4-(4,5-dimethyl-oxazol-2-yl)-cyclohexyl]-5-methyl-5,6-dihydro-4H-2,3,5,10b-tetraaza-benzo[e]azulene, trans-8-Chloro-1-(4-thiazol-2-yl-cyclohexyl)-4H,6H-2,3,5,10b-tetraaza-benzo[e]azulene-5-carboxylic acid tert-butyl ester, trans-8-Chloro-1-(4-thiazol-2-yl-cyclohexyl)-5,6-dihydro-4H-2,3,5,10b-tetraaza-benzo[e]azulene, trans-8-Chloro-5-methyl-1-(4-thiazol-2-yl-cyclohexyl)-5,6-dihydro-4H-2,3,5,10b-tetraaza-benzo[e]azulene, trans-8-Chloro-1-[4-(4-methyl-thiazol-2-yl)-cyclohexyl]-4H,6H-2,3,5,10b-tetraaza-benzo[e]azulene-5-carboxylic acid tert-butyl ester, trans-8-Chloro-1-[4-(4-methyl-thiazol-2-yl)-cyclohexyl]-5,6-dihydro-4H-2,3,5,10b-tetraaza-benzo[e]azulene, trans-8-Chloro-5-methyl-1-[4-(4-methyl-thiazol-2-yl)-cyclohexyl]-5,6-dihydro-4H-2,3,5,10b-tetraaza-benzo[e]azulene, trans-8-Chloro-1-[4-(2-methyl-thiazol-4-yl)-cyclohexyl]-4H,6H-2,3,5,10b-tetraaza-benzo[e]azulene-5-carboxylic acid tert-butyl ester, trans-Chloro-1-[4-(2-methyl-thiazol-4-yl)-cyclohexyl]-5,6-dihydro-4H-2,3,5,10b-tetraaza-benzo[e]azulene, trans-8-Chloro-5-methyl-1-[4-(2-methyl-thiazol-4-yl)-cyclohexyl]-5,6-dihydro-4H-2,3,5,10b-tetraaza-benzo[e]azulene, trans-8-Chloro-1-[4-(5-methyl-isoxazol-3-yl)-cyclohexyl]-4H,6H-2,3,5,10b-tetraaza-benzo[e]azulene-5-carboxylic acid tert-butyl ester, trans-8-Chloro-1-[4-(5-methyl-isoxazol-3-yl)-cyclohexyl]-5,6-dihydro-4H-2,3,5,10b-tetraaza-benzo[e]azulene, trans-8-Chloro-5-methyl-1-[4-(5-methyl-isoxazol-3-yl)-cyclohexyl]-5,6-dihydro-4H-2,3,5,10b-tetraaza-benzo[e]azulene, trans-1-{8-Chloro-1-[4-(5-methyl-isoxazol-3-yl)-cyclohexyl]-4H,6H-2,3,5,10b-tetraaza-benzo[e]azulen-5-yl}-ethanone, trans-8-Chloro-5-methanesulfonyl-1-[4-(5-methyl-isoxazol-3-yl)-cyclohexyl]-5,6-dihydro-4H-2,3,5,10b-tetraaza-benzo[e]azulene, trans-8-Chloro-5-cyclobutyl-1-[4-(5-methyl-isoxazol-3-yl)-cyclohexyl]-5,6-dihydro-4H-2,3,5,10b-tetraaza-benzo[e]azulene, trans-8-Chloro-5-(2,2-difluoro-ethyl)-1-[4-(5-methyl-isoxazol-3-yl)-cyclohexyl]-5,6-dihydro-4H-2,3,5,10b-tetraaza-benzo[e]azulene, trans-8-Chloro-5-(2-methoxy-ethyl)-1-[4-(5-methyl-isoxazol-3-yl)-cyclohexyl]-5,6-dihydro-4H-2,3,5,10b-tetraaza-benzo[e]azulene, trans-(2-{8-Chloro-1-[4-(5-methyl-isoxazol-3-yl)-cyclohexyl]-4H,6H-2,3,5,10b-tetraaza-benzo[e]azulen-5-yl}-ethyl)-methyl-amine, trans-8-Chloro-5-ethyl-1-[4-(5-methyl-isoxazol-3-yl)-cyclohexyl]-5,6-dihydro-4H-2,3,5,10b-tetraaza-benzo[e]azulene, trans-1-{8-Chloro-1-[4-(5-methyl-isoxazol-3-yl)-cyclohexyl]-4H,6H-2,3,5,10b-tetraaza-benzo[e]azulen-5-yl}-2-hydroxy-ethanone, trans-1-{8-Chloro-1-[4-(5-methyl-isoxazol-3-yl)-cyclohexyl]-4H,6H-2,3,5,10b-tetraaza-benzo[e]azulen-5-yl}-2-dimethylamino-ethanone, trans-8-Chloro-5-isopropyl-1-[4-(5-methyl-isoxazol-3-yl)-cyclohexyl]-5,6-dihydro-4H-2,3,5,10b-tetraaza-benzo[e]azulene, trans-8-Chloro-1-[4-(5-methyl-isoxazol-3-yl)-cyclohexyl]-4H,6H-2,3,5,10b-tetraaza-benzo[e]azulene-5-sulfonic acid dimethylamide, trans-8-Fluoro-1-[4-(5-methyl-isoxazol-3-yl)-cyclohexyl]-4H,6H-2,3,5,10b-tetraaza-benzo[e]azulene-5-carboxylic acid tert-butyl ester,
trans-8-Fluoro-1-[4-(5-methyl-isoxazol-3-yl)-cyclohexyl]-5,6-dihydro-4H-2,3,5,10b-tetraaza-benzo[e]azulene,
trans-8-Fluoro-5-methyl-1-[4-(5-methyl-isoxazol-3-yl)-cyclohexyl]-5,6-dihydro-4H-2,3,5,10b-tetraaza-benzo[e]azulene,
trans-8-Chloro-1-[4-(4,5-dimethyl-isoxazol-3-yl)-cyclohexyl]-4H,6H-2,3,5,10b-tetraaza-benzo[e]azulene-5-carboxylic acid tert-butyl ester,
trans-8-Chloro-1-[4-(4,5-dimethyl-isoxazol-3-yl)-cyclohexyl]-5,6-dihydro-4H-2,3,5,10b-tetraaza-benzo[e]azulene,
trans-8-Chloro-1-[4-(4,5-dimethyl-isoxazol-3-yl)-cyclohexyl]-5-methyl-5,6-dihydro-4H-2,3,5,10b-tetraaza-benzo[e]azulene,
trans-8-Chloro-1-[4-(4-chloro-5-methyl-isoxazol-3-yl)-cyclohexyl]-4H,6H-2,3,5,10b-tetraaza-benzo[e]azulene-5-carboxylic acid tert-butyl ester,
trans-8-Chloro-1-[4-(4-chloro-5-methyl-isoxazol-3-yl)-cyclohexyl]-5,6-dihydro-4H-2,3,5,10b-tetraaza-benzo[e]azulene,
trans-8-Chloro-1-[4-(4-chloro-5-methyl-isoxazol-3-yl)-cyclohexyl]-5-methyl-5,6-dihydro-4H-2,3,5,10b-tetraaza-benzo[e]azulene,
trans-8-Chloro-1-[4-(4-fluoro-5-methyl-isoxazol-3-yl)-cyclohexyl]-4H,6H-2,3,5,10b-tetraaza-benzo[e]azulene-5-carboxylic acid tert-butyl ester,
trans-8-Chloro-1-[4-(4-fluoro-5-methyl-isoxazol-3-yl)-cyclohexyl]-5,6-dihydro-4H-2,3,5,10b-tetraaza-benzo[e]azulene,
trans-8-Chloro-1-[4-(4-fluoro-5-methyl-isoxazol-3-yl)-cyclohexyl]-5-methyl-5,6-dihydro-4H-2,3,5,10b-tetraaza-benzo[e]azulene,
cis-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester,
trans-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester,
cis-8-Chloro-1-[4-(5-ethyl-isoxazol-3-yl)-cyclohexyl]-5,6-dihydro-4H-2,3,5,10b-tetraaza-benzo[e]azulene,
cis-8-Chloro-1-[4-(5-ethyl-isoxazol-3-yl)-cyclohexyl]-5-methyl-5,6-dihydro-4H-2,3,5,10b-tetraaza-benzo[e]azulene,
trans-8-Chloro-1-[4-(5-ethyl-isoxazol-3-yl)-cyclohexyl]-5,6-dihydro-4H-2,3,5,10b-tetraaza-benzo[e]azulene,
trans-8-Chloro-1-[4-(5-ethyl-isoxazol-3-yl)-cyclohexyl]-5-methyl-5,6-dihydro-4H-2,3,5,10b-tetraaza-benzo[e]azulene,
trans-8-Chloro-1-[4-(4,5,6,7-tetrahydro-benzo[d]isoxazol-3-yl)-cyclohexyl]-4H,6H-2,3,5,10b-tetraaza-benzo[e]azulene-5-carboxylic acid tert-butyl ester,
trans-8-Chloro-1-[4-(4,5,6,7-tetrahydro-benzo[d]isoxazol-3-yl)-cyclohexyl]-5,6-dihydro-4H-2,3,5,10b-tetraaza-benzo[e]azulene,
trans-8-Chloro-5-methyl-1-[4-(4,5,6,7-tetrahydro-benzo[d]isoxazol-3-yl)-cyclohexyl]-5,6-dihydro-4H-2,3,5,10b-tetraaza-benzo[e]azulene,
cis-8-Chloro-1-[4-(4,5,6,7-tetrahydro-benzo[d]isoxazol-3-yl)-cyclohexyl]-4H,6H-2,3,5,10b-tetraaza-benzo[e]azulene-5-carboxylic acid tert-butyl ester,
cis-8-Chloro-1-[4-(4,5,6,7-tetrahydro-benzo[d]isoxazol-3-yl)-cyclohexyl]-5,6-dihydro-4H-2,3,5,10b-tetraaza-benzo[e]azulene,
cis-8-Chloro-5-methyl-1-[4-(4,5,6,7-tetrahydro-benzo[d]isoxazol-3-yl)-cyclohexyl]-5,6-dihydro-4H-2,3,5,10b-tetraaza-benzo[e]azulene,
trans-8-Chloro-1-[4-(4,5,6,7-tetrahydro-benzo[c]isoxazol-3-yl)-cyclohexyl]-4H,6H-2,3,5,10b-tetraaza-benzo[e]azulene-5-carboxylic acid tert-butyl ester,
trans-8-Chloro-1-[4-(4,5,6,7-tetrahydro-benzo[c]isoxazol-3-yl)-cyclohexyl]-5,6-dihydro-4H-2,3,5,10b-tetraaza-benzo[e]azulene,
trans-8-Chloro-5-methyl-1-[4-(4,5,6,7-tetrahydro-benzo[c]isoxazol-3-yl)-cyclohexyl]-5,6-dihydro-4H-2,3,5,10b-tetraaza-benzo[e]azulene,
trans-8-Chloro-1-[4-(5-methyl-[1,3,4]oxadiazol-2-yl)-cyclohexyl]-4H,6H-2,3,5,10b-tetraaza-benzo[e]azulene-5-carboxylic acid tert-butyl ester,
trans-8-Chloro-1-[4-(5-methyl-[1,3,4]oxadiazol-2-yl)-cyclohexyl]-5,6-dihydro-4H-2,3,5,10b-tetraaza-benzo[e]azulene,
trans-8-Chloro-5-methyl-1-[4-(5-methyl-[1,3,4]oxadiazol-2-yl)-cyclohexyl]-5,6-dihydro-4H-2,3,5,10b-tetraaza-benzo[e]azulene,
trans-8-Chloro-1-[4-(3-methyl-[1,2,4]oxadiazol-5-yl)-cyclohexyl]-4H,6H-2,3,5,10b-tetraaza-benzo[e]azulene-5-carboxylic acid tert-butyl ester,
trans-8-Chloro-1-[4-(3-methyl-[1,2,4]oxadiazol-5-yl)-cyclohexyl]-5,6-dihydro-4H-2,3,5,10b-tetraaza-benzo[e]azulene,
trans-8-Chloro-5-methyl-1-[4-(3-methyl-[1,2,4]oxadiazol-5-yl)-cyclohexyl]-5,6-dihydro-4H-2,3,5,10b-tetraaza-benzo[e]azulene,
trans-8-Chloro-1-[4-(3-methyl-[1,2,4]thiadiazol-5-yl)-cyclohexyl]-4H,6H-2,3,5,10b-tetraaza-benzo[e]azulene-5-carboxylic acid tert-butyl ester,
trans-8-Chloro-1-[4-(3-methyl-[1,2,4]thiadiazol-5-yl)-cyclohexyl]-5,6-dihydro-4H-2,3,5,10b-tetraaza-benzo[e]azulene,
trans-8-Chloro-5-methyl-1-[4-(3-methyl-[1,2,4]thiadiazol-5-yl)-cyclohexyl]-5,6-dihydro-4H-2,3,5,10b-tetraaza-benzo[e]azulene,
trans-8-Chloro-1-[4-(5-methyl-[1,2,4]oxadiazol-3-yl)-cyclohexyl]-4H,6H-2,3,5,10b-tetraaza-benzo[e]azulene-5-carboxylic acid tert-butyl ester,
trans-8-Chloro-1-[4-(5-methyl-[1,2,4]oxadiazol-3-yl)-cyclohexyl]-5,6-dihydro-4H-2,3,5,10b-tetraaza-benzo[e]azulene,
trans-8-Chloro-5-methyl-1-[4-(5-methyl-[1,2,4]oxadiazol-3-yl)-cyclohexyl]-5,6-dihydro-4H-2,3,5,10b-tetraaza-benzo[e]azulene,
trans-8-Chloro-5-ethyl-1-[4-(5-methyl-[1,2,4]oxadiazol-3-yl)-cyclohexyl]-5,6-dihydro-4H-2,3,5,10b-tetraaza-benzo[e]azulene,
trans-8-Chloro-5-isopropyl-1-[4-(5-methyl-[1,2,4]oxadiazol-3-yl)-cyclohexyl]-5,6-dihydro-4H-2,3,5,10b-tetraaza-benzo[e]azulene,
trans-8-Chloro-5-cyclobutyl-1-[4-(5-methyl-[1,2,4]oxadiazol-3-yl)-cyclohexyl]-5,6-dihydro-4H-2,3,5,10b-tetraaza-benzo[e]azulene,
trans-8-Chloro-5-cyclopentyl-1-[4-(5-methyl-[1,2,4]oxadiazol-3-yl)-cyclohexyl]-5,6-dihydro-4H-2,3,5,10b-tetraaza-benzo[e]azulene,
trans-8-Chloro-5-(2,2-difluoro-ethyl)-1-[4-(5-methyl-[1,2,4]oxadiazol-3-yl)-cyclohexyl]-5,6-dihydro-4H-2,3,5,10b-tetraaza-benzo[e]azulene,
trans-1-{8-Chloro-1-[4-(5-methyl-[1,2,4]oxadiazol-3-yl)-cyclohexyl]-4H,6H-2,3,5,10b-tetraaza-benzo[e]azulen-5-yl}-ethanone, trans-8-Chloro-5-methanesulfonyl-1-[4-(5-methyl-[1,2,4]
oxadiazol-3-yl)-cyclohexyl]-5,6-dihydro-4H-2,3,5,10b-
tetraaza-benzo[e]azulene,
cis-8-Chloro-1-[4-(5-methyl-[1,2,4]oxadiazol-3-yl)-cyclo-
hexyl]-4H,6H-2,3,5,10b-tetraaza-benzo[e]azulene-5-car-
boxylic acid tert-butyl ester,
cis-8-Chloro-1-[4-(5-methyl-[1,2,4]oxadiazol-3-yl)-cyclo-
hexyl]-5,6-dihydro-4H-2,3,5,10b-tetraaza-benzo[e]azu-
lene,
cis-8-Chloro-5-methyl-1-[4-(5-methyl-[1,2,4]oxadiazol-3-
yl)-cyclohexyl]-5,6-dihydro-4H-2,3,5,10b-tetraaza-benzo
[e]azulene,
cis-8-Chloro-1-[4-(5-ethyl-[1,2,4]oxadiazol-3-yl)-cyclo-
hexyl]-4H,6H-2,3,5,10b-tetraaza-benzo[e]azulene-5-car-
boxylic acid tert-butyl ester,
trans-8-Chloro-1-[4-(5-ethyl-[1,2,4]oxadiazol-3-yl)-cyclo-
hexyl]-4H,6H-2,3,5,10b-tetraaza-benzo[e]azulene-5-car-
boxylic acid tert-butyl ester,
trans-8-Chloro-1-[4-(5-ethyl-[1,2,4]oxadiazol-3-yl)-cyclo-
hexyl]-5,6-dihydro-4H-2,3,5,10b-tetraaza-benzo[e]azu-
lene,
trans-8-Chloro-1-[4-(5-ethyl-[1,2,4]oxadiazol-3-yl)-cyclo-
hexyl]-5-methyl-5,6-dihydro-4H-2,3,5,10b-tetraaza-
benzo[e]azulene,
cis-8-Chloro-1-[4-(5-ethyl-[1,2,4]oxadiazol-3-yl)-cyclo-
hexyl]-5,6-dihydro-4H-2,3,5,10b-tetraaza-benzo[e]azu-
lene,
cis-8-Chloro-1-[4-(5-ethyl-[1,2,4]oxadiazol-3-yl)-cyclo-
hexyl]-5-methyl-5,6-dihydro-4H-2,3,5,10b-tetraaza-
benzo[e]azulene,
cis-8-Chloro-1-[4-(5-isopropyl-[1,2,4]oxadiazol-3-yl)-cy-
clohexyl]-4H,6H-2,3,5,10b-tetraaza-benzo[e]azulene-5-
carboxylic acid tert-butyl ester,
trans-8-Chloro-1-[4-(5-isopropyl-[1,2,4]oxadiazol-3-yl)-cy-
clohexyl]-4H,6H-2,3,5,10b-tetraaza-benzo[e]azulene-5-
carboxylic acid tert-butyl ester,
trans-8-Chloro-1-[4-(5-isopropyl-[1,2,4]oxadiazol-3-yl)-cy-
clohexyl]-5,6-dihydro-4H-2,3,5,10b-tetraaza-benzo[e]
azulene,
trans-8-Chloro-1-[4-(5-isopropyl-[1,2,4]oxadiazol-3-yl)-cy-
clohexyl]-5-methyl-5,6-dihydro-4H-2,3,5,10b-tetraaza-
benzo[e]azulene,
cis-8-Chloro-1-[4-(5-isopropyl-[1,2,4]oxadiazol-3-yl)-cy-
clohexyl]-5,6-dihydro-4H-2,3,5,10b-tetraaza-benzo[e]
azulene,
cis-8-Chloro-1-[4-(5-isopropyl-[1,2,4]oxadiazol-3-yl)-cy-
clohexyl]-5-methyl-5,6-dihydro-4H-2,3,5,10b-tetraaza-
benzo[e]azulene, and
trans-8-Chloro-5-methyl-1-[4-(5-methyl-[1,2,4]thiadiazol-
3-yl)-cyclohexyl]-5,6-dihydro-4H-2,3,5,10b-tetraaza-
benzo[e]azulene,
or a pharmaceutically acceptable salt thereof.
More specific compounds are selected from the group consisting of
trans-8-Chloro-1-(4-oxazol-2-yl-cyclohexyl)-4H,6H-2,3,5,
10b-tetraaza-benzo[e]azulene-5-carboxylic acid tert-butyl
ester,
trans-8-Chloro-1-(4-oxazol-2-yl-cyclohexyl)-5,6-dihydro-
4H-2,3,5,10b-tetraaza-benzo[e]azulene,
trans-8-Chloro-5-methyl-1-(4-oxazol-2-yl-cyclohexyl)-5,6-
dihydro-4H-2,3,5,10b-tetraaza-benzo[e]azulene,
trans-8-Chloro-1-[4-(4-methyl-oxazol-2-yl)-cyclohexyl]-
4H,6H-2,3,5,10b-tetraaza-benzo[e]azulene-5-carboxylic
acid tert-butyl ester,
trans-8-Chloro-1-[4-(4-methyl-oxazol-2-yl)-cyclohexyl]-5,
6-dihydro-4H-2,3,5,10b-tetraaza-benzo[e]azulene,
trans-8-Chloro-5-methyl-1-[4-(4-methyl-oxazol-2-yl)-cy-
clohexyl]-5,6-dihydro-4H-2,3,5,10b-tetraaza-benzo[e]
azulene,
trans-8-Chloro-1-[4-(5-methyl-oxazol-2-yl)-cyclohexyl]-
4H,6H-2,3,5,10b-tetraaza-benzo[e]azulene-5-carboxylic
acid tert-butyl ester,
trans-8-Chloro-1-[4-(5-methyl-oxazol-2-yl)-cyclohexyl]-5,
6-dihydro-4H-2,3,5,10b-tetraaza-benzo[e]azulene,
trans-8-Chloro-5-methyl-1-[4-(5-methyl-oxazol-2-yl)-cy-
clohexyl]-5,6-dihydro-4H-2,3,5,10b-tetraaza-benzo[e]
azulene,
trans-8-Chloro-1-[4-(4,5-dimethyl-oxazol-2-yl)-cyclo-
hexyl]-4H,6H-2,3,5,10b-tetraaza-benzo[e]azulene-5-car-
boxylic acid tert-butyl ester,
trans-8-Chloro-1-[4-(4,5-dimethyl-oxazol-2-yl)-cyclo-
hexyl]-5,6-dihydro-4H-2,3,5,10b-tetraaza-benzo[e]azu-
lene,
trans-8-Chloro-1-[4-(4,5-dimethyl-oxazol-2-yl)-cyclo-
hexyl]-5-methyl-5,6-dihydro-4H-2,3,5,10b-tetraaza-
benzo[e]azulene,
trans-8-Chloro-1-(4-thiazol-2-yl-cyclohexyl)-4H,6H-2,3,5,
10b-tetraaza-benzo[e]azulene-5-carboxylic acid tert-butyl
ester,
trans-8-Chloro-1-(4-thiazol-2-yl-cyclohexyl)-5,6-dihydro-
4H-2,3,5,10b-tetraaza-benzo[e]azulene,
trans-8-Chloro-5-methyl-1-(4-thiazol-2-yl-cyclohexyl)-5,6-
dihydro-4H-2,3,5,10b-tetraaza-benzo[e]azulene,
trans-8-Chloro-1-[4-(4-methyl-thiazol-2-yl)-cyclohexyl]-
4H,6H-2,3,5,10b-tetraaza-benzo[e]azulene-5-carboxylic
acid tert-butyl ester,
trans-8-Chloro-1-[4-(4-methyl-thiazol-2-yl)-cyclohexyl]-5,
6-dihydro-4H-2,3,5,10b-tetraaza-benzo[e]azulene,
trans-8-Chloro-5-methyl-1-[4-(4-methyl-thiazol-2-yl)-cy-
clohexyl]-5,6-dihydro-4H-2,3,5,10b-tetraaza-benzo[e]
azulene,
trans-8-Chloro-1-[4-(2-methyl-thiazol-4-yl)-cyclohexyl]-
4H,6H-2,3,5,10b-tetraaza-benzo[e]azulene-5-carboxylic
acid tert-butyl ester,
trans-Chloro-1-[4-(2-methyl-thiazol-4-yl)-cyclohexyl]-5,6-
dihydro-4H-2,3,5,10b-tetraaza-benzo[e]azulene,
trans-8-Chloro-5-methyl-1-[4-(2-methyl-thiazol-4-yl)-cy-
clohexyl]-5,6-dihydro-4H-2,3,5,10b-tetraaza-benzo[e]
azulene,
trans-8-Chloro-1-[4-(5-methyl-isoxazol-3-yl)-cyclohexyl]-
4H,6H-2,3,5,10b-tetraaza-benzo[e]azulene-5-carboxylic
acid tert-butyl ester,
trans-8-Chloro-1-[4-(5-methyl-isoxazol-3-yl)-cyclohexyl]-
5,6-dihydro-4H-2,3,5,10b-tetraaza-benzo[e]
azulene*HCl,
trans-8-Chloro-5-methyl-1-[4-(5-methyl-isoxazol-3-yl)-cy-
clohexyl]-5,6-dihydro-4H-2,3,5,10b-tetraaza-benzo[e]
azulene,
trans-1-{8-Chloro-1-[4-(5-methyl-isoxazol-3-yl)-cyclo-
hexyl]-4H,6H-2,3,5,10b-tetraaza-benzo[e]azulen-5-yl}-
ethanone,
trans-8-Chloro-5-methanesulfonyl-1-[4-(5-methyl-isoxazol-
3-yl)-cyclohexyl]-5,6-dihydro-4H-2,3,5,10b-tetraaza-
benzo[e]azulene,
trans-8-Chloro-5-cyclobutyl-1-[4-(5-methyl-isoxazol-3-yl)-
cyclohexyl]-5,6-dihydro-4H-2,3,5,10b-tetraaza-benzo[e]
azulene,
trans-8-Chloro-5-(2,2-difluoro-ethyl)-1-[4-(5-methyl-isox-
azol-3-yl)-cyclohexyl]-5,6-dihydro-4H-2,3,5,10b-tet-
raaza-benzo[e]azulene,
trans-8-Chloro-5-(2-methoxy-ethyl)-1-[4-(5-methyl-isox-
azol-3-yl)-cyclohexyl]-5,6-dihydro-4H-2,3,5,10b-tet-
raaza-benzo[e]azulene, trans-(2-{8-Chloro-1-[4-(5-methyl-isoxazol-3-yl)-cyclohexyl]-4H,6H-2,3,5,10b-tetraaza-benzo[e]azulen-5-yl}-ethyl)-methyl-amine,
trans-8-Chloro-5-ethyl-1-[4-(5-methyl-isoxazol-3-yl)-cyclohexyl]-5,6-dihydro-4H-2,3,5,10b-tetraaza-benzo[e]azulene,
trans-1-{8-Chloro-1-[4-(5-methyl-isoxazol-3-yl)-cyclohexyl]-4H,6H-2,3,5,10b-tetraaza-benzo[e]azulen-5-yl}-2-hydroxy-ethanone,
trans-1-{8-Chloro-1-[4-(5-methyl-isoxazol-3-yl)-cyclohexyl]-4H,6H-2,3,5,10b-tetraaza-benzo[e]azulen-5-yl}-2-dimethylamino-ethanone hydrofumate,
trans-8-Chloro-5-isopropyl-1-[4-(5-methyl-isoxazol-3-yl)-cyclohexyl]-5,6-dihydro-4H-2,3,5,10b-tetraaza-benzo[e]azulene,
trans-8-Chloro-1-[4-(5-methyl-isoxazol-3-yl)-cyclohexyl]-4H,6H-2,3,5,10b-tetraaza-benzo[e]azulene-5-sulfonic acid dimethylamide,
trans-8-Fluoro-1-[4-(5-methyl-isoxazol-3-yl)-cyclohexyl]-4H,6H-2,3,5,10b-tetraaza-benzo[e]azulene-5-carboxylic acid tert-butyl ester,
trans-8-Fluoro-1-[4-(5-methyl-isoxazol-3-yl)-cyclohexyl]-5,6-dihydro-4H-2,3,5,10b-tetraaza-benzo[e]azulene,
trans-8-Fluoro-5-methyl-1-[4-(5-methyl-isoxazol-3-yl)-cyclohexyl]-5,6-dihydro-4H-2,3,5,10b-tetraaza-benzo[e]azulene,
trans-8-Chloro-1-[4-(4,5-dimethyl-isoxazol-3-yl)-cyclohexyl]-4H,6H-2,3,5,10b-tetraaza-benzo[e]azulene-5-carboxylic acid tert-butyl ester,
trans-8-Chloro-1-[4-(4,5-dimethyl-isoxazol-3-yl)-cyclohexyl]-5,6-dihydro-4H-2,3,5,10b-tetraaza-benzo[e]azulene,
trans-8-Chloro-1-[4-(4,5-dimethyl-isoxazol-3-yl)-cyclohexyl]-5-methyl-5,6-dihydro-4H-2,3,5,10b-tetraaza-benzo[e]azulene,
trans-8-Chloro-1-[4-(4-chloro-5-methyl-isoxazol-3-yl)-cyclohexyl]-4H,6H-2,3,5,10b-tetraaza-benzo[e]azulene-5-carboxylic acid tert-butyl ester,
trans-8-Chloro-1-[4-(4-chloro-5-methyl-isoxazol-3-yl)-cyclohexyl]-5,6-dihydro-4H-2,3,5,10b-tetraaza-benzo[e]azulene,
trans-8-Chloro-1-[4-(4-chloro-5-methyl-isoxazol-3-yl)-cyclohexyl]-5-methyl-5,6-dihydro-4H-2,3,5,10b-tetraaza-benzo[e]azulene,
trans-8-Chloro-1-[4-(4-fluoro-5-methyl-isoxazol-3-yl)-cyclohexyl]-4H,6H-2,3,5,10b-tetraaza-benzo[e]azulene-5-carboxylic acid tert-butyl ester,
trans-8-Chloro-1-[4-(4-fluoro-5-methyl-isoxazol-3-yl)-cyclohexyl]-5,6-dihydro-4H-2,3,5,10b-tetraaza-benzo[e]azulene,
trans-8-Chloro-1-[4-(4-fluoro-5-methyl-isoxazol-3-yl)-cyclohexyl]-5-methyl-5,6-dihydro-4H-2,3,5,10b-tetraaza-benzo[e]azulene,
cis-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester,
trans-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester,
cis-8-Chloro-1-[4-(5-ethyl-isoxazol-3-yl)-cyclohexyl]-5,6-dihydro-4H-2,3,5,10b-tetraaza-benzo[e]azulene*HCl,
cis-8-Chloro-1-[4-(5-ethyl-isoxazol-3-yl)-cyclohexyl]-5-methyl-5,6-dihydro-4H-2,3,5,10b-tetraaza-benzo[e]azulene,
trans-8-Chloro-1-[4-(5-ethyl-isoxazol-3-yl)-cyclohexyl]-5,6-dihydro-4H-2,3,5,10b-tetraaza-benzo[e]azulene*HCl,
trans-8-Chloro-1-[4-(5-ethyl-isoxazol-3-yl)-cyclohexyl]-5-methyl-5,6-dihydro-4H-2,3,5,10b-tetraaza-benzo[e]azulene,
trans-8-Chloro-1-[4-(4,5,6,7-tetrahydro-benzo[d]isoxazol-3-yl)-cyclohexyl]-4H,6H-2,3,5,10b-tetraaza-benzo[e]azulene-5-carboxylic acid tert-butyl ester,
trans-8-Chloro-1-[4-(4,5,6,7-tetrahydro-benzo[d]isoxazol-3-yl)-cyclohexyl]-5,6-dihydro-4H-2,3,5,10b-tetraaza-benzo[e]azulene,
trans-8-Chloro-5-methyl-1-[4-(4,5,6,7-tetrahydro-benzo[d]isoxazol-3-yl)-cyclohexyl]-5,6-dihydro-4H-2,3,5,10b-tetraaza-benzo[e]azulene,
cis-8-Chloro-1-[4-(4,5,6,7-tetrahydro-benzo[d]isoxazol-3-yl)-cyclohexyl]-4H,6H-2,3,5,10b-tetraaza-benzo[e]azulene-5-carboxylic acid tert-butyl ester,
cis-8-Chloro-1-[4-(4,5,6,7-tetrahydro-benzo[d]isoxazol-3-yl)-cyclohexyl]-5,6-dihydro-4H-2,3,5,10b-tetraaza-benzo[e]azulene,
cis-8-Chloro-5-methyl-1-[4-(4,5,6,7-tetrahydro-benzo[d]isoxazol-3-yl)-cyclohexyl]-5,6-dihydro-4H-2,3,5,10b-tetraaza-benzo[e]azulene,
trans-8-Chloro-1-[4-(4,5,6,7-tetrahydro-benzo[c]isoxazol-3-yl)-cyclohexyl]-4H,6H-2,3,5,10b-tetraaza-benzo[e]azulene-5-carboxylic acid tert-butyl ester,
trans-8-Chloro-1-[4-(4,5,6,7-tetrahydro-benzo[c]isoxazol-3-yl)-cyclohexyl]-5,6-dihydro-4H-2,3,5,10b-tetraaza-benzo[e]azulene,
trans-8-Chloro-5-methyl-1-[4-(4,5,6,7-tetrahydro-benzo[c]isoxazol-3-yl)-cyclohexyl]-5,6-dihydro-4H-2,3,5,10b-tetraaza-benzo[e]azulene,
trans-8-Chloro-1-[4-(5-methyl-[1,3,4]oxadiazol-2-yl)-cyclohexyl]-4H,6H-2,3,5,10b-tetraaza-benzo[e]azulene-5-carboxylic acid tert-butyl ester,
trans-8-Chloro-1-[4-(5-methyl-[1,3,4]oxadiazol-2-yl)-cyclohexyl]-5,6-dihydro-4H-2,3,5,10b-tetraaza-benzo[e]azulene,
trans-8-Chloro-5-methyl-1-[4-(5-methyl-[1,3,4]oxadiazol-2-yl)-cyclohexyl]-5,6-dihydro-4H-2,3,5,10b-tetraaza-benzo[e]azulene,
trans-8-Chloro-1-[4-(3-methyl-[1,2,4]oxadiazol-5-yl)-cyclohexyl]-4H,6H-2,3,5,10b-tetraaza-benzo[e]azulene-5-carboxylic acid tert-butyl ester,
trans-8-Chloro-1-[4-(3-methyl-[1,2,4]oxadiazol-5-yl)-cyclohexyl]-5,6-dihydro-4H-2,3,5,10b-tetraaza-benzo[e]azulene*HCl,
trans-8-Chloro-5-methyl-1-[4-(3-methyl-[1,2,4]oxadiazol-5-yl)-cyclohexyl]-5,6-dihydro-4H-2,3,5,10b-tetraaza-benzo[e]azulene,
trans-8-Chloro-1-[4-(3-methyl-[1,2,4]thiadiazol-5-yl)-cyclohexyl]-4H,6H-2,3,5,10b-tetraaza-benzo[e]azulene-5-carboxylic acid tert-butyl ester,
trans-8-Chloro-1-[4-(3-methyl-[1,2,4]thiadiazol-5-yl)-cyclohexyl]-5,6-dihydro-4H-2,3,5,10b-tetraaza-benzo[e]azulene,
trans-8-Chloro-5-methyl-1-[4-(3-methyl-[1,2,4]thiadiazol-5-yl)-cyclohexyl]-5,6-dihydro-4H-2,3,5,10b-tetraaza-benzo[e]azulene,
trans-8-Chloro-1-[4-(5-methyl-[1,2,4]oxadiazol-3-yl)-cyclohexyl]-4H,6H-2,3,5,10b-tetraaza-benzo[e]azulene-5-carboxylic acid tert-butyl ester,
trans-8-Chloro-1-[4-(5-methyl-[1,2,4]oxadiazol-3-yl)-cyclohexyl]-5,6-dihydro-4H-2,3,5,10b-tetraaza-benzo[e]azulene*HCl,
trans-8-Chloro-5-methyl-1-[4-(5-methyl-[1,2,4]oxadiazol-3-yl)-cyclohexyl]-5,6-dihydro-4H-2,3,5,10b-tetraaza-benzo[e]azulene, trans-8-Chloro-5-ethyl-1-[4-(5-methyl-[1,2,4]oxadiazol-3-yl)-cyclohexyl]-5,6-dihydro-4H-2,3,5,10b-tetraaza-benzo[e]azulene, trans-8-Chloro-5-isopropyl-1-[4-(5-methyl-[1,2,4]oxadiazol-3-yl)-cyclohexyl]-5,6-dihydro-4H-2,3,5,10b-tetraaza-benzo[e]azulene, trans-8-Chloro-5-cyclobutyl-1-[4-(5-methyl-[1,2,4]oxadiazol-3-yl)-cyclohexyl]-5,6-dihydro-4H-2,3,5,10b-tetraaza-benzo[e]azulene, trans-8-Chloro-5-cyclopentyl-1-[4-(5-methyl-[1,2,4]oxadiazol-3-yl)-cyclohexyl]-5,6-dihydro-4H-2,3,5,10b-tetraaza-benzo[e]azulene, trans-8-Chloro-5-(2,2-difluoro-ethyl)-1-[4-(5-methyl-[1,2,4]oxadiazol-3-yl)-cyclohexyl]-5,6-dihydro-4H-2,3,5,10b-tetraaza-benzo[e]azulene, trans-1-{8-Chloro-1-[4-(5-methyl-[1,2,4]oxadiazol-3-yl)-cyclohexyl]-4H,6H-2,3,5,10b-tetraaza-benzo[e]azulen-5-yl}-ethanone, trans-8-Chloro-5-methanesulfonyl-1-[4-(5-methyl-[1,2,4]oxadiazol-3-yl)-cyclohexyl]-5,6-dihydro-4H-2,3,5,10b-tetraaza-benzo[e]azulene, cis-8-Chloro-1-[4-(5-methyl-[1,2,4]oxadiazol-3-yl)-cyclohexyl]-4H,6H-2,3,5,10b-tetraaza-benzo[e]azulene-5-carboxylic acid tert-butyl ester, cis-8-Chloro-1-[4-(5-methyl-[1,2,4]oxadiazol-3-yl)-cyclohexyl]-5,6-dihydro-4H-2,3,5,10b-tetraaza-benzo[e]azulene*HCl, cis-8-Chloro-5-methyl-1-[4-(5-methyl-[1,2,4]oxadiazol-3-yl)-cyclohexyl]-5,6-dihydro-4H-2,3,5,10b-tetraaza-benzo[e]azulene, cis-8-Chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester, trans-8-Chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester, trans-8-Chloro-1-[4-(5-ethyl-[1,2,4]oxadiazol-3-yl)-cyclohexyl]-5,6-dihydro-4H-2,3,5,10b-tetraaza-benzo[e]azulene*HCl, trans-8-Chloro-1-[4-(5-ethyl-[1,2,4]oxadiazol-3-yl)-cyclohexyl]-5-methyl-5,6-dihydro-4H-2,3,5,10b-tetraaza-benzo[e]azulene, cis-8-Chloro-1-[4-(5-ethyl-[1,2,4]oxadiazol-3-yl)-cyclohexyl]-5,6-dihydro-4H-2,3,5,10b-tetraaza-benzo[e]azulene*HCl, cis-8-Chloro-1-[4-(5-ethyl-[1,2,4]oxadiazol-3-yl)-cyclohexyl]-5-methyl-5,6-dihydro-4H-2,3,5,10b-tetraaza-benzo[e]azulene, cis-8-Chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester, trans-8-Chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester, trans-8-Chloro-1-[4-(5-isopropyl-[1,2,4]oxadiazol-3-yl)-cyclohexyl]-5,6-dihydro-4H-2,3,5,10b-tetraaza-benzo[e]azulene*HCl, trans-8-Chloro-1-[4-(5-isopropyl-[1,2,4]oxadiazol-3-yl)-cyclohexyl]-5-methyl-5,6-dihydro-4H-2,3,5,10b-tetraaza-benzo[e]azulene, cis-8-Chloro-1-[4-(5-isopropyl-[1,2,4]oxadiazol-3-yl)-cyclohexyl]-5,6-dihydro-4H-2,3,5,10b-tetraaza-benzo[e]azulene*HCl, cis-8-Chloro-1-[4-(5-isopropyl-[1,2,4]oxadiazol-3-yl)-cyclohexyl]-5-methyl-5,6-dihydro-4H-2,3,5,10b-tetraaza-benzo[e]azulene, and trans-8-Chloro-5-methyl-1-[4-(5-methyl-[1,2,4]thiadiazol-3-yl)-cyclohexyl]-5,6-dihydro-4H-2,3,5,10b-tetraaza-benzo[e]azulene, or a pharmaceutically acceptable salt thereof.

Most particular compounds are selected from the group consisting of trans-8-Chloro-1-[4-(5-ethyl-isoxazol-3-yl)-cyclohexyl]-5,6-dihydro-4H-2,3,5,10b-tetraaza-benzo[e]azulene*HCl, trans-8-Chloro-1-[4-(5-ethyl-isoxazol-3-yl)-cyclohexyl]-5-methyl-5,6-dihydro-4H-2,3,5,10b-tetraaza-benzo[e]azulene, trans-8-Chloro-1-[4-(5-methyl-[1,2,4]oxadiazol-3-yl)-cyclohexyl]-5,6-dihydro-4H-2,3,5,10b-tetraaza-benzo[e]azulene*HCl, trans-8-Chloro-5-methyl-1-[4-(5-methyl-[1,2,4]oxadiazol-3-yl)-cyclohexyl]-5,6-dihydro-4H-2,3,5,10b-tetraaza-benzo[e]azulene, trans-8-Chloro-1-[4-(5-methyl-isoxazol-3-yl)-cyclohexyl]-5,6-dihydro-4H-2,3,5,10b-tetraaza-benzo[e]azulene*HCl, trans-8-Chloro-5-methyl-1-[4-(5-methyl-isoxazol-3-yl)-cyclohexyl]-5,6-dihydro-4H-2,3,5,10b-tetraaza-benzo[e]azulene, trans-8-Chloro-5-methyl-1-[4-(5-methyl-[1,2,4]thiadiazol-3-yl)-cyclohexyl]-5,6-dihydro-4H-2,3,5,10b-tetraaza-benzo[e]azulene, trans-8-Chloro-5-cyclobutyl-1-[4-(5-methyl-[1,2,4]oxadiazol-3-yl)-cyclohexyl]-5,6-dihydro-4H-2,3,5,10b-tetraaza-benzo[e]azulene, trans-8-Chloro-5-methyl-1-[4-(4-methyl-oxazol-2-yl)-cyclohexyl]-5,6-dihydro-4H-2,3,5,10b-tetraaza-benzo[e]azulene, trans-8-Chloro-5-methyl-1-[4-(5-methyl-oxazol-2-yl)-cyclohexyl]-5,6-dihydro-4H-2,3,5,10b-tetraaza-benzo[e]azulene, trans-8-Chloro-5-methyl-1-[4-(4-methyl-thiazol-2-yl)-cyclohexyl]-5,6-dihydro-4H-2,3,5,10b-tetraaza-benzo[e]azulene, trans-8-Chloro-1-[4-(4-chloro-5-methyl-isoxazol-3-yl)-cyclohexyl]-5,6-dihydro-4H-2,3,5,10b-tetraaza-benzo[e]azulene, trans-8-Chloro-1-[4-(4,5-dimethyl-isoxazol-3-yl)-cyclohexyl]-5,6-dihydro-4H-2,3,5,10b-tetraaza-benzo[e]azulene, trans-8-Chloro-1-[4-(4-chloro-5-methyl-isoxazol-3-yl)-cyclohexyl]-5-methyl-5,6-dihydro-4H-2,3,5,10b-tetraaza-benzo[e]azulene, trans-8-Chloro-1-[4-(4,5-dimethyl-isoxazol-3-yl)-cyclohexyl]-5-methyl-5,6-dihydro-4H-2,3,5,10b-tetraaza-benzo[e]azulene, trans-8-Chloro-1-[4-(4,5-dimethyl-oxazol-2-yl)-cyclohexyl]-5,6-dihydro-4H-2,3,5,10b-tetraaza-benzo[e]azulene, trans-8-Chloro-1-[4-(4-fluoro-5-methyl-isoxazol-3-yl)-cyclohexyl]-5,6-dihydro-4H-2,3,5,10b-tetraaza-benzo[e]azulene, trans-8-Chloro-1-[4-(4,5-dimethyl-oxazol-2-yl)-cyclohexyl]-5-methyl-5,6-dihydro-4H-2,3,5,10b-tetraaza-benzo[e]azulene, trans-8-Chloro-1-[4-(4-fluoro-5-methyl-isoxazol-3-yl)-cyclohexyl]-5-methyl-5,6-dihydro-4H-2,3,5,10b-tetraaza-benzo[e]azulene, trans-1-{8-Chloro-1-[4-(5-methyl-isoxazol-3-yl)-cyclohexyl]-4H,6H-2,3,5,10b-tetraaza-benzo[e]azulen-5-yl}-ethanone, trans-8-Chloro-5-methanesulfonyl-1-[4-(5-methyl-isoxazol-3-yl)-cyclohexyl]-5,6-dihydro-4H-2,3,5,10b-tetraaza-benzo[e]azulene, trans-8-Chloro-5-cyclobutyl-1-[4-(5-methyl-isoxazol-3-yl)-cyclohexyl]-5,6-dihydro-4H-2,3,5,10b-tetraaza-benzo[e]azulene, and trans-8-Chloro-5-(2,2-difluoro-ethyl)-1-[4-(5-methyl-isoxazol-3-yl)-cyclohexyl]-5,6-dihydro-4H-2,3,5,10b-tetraaza-benzo[e]azulene.

A certain embodiment of the invention is a compound as described in any of the embodiments obtainable by a process according as described herein.

A certain embodiment of the invention is a compound as described in any of the embodiments, whenever obtained by a process according as described herein.

A certain embodiment of the invention is a compound as described in any of the embodiments for the use as therapeutically active substance.

A certain embodiment of the invention is a compound as described in any of the embodiments for a use in the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is a pharmaceutical composition comprising a compound as described in any of the embodiments.

A certain embodiment of the invention is a pharmaceutical composition comprising a compound as described in any of the embodiments, wherein it is useful for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is the use of a compound as described in any of the embodiments for the preparation of a medicament.

A certain embodiment of the invention is the use of a compound as described in any of the embodiments for the preparation of a medicament, wherein the medicament is useful for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is the use of a compound as described in any of the embodiments for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention is a method for the therapeutic and/or prophylactic treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior, which method comprises administering a compound as defined in any if the embodiments to a human being or animal.

In a certain embodiment, the compounds of formula I of the invention can be manufactured according to a process comprising the step of reacting a compound of formula II

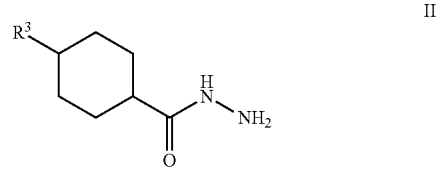

with a compound of formula III

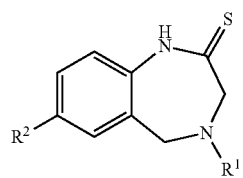

to obtain a compound of formula I wherein $R^1$, $R^2$ and $R^3$ are as defined hereinabove for formula I.

The processes are described in more detail with the following general schemes and procedures A to R.

Scheme 1: General Scheme A

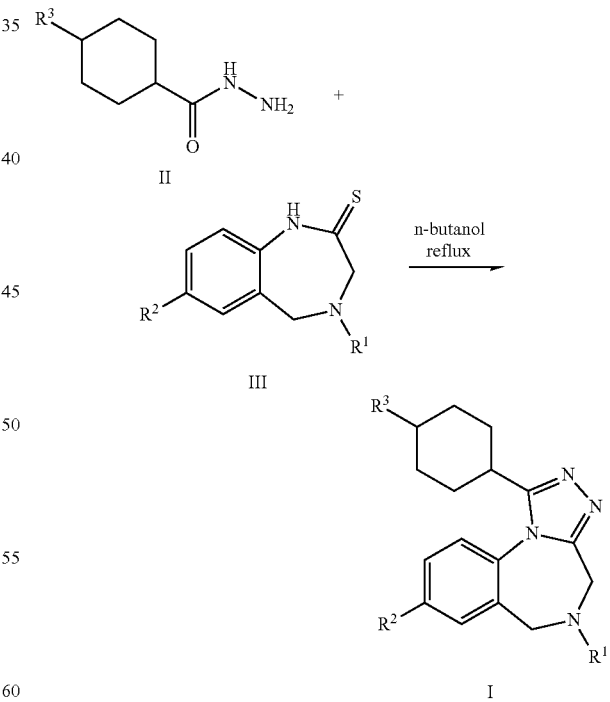

Compounds of formula I can be prepared by thermal condensation of a hydrazide of formula II and a thiolactam of formula III. The synthesis of compounds of formula II is outlined in general schemes D-R hereinafter. Compounds of formula III can be prepared following the procedures described in general scheme C as described hereinafter. General scheme A is hereinafter further illustrated with general procedure XV.

Scheme 2: General Scheme B

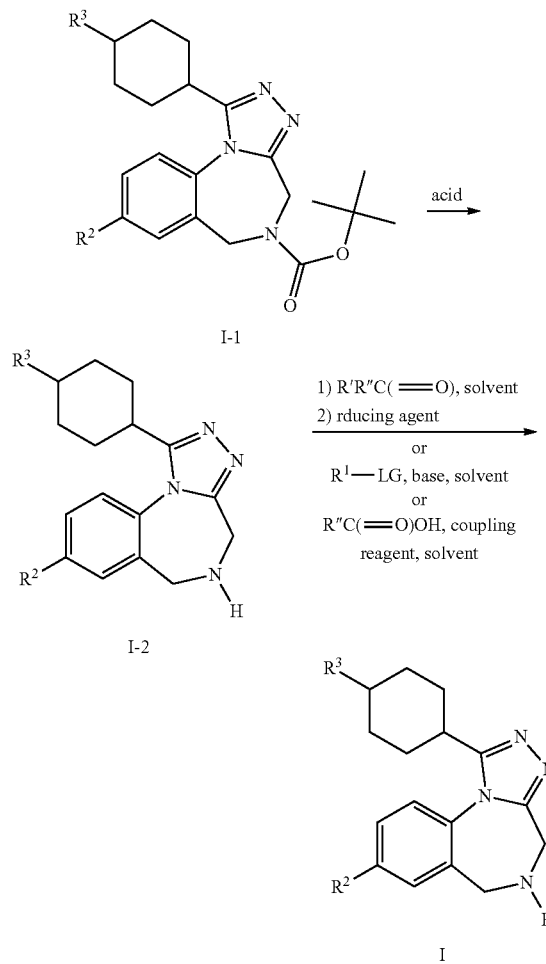

R' = H, $C_a$-alkyl, optionally substituted,
R'' = $C_b$-alkyl, optionally substituted,
or R' and R'' form together an optionally substituted cycloalkyl,
and a + b are $\le$ = 5.

Compounds of formula I with $R^1$ different from H can be prepared from compounds of formula I-2 (compounds of formula I wherein $R^1$ is H) according to methods known in the art, e.g. by treating a compound of formula I-2 with an inorganic base such as a carbonate salt or an organic base such as a tertiary amine and an electrophilic reactant $R^1$-LG (wherein LG is a leaving group like. halogen or sulfonyl) which is either commercially available or easily prepared according to methods and starting materials well known in the art. Alternatively, compounds of formula I can be obtained via reductive alkylation by consecutively treating a compound of formula I-2 with a ketone or aldehyde and a suitable reducing agent like a borohydride derivative such as sodium borohydride, sodium cyanoborohydride or sodium triacetoxyborohydride. Alternatively, compounds of formula I, in which $R^1$ is an acyl group, can be manufactured by coupling an amine of formula I-2 with a carboxylic acid. The usual reagents and protocols known in the art can be used to effect the amide coupling. Compounds of formula I-2 can be obtained by cleavage of the substituent $R^1$ of a compound of formula I using methods known in the art. Compounds of formula I-2 are conveniently obtained as the salt or the free base after basic aqueous work-up by treatment of compounds of formula I-1 (compounds of formula I in which $R^1$ is tert-butoxycarbonyl) with an acid in a suitable solvent like methanesulphonic acid or trifluoroacetic acid in dichloromethane or tetrahydrofuran or hydrochloric acid in methanol. General scheme B is hereinafter further illustrated with general procedures XVI and XVII.

Scheme 3: General Scheme C

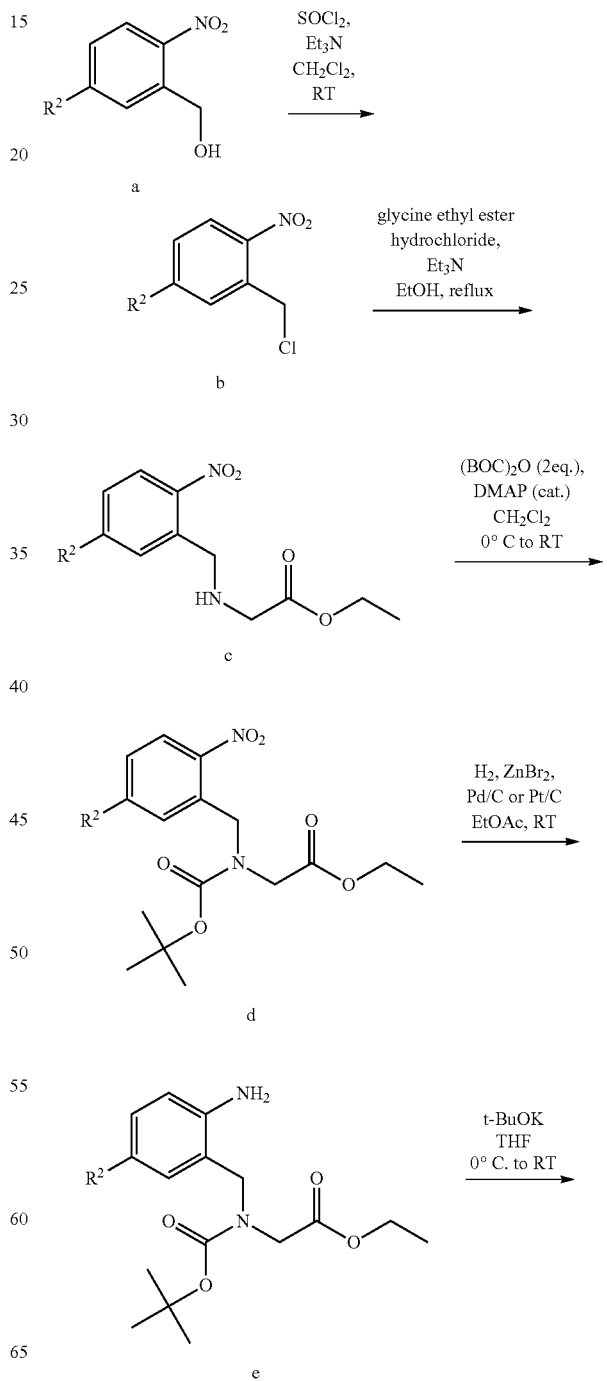

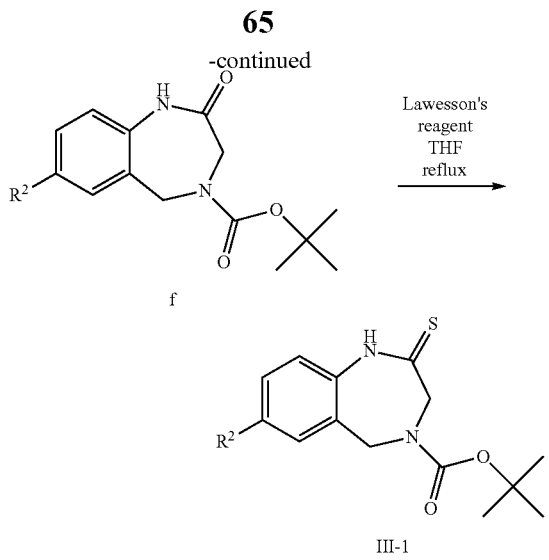

A thiolactam of formula III-1 (compounds of formula III in which $R^1$ is tert-butoxycarbonyl) can be obtained as follows: Transformation of a 2-nitrobenzyl alcohol of formula a to a benzylic chloride of formula b can be affected by a chlorinating reagent such as thionyl chloride in the presence of an organic tertiary amine base. Alkylation of a compound of formula b with glycine ethyl ester hydrochloride in the presence of an organic tertiary amine base and N-protection of the resulting compound of formula c using di-tert-butyl dicarbonate and a catalytic amount of 4-N,N-dimethylaminopyridine gives compounds of formula d. The nitro group can be reduced selectively by hydrogenation over palladium or platinum on charcoal, which has been pretreated with a zinc halide such as zinc bromide, to give aniline intermediates of formula e. Cyclization to lactams of formula f is achieved by treatment of compounds of formula e with a suitable base, e.g. potassium tert-butoxide, in tetrahydrofuran. A thiolactam of formula III-1 is obtained by treatment of a compound of formula f with Lawesson's reagent or phosphorous pentasulphide at elevated temperature.

Scheme 4: General Scheme D

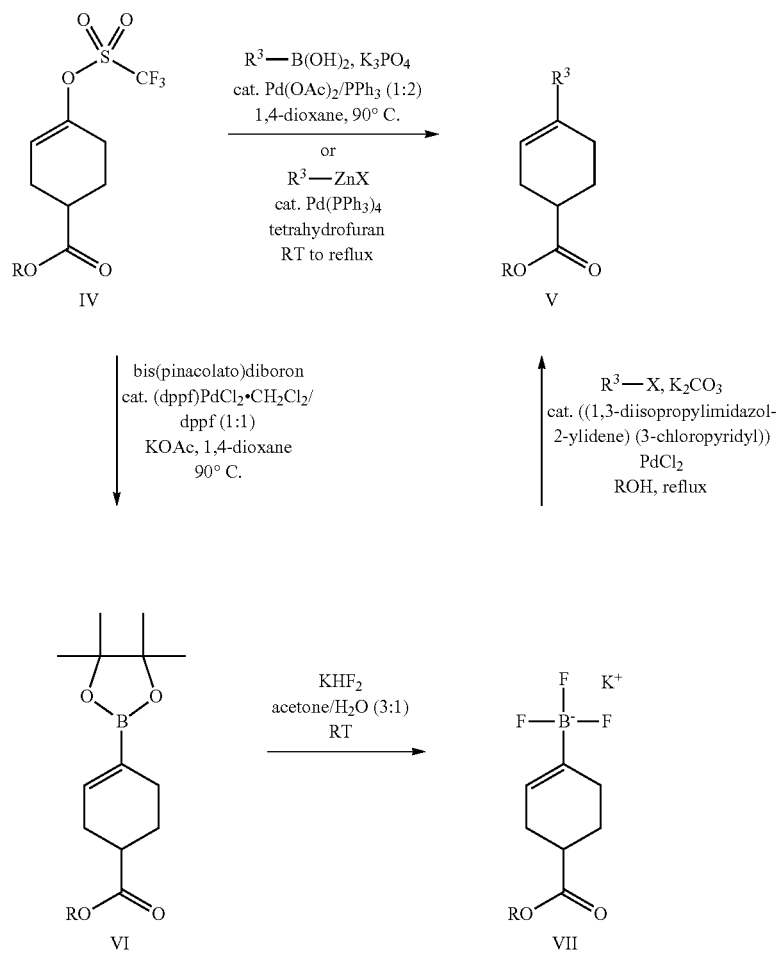

R = Me, Et
X = halogen
dppf = 1,1'-bis(diphenylphosphino)ferrocene

4-Heteroaryl-cyclohex-3-enecarboxylic acid ester intermediates of formula V can be prepared under the conditions of the Suzuki reaction from a 4-trifluoromethanesulfonyloxy-cyclohex-3-enecarboxylic acid ester of formula IV and a heteroaryl boronic acid, a heteroaryl boronic acid ester or a heteroaryl trifluoroborate salt in a suitable organic solvent such as 1,4-dioxane, tetrahydrofuran or toluene in the presence of catalytic amounts of a 1:2 mixture of palladium(II) acetate and triphenylphosphine or a 1:1 mixture of palladium (II) acetate and a bisphosphine ligand or tetrakis(triphenylphosphine)palladium(0) and in the presence of a base such as potassium phosphate or potassium carbonate, which is used neat or as an aqueous solution, at a reaction temperature between room temperature and reflux. Alternatively 4-heteroaryl-cyclohex-3-enecarboxylic acid ester intermediates of formula V can be prepared under the conditions of the Negishi reaction from a 4-trifluoromethanesulfonyloxy-cyclohex-3-enecarboxylic acid ester of formula IV and a heteroaryl zinc halide in a suitable organic solvent such as tetrahydrofuran and Pd(PPh)$_3$ at a reaction temperature between room temperature and reflux. Alternatively compounds of formula V can be prepared by coupling a potassium trifluoroborate salt of formula VII with a heteroaryl halide $R^3$—X in the presence of a base such as potassium carbonate and a suitable palladium catalyst such as (1,3-diisopropylimidazol-2-ylidene)(3-chloropyridyl)palladium (II) chloride in a suitable solvent such as an alcohol at reflux. A potassium trifluoroborate salt of formula VII can be prepared by treatment of an (RS)-4-(4,4,5,5-tetramethyl-[1,3,2]dioxaborolan-2-yl)-cyclohex-3-enecarboxylic acid ester of formula VI with potassium hydrogen difluoride in a mixture of acetone and water at room temperature. Compounds of formula VI can be obtained by coupling a compound of formula IV with bis (pinacolato)diboron in the presence of a suitable base such as potassium acetate and a suitable palladium catalyst such as a 1:1 mixture of 1,1'-bis(diphenylphosphino)ferrocene and dichloro(1,1'-bis(diphenylphosphino)ferrocene) palladium (II) dichloromethane adduct in a suitable solvent such as 1,4-dioxane at 90° C. General scheme D is hereinafter further illustrated with general procedures I and III.

Scheme 5: General Scheme E

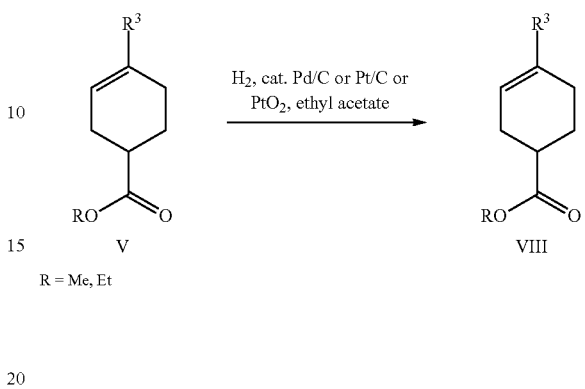

R = Me, Et

4-Heteroaryl-cyclohexane carboxylic acid ester intermediates of formula VIII are usually obtained as a mixture of the cis and the trans isomer by reduction of 4-heteroaryl-cyclohex-3-enyl carboxylic acid ester intermediates of formula V under an atmosphere of hydrogen gas (1 bar) in a suitable solvent such as ethyl acetate or an alcohol in the presence of a catalytic amount of palladium or platinum on charcoal or platinum(IV) oxide at room temperature. Compounds of formula V and VIII, the residue $R^3$ of which is substituted with one or more halide substituents other than fluorine may undergo partial or complete dehalogenation under these reaction conditions. The acid formed as a consequence of the dehalogenation reaction may be neutralized by addition of a base such as a trialkyl amine to the reaction mixture. Pretreatment of the palladium or platinum catalyst with a zinc halide may in some cases prevent or reduce dehalogenation of compounds of formula V and VIII, the residue $R^3$ of which is substituted with one or more halide substituents other than fluorine. General scheme E is hereinafter further illustrated with general procedures VIII to IX.

Scheme 6: General Scheme F

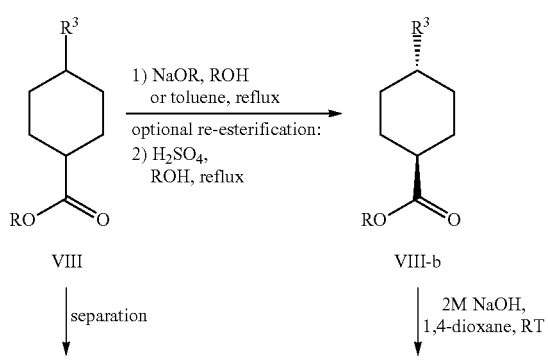

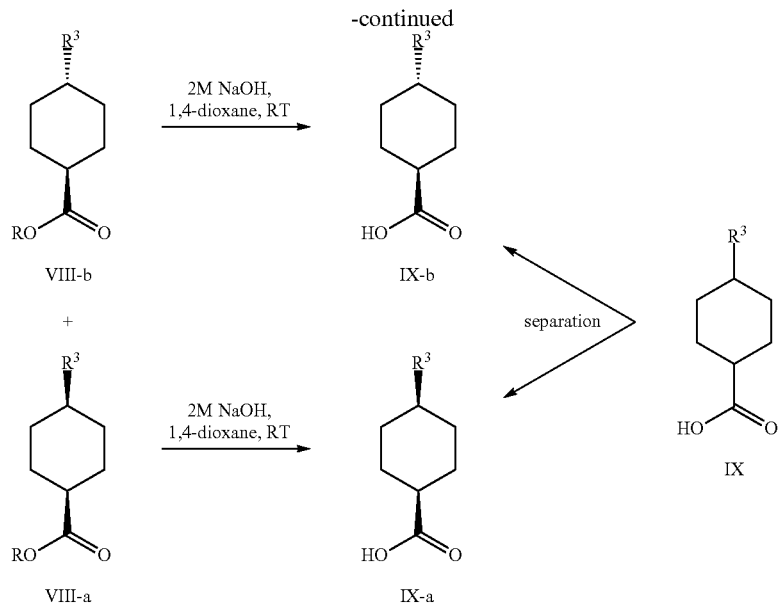

Cis/trans mixtures of 4-heteroaryl-cyclohexane carboxylic acid ester intermediates of formula VIII may in some cases be separable by the usual methods such as silica gel column or high performance chromatography or crystallization into pure cis-4-heteroaryl-cyclohexane carboxylic acid ester intermediates of formula VIII-a and trans-4-heteroaryl-cyclohexane carboxylic acid ester intermediates of formula VIII-b, which can be saponified to pure cis-4-heteroaryl-cyclohexane carboxylic acid intermediates of formula IX-a and trans-4-heteroaryl-cyclohexane carboxylic acid intermediates of formula IX-b under standard conditions such as stirring in a mixture of aqueous sodium hydroxide solution and an etheral solvent such as 1,4-dioxane, tetrahydrofuran or diethyl ether a room temperature. Alternatively, trans-4-heteroaryl-cyclohexane carboxylic acid intermediates of formula IX-b can be obtained by epimerization of the cis isomer of cis/trans-mixtures of 4-heteroaryl-cyclohexane carboxylic acid ester intermediates of formula VIII using a suitable base, e.g. an alkali metal alkoxide such as sodium or potassium methylate or ethylate, in a suitable solvent such as methanol, ethanol or toluene at reflux followed by saponification of the crude reaction mixture, which may consist of a mixture of a trans-4-heteroaryl-cyclohexane carboxylic acid intermediate of formula IX-b and a trans-4-heteroaryl-cyclohexane carboxylic acid ester intermediate of formula VIII-b, under standard conditions such as stirring in a mixture of aqueous sodium hydroxide solution and an etheral solvent such as 1,4-dioxane, tetrahydrofuran or diethyl ether at room temperature. In case the epimerization reaction was carried out in an alcohol as solvent, the crude reaction mixture can alternatively be acidified by the addition of concentrated sulfuric acid and heated to reflux to obtain a trans-4-heteroaryl-cyclohexane carboxylic acid ester intermediate of formula VIII-b. Cis/trans mixtures of 4-heteroaryl-cyclohexane carboxylic acid intermediates of formula IX may in some cases be separable by the usual methods such as silica gel column or high performance chromatography or crystallization into pure cis-4-heteroaryl-cyclohexane carboxylic acid intermediates of formula IX-a and trans-4-heteroaryl-cyclohexane carboxylic acid intermediates of formula IX-b. General scheme F is hereinafter further illustrated with general procedures X and XII.

Scheme 7: General Scheme G

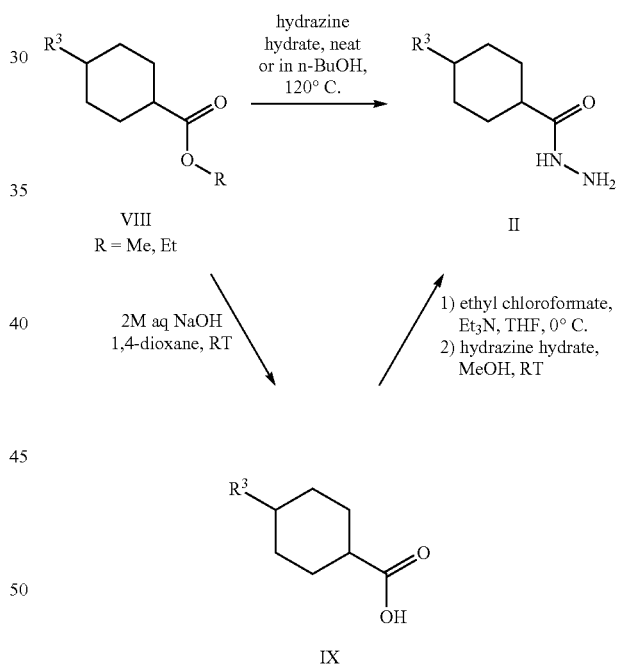

A 4-heteroaryl-cyclohexanecarboxylic acid ester intermediate of formula VIII can be converted to a hydrazide of formula II by heating with hydrazine hydrate. Alternatively, an ester of formula VIII can be hydrolyzed to a carboxylic acid of formula IX using a biphasic mixture of aqueous sodium or potassium hydroxide solution and an etheral solvent such as dioxane, tetrahydrofuran or diethyl ether. A hydrazide of formula II can be obtained by activating an acid intermediate of formula IX, e.g. with ethyl chloroformate, thionyl chloride, oxalyl chloride or a peptide coupling reagent, and subsequent coupling with hydrazine. General scheme G is hereinafter further illustrated with general procedures XIII and XIV.

Scheme 8: General Scheme H

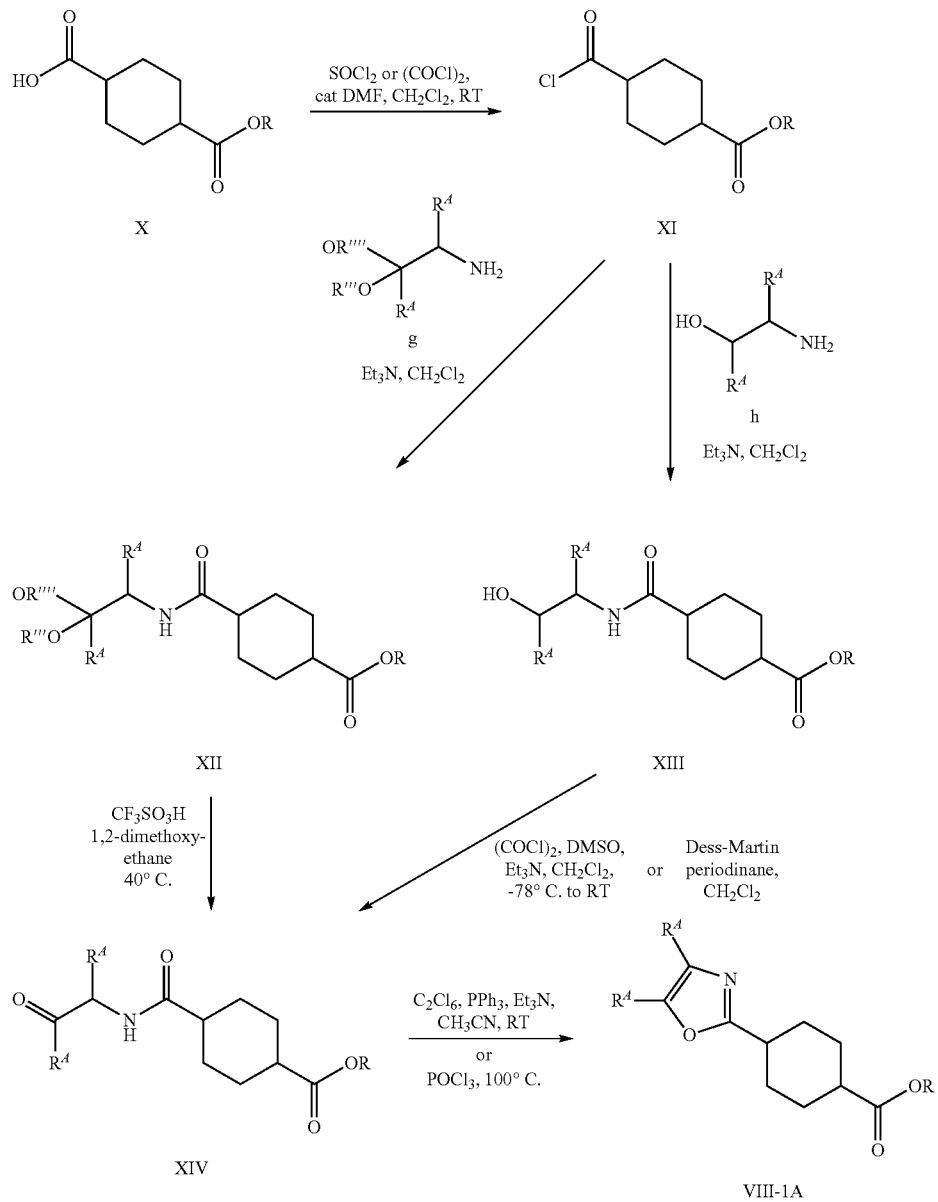

R = Me, Et
$R^A$ = H, $C_{1-6}$-alkyl
R''', R'''' = $C_{1-6}$-alkyl, or
R''' and R'''' form together a ring A cyclohexane-1,4-dicarboxylic acid mono ester of formula X can be converted to a chlorocarbonyl-cyclohexanecarboxylic acid ester of formula XI using the usual methods to convert a carboxylic acid to a carboxylic acid chloride, such as thionyl chloride or oxalyl chloride in the presence of a catalytic amount of DMF in a suitable solvent such as dichloromethane. An acid chloride of formula XI can be converted to an amide of formula XII by coupling with an amine of formula g or to an amide of formula XIII by coupling with an amine of formula h in the presence of a base such as triethylamine in a suitable solvent such as dichloromethane or tetrahydrofuran. A carbonyl derivative of formula XIV can be obtained either by treatment of an acetal derivative of formula XII with an acid such as trifluoromethylsulfonic acid or by oxidation of the alcohol group using the usual methods known in the art, e.g. treatment with oxalyl chloride, DMSO and a base such as triethylamine or with Dess-Martin periodinane. Cyclization of a compound of formula XIV to an oxazole derivative of formula VIII-1A can be effected by treatment with a suitable dehydrating agent such as phosphorus oxychloride or a mixture of hexachloroethane, triphenylphosphine and a base such as triethylamine in a suitable solvent such as acetonitrile. General scheme H is hereinafter further illustrated with general procedures III, IV and VII.

Scheme 9: General Scheme I

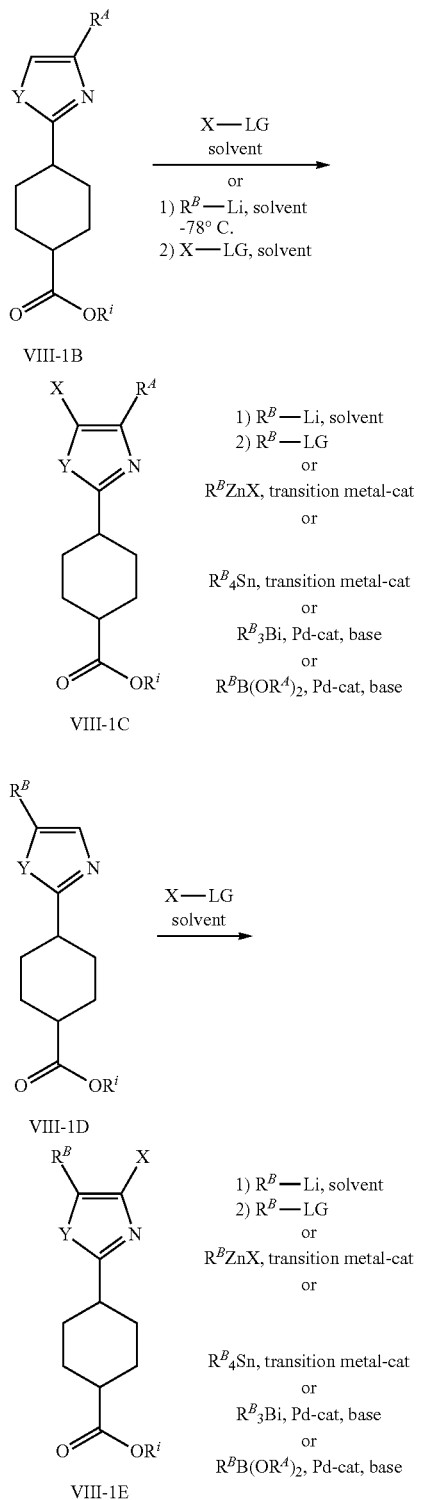

$R^i$ = H, Me, Et
X = halogen
Y = S, O
LG = leaving group
$R^A$ = H, $C_{1-6}$-alkyl
$R^B$ = $C_{1-6}$-alkyl A compound of formula VIII-1B can be halogenated to give a compound of formula VIII-1C either by direct treatment with an electrophilic halogenation reagent X-LG, in which X is halogen and LG a suitable leaving group, or by consecutive deprotonation with a strong base such as an alkyl lithium reagent at low temperature and treatment with an electrophilic halogenation reagent X-LG. Examples of halogenation reagents X-LG are Selectfluor®, N-fluorodibenzenesulfonimide (NFSI), 1-fluoropyridinium salts, bromine, iodine, N-chlorosuccinimide, N-bromosuccinimide, N-iododsuccinimide, 1,3-dibromo-5,5-dimethylhydantoin or a tetraalkylammonium trihalide salt. Likewise a compound of formula VIII-1D can be halogenated to give a compound of formula VIII-1E by treatment with an electrophilic halogenation reagent X-LG.

A halogenated compound of formula VIII-1C can be converted to a compound of formula VIII-1F and a halgogenated compound of formula VIII-1E can be converted to a compound of formula VIII-1G under one of the following conditions: Sequential treatment of a halogenated compound of formula VIII-1C or VIII-1E with an alkyl-lithium reagent such as n-butyllithium, sec-butyllithium or tert-butyllithium in a suitable solvent, typically an etheral solvent such as tetrahydrofuran or diethyl ether, usually under cooling between −78° C. and 0° C., followed by the addition of an alkylating agent $R^B$-LG, in which LG is a suitable leaving group, gives an alkylated compound of formula VIII-1F or VIII-1G, respectively. Alternatively, an alkylated compound of formula VIII-1F or VIII-1G can be obtained by reacting a halogenated compound of formula VIII-1C or VIII-1E, respectively, either with a tetraalkyltin reagent of formula $R^B_4Sn$ in the presence of a suitable palladium catalyst or pre-catalyst and optionally in the presence of a co-catalysts such as copper(I) iodide in a suitable solvent such as N,N-dimethylacetamide, or with an alkylzinc halide of formula $R^BZnX$ in the presence of a suitable transition metal catalyst or pre-catalyst, e.g. a nickel or palladium complex. e.g. bis (triphenylphosphine)dichloronickel(II) or (1,3-diisopropylimidazol-2-ylidene)(3-chloropyridyl)palladium(II) chloride, in a suitable solvent or solvent mixture such as N,N-dimethylacetamide or tetrahydrofuran or a mixture of tetrahydrofuran and 1,3-dimethyl-2-imidazolidinone, or with an alkylboronic acid $R^BB(OH)_2$ or and alkylboronic acid ester or a trialklybismuth derivative $R^B_3Bi$ in the presence of a suitable palladium catalyst or pre-catalyst such as tetrakis (triphenylphosphine)palladium or a mixture of palladium(II) acetate and a mono- or diphosphine derivative in the presence of a suitable base such as potassium or sodium carbonate in a suitable solvent such as N,N-dimethylformamide, toluene or tetrahydrofuran or a mixture of such a solvent with water.

Scheme 10: General Scheme J

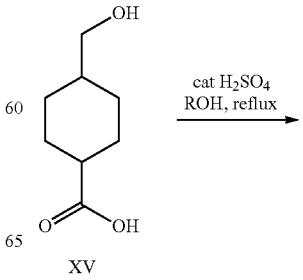

XV

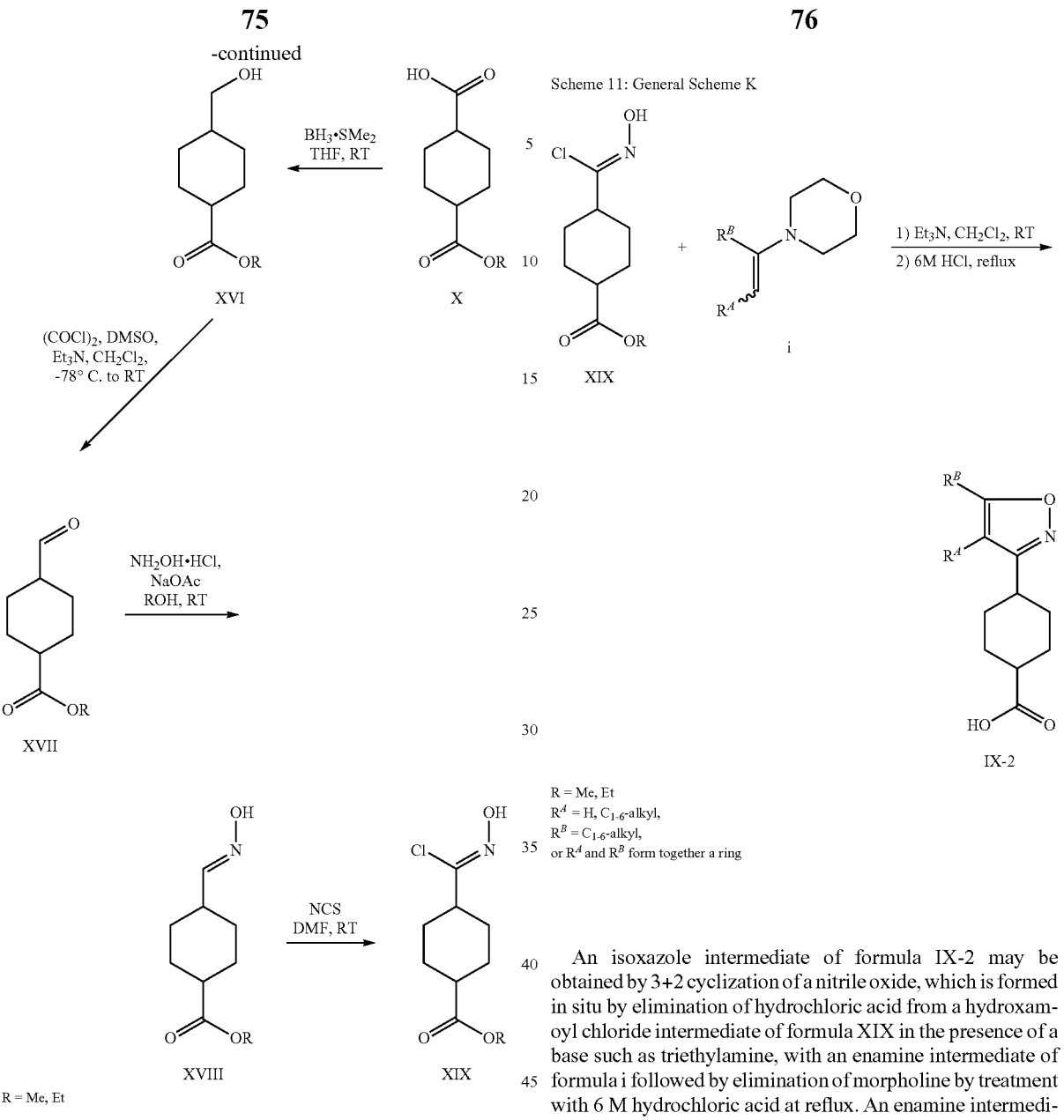

A 4-hydroxymethyl-cyclohexanecarboxylic acid ester of formula XVI can either be prepared by esterification of 4-hydroxymethyl-cyclohexanecarboxylic acid XV in an alcohol in the presence of a catalytic amount of an acid such as concentrated sulfuric acid at elevated temperature, usually reflux, or by reduction of a cyclohexane-1,4-dicarboxylic acid mono ester of formula X using the usual methods known in the art, e.g. a borane derivative such as borane-dimethylsulfide complex. An alcohol intermediate of formula XVI can be oxidized to an aldehyde intermediate of formula XVII using the usual methods known in the art for the oxidation of a primary alcohol group, e.g. treatment with oxalyl chloride, DMSO and a base such as triethylamine. A hydroxamoyl chloride intermediate of formula XIX can be prepared by chlorination of an aldoxime intermediate of formula XVIII, which can be obtained by treatment of an aldehyde intermediate of formula XVII with hydroxylamine hydrochloride in the presence of sodium acetate.

An isoxazole intermediate of formula IX-2 may be obtained by 3+2 cyclization of a nitrile oxide, which is formed in situ by elimination of hydrochloric acid from a hydroxamoyl chloride intermediate of formula XIX in the presence of a base such as triethylamine, with an enamine intermediate of formula i followed by elimination of morpholine by treatment with 6 M hydrochloric acid at reflux. An enamine intermediate of formula i may can be obtained by reacting a ketone with morpholine under the usual conditions known in the art, e.g. in the presence of a titanium reagent such as titanium tetrachloride or tetraisopropoxide.

Scheme 12: General Scheme L

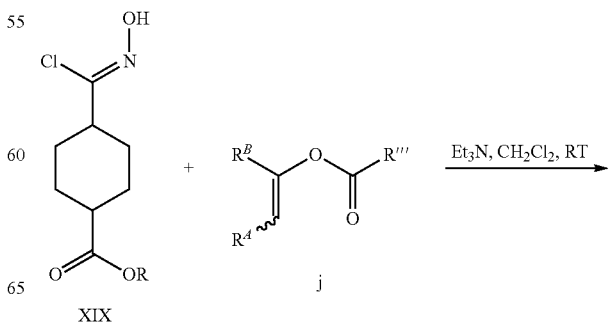

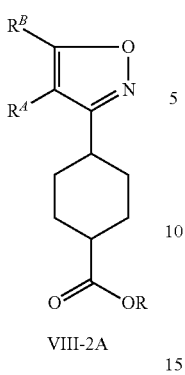

VIII-2A

R = Me, Et
$R^A$ = H, $C_{1-6}$-alkyl,
$R^B$ = $C_{1-6}$-alkyl,
or $R^A$ and $R^B$ form together a ring
R''' = optionally substituted $C_{1-6}$-alkyl or aryl

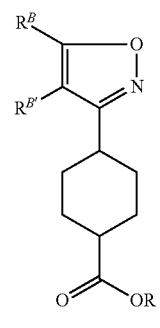

VIII-2E

R = Me, Et
X = halogen
X' = Br, I
$R^B$, $R^{B'}$ = $C_{1-6}$-alkyl

An isoxazole intermediate of formula IX-2A may be obtained by 3+2 cyclization of a nitrile oxide, which is formed in situ by elimination of hydrochloric acid from a hydroxamoyl chloride intermediate of formula XIX in the presence of a base such as triethyl amine, with an enol ester intermediate of formula j followed by spontaneous elimination of a carboxylic acid R''' COOH under the reaction conditions.

Scheme 13: General Scheme M

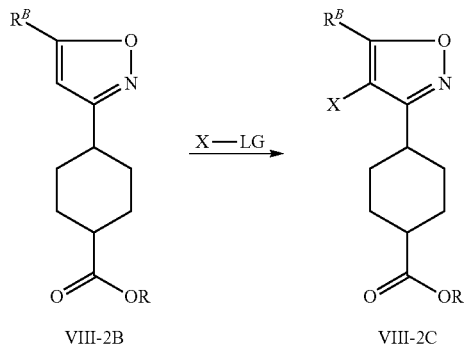

VIII-2B → VIII-2C

A compound of formula VIII-2B can be halogenated to give a compound of formula VIII-2C by treatment with an electrophilic halogenation reagent X-LG, in which X is halogen and LG a suitable leaving group. Examples of halogenation reagents X-LG are Selectfluor®, N-fluorodibenzenesulfonimide (NFSI), 1-fluoropyridinium salts, bromine, iodine, N-chlorosuccinimide, N-bromosuccinimide, N-iododsuccinimide, 1,3-dibromo-5,5-dimethylhydantoin or a tetraalkylammonium trihalide salt. A compound of formula VIII-2D, in which X' is bromine or iodine, can be transformed to a compound of formula VIII-2E by coupling with an alkyl zinc halide $R^{B'}$—ZnX in the presence of a suitable catalyst such as ((1,3-diisopropylimidazol-2-ylidene)(3-chloropyridyl))palladium dichloride in a suitable solvent or solvent mixture, e.g. a 4:1 mixture of tetrahydrofuran and 1,3-dimethyl-2-imidazolidinone.

Scheme 14: General Scheme N

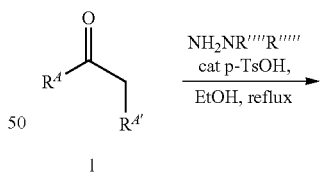

l

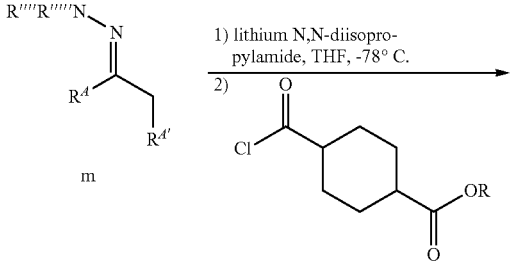

m → XI

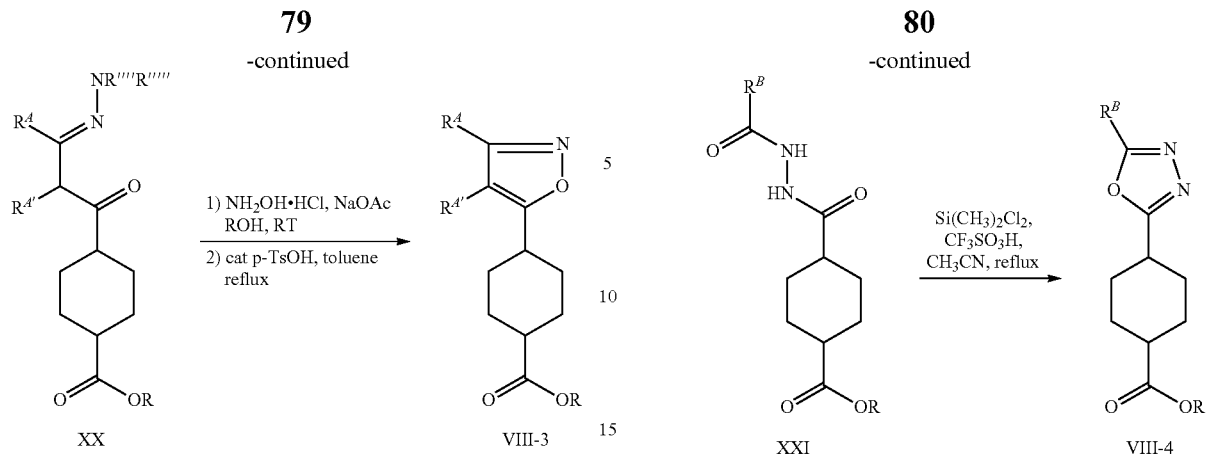

R = Me, Et
$R^4$, $R^{4'}$ = H, $C_{1-6}$-alkyl, or
$R^4$ and $R^{4'}$ form a ring
$R''''$, $R'''''$ = $C_{1-6}$-alkyl, or
$R''''$ and $R'''''$ form a ring Isoxazole intermediates of formula VIII-3 may be obtained from intermediates of formula XX by consecutive treatment with hydroxylamine hydrochloride and sodium acetate and heating at reflux in toluene in the presence of a catalytic amount of para-toluenesulfonic acid. Compounds of formula XX can be obtained by deprotonation of a hydrazone of formula m with a strong base such as lithium N,N-diisopropylamide at low temperature followed by acylation with a compound of formula XI. Compounds of formula m can be obtained from a ketone of formula I by the usual methods, e.g. by treatment with a hydrazine derivative NH2-NR""R""" in the presence of a catalytic amount of an acid such as para-toluenesulfonic acid in a suitable solvent such as ethanol.

Scheme 15: General Scheme O

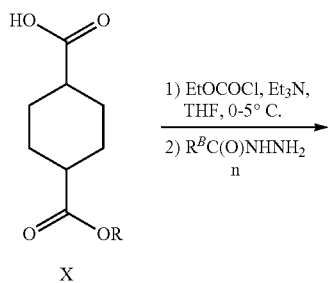

R = Me, Et
$R^B$ = $C_{1-6}$-alkyl

An oxadiazole intermediate of formula VIII-4 may be obtained by cyclization of a diacyl hydrazine intermediate of formula XXI in the presence of trifluoromethanesulfonic acid and dimethyldichlorosilane in acetonitrile at reflux. A diacyl hydrazine intermediate of formula XXI can be prepared by consecutive transformation of a cyclohexane-1,4-dicarboxylic acid mono ester of formula X to an anhydride by the usual methods, e.g. treatment with ethyl chloroformate in the presence of a base such as triethylamine, or to another activated form such as an acid chloride of formula XI followed by treatment with a hydrazide intermediate of formula n.

Scheme 16: General Scheme P

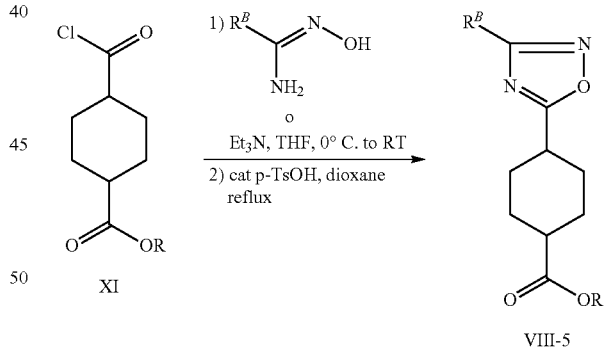

R = Me, Et
$R^B$ = $C_{1-6}$-alkyl

An oxadiazole intermediate of formula VIII-5 may be obtained by treatment of an acid chloride intermediate of formula XI with an N-hydroxamidine derivative of formula o in the presence of a base such as triethylamine followed by heating at reflux in the presence of a catalytic amount of an acid such as para-toluenesulfonic acid in a suitable solvent such as dioxane.

Scheme 17: General Scheme Q

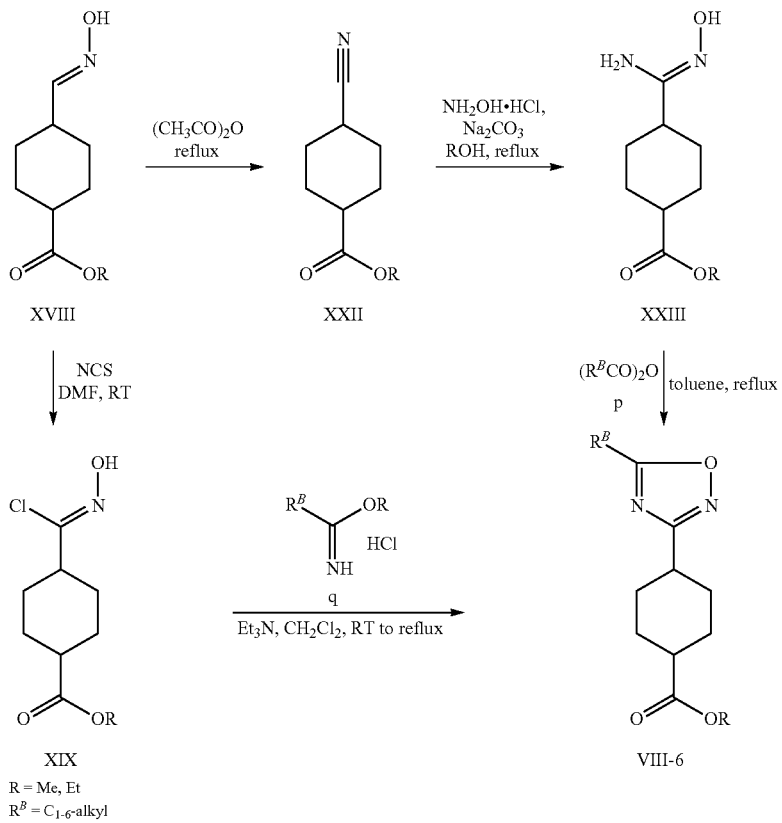

R = Me, Et
$R^B = C_{1-6}$-alkyl

An oxadiazole intermediate of formula VIII-6 may be obtained either by treatment of an N-hydroxamidine intermediate of formula XXIII with a carboxylic acid anhydride of formula p in a suitable solvent such as toluene at reflux or by treatment of a hydroxamoyl chloride intermediate of formula XIX with an imidate salt of formula q in the presence of a base such as triethylamine in a suitable solvent such as dichloromethane. An N-hydroxamidine intermediate of formula XXIII can be prepared by dehydration of an aldoxime intermediate of formula XVIII with acetic anhydride at reflux and treatment of the resulting nitrile intermediate of formula XXII with hydroxylamine hydrochloride in the presence of a base such as sodium carbonate in suitable solvent such as an alcohol at elevated temperature, typically at reflux. General scheme Q is hereinafter further illustrated with general procedures V, VI and XI.

Scheme 18: General Scheme R

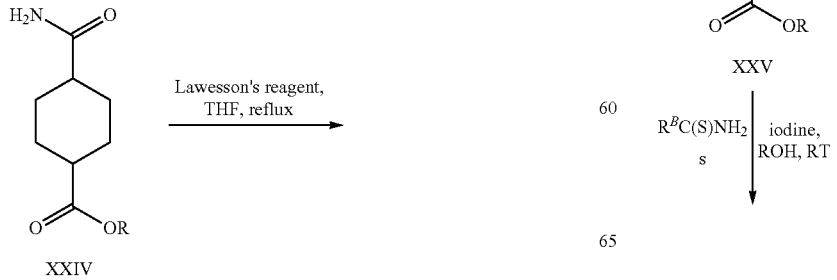

-continued

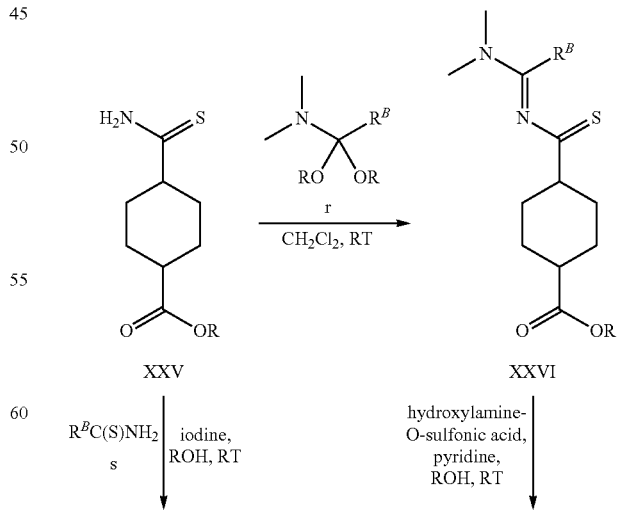

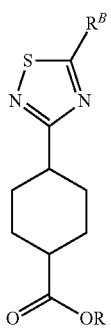

VIII-7

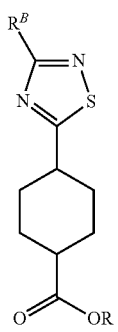

VIII-8

R = Me, Et
R$^B$ = C$_{1-6}$-alkyl

By treatment with Lawesson's reagent a 4-carbamoyl-cyclohexanecarboxylic acid ester of formula XXIV can be converted to a 4-thiocarbamoyl-cyclohexanecarboxylic acid ester of formula XXV, which may be cyclized to a thiadiazole intermediate of formula VIII-7 by treatment with a thioamide derivative of formula s in the presence of iodine in a suitable solvent such as an alcohol. Alternatively, a 4-thiocarbamoyl-cyclohexanecarboxylic acid ester of formula XXV may be converted to a N-[1-dimethylamino-ethylidene]-thioacetamide intermediate of formula XXVI condensation with an N,N-dimethylcarboxylic acid acetal of formula r. A thiadiazole intermediate of formula VIII-8 may be obtained by cyclization of an intermediate of formula XXVI with hydroxylamine-O-sulfonic acid in the presence of pyridine in a suitable solvent such as an alcohol.

Scheme 19: General Scheme S

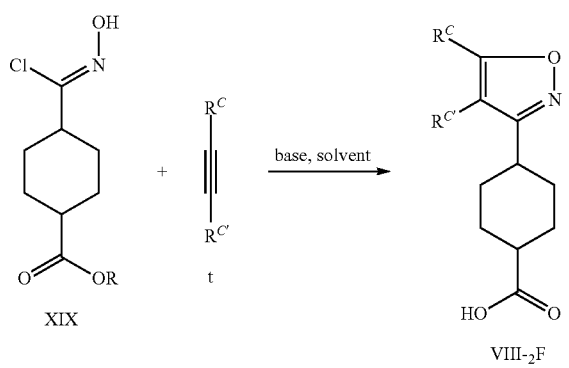

XIX     t     VIII-$_2$F

R = Me, Et
RC, RC' = H, R*, CO$_2$R''', SiR'''$_3$
R''' = optionally substituted C$_{1-6}$-alkyl or aryl An isoxazole intermediate of formula VIII-2F may be obtained by 3+2 cyclization of an alkyne derivate of formula t with a nitrile oxide, which is formed in situ by elimination of hydrochloric acid from a hydroxamoyl chloride intermediate of formula XIX in the presence of a suitable base such as an amine base, e.g. triethyl amine or ethyldiisopropylamine, or a carbonate base, e.g. potassium or sodium carbonate, in a suitable organic solvent, e.g. diethyl ether, tetrahydrofuran, dichloromethane, chloroform, toluene, benzene, hexane or ethyl acetate, or a mixture of such an organic solvent with water.

Scheme 10: General Scheme T

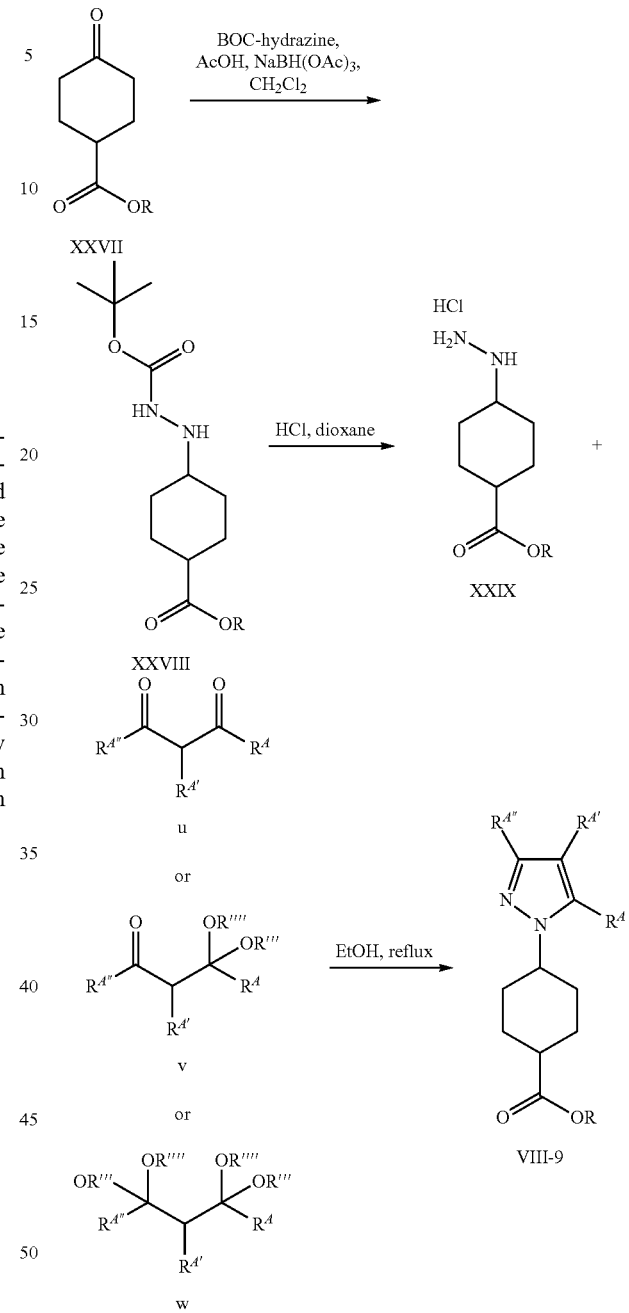

R = Me, Et
R$^A$, R$^{A'}$, R$^{A''}$ = H, C$_{1-6}$-alkyl, or
R$^A$ and R$^{A'}$ or R$^{A'}$ and R$^{A''}$ form a ring
R''', R'''' = C$_{1-6}$-alkyl, or
R''' and R'''' form a ring A 4-(N'-tert-butoxycarbonyl-hydrazino)-cyclohexanecarboxylic acid ester of formula XXVIII can be prepared from a 4-oxo-cyclohexanecarboxylic acid ester of formula XXVII by reductive amination with tert-butyl hydrazinecarboxylate and a suitable reducing agent, e.g. a mixture of sodium triacetoxyborohydride and acetic acid, in a suitable solvent such as dichloromethane. Cleavage of the N'-tert-butoxycarbonyl group of an intermediate of formula XXVIII by treatment with hydrochloric acid in a suitable organic solvent such as dioxane, diethyl ether or methanol gives rise to 4-hydrazino-cyclohexanecarboxylic acid ester hydrochloride salt of formula XXIX. A 4-pyrazol-1-yl-cyclohexanecarboxylic acid ester of formula VIII-9 can be obtained by condensation of a 4-hydrazino-cyclohexanecarboxylic acid ester hydrochloride salt of formula XXIX with a 1,3-dicarbonyl derivative of formula u, a mono-protected 1,3-dicarbonyl derivative of formula v or a di-protected 1,3-dicarbonyl derivative of formula w in a suitable solvent such as an alcohol, e.g. ethanol, usually at reflux temperature.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of formula I in this invention can be derivatised at functional groups to provide derivatives which are capable of conversion back to the parent compound in vivo.

Pharmacological Tests

The compounds of the present invention exhibit V1a activity. They are selective inhibitors of the V1a receptor and are therefore likely to have 125 a low potential to cause unwanted off-target related side-effects. The V1a activity can be detected as described below.

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are resuspended in 30 ml freshly prepared ice cold Lysis buffer (50 mM HEPES, 1 mM EDTA, 10 mM magnesium dichloride adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43,000 g at 4° C. (19,000 rpm). The pellet is resuspended in 12.5 ml Lysis buffer+12.5 ml sucrose 20% and homogenized using a Polytron for 1-2 min. The protein concentration is determined by the Bradford method and aliquots are stored at −80° C. until use. For binding studies 60 mg Yttrium silicate SPA beads (Amersham®) are mixed with an aliquot of membrane in binding buffer (50 mM Tris, 120 mM sodium chloride, 5 mM potassium chloride, 2 mM calcium dichloride, 10 mM magnesium dichloride) for 15 minutes with mixing. 50 µl of bead/membrane mixture is then added to each well of a 96 well plate, followed by 50 µl of 4 nM 3H-Vasopressin (American Radiolabeled Chemicals). For total binding measurement 100 µl of binding buffer are added to the respective wells, for non-specific binding 100 µl of 8.4 mM cold vasopressin and for compound testing 100 µl of a serial dilution of each compound in 2% dimethyl sulfoxide. The plate is incubated 1 h at room temperature, centrifuged 1 min at 1000 g and counted on a Packard Top-Count. Non-specific binding counts are subtracted from each well and data is normalized to the maximum specific binding set at 100%. To calculate an $IC_{50}$ the curve is fitted using a non-linear regression model (XLfit) and the Ki is calculated using the Cheng-Prussoff equation.

The following representative data show the antagonistic activity against human $V_{1a}$ receptor of compounds according to present invention.

TABLE 3 human V1a pKi of selected examples

| Ex# | pKi (hV1a) |
|---|---|
| 1 | 9.00 |
| 2 | 7.27 |
| 3 | 7.98 |
| 4 | 9.40 |
| 5 | 7.49 |
| 6 | 8.48 |
| 7 | 9.22 |
| 8 | 7.73 |
| 9 | 8.66 |
| 10 | 9.28 |
| 11 | 8.26 |
| 12 | 9.07 |
| 13 | 9.00 |
| 14 | 7.55 |
| 15 | 8.48 |
| 16 | 9.52 |
| 17 | 8.12 |
| 18 | 8.77 |
| 19 | 9.70 |
| 20 | 7.91 |
| 21 | 8.77 |
| 22 | 9.52 |
| 23 | 8.19 |
| 24 | 8.92 |
| 25 | 8.76 |
| 26 | 9.45 |
| 27 | 9.37 |
| 28 | 9.22 |
| 29 | 8.80 |
| 30 | 7.60 |
| 31 | 8.76 |
| 32 | 8.54 |
| 33 | 8.70 |
| 34 | 9.56 |
| 35 | 9.30 |
| 36 | 9.11 |
| 37 | 7.04 |
| 38 | 7.73 |
| 39 | 9.70 |
| 40 | 8.32 |
| 41 | 9.30 |
| 42 | 9.40 |
| 43 | 8.23 |
| 44 | 9.22 |
| 45 | 9.14 |
| 46 | 8.07 |
| 47 | 9.24 |
| 48 | 8.08 |
| 49 | 8.39 |
| 50 | 6.74 |
| 51 | 7.81 |
| 52 | 8.20 |

TABLE 3-continued human V1a pKi of selected examples

| Ex# | pKi (hV1a) |
|---|---|
| 53 | 8.92 |
| 54 | 8.02 |
| 55 | 8.23 |
| 56 | 8.80 |
| 57 | 7.33 |
| 58 | 6.72 |
| 59 | 8.09 |
| 60 | 7.81 |
| 61 | 7.52 |
| 62 | 8.20 |
| 63 | 8.80 |
| 64 | 6.69 |
| 65 | 7.80 |
| 66 | 8.54 |
| 67 | 7.17 |
| 68 | 8.18 |
| 69 | 8.82 |
| 70 | 6.89 |
| 71 | 7.82 |
| 72 | 9.15 |
| 73 | 7.80 |
| 74 | 8.49 |
| 75 | 8.17 |
| 76 | 8.00 |
| 77 | 8.82 |
| 78 | 8.23 |
| 79 | 8.47 |
| 80 | 7.64 |
| 81 | 8.37 |
| 82 | 7.83 |
| 83 | 6.21 |
| 84 | 6.87 |
| 85 | 7.39 |
| 86 | 8.51 |
| 87 | 6.84 |
| 88 | 7.84 |
| 89 | 5.56 |
| 90 | 6.53 |
| 91 | 7.46 |
| 92 | 8.51 |
| 93 | 6.58 |
| 94 | 7.71 |
| 95 | 5.53 |
| 96 | 6.69 |
| 97 | 8.54 |
| 98 | 8.96 |
| 99 | 8.27 |
| 100 | 8.96 |
| 101 | 8.89 |
| 102 | 8.42 |
| 103 | 8.80 |
| 104 | 9.10 |
| 105 | 7.66 |
| 106 | 8.64 |
| 107 | 8.80 |
| 108 | 7.90 |
| 109 | -. |
| 110 | 7.37 |
| 111 | 7.77 |
| 112 | 7.12 |
| 113 | 6.10 |
| 114 | 6.10 |
| 115 | 9.77 |
| 116 | 7.14 |
| 117 | 8.16 |
| 118 | 9.08 |
| 119 | 8.66 |
| 120 | 8.71 |

Pharmaceutical Compositions

The compounds of formula I as well as their pharmaceutically acceptable salts can be used as therapeutics, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injectable solutions.

The compounds of formula I and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

Examples of compositions according to the invention are, but are not limited to:

EXAMPLE A

Tablets of the following composition are manufactured in the usual manner:

TABLE 4 possible tablet composition

| ingredient | mg/tablet | | | |
|---|---|---|---|---|
| | 5 | 25 | 100 | 500 |
| 1. compound of formula I | 5 | 25 | 100 | 500 |
| 2. lactose | 45 | 105 | 30 | 150 |
| 3. corn starch | 15 | 6 | 6 | 60 |
| 4. microcrystalline cellulose | 34 | 30 | 30 | 450 |
| 5. magnesium stearate | 1 | 1 | 1 | 1 |
| total | 100 | 167 | 167 | 831 |

Manufacturing Procedure

1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 5 possible capsule ingredient composition

| ingredient | mg/capsule | | | | |
|---|---|---|---|---|---|
|  | 5 | 10 | 25 | 100 | 500 |
| 1. compound of formula I | 5 | 10 | 25 | 100 | 500 |
| 2. lactose | 159 | 155 | 123 | 148 | — |
| 3. corn starch | 25 | 30 | 35 | 40 | 70 |
| 4. talc | 10 | 5 | 15 | 10 | 25 |
| 5. magnesium stearate | 1 | — | 2 | 2 | 5 |
| total | 200 | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer, the talc (and magnesium stearate) is added thereto and mixed thoroughly. The mixture is filled by machine into suitable capsules, e.g. hard gelatin capsules.

EXAMPLE B-2

Soft Gelatin Capsules of the following composition are manufactured:

TABLE 6 possible soft gelatin capsule ingredient composition

| ingredient | mg/capsule |
|---|---|
| compound of formula I | 5 |
| yellow wax | 8 |
| hydrogenated soybean oil | 8 |
| partially hydrogenated plant oils | 34 |
| soybean oil | 110 |
| total | 165 |

TABLE 7 possible soft gelatin capsule composition

| ingredient | mg/capsule |
|---|---|
| gelatin | 75 |
| glycerol 85% | 32 |
| karion 83 | 8 (dry matter) |
| titanium dioxide | 0.4 |
| iron oxide yellow | 1.1 |
| total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 8 possible suppository composition

| ingredient | mg/supp. |
|---|---|
| compound of formula I | 15 |
| suppository mass | 1285 |
| total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

EXAMPLE D

Injection solutions of the following composition are manufactured:

TABLE 9 possible injection solution composition

| ingredient | mg/injection solution. |
|---|---|
| compound of formula I | 3 |
| polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 10 possible sachet composition

| ingredient | mg/sachet |
|---|---|
| compound of formula I | 50 |
| lactose, fine powder | 1015 |
| microcrystalline cellulose (AVICEL PH 102) | 1400 |
| sodium carboxymethyl cellulose | 14 |
| polyvinylpyrrolidon K 30 | 10 |
| magnesium stearate | 10 |
| flavoring additives | 1 |
| total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXAMPLES

The following examples are provided for illustration of the invention. They should not be considered as limiting the scope of the invention, but merely as being representative thereof.

Intermediate of Formula IV (RS)-4-Trifluoromethanesulfonyloxy-cyclohex-3-enecarboxylic acid ethyl ester

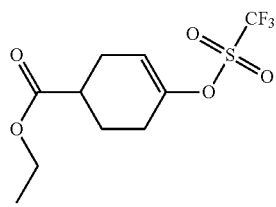 [SMILES: CCOC(=O)C1CC=C(OS(=O)(=O)C(F)(F)F)CC1]

To a solution of ethyl-4-cyclohexanonecarboxylate (25.0 g, 147 mmol) in tetrahydrofuran (580 ml) was added a 1M solution of lithium bis(trimethylsilyl)amid in tetrahydrofuran (154 ml, 154 mmol) at −78° C. Stirring for 1 h was followed by addition of a solution of N-phenyl-bis(trifluoromethanesulfonimide) (55.1 g, 154 mmol) in tetrahydrofuran (80 ml). The cooling bath was removed 30 minutes after completed addition, and the reaction mixture was stirred for 12 h at room temperature. The mixture was quenched with 1 M aqueous sodium hydrogen sulfate solution (154 ml, 154 mmol). The solvent was removed by rotary evaporation (water bath of 40° C.). The residue was partitioned between tert-butyl methyl ether (500 ml) and 0.5 M aqueous sodium hydroxide solution (400 ml). The organic layer was washed with two 400-ml portions of 0.5 M aqueous sodium hydroxide solution, one 200-ml portion of saturated ammonium chloride solution and one 100-ml portion of brine, dried over anhydrous sodium sulfate and concentrated in vacuo to give the title compound (41.8 g, 94.2%) as yellow oil, which was used in the following steps without further purification. MS m/e: 273 ([M−C$_2$H$_5$]$^-$).

Intermediate of Formula (VI)

(RS)-4-(4,4,5,5-Tetramethyl-[1,3,2]dioxaborolan-2-yl)-cyclohex-3-enecarboxylic acid ethyl ester

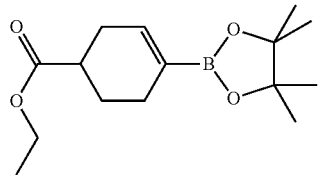 [SMILES: CCOC(=O)C1CC=C(B2OC(C)(C)C(C)(C)O2)CC1]

A mixture of (RS)-4-trifluoromethanesulfonyloxy-cyclohex-3-enecarboxylic acid ethyl ester (3.0 g, 9.92 mmol), potassium acetate (2.92 g, 29.8 mmol) and bis(pinacolato) diboron (3.78 g, 14.9 mmol) in 1,4-dioxane (30 ml) was purged with argon. Addition of 1,1'-bis(diphenylphosphino) ferrocene (0.17 g, 0.30 mmol) and dichloro(1,1'-bis(diphenylphosphino)ferrocene)palladium(II) dichloromethane adduct (0.22 g, 0.30 mmol) was followed by stirring at 90° C. for 18 h. The reaction mixture was partitioned between ethyl acetate (200 ml) and water (150 ml). The layers were separated. The organic layer was washed with one portion of brine, dried over anhydrous sodium sulfate and concentrated to dryness. Flash-chromatography with n-heptane/ethyl acetate as eluent gave the title compound (1.95 g, 70%) as light yellow oil. MS m/e: 281 ([M+H]$^+$)

Intermediate of Formula (VII)

Potassium (RS)-(4-(ethoxycarbonyl)cyclohex-1-enyl)trifluoroborate

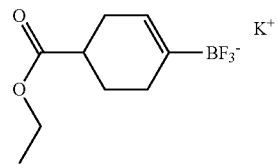

To a solution of (RS)-4-(4,4,5,5-tetramethyl-[1,3,2]dioxaborolan-2-yl)-cyclohex-3-enecarboxylic acid ethyl ester (0.37 g, 1.32 mmol) in acetone (9 ml) and water (3 ml) was added potassium hydrogen difluoride (0.41 g, 5.28 mmol). Stirring for 4 h at room temperature was followed by evaporation of the solvent mixture. The residue was triturated in warm acetonitrile (20 ml). The solids were removed by filtration. The filtrate was concentrated to dryness to give the title compound (0.35 g, quantitative) as white solid which was used without further purification in the next step.

4-Heteroaryl-cyclohex-3-enecarboxylic acid ester Intermediates of Formula (V)

General Procedure (I):
A mixture of (RS)-4-trifluoromethanesulfonyloxy-cyclohex-3-enecarboxylic acid ethyl ester (1 eq), a heteroaryl zinc halide (1-1.2 eq) and tetrakis(triphenylphosphine)palladium (0.05 eq) in dry tetrahydrofuran (0.3 M) is stirred at reflux for 14-20 h. After cooling to room temperature the reaction mixture is partitioned between an organic solvent such as tert-butyl methyl ether or ethyl acetate and water. The layers are separated. The aqueous layer is extracted with two or three portions of organic solvent. The combined organic layers are dried over anhydrous sodium sulfate and concentrated to dryness. Purification by flash-chromatography gives a 4-heteroaryl-cyclohex-3-enecarboxylic acid ester intermediate of formula V.

General Procedure (II):
To a mixture of potassium (RS)-(4-(ethoxycarbonyl)cyclohex-1-enyl)trifluoroborate (1 eq), a heteroaryl halide (1.2 eq) and potassium carbonate (3 eq) in an alcohol such as ethanol or methanol (0.2 M) is added (1,3-diisopropylimidazol-2-ylidene)(3-chloropyridyl)palladium(II) chloride (0.02 eq). The mixture is stirred at reflux for 1-20 h. After cooling to room temperature the solvent is evaporated. The residue is triturated in an organic solvent such as tert-butyl methyl ether or ethyl acetate. The precipitates are removed by filtration. The filtrate is concentrated to dryness. Purification by flash-chromatography gives a 4-heteroaryl-cyclohex-3-enecarboxylic acid ester intermediate of formula V.

4-Heteroaryl-cyclohex-3-enecarboxylic acid ester 1

(RS)-4-Thiazol-2-yl-cyclohex-3-enecarboxylic acid ethyl ester

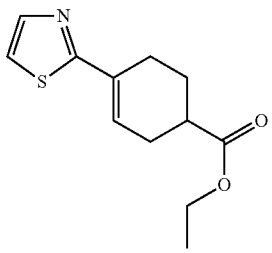 [SMILES: CCOC(=O)C1CC=C(c2nccs2)CC1]

The title compound was obtained as yellow oil in 33% yield from 2-bromothiazole according to general procedure (II). MS m/e: 238 ([M+H]$^+$)

4-Heteroaryl-cyclohex-3-enecarboxylic acid ester 2

(RS)-4-(4-Methyl-thiazol-2-yl)-cyclohex-3-enecarboxylic acid ethyl ester

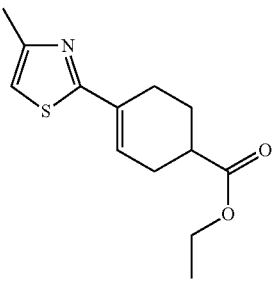 [SMILES: CCOC(=O)C1CC=C(c2nc(C)cs2)CC1]

The title compound was obtained as yellow oil in 41% yield from 2-chloro-4-methylthiazole according to general procedure (II). MS m/e: 252 ([M+H]$^+$)

4-Heteroaryl-cyclohex-3-enecarboxylic acid ester 3

(RS)-4-(2-Methyl-thiazol-4-yl)-cyclohex-3-enecarboxylic acid ethyl ester

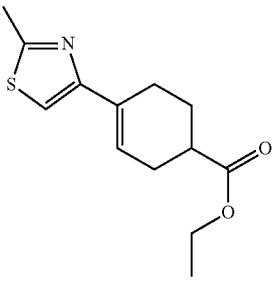 [SMILES: CCOC(=O)C1CC=C(c2csc(C)n2)CC1]

The title compound was obtained as light yellow oil in 66% yield from 4-bromo-2-methylthiazole according to general procedure (II). MS m/e: 252 ([M+H]$^+$)

Intermediate of Formula (XI)

trans-4-Chlorocarbonyl-cyclohexanecarboxylic acid methyl ester

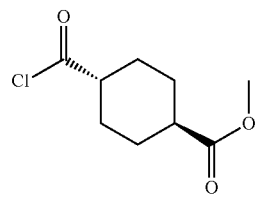

To a solution of trans-1,4-cycloxanedicarboxylic acid monomethylester (2.0 g, 11 mmol) in dichloromethane (30 ml) was added oxalyl chloride (1.1 ml, 13 mmol) and a catalytic amount of N,N-dimethylformamide at 0-5°. The cooling bath was removed, and the reaction mixture was stirred for 24 h at room temperature. After evaporation of the solvent the residue was triturated in n-hexane (100 ml). The precipitate was removed by filtration. The filtrate was concentrated in vacuo to give the title compound (2.2 g, quantitative) as colorless oil which was used in the next step without further purification.

Amide Intermediates of Formula (XII), (XIII) and (XIV)

General Procedure (III): Amide Coupling

To a solution of an amine of formula g or h (1.1-1.5 eq) and triethylamine (1.1 eq) in dichloromethane (0.2 M) is added a solution of an acid chloride of formula XI (1 eq) in dichloromethane (0.2-1.0 M) at 0-5° C. The cooling bath is removed and the reaction mixture is allowed to warm to room temperature. After 2 h the reaction mixture is partitioned between an organic solvent such ethyl acetate or tert-butyl methyl ether and water. The layers are separated. The aqueous layer is extracted with two portions of organic solvent. The combined organic layers are washed with one portion of saturated ammonium chloride solution, dried over anhydrous sodium sulfate and concentrated in vacuo to give an amide intermediate of formula XII or XIII, respectively.

General Procedure (IV): Swern Oxidation

To a solution of dimethylsulfoxide (2.4 eq) in dry dichloromethane (0.1-0.2 M) at −78° C. is added oxalyl chloride (1.2 eq). The cooling bath is removed and the reaction mixture is stirred at −50° C. for 5 min. A solution of an amide intermediate of formula XIII (1 eq) in dichloromethane (0.2-0.5 M) is added at −65° C. Stirring for 30 minutes is followed by addition of triethylamine (5.0 eq). The cooling bath is removed 30 minutes after completed addition, and the reaction mixture is quenched with 1 M aqueous hydrochloric acid solution (3 eq) at −30° C. to −10° C. The mixture is partitioned between an organic solvent such as ethyl acetate and water. The layers are separated. The aqueous layer is extracted with one or two portions of organic solvent. The combined organic layers are washed with one portion of brine or saturated ammonium chloride solution, dried over anhydrous sodium sulfate and concentrated in vacuo to give an intermediate of formula XIV.

Amide 1 trans-4-(2,2-Diethoxy-ethylcarbamoyl)-cyclohexanecarboxylic acid methyl ester

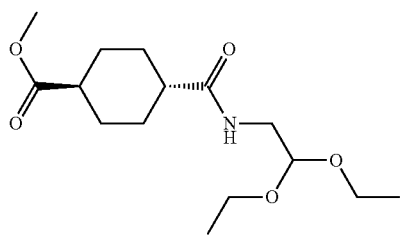 [SMILES: CCOC(CNC(=O)[C@H]1CC[C@H](C(=O)OC)CC1)OCC]

The title compound was obtained as white solid in quantitative yield from amino acetaldehyde diethyl acetal and trans-4-chlorocarbonyl-cyclohexanecarboxylic acid methyl ester according to general procedure (III). MS m/e: 302 ([M+H]$^+$)

Amide 2 trans-4-(2-Oxo-ethylcarbamoyl)-cyclohexanecarboxylic acid methyl ester

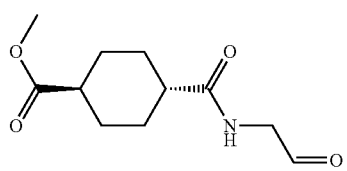 [SMILES: COC(=O)[C@H]1CC[C@H](C(=O)NCC=O)CC1]

A solution of trans-4-(2,2-diethoxy-ethylcarbamoyl)-cyclohexanecarboxylic acid methyl ester (900 mg, 2.99 mmol) and trifluoromethanesulfonic acid (996 mg, 4.48 mmol) in 1,2-dimethoxyethane (30 ml) was heated at 40° C. for 4 h. After cooling to room temperature the reaction mixture was partitioned between ethyl acetate (100 ml) and saturated aqueous sodium bicarbonate solution (50 ml). The layers were separated. The aqueous layer was extracted with two 100 ml-portions of ethyl acetate. The combined organic layers were dried over anhydrous sodium sulfate and concentrated in vacuo to give the title compound (740 mg, quantitative) as light brown viscous oil, which was used in the next step without further purifications. MS m/e: 228 ([M+H]$^+$)

Amide 3 trans-4-((S)-2-Hydroxy-1-methyl-ethylcarbamoyl)-cyclohexanecarboxylic acid methyl ester

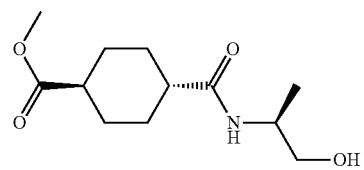 [SMILES: COC(=O)[C@H]1CC[C@H](C(=O)N[C@@H](C)CO)CC1]

The title compound was obtained as white solid in 56% yield from S-(+)-2-amino-1-propanol and trans-4-chlorocarbonyl-cyclohexanecarboxylic acid methyl ester according to general procedure (III). MS m/e: 244 ([M+H]$^+$)

Amide 4 trans-4-((S)-1-Methyl-2-oxo-ethylcarbamoyl)-cyclohexanecarboxylic acid methyl ester

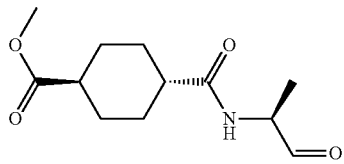 [SMILES: COC(=O)[C@H]1CC[C@H](C(=O)N[C@@H](C)C=O)CC1]

The title compound was obtained as white solid in quantitative yield from trans-4-((S)-2-hydroxy-1-methyl-ethylcarbamoyl)-cyclohexanecarboxylic acid methyl ester according to general procedure (IV). MS m/e: 240 ([M−H]$^-$)

Amide 5 trans-4-((S)-2-Hydroxy-propylcarbamoyl)-cyclohexanecarboxylic acid methyl ester

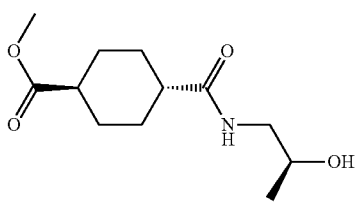 [SMILES: COC(=O)[C@H]1CC[C@H](C(=O)NC[C@H](C)O)CC1]

The title compound was obtained as white solid in 57% yield from (S)-1-aminopropan-2-ol and trans-4-chlorocarbonyl-cyclohexanecarboxylic acid methyl ester according to general procedure (III). MS m/e: 244 ([M+H]$^+$)

Amide 6 trans-4-(2-Oxo-propylcarbamoyl)-cyclohexanecarboxylic acid methyl ester

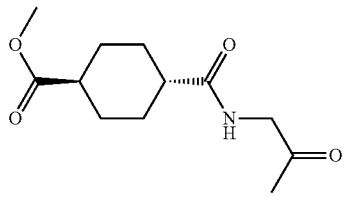 [SMILES: COC(=O)[C@H]1CC[C@H](C(=O)NCC(C)=O)CC1]

The title compound was obtained as white solid in quantitative yield from trans-4-((S)-2-hydroxy-propylcarbamoyl)- cyclohexanecarboxylic acid methyl ester according to general procedure (IV). MS m/e: 242 ([M+H]⁺)

Amide 7 trans-4-(2-Hydroxy-1-methyl-propylcarbamoyl)-cyclohexanecarboxylic acid methyl ester

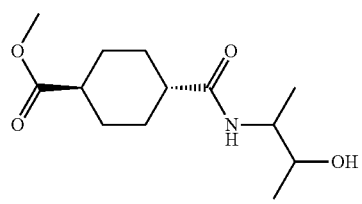 [SMILES: COC(=O)[C@H]1CC[C@H](C(=O)NC(C)C(C)O)CC1]

The title compound was obtained as white solid in 72% yield from 3-aminobutan-2-ol and trans-4-chlorocarbonyl-cyclohexanecarboxylic acid methyl ester according to general procedure (III). MS m/e: 258 ([M+H]⁺)

Amide 8 trans-4-(1-Methyl-2-oxo-propylcarbamoyl)-cyclohexanecarboxylic acid methyl ester

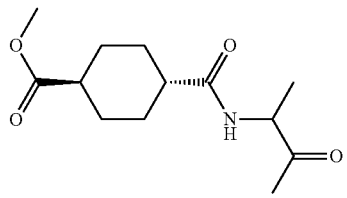 [SMILES: COC(=O)[C@H]1CC[C@H](C(=O)NC(C)C(C)=O)CC1]

The title compound was obtained as white solid in quantitative yield from trans-4-(2-hydroxy-1-methyl-propylcarbamoyl)-cyclohexanecarboxylic acid methyl ester according to general procedure (IV). MS m/e: 256 ([M+H]⁺)

Intermediates of Formula (XVI)

4-Hydroxymethyl-cyclohexanecarboxylic acid ester 1 cis/trans-4-Hydroxymethyl-cyclohexanecarboxylic acid ethyl ester (3:1)

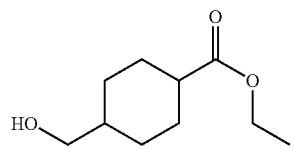

To a solution of cis/trans-4-(hydroxymethyl)cyclohexanecarboxylic acid (10.0 g, 63.2 mmol) in ethanol (316 ml) was added a catalytic amount of sulfuric acid. The reaction mixture was heated at reflux for 20 h. The solvent was evaporated. The residue was partitioned between ethyl acetate (150 ml) and 2 M aqueous sodium carbonate solution (100 ml). The aqueous layer was separated. The organic layer was washed with one 100-ml portion of water and one 50-ml portion of brine. The combined aqueous layers were extracted with one 100-ml portion of ethyl acetate. The combined organic layers were dried over anhydrous sodium sulfate and concentrated in vacuo to give the tile compound as colorless oil (11.5 g, 98.1%). MS m/e: 187 ([M+H]⁺)

4-Hydroxymethyl-cyclohexanecarboxylic acid ester 2 trans-4-Hydroxymethyl-cyclohexanecarboxylic acid methyl ester

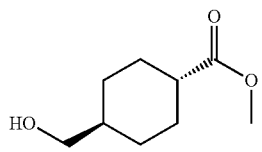

To a solution of trans-4-(methoxycarbonyl)cyclohexanecarboxylic acid (10.0 g, 53.7 mmol) in tetrahydrofuran (540 ml) was added borane-dimethylsulfide complex (6.80 g, 80.6 mmol) at 0-5° C. The cooling bath was removed after 15 minutes and the mixture was stirred for 4 h. The reaction mixture was quenched with methanol (17.2 g, 537 mmol), stirred for 20 minutes and concentrated in vacuo. The residue was triturated in tert-butyl methyl ether (300 ml) and filtrated over a pad of Decalite. The filtrate was concentrated in vacuo. The residue was partitioned between ethyl acetate (300 ml) and 1 M aqueous sodium hydroxide solution (100 ml). The layers were separated. The organic layer was washed with one 100 ml-portion of water. The combined aqueous layers were extracted with one 150-ml portion of ethyl acetate. The combined organic layers were washed with one 50 ml-portion of brine, dried over anhydrous sodium sulfate and concentrated in vacuo to give the title compound (8.75 g, 94.6%) as colorless oil, which can be used without further purification. MS m/e: 172 (M⁺)

Intermediates of Formula (XVII)

4-Formyl-cyclohexanecarboxylic acid ester 1 cis/trans-4-Formyl-cyclohexanecarboxylic acid ethyl ester

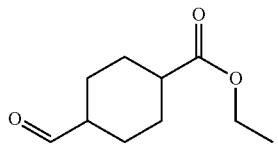

To a solution of oxalyl chloride (2.8 ml, 32 mmol) in dichloromethane (150 ml) was added dimethylsulfoxide (5.0 ml, 64 mmol) at −78° C. The mixture was stirred for 5 minutes at −50° C. A solution of cis/trans-4-hydroxymethyl-cyclohexanecarboxylic acid ethyl ester (3:1) (5.0 g, 27 mmol) in dichloromethane (30 ml) was added at −65° C. Stirring for 30 minutes was followed by addition of triethylamine (18.7 ml, 134 mmol). The cooling bath was removed 15 minutes after completed addition, and the reaction mixture was stirred for 2 h. The reaction mixture was concentrated to approximately 20-30 ml by rotating evaporation. The residue was partitioned between ethyl acetate (200 ml) and 0.5 M aqueous hydrochloric acid solution (100 ml). The layers were separated. The aqueous layer was extracted with one 100-portion of ethyl acetate. The combined organic layers were washed with one 100-ml portion of brine, dried over anhydrous sodium sulfate and concentrated in vacuo to give the title compound (4.9 g, 98%) as light yellow oil, which was used in the next step without further purification. MS m/e: 185 ([M+H]$^+$)

4-Formyl-cyclohexanecarboxylic acid ester 2 trans-4-Formyl-cyclohexanecarboxylic acid methyl ester

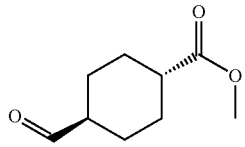

To a solution of dimethylsulfoxide (9.53 g, 122 mmol) in dry dichloromethane (400 ml) was slowly added oxalyl chloride (7.74 g, 61.0 mmol) at −78° C. The cooling bath was removed and the reaction mixture was stirred at −50° C. for 5 min. A solution of trans-4-hydroxymethyl-cyclohexanecarboxylic acid methyl ester (8.75 g, 50.8 mmol) in dichloromethane (108 ml) was added at −65° C. Stirring for 30 minutes was followed by addition of triethylamine (25.7 g, 254 mmol). The cooling bath was removed 15 minutes after completed addition. The reaction mixture was quenched with 1 M aqueous hydrochloric acid solution (152 ml, 152 mmol) at −10° C. The layer were separated. The organic layer was washed with two 250 ml-portions of water and one 100-ml portion of brine, dried over anhydrous sodium sulfate and concentrated in vacuo to give the title compound as yellow oil (9.3 g, quantitative), which was used in the next step without further purification.

Intermediates of Formula (XVIII)

4-(Hydroxyimino-methyl)-cyclohexanecarboxylic acid ester 1 cis/trans-(E/Z)-4-(Hydroxyimino-methyl)-cyclohexanecarboxylic acid ethyl ester

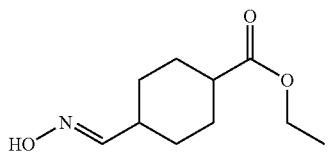

To a solution of cis/trans-4-formyl-cyclohexanecarboxylic acid ethyl ester (4.56 g, 24.8 mmol) in ethanol (248 ml) were added sodium acetate (2.44 g, 29.7 mmol) and hydroxylamine hydrochloride (2.06 g, 29.7 mmol). Stirring for 16 h at room temperature was followed by evaporation of the solvent. The residue was partitioned between ethyl acetate (200 ml) and 1 M aqueous sodium carbonate solution (100 ml). The layers were separated. The aqueous layer was extracted with one 200-ml portion of ethyl acetate. The combined organic layers were washed with one 100-ml portion of brine, dried over anhydrous sodium sulfate and concentrated in vacuo to give the title compound (5.15 g, quantitative) as light yellow oil, which was used in the next step without further purification. MS m/e: 200 ([M+H]$^+$)

4-(Hydroxyimino-methyl)-cyclohexanecarboxylic acid ester 2 trans-(E/Z)-4-(Hydroxyimino-methyl)-cyclohexanecarboxylic acid methyl ester

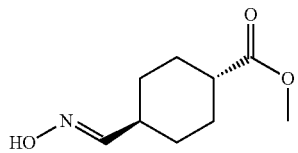

To a solution of trans-4-formyl-cyclohexanecarboxylic acid methyl ester (8.65 g, 50.8 mmol) in methanol (250 ml) was added sodium acetate (12.5 g, 152 mmol) and subsequently hydroxylamine hydrochloride (10.6 g, 152 mmol) at 0-5° C. The cooling bath was removed 10 minutes after completed addition, and the mixture was stirred for 20 h. The reaction mixture was concentrated in vacuo. The residue was partitioned between ethyl acetate (300 ml) and of 0.5 M aqueous sodium hydroxide solution. The layers were separated. The organic layer was washed with one 150-ml portion of 0.5 M aqueous sodium hydroxide solution. The combined aqueous layers were extracted with one 150 ml-portion of ethyl acetate. The combined organic layers were washed with one 150 ml-portion of 0.5 M aqueous hydrochloric acid solution and one 100-ml portion of brine, dried over anhydrous sodium sulfate and concentrated in vacuo to give the title compound (8.5 g, 90%) as colorless oil, which was used in the next step without further purification. MS m/e: 185 (M$^+$)

Intermediates of Formula (XIX)

4-(Chloro(hydroxyimino)methyl)-cyclohexanecarboxylic acid ester 1 cis/trans-Ethyl 4-(chloro(hydroxyimino)methyl)cyclohexanecarboxylate

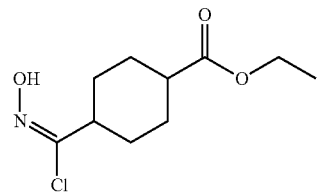

To a solution of cis/trans-(E/Z)-4-(hydroxyimino-methyl)-cyclohexanecarboxylic acid ethyl ester (0.50 g, 2.5 mmol) in N,N-dimethylformamide (12.5 ml) was added N-chlorosuccinimide (0.37 g, 2.8 mmol) at 0° C. The cooling bath was removed 10 minutes after completed addition, and the mixture was stirred for 1 h at room temperature. The reaction mixture was partitioned between diethyl ether (150 ml) and water (50 ml). The layers were separated. The organic layer was washed with one 50-ml portion of water and one 30-ml portion of brine, dried over anhydrous sodium sulfate and concentrated in vacuo to give the title compound (0.58 g, 99%) as colorless oil, which was used in the next step without further purification. MS m/e: 198 ([M−Cl]⁺)

4-(Chloro(hydroxyimino)methyl)-cyclohexanecarboxylic acid ester 2 trans-Methyl 4-(chloro(hydroxyimino)methyl)cyclohexanecarboxylate

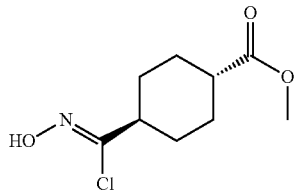

To a solution of trans-(E/Z)-4-(hydroxyimino-methyl)-cyclohexanecarboxylic acid methyl ester (5.0 g, 27 mmol) in N,N-dimethylformamide (135 ml) was added N-chlorosuccinimide (3.78 g, 28.3 mmol) at 0-5° C. The cooling bath was removed, and the mixture was stirred for 1 h. The reaction mixture was partitioned between diethyl ether (250 ml) and an ice-water mixture (200 ml). The organic layer was washed with two 200 ml-portions of water and one 100 ml-portion of brine. The combined aqueous layers were extracted with one 150-ml portion of diethyl ether. The combined organic layers were dried over anhydrous sodium sulfate and concentrated in vacuo to give the title compound (6.1 g, quantitative) as colorless viscous oil, which was used in the next step without further purification.

Intermediate of Formula (XX)

trans-4-[2-(Dimethyl-hydrazono)-cyclohexanecarbonyl]-cyclohexanecarboxylic acid methyl ester a) N'-Cyclohexylidene-N,N-dimethyl-hydrazine

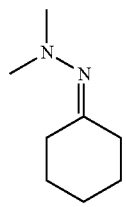

To solution of cyclohexanone (2.00 g, 20.4 mmol) and N,N-dimethylhydrazine (1.50 ml, 20.4 mmol) in ethanol (20 ml) was added a catalytic amount of toluene-4-sulfonic acid monohydrate. The reaction mixture was stirred at 70° C. for 72 h. The solvent was evaporated, and the residue was purified by Kugelrohr distillation (60-80° C., 5 mbar) to give the title compound (2.50 g, 87%) as colorless oil. MS m/e: 141 ([M+H]⁺)

a) trans-(RS)-4-[2-(Dimethyl-hydrazono)-cyclohexanecarbonyl]-cyclohexanecarboxylic acid methyl ester

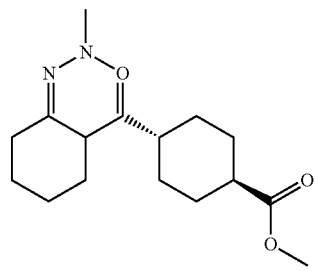

To a solution of N,N-diisopropylamine (1.59 ml, 11.2 mmol) in dry tetrahydrofuran (10 ml) was added 1.6 M n-butyl lithium in n-hexane (7.00 ml, 11.2 mmol) at 0-5° C. Addition of N'-cyclohexylidene-N,N-dimethyl-hydrazine (1.50 g, 10.7 mmol) after 15 minutes was followed by stirring for 90 minutes. The resulting solution was cannulated dropwise to a solution of trans-4-chlorocarbonyl-cyclohexanecarboxylic acid methyl ester (2.19 g, 10.7 mmol) in dry tetrahydrofuran (50 ml) at −65° C. The reaction mixture was stirred for 20 h at −78° C. The cooling bath was removed and the reaction mixture was quenched by addition of acetic acid (0.65 ml, 11 mmol) at −5° C. The mixture was partitioned between ethyl acetate (150 ml) and saturated ammonium chloride solution (100 ml). The layers were separated. The aqueous layer was extracted with one 100-ml portion of ethyl acetate. The combined organic layers were washed with one 50-ml portion of brine, dried over anhydrous sodium sulfate and concentrated in vacuo. Purification with n-heptane/ethyl acetate as eluent gave the title compound (0.98 g, 30%) as light yellow oil with a purity of 60%. MS m/e: 309 ([M+H]⁺)

Intermediate of Formula (XXI)

trans-4-(N'-Acetyl-hydrazinocarbonyl)-cyclohexanecarboxylic acid methyl ester

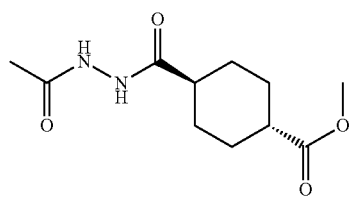 [SMILES: COC(=O)[C@H]1CC[C@H](C(=O)NNC(C)=O)CC1]

To a solution of trans-1,4-cycloxanedicarboxylic acid monomethylester (1.0 g, 5.4 mmol) and triethylamine (1.6 ml, 11 mmol) in dry tetrahydrofuran was added ethyl chloroformate (0.54 ml, 5.6 mmol) at 0-5° C. After 1 h the precipitated ammonium salts were removed by filtration. To the filtrate was added a solution of acetyl hydrazide (0.46 g, 5.6 mmol) in tetrahydrofuran (5 ml) at room temperature, and the mixture was stirred for 48 h. The reaction mixture was partitioned between ethyl acetate (250 ml) and water (250 ml). The layers were separated. The aqueous layer was extracted with two 250-ml portions and further six 150-ml portions of ethyl acetate. The combined organic layers were dried over anhydrous sodium sulfate and concentrated in vacuo to give the title compound (0.83 g, 64%) as white solid. MS m/e: 241 ([M−H]⁻)

Intermediates of Formula (XXII)

General Procedure (V)

A solution of an aldoxime intermediate of formula XVIII (1 eq) in acetic anhydride (21 eq) is heated at reflux for 16-24 h. After cooling to room temperature the reaction mixture is partitioned between 2 M aqueous sodium hydroxide solution and ethyl acetate. The layers are separated. The aqueous layer is extracted with an organic solvent such as ethyl acetate or tert-butyl methyl ether. The combined organic layers are dried over anhydrous sodium sulfate and concentrated in vacuo. Flash-chromatography gives a nitrile intermediate of formula XXII.

4-Cyano-cyclohexanecarboxylic acid ester 1 cis-4-Cyano-cyclohexanecarboxylic acid ethyl ester

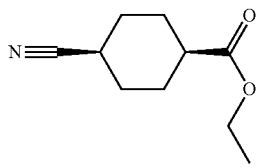

and

4-Cyano-cyclohexanecarboxylic acid ester 2 trans-4-Cyano-cyclohexanecarboxylic acid ethyl ester

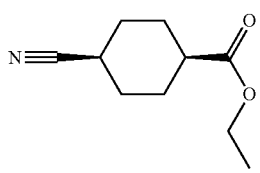

cis-4-Cyano-cyclohexanecarboxylic acid ethyl ester and trans-4-cyano-cyclohexanecarboxylic acid ethyl ester were obtained from cis/trans-(E/Z)-4-(hydroxyimino-methyl)-cyclohexanecarboxylic acid ethyl ester according to general procedure (V) after chromatographic separation.

cis-4-Cyano-cyclohexanecarboxylic acid ethyl ester was obtained as colorless liquid in 70% yield. MS m/e: 181 (M⁺)

trans-4-Cyano-cyclohexanecarboxylic acid ethyl ester was obtained as colorless liquid in 15% yield. MS m/e: 181 (M⁺)

4-Cyano-cyclohexanecarboxylic acid ester 3 cis/trans-4-Cyano-cyclohexanecarboxylic acid ethyl ester (4:1)

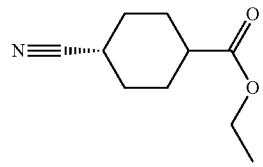

The title compound was obtained from cis/trans-(E/Z)-4-(hydroxyimino-methyl)-cyclohexanecarboxylic acid ethyl ester as light yellow liquid in 88% yield according to general procedure (V). MS m/e: 181 (M⁺)

Intermediates of Formula (XXIII)

General Procedure (VI)

A mixture of a nitrile intermediate of formula XXII (1.0 eq), sodium carbonate (1.0-1.2 eq) and hydroxylamine hydrochloride (1.0-1.2 eq) in ethanol (0.2 M) is heated at reflux for 24-72 h. The solvent is evaporated. The residue is triturated in ethyl acetate. The solids are removed by filtration and washed with ethyl acetate. The filtrate is extracted with three portions of 0.1 M aqueous hydrochloric acid solution. The combined aqueous layers are adjusted to pH 8 by addition of a base such as sodium carbonate or sodium hydroxide and extracted with two portions of ethyl acetate. The combined organic extracts are dried over anhydrous sodium sulfate and concentrated in vacuo to give a hydroxamidine intermediate of formula XXIII.

4-(N-Hydroxycarbamimidoyl)-cyclohexanecarboxylic acid ester 1 cis-4-(N-Hydroxycarbamimidoyl)-cyclohexanecarboxylic acid ethyl ester

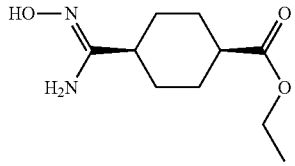

The title compound was obtained as off-white solid in 32% yield from cis-4-cyano-cyclohexanecarboxylic acid ethyl ester according to general procedure (VI). MS m/e: 215 ([M+H]⁺)

4-(N-Hydroxycarbamimidoyl)-cyclohexanecarboxylic acid ester 2 cis/trans-4-(N-Hydroxycarbamimidoyl)-cyclohexanecarboxylic acid ethyl ester

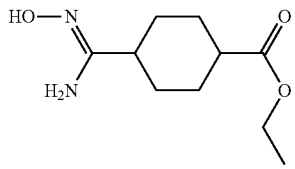

The title compound was obtained as white solid in 28% yield from cis/trans-4-cyano-cyclohexanecarboxylic acid ethyl ester according to general procedure (VI). MS m/e: 215 ([M+H]⁺)

Intermediate of Formula (XXV)

trans-4-Thiocarbamoyl-cyclohexanecarboxylic acid methyl ester

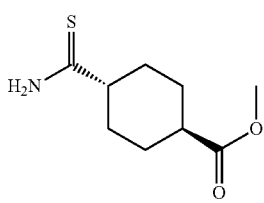

A solution of trans-4-carbamoyl-cyclohexanecarboxylic acid methyl ester (2.00 g, 10.8 mmol) and Lawesson's reagent (2.2 g, 5.4 mmol) in tetrahydrofuran (55 ml) was heated at reflux for 3.5 h. The heating bath was removed and the solvent was evaporated. The residue was purified by flash-chromatography with n-heptane/ethyl acetate as eluent to give a pink solid, which was triturated in toluene (10 ml). The precipitate was collected by filtration and dried in vacuo to give the title compound (1.04 g, 48%) as off-white solid. MS m/e: 202 ([M+H]⁺)

Intermediate of Formula (XXVI)

trans-4-[1-Dimethylamino-ethylidenethiocarbamoyl]-cyclohexanecarboxylic acid methyl ester

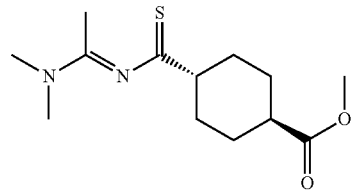

A mixture of trans-4-thiocarbamoyl-cyclohexanecarboxylic acid methyl ester (0.72 g, 3.6 mmol) and N,N-dimethylacetamide dimethyl acetal (0.95 g, 7.2 mmol) was stirred at room temperature over night. The solvent was evaporated. Flash-chromatography with n-heptane/ethyl acetate as eluent gave the title compound (0.90 g, 93%) as yellow oil. MS m/e: 271 ([M+H]⁺)

Intermediates of Formula (XXVIII)

4-(N'-tert-Butoxycarbonyl-hydrazino)-cyclohexanecarboxylic acid ester 1 cis-4-(N'-tert-Butoxycarbonyl-hydrazino)-cyclohexanecarboxylic acid ethyl ester

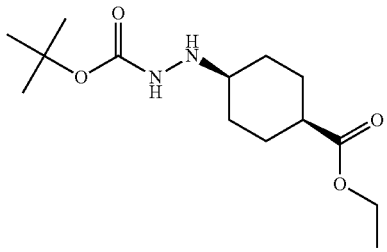 [SMILES: CCOC(=O)[C@H]1CC[C@@H](NNC(=O)OC(C)(C)C)CC1]

and 4-(N'-tert-Butoxycarbonyl-hydrazino)-cyclohexanecarboxylic acid ester 2 trans-4-(N'-tert-Butoxycarbonyl-hydrazino)-cyclohexanecarboxylic acid ethyl ester

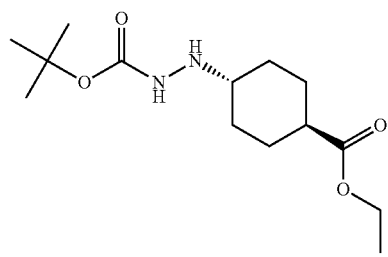 [SMILES: CCOC(=O)[C@H]1CC[C@H](NNC(=O)OC(C)(C)C)CC1]

A solution of ethyl 4-oxo-cyclohexanecarboxylate (1.00 g, 5.88 mmol), tert-butyl hydrazinecarboxylate (1.16 g, 8.81 mmol) and acetic acid (0.34 ml, 5.9 mmol) in dichloromethane (29 ml) was stirred for 1 h at room temperature and subsequently cooled to 0° C. on an ice-water bath. Sodium triacetoxyborohydride (2.49 g, 11.8 mmol) was added at 0-5° C. The cooling bath was removed after completed addition. Stirring at room temperature for 20 h was followed by quenching with ethanol (5 ml). The reaction mixture was washed with one 50-ml portion of water. The aqueous layer (pH 4) was extracted with two 50-ml portions of dichloromethane. The combined organic layers were washed with one 50 ml-portion of aqueous 2 M sodium carbonate solution, dried over anhydrous sodium sulfate and concentrated in vacuo. Flash-chromatography with n-heptane/ethyl acetate as eluent gave cis-4-(N'-tert-butoxycarbonyl-hydrazino)-cyclohexanecarboxylic acid ethyl ester (1.05 g, 62%) and trans-4-(N'-tert-butoxycarbonyl-hydrazino)-cyclohexanecarboxylic acid ethyl ester (0.63 g, 37%).

cis-4-(N'-tert-Butoxycarbonyl-hydrazino)-cyclohexanecarboxylic acid ethyl ester was obtained as viscous colorless oil. MS m/e: 287 ([M+H]⁺).

trans-4-(N'-tert-Butoxycarbonyl-hydrazino)-cyclohexanecarboxylic acid ethyl ester was obtained as white solid. MS m/e: 287 ([M+H]⁺).

Intermediates of Formula (XXIX)

4-Hydrazino-cyclohexanecarboxylic acid ester hydrochloride 1 trans-4-Hydrazino-cyclohexanecarboxylic acid ethyl ester hydrochloride

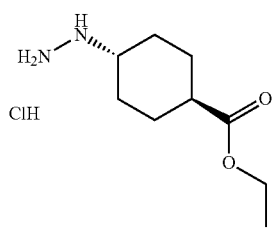

A solution of trans-4-(N'-tert-butoxycarbonyl-hydrazino)-cyclohexanecarboxylic acid ethyl ester (0.625 g, 2.18 mmol) in 4 M hydrogen chloride solution in 1,4-dioxane (5.5 ml, 22 mmol) was stirred at room temperature for 3 days. The precipitate was collected by filtration, washed with tert-butyl methyl ether and dried in vacuo to give the title compound as white solid in quantitative yield. MS m/e: 187 ([M+H]$^+$).

4-Hydrazino-cyclohexanecarboxylic acid ester hydrochloride 2 cis-4-Hydrazino-cyclohexanecarboxylic acid ethyl ester hydrochloride

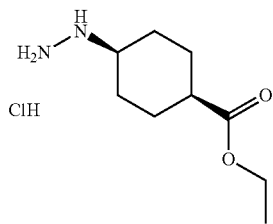

A solution of cis-4-(N'-tert-butoxycarbonyl-hydrazino)-cyclohexanecarboxylic acid ethyl ester (1.03 g, 3.60 mmol) in 4 M hydrogen chloride solution in 1,4-dioxane (9.0 ml, 36 mmol) was stirred at room temperature for 3 days. The precipitate was collected by filtration, washed with tert-butyl methyl ether and dried in vacuo to give the title compound as white solid in quantitative yield. MS m/e: 187 ([M+H]$^+$).

4-Heteroaryl-cyclohexanecarboxylic acid ester intermediates of formula (VIII)

General Procedure (VII): Oxazole Formation

To a solution of a keto-amide intermediate of formula XIV (1 eq), hexachloroethane (3 eq) and triethylamine (6 eq) in acetonitrile (0.1 M) is added triphenylphosphine (3 eq) in small portions at 0-5° C. The cooling bath is removed 10 minutes after completed addition, and stirring is continued for 2 h. The reaction mixture is partitioned between an organic solvent such as ethyl acetate and saturated aqueous ammonium chloride solution. The layers are separated. The aqueous layer is extracted with two portions of organic solvent. The combined organic layers are washed with one portion of brine, dried over anhydrous sodium sulfate and concentrated in vacuo. Purification by flash-chromatography gives an oxazole intermediate of formula VIII-1A.

General Procedure (VIII): Platinum(IV)Oxide Catalyzed Hydrogenation

A solution of a 4-heteroaryl-cyclohex-3-enecarboxylic acid ester intermediate of formula V in ethyl acetate (0.1 M) is purged with argon. Addition of platinum(IV) oxide (0.3 eq) is followed by filling the flask with hydrogen. The reaction mixture is stirred at room temperature under an atmosphere of hydrogen (1 bar) for 1-16 h. The catalyst is removed by filtration over Decalite®. The filtrate is concentrated to dryness to give a cis/trans mixture of a crude 4-heteroaryl-cyclohexanecarboxylic acid ester intermediate of formula VIII, which can usually be used in the next step without further purification.

General Procedure (IX): Palladium on Charcoal Catalyzed Hydrogenation

A solution of a 4-heteroaryl-cyclohex-3-enecarboxylic acid ester intermediate of formula V and optionally an base such as triethylamine (1 eq) in an organic solvent such as ethyl acetate or toluene (0.1 M) is purged with argon. Addition of 10% palladium on activated charcoal (0.05 eq) is followed by filling the flask with hydrogen. The reaction mixture is stirred at room temperature under an atmosphere of hydrogen (1 bar) for 20-72 h. The catalyst is removed by filtration over Decalite®. The filtrate is washed with one portion of water. The aqueous layer is extracted with one or two portions of ethyl acetate. The combined organic layers are dried over anhydrous sodium sulfate and concentrated to dryness to give a cis/trans mixture of a crude 4-heteroaryl-cyclohexanecarboxylic acid ester intermediate of formula VIII, which can usually be used in the next step without further purification.

General Procedure (X): Epimerization Followed by Re-esterification

A mixture of cis/trans-4-heteroaryl-cyclohexanecarboxylic acid ester intermediate of formula VIII and sodium ethylate (3-6 eq) in ethanol is heated at reflux for 20-72 h. Under these reaction conditions partial saponification of the resulting trans-4-heteroaryl-cyclohexanecarboxylic acid ester intermediate of formula VIII-b to a trans-4-heteroaryl-cyclohexanecarboxylic acid intermediate of formula IX-b may occur. Such a trans-4-heteroaryl-cyclohexanecarboxylic acid intermediate of formula IX-b can be reconverted to a trans-4-heteroaryl-cyclohexanecarboxylic acid ester intermediate of formula VIII-b by consecutive cooling of the mixture to 0-5° C., addition of concentrated sulfuric acid (7-9 eq) and heating of the mixture at reflux for 1-2 h. After cooling to room temperature the reaction mixture is partitioned between an organic solvent such as ethyl acetate or tert-butyl methyl ether and 2M aqueous sodium carbonate solution. The layers are separated. The aqueous layer is extracted with two or three portions of organic solvent. The combined organic layers are dried over anhydrous sodium sulfate and concentrated to dryness. Purification by flash-chromatography gives a trans-4-heteroaryl-cyclohexanecarboxylic acid ester intermediate of formula VIII-b.

General Procedure (XI): 1,2,4-Oxadiazole Formation

A solution of a hydroxamidine intermediate of formula XXIII (1 eq) and carboxylic acid anhydride of formula p (3 eq) in toluene (0.1 M) is heated at reflux for 16-24 h. After cooling to room temperature the reaction mixture is neutralized by addition of solid sodium carbonate. The solvent is evaporated. The residue is triturated in an organic solvent such as tert-butyl methyl ether or ethyl acetate. The solids are removed by filtration. The residue is concentrated in vacuo. Flash-chromatography gives a 1,2,4-oxadiazole intermediate of formula VIII-6.

General Procedure (XIX): Pyrazole Formation

A mixture of a 4-hydrazino-cyclohexanecarboxylic acid ester hydrochloride of formula XXIX (1 eq) and a dicarbonyl derivative of formula u, v or w (1-1.1 eq) in ethanol (0.1 M) is heated at reflux for 1-2 h. After cooling to room temperature the reaction mixture is partitioned between an organic solvent such as ethyl acetate or dichloromethane and aqueous saturated bicarbonate solution. The layers are separated and the aqueous layer is extracted with two portions of organic solvent. The combined organic layers are dried over anhydrous sodium sulfate and concentrated in vacuo to give a pyrazole intermediate of formula (VIII-9), which is usually used in the following step without further purification.

4-Heteroaryl-cyclohexanecarboxylic acid ester 1 trans-4-Oxazol-2-yl-cyclohexanecarboxylic acid methyl ester

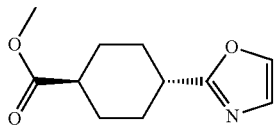

A mixture of trans-4-(2-oxo-ethylcarbamoyl)-cyclohexanecarboxylic acid methyl ester (830 mg, 3.65 mmol) and phosphorus oxychloride (2.80 g, 18.3 mmol) was heated at 100° C. for 20 h. After cooling to room temperature the reaction mixture was poured on crushed ice and basified to pH 7-8 by addition of 1 M aqueous sodium hydroxide solution. The mixture was extracted with three 100 ml-portions of ethyl acetate. The combined organic layers were washed with one 50 ml-portion of brine, dried over anhydrous sodium sulfate and concentrated in vacuo. Purification with n-heptane/ethyl acetate as eluent gave the title compound (175 mg, 23%) as white solid, with a purity of 90% according to GC. MS m/e: 210 ([M+H]$^+$)

4-Heteroaryl-cyclohexanecarboxylic acid ester 2 trans-4-(4-Methyl-oxazol-2-yl)-cyclohexanecarboxylic acid methyl ester

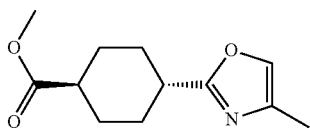 [SMILES: COC(=O)[C@H]1CC[C@H](c2nc(C)co2)CC1]

The title compound was obtained as white solid in 38% yield from trans-4-((S)-1-methyl-2-oxo-ethylcarbamoyl)-cyclohexanecarboxylic acid methyl ester according to general procedure (VII). MS m/e: 224 ([M+H]$^+$)

4-Heteroaryl-cyclohexanecarboxylic acid ester 3 trans-4-(5-Methyl-oxazol-2-yl)-cyclohexanecarboxylic acid methyl ester

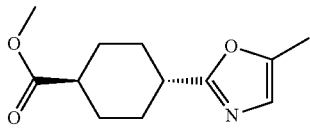 [SMILES: COC(=O)[C@H]1CC[C@H](c2ncc(C)o2)CC1]

The title compound was obtained as off-white solid in 76% yield from trans-4-(2-oxo-propylcarbamoyl)-cyclohexanecarboxylic acid methyl ester according to general procedure (VII). MS m/e: 224 ([M+H]$^+$)

4-Heteroaryl-cyclohexanecarboxylic acid ester 4 trans-4-(4,5-Dimethyl-oxazol-2-yl)-cyclohexanecarboxylic acid methyl ester

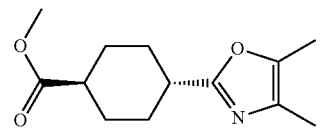 [SMILES: COC(=O)[C@H]1CC[C@H](c2nc(C)c(C)o2)CC1]

The title compound was obtained as light brown solid in 62% yield from trans-4-(1-methyl-2-oxo-propylcarbamoyl)-cyclohexanecarboxylic acid methyl ester according to general procedure (VII). MS m/e: 238 ([M+H]$^+$)

4-Heteroaryl-cyclohexanecarboxylic acid ester 5 cis/trans-4-Thiazol-2-yl-cyclohexanecarboxylic acid ethyl ester (3:1)

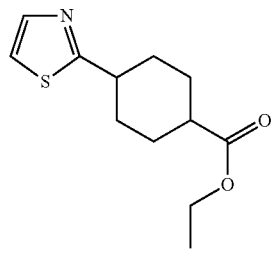 [SMILES: CCOC(=O)C1CCC(c2nccs2)CC1]

The title compound was obtained as colorless oil in 62% yield from (RS)-4-thiazol-2-yl-cyclohex-3-enecarboxylic acid ethyl ester according to general procedure (VIII). MS m/e: 240 ([M+H]$^+$)

4-Heteroaryl-cyclohexanecarboxylic acid ester 6 cis/trans-4-(4-Methyl-thiazol-2-yl)-cyclohexanecarboxylic acid ethyl ester (4:1)

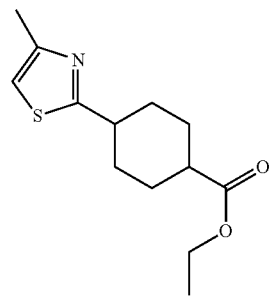 [SMILES: CCOC(=O)C1CCC(c2nc(C)cs2)CC1]

The title compound was obtained as colorless oil in 54% yield from (RS)-4-(4-methyl-thiazol-2-yl)-cyclohex-3-enecarboxylic acid ethyl ester according to general procedure (VIII). MS m/e: 254 ([M+H]+)

4-Heteroaryl-cyclohexanecarboxylic acid ester 7 cis/trans-4-(2-Methyl-thiazol-4-yl)-cyclohexanecarboxylic acid ethyl ester (3:1)

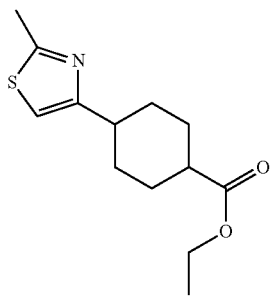 [SMILES: CCOC(=O)C1CCC(c2csc(C)n2)CC1]

The title compound was obtained as colorless oil in 52% yield from (RS)-4-(2-methyl-thiazol-4-yl)-cyclohex-3-enecarboxylic acid ethyl ester according to general procedure (VIII). MS m/e: 254 ([M+H]+)

4-Heteroaryl-cyclohexanecarboxylic acid ester 8 trans-4-(5-Methyl-isoxazol-3-yl)-cyclohexanecarboxylic acid methyl ester

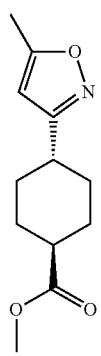

To a solution of trans-methyl 4-(chloro(hydroxyimino)methyl)cyclohexanecarboxylate (5.90 g, 26.9 mmol) and isopropenyl acetate (53.8 g, 537 mmol) in dichloromethane (134 ml) was added triethylamine (5.44 g, 53.7 mmol) at 0-5° C. The cooling bath was removed 15 minutes after completed addition, and the mixture was stirred for 20 h. The reaction mixture was concentrated in vacuo. The residue was partitioned between ethyl acetate (250 ml) and 0.1 M aqueous hydrochloric acid solution (200 ml). The organic layer was washed with one 100 ml-portion of 0.1 M aqueous hydrochloric acid solution. The combined aqueous layers were extracted with one 150 ml-portion of ethyl acetate. The combined organic layers were washed with one 200 ml-portion of 2 M sodium carbonate and one 100-ml portion of brine, dried over anhydrous sodium sulfate and concentrated in vacuo. Purification with n-heptane/ethyl acetate as eluent gave the title compound (3.00 g, 50%) as off-white solid. MS m/e: 224 ([M+H]+)

4-Heteroaryl-cyclohexanecarboxylic acid ester 9 trans-4-(4-Bromo-5-methyl-isoxazol-3-yl)-cyclohexanecarboxylic acid methyl ester

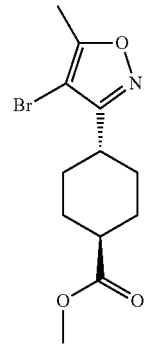

A solution of trans-4-(5-methyl-isoxazol-3-yl)-cyclohexanecarboxylic acid methyl ester (295 mg, 1.32 mmol) and N-bromosuccinimde (235 mg, 1.32 mmol) in N,N-dimethylformamide (2.6 ml) was stirred at room temperature for 16 h. The reaction mixture was partitioned between ethyl acetate (50 ml) and 0.1 M aqueous sodium hydroxide solution (50 ml). The layers were separated. The aqueous layer was extracted with one 50 ml-portion of ethyl acetate. The combined organic layers were dried over anhydrous sodium sulfate and concentrated in vacuo to give the title compound (399 mg, 100%) as light yellow oil, which was used in the next step without further purification. MS m/e: 302 ([M+H]+)

4-Heteroaryl-cyclohexanecarboxylic acid ester 10 trans-4-(4,5-Dimethyl-isoxazol-3-yl)-cyclohexanecarboxylic acid methyl ester

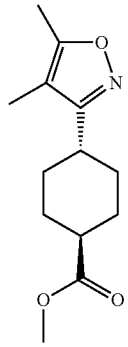

To a solution of trans-4-(4-bromo-5-methyl-isoxazol-3-yl)-cyclohexanecarboxylic acid methyl ester (660 mg, 2.18 mmol) and 2 M methyl zinc chloride solution in tetrahydrofuran (1.64 ml, 3.28 mmol) in a 4:1 mixture of tetrahydrofuran and 1,3-dimethyl-2-imidazolidinone (12 ml) was added (1,3-diisopropylimidazol-2-ylidene)(3-chloropyridyl)palladium(II) chloride (29.7 mg, 43.7 μmol) at room temperature. The reaction mixture was heated at 50° C. for 2 h. The reaction mixture was partitioned between tert-butyl methyl ether (100 ml) and 0.1 M aqueous hydrochloric acid solution (100 ml). The layers were separated. The aqueous layer was extracted with one 100 ml-portion of tert-butyl methyl ether. The combined organic layers were washed with two 50 ml-portions of water and one 50-ml portion of brine, dried over 4-Heteroaryl-cyclohexanecarboxylic acid ester 11 trans-4-(4-Chloro-5-methyl-isoxazol-3-yl)-cyclohexanecarboxylic acid methyl ester

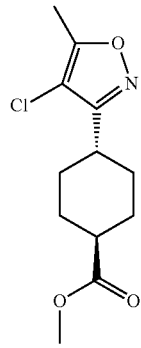

A solution of trans-4-(5-methyl-isoxazol-3-yl)-cyclohexanecarboxylic acid methyl ester (250 mg, 1.12 mmol) and N-chlorosuccinimide (164 mg, 1.23 mmol) in N,N-dimethylformamide (2.2 ml) was stirred for 24 h at room temperature. The reaction mixture was partitioned between tert-butyl methyl ether (50 ml) and water (50 ml). The layers were separated. The aqueous layer was extracted with one 50 ml-portion of tert-butyl methyl ether. The combined organic layers were washed with one 50 ml-portion of 0.1 M aqueous sodium hydroxide solution, one 50 ml-portion of water and one 30 ml-portion of brine, dried over anhydrous sodium sulfate and concentrated in vacuo to give the crude title compound (275 mg, 95%) as light yellow oil, which was used in the next step without further purification. MS m/e: 257 (M+)

4-Heteroaryl-cyclohexanecarboxylic acid ester 12 trans-4-(4-Fluoro-5-methyl-isoxazol-3-yl)-cyclohexanecarboxylic acid methyl ester

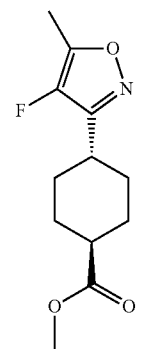

A mixture of trans-4-(5-methyl-isoxazol-3-yl)-cyclohexanecarboxylic acid methyl ester (250 mg, 1.12 mmol) and Selectfluor® (476 mg, 1.34 mmol) in acetonitrile (5.6 ml) was heated at 90° C. for 20 h. After cooling to room temperature the reaction mixture was partitioned between ethyl acetate (50 ml) and water (25 ml). The layers were separated. The aqueous layer was extracted with two 50 ml-portions of ethyl acetate. The combined organic layers were washed with one 25 ml-portion of water/brine (1:1), dried over anhydrous sodium sulfate and concentrated in vacuo. Purification with n-heptane/tert-butyl methyl ether as eluent gave the title compound (35 mg, 13%) as light yellow oil. MS m/e: 241 ([M+H]+)

4-Heteroaryl-cyclohexanecarboxylic acid ester 13 trans-4-(4,5,6,7-Tetrahydro-benzo[c]isoxazol-3-yl)-cyclohexanecarboxylic acid methyl ester

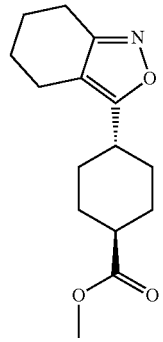 [SMILES: COC(=O)[C@H]1CC[C@H](c2onc3c2CCCC3)CC1]

A mixture of trans-4-[2-(dimethyl-hydrazono)-cyclohexanecarbonyl]-cyclohexanecarboxylic acid methyl ester (0.95 g, 3.1 mmol), sodium acetate (0.28 g, 3.4 mmol) and hydroxylamine hydrochloride (0.24 g, 3.4 mmol) in methanol (15 ml) was stirred at room temperature for 16 h. The reaction mixture was partitioned between ethyl acetate (100 ml) and water (50 ml). The layers were separated. The aqueous layer was extracted with two 100-ml portions of ethyl acetate. The combined organic layers were dried over anhydrous sodium sulfate and concentrated in vacuo. The residue (0.88 g) was dissolved in toluene (15 ml). After addition of a catalytic amount of toluene-4-sulfonic acid monohydrate the mixture was heated at reflux for 3 h. The solvent was evaporated. Purification with n-heptane/ethyl acetate as eluent gave the title compound (0.58 g, 72%) with a regioisomeric purity of approx. 90% according to 13C-NMR. MS m/e: 264 ([M+H]+)

4-Heteroaryl-cyclohexanecarboxylic acid ester 14 trans-4-(5-Methyl-[1,3,4]oxadiazol-2-yl)-cyclohexanecarboxylic acid methyl ester

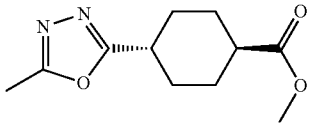 [SMILES: COC(=O)[C@H]1CC[C@H](c2nnc(C)o2)CC1]

To a solution of trans-4-(N'-acetyl-hydrazinocarbonyl)-cyclohexanecarboxylic acid methyl ester (0.55 g, 2.3 mmol) in acetonitrile (23 ml) was consecutively added trifluoromethanesulfonic acid (0.51 ml, 5.9 mmol) and dimethyldichlorosilane (0.30 ml, 2.5 mmol) at room temperature. The mixture was heated at reflux for 16 h. After cooling to room temperature the mixture was poured on ice. The pH was adjusted to 3 by addition of 1 M aqueous sodium hydroxide solution (2.3 ml, 2.3 mmol). The aqueous layer was extracted with three 150-ml portions of ethyl acetate. The combined organic layers were washed with one 50-ml portion of brine, dried over anhydrous sodium sulfate and concentrated in vacuo to give a first batch of crude product (0.23 g). A second batch (0.37 g) was obtained analogously from 0.33 g of trans-4-(N'-acetyl-hydrazinocarbonyl)-cyclohexanecarboxylic acid methyl ester. The two batches were combined and purified by flash-chromatography with n-heptane/ethyl acetate as eluent to give the title compound (0.23 mg, 46%) as white solid. MS m/e: 225 ([M+H]$^+$)

4-Heteroaryl-cyclohexanecarboxylic acid ester 15 trans-4-(3-Methyl-[1,2,4]oxadiazol-5-yl)-cyclohexanecarboxylic acid methyl ester

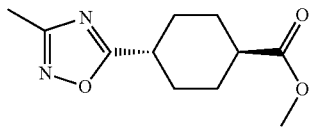 [SMILES: COC(=O)[C@H]1CC[C@H](c2nc(C)no2)CC1]

To a solution of acetamide oxime (0.19 g, 2.6 mmol) and triethylamine (0.36 ml, 2.6 mmol) in tetrahydrofuran (24 ml) was added trans-4-chlorocarbonyl-cyclohexanecarboxylic acid methyl ester (0.50 g, 2.4 mmol) at 0-5° C. After completed addition the cooling bath was removed, and the mixture was stirred for 30 minutes. The precipitated ammonium salts were removed by filtration and washed with tetrahydrofuran. The filtrate was concentrated to dryness. The residue was redissolved in 1,4-dioxane (24 ml). The mixture was treated with a catalytic amount of toluene-4-sulfonic acid monohydrate and heated at reflux over night (16 h). The solvent was evaporated. Flash-chromatography with n-heptane/ethyl acetate as eluent gave the title compound (0.48 g, 88%) as light brown oil. MS m/e: 225 ([M+H]$^+$)

4-Heteroaryl-cyclohexanecarboxylic acid ester 16 trans-4-(3-Methyl-[1,2,4]thiadiazol-5-yl)-cyclohexanecarboxylic acid methyl ester

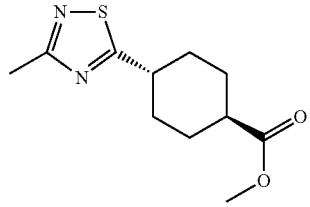 [SMILES: COC(=O)[C@H]1CC[C@H](c2nc(C)ns2)CC1]

To a solution of trans-4-[1-dimethylamino-ethylidenethiocarbamoyl]-cyclohexanecarboxylic acid methyl ester (0.87 g, 3.2 mmol) and pyridine (0.52 ml, 6.5 mmol) in ethanol (6 ml) was added a solution of hydroxylamine-O-sulfonic acid (0.45 g; 3.6 mmol) in methanol (3 ml) at room temperature. After stirring over night the reaction mixture was partitioned between 1 M aqueous hydrochloric acid solution (100 ml) and ethyl acetate (100 ml). The layers were separated. The aqueous layer was extracted with one 100-ml portion of ethyl acetate. The combined organic layers were dried over anhydrous sodium sulfate and concentrated in vacuo. Flash-chromatography with n-heptane/ethyl acetate as eluent gave the title compound (0.68 g, 88%) as yellow oil. MS m/e: 241 ([M+H]$^+$)

4-Heteroaryl-cyclohexanecarboxylic acid ester 17 cis/trans-4-(5-Methyl-[1,2,4]oxadiazol-3-yl)-cyclohexanecarboxylic acid ethyl ester

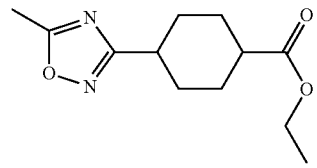

To a suspension of cis/trans-ethyl 4-(chloro(hydroxyimino)methyl)cyclohexanecarboxylate (1.85 g, 7.92 mmol) and ethyl acetimidate hydrochloride (1.96 g, 15.8 mmol) in dichloromethane (40 ml) was added triethylamine (2.2 ml, 16 mmol) at 0-5° C. The cooling bath was removed 15 minutes after completed addition, and stirring for 18 h at room temperature was followed by heating at reflux for 4 h. The reaction mixture was washed with one 50-ml portion of 1 M aqueous hydrochloric acid solution. The aqueous layer was extracted with two 50-ml portions of dichloromethane. The combined organic layers were dried over anhydrous sodium sulfate and concentrated in vacuo. Flash-chromatography with n-heptane/tert-butyl methyl ether as eluent gave the title compound (1.05 g, 56%) as colorless oil. MS m/e: 239 ([M+H]$^+$)

4-Heteroaryl-cyclohexanecarboxylic acid ester 18 cis-4-(5-Methyl-[1,2,4]oxadiazol-3-yl)-cyclohexanecarboxylic acid ethyl ester

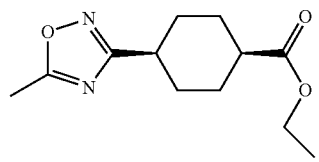 [SMILES: CCOC(=O)[C@H]1CC[C@@H](c2noc(C)n2)CC1]

The title compound was obtained as light yellow oil in 75% yield from cis-4-(N-hydroxycarbamimidoyl)-cyclohexanecarboxylic acid ethyl ester and acetic anhydride according to general procedure (XI). MS m/e: 239 ([M+H]$^+$)

4-Heteroaryl-cyclohexanecarboxylic acid ester 19 cis/trans-4-(5-Ethyl-[1,2,4]oxadiazol-3-yl)-cyclohexanecarboxylic acid ethyl ester

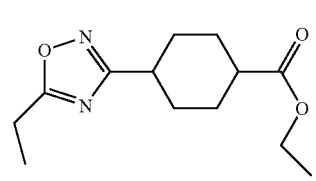 [SMILES: CCOC(=O)C1CCC(c2noc(CC)n2)CC1]

The title compound was obtained as yellow liquid in 92% yield from cis/trans-4-(N-hydroxycarbamimidoyl)-cyclohexanecarboxylic acid ethyl ester and propionic anhydride according to general procedure (XI). MS m/e: 253 ([M+H]$^+$)

4-Heteroaryl-cyclohexanecarboxylic acid ester 20 cis/trans-4-(5-Isopropyl-[1,2,4]oxadiazol-3-yl)-cyclohexanecarboxylic acid ethyl ester

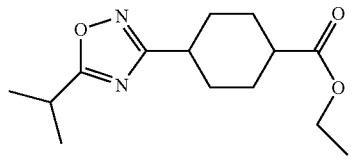 [SMILES: CCOC(=O)C1CCC(c2noc(C(C)C)n2)CC1]

The title compound was obtained as yellow liquid in 92% yield from cis/trans-4-(N-hydroxycarbamimidoyl)-cyclohexanecarboxylic acid ethyl ester and isobutyric anhydride according to general procedure (XI). MS m/e: 267 ([M+H]$^+$)

4-Heteroaryl-cyclohexanecarboxylic acid ester 21 trans-4-(5-Methyl-[1,2,4]thiadiazol-3-yl)-cyclohexanecarboxylic acid methyl ester

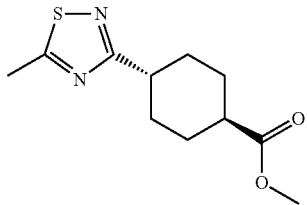

To a solution of trans-4-thiocarbamoyl-cyclohexanecarboxylic acid methyl ester (0.30 g, 1.5 mmol) and thioacetamide (0.67 g, 8.9 mmol) in methanol (7 ml) was added a solution of iodine (2.65 g, 10.4 mmol) in methanol (15 ml) at room temperature. After stirring for 48 h the reaction mixture was partitioned between 0.1 M sodium thiosulfate solution (100 ml) and ethyl acetate (100 ml). The layers were separated. The aqueous layer was extracted with two 50-ml portions of ethyl acetate. The combined organic layers were dried over anhydrous sodium sulfate and concentrated in vacuo. The residue was purified by Kugelrohr distillation. The distillate was purified by flash-chromatography with n-heptane/tert-butyl methyl ether as eluent to give the title compound (0.021 g, 5%) as light yellow oil, which was contaminated with 20% trans-4-(3-methyl-[1,2,4]thiadiazol-5-yl)-cyclohexanecarboxylic acid methyl ester. MS m/e: 241 ([M+H]$^+$)

4-Heteroaryl-cyclohexanecarboxylic acid ester 22 trans-4-(5-Chloro-4-methyl-oxazol-2-yl)-cyclohexanecarboxylic acid methyl ester

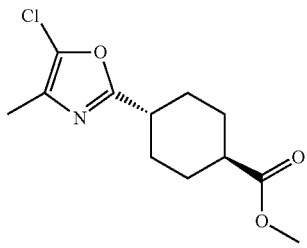

A solution of trans-4-(4-methyl-oxazol-2-yl)-cyclohexanecarboxylic acid methyl ester (277 mg, 1.24 mmol) and N-chlorosuccinimide (182 mg, 1.36 mmol) in N,N-dimethylformamide (2.5 ml) was stirred for 6 h at room temperature. The reaction mixture was partitioned between tert-butyl methyl ether (25 ml) and 0.1 M aqueous sodium hydroxide solution (25 ml). The layers were separated. The aqueous layer was extracted with one 25-ml portion of tert-butyl methyl ether. The combined organic layers were washed with three 25-ml portions of water, dried over anhydrous sodium sulfate and concentrated in vacuo to give the crude title compound (285 mg, 89%) as light yellow solid, which was used in the next step without further purification. MS m/e: 258 ([M+H]$^+$)

4-Heteroaryl-cyclohexanecarboxylic acid ester 23 cis/trans-4-(4-Methyl-thiazol-2-yl)-cyclohexanecarboxylic acid ethyl ester (1:5)

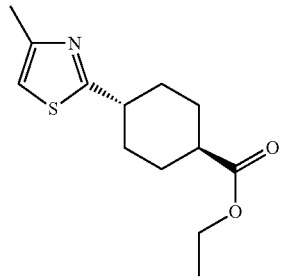 [SMILES: CCOC(=O)[C@H]1CC[C@H](c2nc(C)cs2)CC1]

The title compound was obtained as yellow oil in 97% yield from cis/trans-4-(4-methyl-thiazol-2-yl)-cyclohexanecarboxylic acid ethyl ester (4:1) according to general procedure (X). MS m/e: 254 ([M+H]$^+$)

4-Heteroaryl-cyclohexanecarboxylic acid ester 24 cis/trans-4-(5-Chloro-4-methyl-thiazol-2-yl)-cyclohexanecarboxylic acid ethyl ester (1:5)

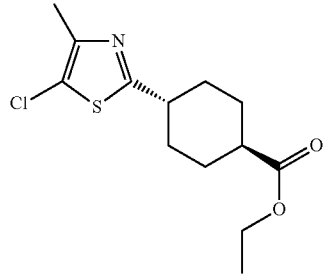 [SMILES: CCOC(=O)[C@H]1CC[C@H](c2nc(C)c(Cl)s2)CC1]

A solution of cis/trans-4-(4-methyl-thiazol-2-yl)-cyclohexanecarboxylic acid ethyl ester (1:5) (200 mg, 0.789 mmol) and N-chlorosuccinimide (116 mg, 0.868 mmol) in N,N-dimethylformamide (1.6 ml) was stirred for 1 h at 50° C. The reaction mixture was partitioned between tert-butyl methyl ether (25 ml) and 0.1 M aqueous sodium hydroxide solution (25 ml). The layers were separated. The aqueous layer was extracted with one 25-ml portion of tert-butyl methyl ether. The combined organic layers were washed with three 25-ml portions of water, dried over anhydrous sodium sulfate and concentrated in vacuo to give the crude title compound (209 mg, 92%) as light yellow solid, which was used in the next step without further purification. MS m/e: 288 ([M+H]$^+$)

4-Heteroaryl-cyclohexanecarboxylic acid ester 25 cis/trans-4-(5-Bromo-4-methyl-thiazol-2-yl)-cyclohexanecarboxylic acid ethyl ester (1:5)

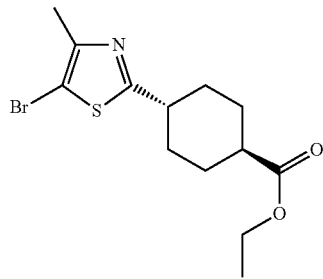

A solution of cis/trans-4-(4-methyl-thiazol-2-yl)-cyclohexanecarboxylic acid ethyl ester (1:5) (319 mg, 1.26 mmol) and N-bromosuccinimide (247 mg, 1.38 mmol) in N,N-dimethylformamide (1.6 ml) was stirred for 1 h at room temperature. The reaction mixture was partitioned between tert-butyl methyl ether (25 ml) and 0.1 M aqueous sodium hydroxide solution (25 ml). The layers were separated. The aqueous layer was extracted with two 25-ml portions of tert-butyl methyl ether. The combined organic layers were washed with two 25-ml portions of water, dried over anhydrous sodium sulfate and concentrated in vacuo to give the crude title compound (371 mg, 89%) as light yellow solid, which was used in the next step without further purification. MS m/e: 334 ([M+H]$^+$)

4-Heteroaryl-cyclohexanecarboxylic acid ester 26 cis/trans-4-(4,5-Dimethyl-thiazol-2-yl)-cyclohexanecarboxylic acid ethyl ester (1:7)

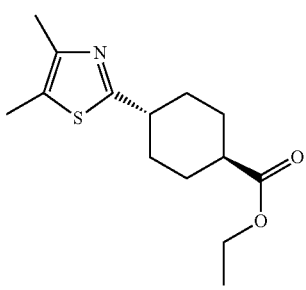 [SMILES: CCOC(=O)[C@H]1CC[C@H](c2nc(C)c(C)s2)CC1]

To a solution of cis/trans-4-(5-bromo-4-methyl-thiazol-2-yl)-cyclohexanecarboxylic acid ethyl ester (1:5) (371 mg, 1.12 mmol) and 2 M methyl zinc chloride solution in tetrahydrofuran (0.837 ml, 1.67 mmol) in a 5:1 mixture of tetrahydrofuran and 1,3-dimethyl-2-imidazolidinone (6 ml) was added (1,3-diisopropylimidazol-2-ylidene)(3-chloropyridyl) palladium(II) chloride (15.2 mg, 22.3 µmol) at room temperature. The reaction mixture was heated at 50° C. for 2 h. After cooling to room temperature the reaction mixture was partitioned between tert-butyl methyl ether (25 ml) and 0.1 M aqueous sodium hydroxide solution (25 ml). The layers were separated. The aqueous layer was extracted with two 25-ml portions of tert-butyl methyl ether. The combined organic layers were washed with two 25-ml portions of water, dried over anhydrous sodium sulfate and concentrated in vacuo. Purification with n-heptane/ethyl acetate as eluent gave the title compound (170 mg, 57%) as colorless oil, with a purity of 80% according to GC. MS m/e: 268 ([M+H]$^+$)

4-Heteroaryl-cyclohexanecarboxylic acid ester 27 trans-4-(4,5-Bis-hydroxymethyl-isoxazol-3-yl)-cyclohexanecarboxylic acid methyl ester

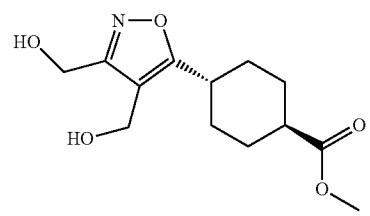 [SMILES: COC(=O)[C@H]1CC[C@H](c2onc(CO)c2CO)CC1]

To a mixture of trans-methyl 4-(chloro(hydroxyimino)methyl)cyclohexanecarboxylate (0.900 g, 4.10 mmol) and but-2-yne-1,4-diol (0.370 g, 4.30 mmol) in 1,2-dichloroethane (41.0 ml) was added chloro(1,5-cyclooctadiene)(pentamethylcyclopentadienyl)ruthenium(II) (0.0778 g, 205 µmol) and triethylamine (0.713 ml, 5.12 mmol) at room temperature. The reaction mixture was stirred for 20 h. The solvent was evaporated. The residue was triturated in ethyl acetate (50 ml). The solids were removed by filtration and washed with ethyl acetate. The filtrate was concentrated in vacuo. Flash chromatography with n-heptane/ethyl acetate as eluent gave the title compound (0.758 g, 69%) as light brown oil.

4-Heteroaryl-cyclohexanecarboxylic acid ester 28 trans-4-Pyrazol-1-yl-cyclohexanecarboxylic acid ethyl ester

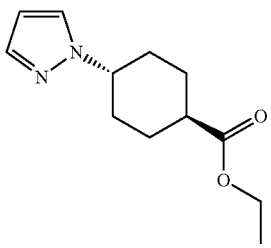 [SMILES: CCOC(=O)[C@H]1CC[C@H](n2cccn2)CC1]

The title compound was obtained as brown oil in quantitative yield from trans-4-hydrazino-cyclohexanecarboxylic acid ethyl ester hydrochloride and 1,1,3,3-tetraethoxypropane according to general procedure (XIX). MS m/e: 223 ([M+H]$^+$).

4-Heteroaryl-cyclohexanecarboxylic acid ester 29 cis-4-Pyrazol-1-yl-cyclohexanecarboxylic acid ethyl ester

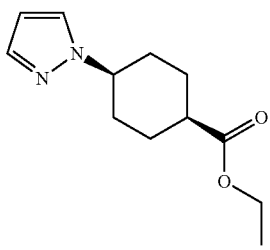 [SMILES: CCOC(=O)[C@H]1CC[C@@H](n2cccn2)CC1]

The title compound was obtained as brown oil in quantitative yield from cis-4-hydrazino-cyclohexanecarboxylic acid ethyl ester hydrochloride and 1,1,3,3-tetraethoxypropane according to general procedure (XIX). MS m/e: 223 ([M+H]$^+$).

4-Heteroaryl-cyclohexanecarboxylic acid ester 30 trans-4-(3,5-Dimethyl-pyrazol-1-yl)-cyclohexanecarboxylic acid ethyl ester

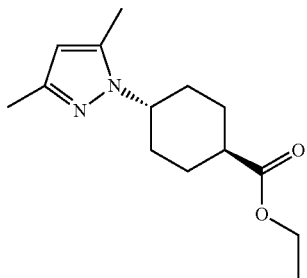 [SMILES: CCOC(=O)[C@H]1CC[C@H](n2nc(C)cc2C)CC1]

The title compound was obtained as off-white solid in 96% yield from trans-4-hydrazino-cyclohexanecarboxylic acid ethyl ester hydrochloride and pentane-2,4-dione according to general procedure (XIX). MS m/e: 251 ([M+H]$^+$).

4-Heteroaryl-cyclohexanecarboxylic acid ester 31 trans-4-(3,4,5-Trimethyl-pyrazol-1-yl)-cyclohexanecarboxylic acid ethyl ester

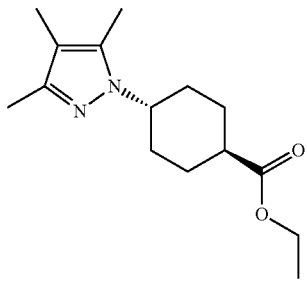 [SMILES: CCOC(=O)[C@H]1CC[C@H](n2nc(C)c(C)c2C)CC1]

The title compound was obtained as light brown solid in quantitative yield from trans-4-hydrazino-cyclohexanecarboxylic acid ethyl ester hydrochloride and 3-methylpentane-2,4-dione according to general procedure (XIX). MS m/e: 265 ([M+H]$^+$).

4-Heteroaryl-cyclohexanecarboxylic acid Intermediates of Formula (IX)

General Procedure (XII): Epimerization Followed by Saponification

A mixture of cis/trans-4-heteroaryl-cyclohexanecarboxylic acid ester intermediate of formula VIII and sodium ethylate (3-6 eq) in ethanol is heated at reflux for 20-72 h. Under these reaction conditions partial saponification of the resulting trans-4-heteroaryl-cyclohexanecarboxylic acid ester intermediate of formula VIII-b to a trans-4-heteroaryl-cyclohexanecarboxylic acid intermediate of formula IX-b may occur. The reaction mixture is partitioned between 0.5 M hydrochloric acid solution and an organic solvent such as ethyl acetate or tert-butyl methyl ether. The pH of the aqueous layer is adjusted to 1-3. The layers are separated. The aqueous layer is extracted with one or two portions of organic solvent. The combined organic layers are dried over anhydrous sodium sulfate and concentrated in vacuo to give a mixture of a trans-4-heteroaryl-cyclohexanecarboxylic acid ester intermediate of formula VIII-b and a trans-4-heteroaryl-cyclohexanecarboxylic acid intermediate of formula IX-b. The mixture is redissolved in 1,4-dioxane (0.1-0.2 M) and 2 M aqueous sodium hydroxide solution (10-20 eq) and stirred at room temperature for 16-24 h. The reaction mixture is partitioned between 0.5 M hydrochloric acid solution and an organic solvent such as ethyl acetate or tert-butyl methyl ether. The pH is adjusted to 1-3. The layers are separated. The aqueous layer is extracted with one or two portions of organic solvent. The combined organic layers are dried over anhydrous sodium sulfate and concentrated to dryness to give a trans-4-heteroaryl-cyclohexanecarboxylic acid intermediate of formula IX-b.

4-Heteroaryl-cyclohexanecarboxylic acid Intermediate 1 trans-4-Thiazol-2-yl-cyclohexanecarboxylic acid

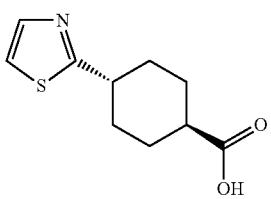 [SMILES: O=C(O)[C@H]1CC[C@H](c2nccs2)CC1]

The title compound was obtained as light brown solid in 60% yield from cis/trans-4-thiazol-2-yl-cyclohexanecarboxylic acid ethyl ester (3:1) according to general procedure (XII). MS m/e: 210 ([M−H]$^-$)

4-Heteroaryl-cyclohexanecarboxylic acid Intermediate 2 trans-4-(4-Methyl-thiazol-2-yl)-cyclohexanecarboxylic acid

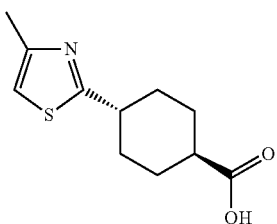

The title compound was obtained as colorless oil in 90% yield from cis/trans-4-(4-methyl-thiazol-2-yl)-cyclohexanecarboxylic acid ethyl ester (4:1) according to general procedure (XII). MS m/e: 226 ([M+H]$^+$)

4-Heteroaryl-cyclohexanecarboxylic acid Intermediate 3 trans-4-(2-Methyl-thiazol-4-yl)-cyclohexanecarboxylic acid

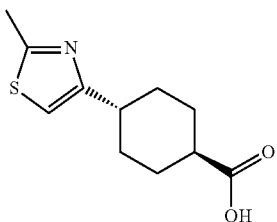

The title compound was obtained as light brown solid in 71% yield from cis/trans-4-(2-methyl-thiazol-4-yl)-cyclohexanecarboxylic acid ethyl ester (3:1) according to general procedure (XII). MS m/e: 224 ([M−H]$^-$)

4-Heteroaryl-cyclohexanecarboxylic acid Intermediate 4 cis/trans-4-(5-Ethyl-isoxazol-3-yl)-cyclohexanecarboxylic acid (3:7)

a) 4-(1-Methylene-propyl)-morpholine

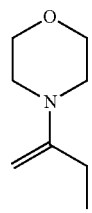

To a solution of 2-butanone (6.2 ml, 69 mmol) and morpholine (18.1 ml, 208 mmol) in n-pentane (400 ml) was added dropwise 1 M titanium tetrachloride solution in dichloromethane (38.1 ml, 38.1 mmol) at 0-5° C. The cooling bath was removed and the mixture was stirred for 20 h. The precipitate was removed by filtration and washed with two 100-ml portions of diethyl ether. The filtrate was concentrated in vacuo. The residue was distilled over a vigreux column in a Kugelrohr oven (1 mbar, 40-70° C.) to give the title compound (5.1 g, 52%) as colorless oil.

b) cis/trans-4-(5-Ethyl-isoxazol-3-yl)-cyclohexanecarboxylic acid (3:7)

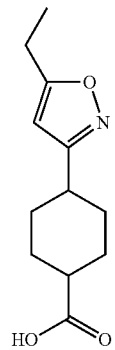

To a solution of cis/trans-ethyl 4-(chloro(hydroxyimino)methyl)cyclohexanecarboxylate (2.35 g, 10.1 mmol) and 4-(1-methylene-propyl)-morpholine (4.26 g, 30.2 mmol) in dichloromethane (100 ml) was added triethylamine (1.40 ml, 10.1 mmol at 0-5° C. The cooling bath was removed 30 minutes after completed addition. After stirring for 20 h the solvent was evaporated. The residue was redissolved in 6 M aqueous hydrochloric acid solution (100 ml), and the mixture was heated at reflux for 3 h. After cooling to room temperature the reaction mixture was partitioned between crushed ice (300 g) and ethyl acetate (100 ml). The layers were separated. The aqueous layer was extracted with two 100-ml portions of ethyl acetate. The combined organic layers were dried over anhydrous sodium sulfate and concentrated in vacuo. Purification with n-heptane/tert-butyl methyl ether as eluent gave the title compound (0.42 g, 19%) as white solid. MS m/e: 222 ([M−H]$^-$)

4-Heteroaryl-cyclohexanecarboxylic acid Intermediate 5 cis-4-(4,5,6,7-Tetrahydro-benzo[d]isoxazol-3-yl)-cyclohexanecarboxylic acid

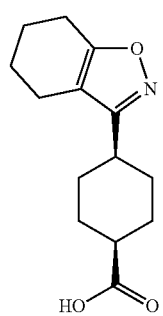 [SMILES: O=C(O)[C@H]1CC[C@@H](c2noc3c2CCCC3)CC1]

4-Heteroaryl-cyclohexanecarboxylic acid
Intermediate 6 trans-4-(4,5,6,7-Tetrahydro-benzo[d]isoxazol-3-yl)-cyclohexanecarboxylic acid

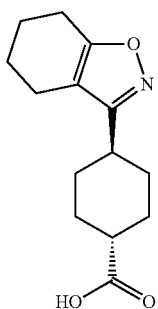 [SMILES: O=C(O)[C@H]1CC[C@H](c2noc3c2CCCC3)CC1]

To a solution of cis/trans-ethyl 4-(chloro(hydroxyimino)methyl)cyclohexanecarboxylate (1.20 g, 5.13 mmol) and 1-morpholinocyclohexene (1.72 g, 10.3 mmol) in dichloromethane (50 ml) was added triethylamine (0.72 ml, 5.1 mmol) at 0-5° C. The cooling bath was removed 30 minutes after completed addition. After stirring for 4 h the solvent was evaporated. The residue was redissolved in 6 M aqueous hydrochloric acid solution (50 ml), and the mixture was and heated at reflux for 1 h. After cooling to room temperature the reaction mixture was partitioned between crushed ice (100 g) and ethyl acetate (50 ml). The layers were separated. The aqueous layer was extracted with two 50-ml portions of ethyl acetate. The combined organic layers were dried over anhydrous sodium sulfate and concentrated in vacuo. Purification with n-heptane/ethyl acetate as eluent gave cis-4-(4,5,6,7-tetrahydro-benzo[d]isoxazol-3-yl)-cyclohexanecarboxylic acid (0.40 g, 31%) as white solid (MS m/e: 248 ([M−H]$^-$)) and trans-4-(4,5,6,7-tetrahydro-benzo[d]isoxazol-3-yl)-cyclohexanecarboxylic acid (0.09 g, 7%) as white solid (MS m/e: 248 ([M−H]$^-$)).

4-Heteroaryl-cyclohexanecarboxylic acid
Intermediate 7 trans-4-(5-Chloro-4-methyl-oxazol-2-yl)-cyclohexanecarboxylic acid

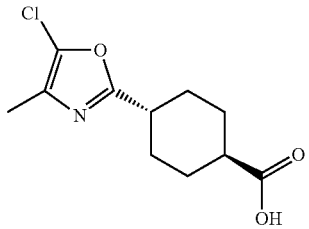 [SMILES: Cc1nc([C@H]2CC[C@H](C(=O)O)CC2)oc1Cl]

A mixture of trans-4-(5-chloro-4-methyl-oxazol-2-yl)-cyclohexanecarboxylic acid methyl ester (285 mg, 1.11 mmol) in 1,4-dioxane (5.5 ml) and 2 M aqueous sodium hydroxide solution (5.5 ml, 11 mmol) was stirred for 4 h at room temperature. The reaction mixture was partitioned between ethyl acetate (25 ml) and water (25 ml). The aqueous layer was acidified to pH 2. The layers were separated. The aqueous layer was extracted with two 25-ml portions of ethyl acetate. The combined organic layers were washed with one 10-ml portion of brine, dried over anhydrous sodium sulfate and concentrated in vacuo to give the title compound (245 mg, 91%) as white solid. MS m/e: 242 ([M−H]$^-$)

4-Heteroaryl-cyclohexanecarboxylic acid
Intermediate 8 cis/trans-4-(5-Chloro-4-methyl-thiazol-2-yl)-cyclohexanecarboxylic acid (1:5)

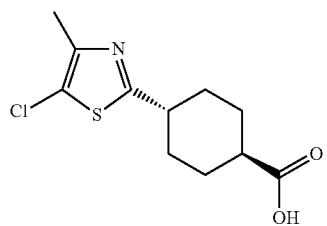 [SMILES: Cc1nc([C@H]2CC[C@H](C(=O)O)CC2)sc1Cl]

A mixture of cis/trans-4-(5-chloro-4-methyl-thiazol-2-yl)-cyclohexanecarboxylic acid ethyl ester (1:5) (209 mg, 0.726 mmol) in 1,4-dioxane (7.3 ml) and 2 M aqueous sodium hydroxide solution (3.6 ml, 7.3 mmol) was stirred for 12 h at room temperature. The reaction mixture was partitioned between ethyl acetate (25 ml) and 0.1 M aqueous hydrogen chloride solution (25 ml). The layers were separated. The aqueous layer (pH 2) was extracted with two 25-ml portions of ethyl acetate. The combined organic layers were washed with one 10-ml portion of brine, dried over anhydrous sodium sulfate and concentrated in vacuo to give the title compound (170 mg, 90%) as white solid. MS m/e: 258 ([M−H]$^-$)

4-Heteroaryl-cyclohexanecarboxylic acid
Intermediate 9 cis/trans-4-(4,5-Dimethyl-thiazol-2-yl)-cyclohexanecarboxylic acid

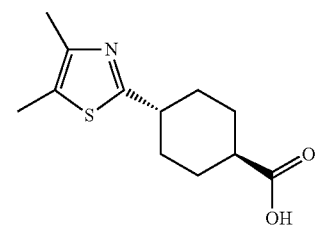 [SMILES: Cc1nc([C@H]2CC[C@H](C(=O)O)CC2)sc1C]

A mixture of cis/trans-4-(4,5-dimethyl-thiazol-2-yl)-cyclohexanecarboxylic acid ethyl ester (1:7) (170 mg, 0.636 mmol) in 1,4-dioxane (6.4 ml) and 2 M aqueous sodium hydroxide solution (3.2 ml, 6.4 mmol) was stirred for 24 h at room temperature. The reaction mixture was partitioned between ethyl acetate (25 ml) and water (25 ml). The aqueous layer was acidified to pH 4-5 by addition of 2 M aqueous hydrogen chloride solution (3.2 ml). The layers were separated. The aqueous layer was extracted with two 25-ml portions of ethyl acetate. The combined organic layers were washed with one 20-ml portion of brine, dried over anhydrous

4-Heteroaryl-cyclohexanecarboxylic acid Intermediate 10 trans-4-(5,6-Dihydro-4H-cyclopenta[d]isoxazol-3-yl)-cyclohexanecarboxylic acid

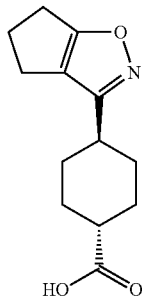 [SMILES: O=C(O)[C@H]1CC[C@H](c2noc3c2CCC3)CC1]

To a solution of trans-methyl 4-(chloro(hydroxyimino)methyl)cyclohexanecarboxylate (0.900 g, 4.10 mmol) and 4-cyclopentenylmorpholine (1.23 ml, 8.19 mmol) in dichloromethane (21 ml) was added triethylamine (0.714 ml, 5.12 mmol) at 0-5° C. The reaction mixture was allowed to warm to room temperature and stirred for 20 h. The solvent was evaporated. The residue was redissolved in 6 M aqueous hydrogen chloride solution (20.5 ml) and stirred at reflux for 4 h. After cooling to room temperature the reaction mixture was poured on ice, basified with 2 M aqueous sodium hydroxide solution (80 ml) and washed with two 50-ml portions of ethyl acetate. The combined organic layers were extracted with two 50-ml portions of 1 M aqueous sodium hydroxide solution. The combined aqueous layers were acidified to pH 2-3 by addition of concentrated hydrochloric acid and extracted with three 100-ml portions of ethyl acetate. The combined organic extracts were dried over anhydrous sodium sulfate and concentrated in vacuo. The residue was triturated in tert-butyl methyl ether (50 ml). The precipitate was removed by filtration. The filtrate was concentrated in vacuo. The residue was purified by flash chromatography with n-heptane/ethyl acetate as eluent to give the title compound (0.060 g, 6%) as off-white solid. MS m/e: 234 ([M−H]$^-$)

4-Heteroaryl-cyclohexanecarboxylic acid Intermediate 11 trans-4-Pyrazol-1-yl-cyclohexanecarboxylic acid

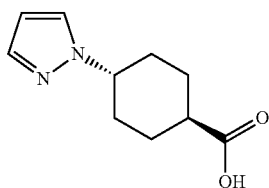 [SMILES: O=C(O)[C@H]1CC[C@H](n2cccn2)CC1]

A solution of trans-4-pyrazol-1-yl-cyclohexanecarboxylic acid ethyl ester (95 mg, 0.43 mmol) in 1,4-dioxane (4.3 ml) and 2 M aqueous sodium hydroxide solution (2.2 ml, 4.4 mmol) was stirred at room temperature for 20 h. The pH was adjusted to 2 by addition of 2 M aqueous hydrochloric acid. The mixture was partitioned between ethyl acetate (25 ml) and water (25 ml). The layers were separated. The aqueous layer was extracted with two 25-ml portions of ethyl acetate. The combined organic layers were dried over anhydrous sodium sulfate and concentrated in vacuo to give the title compound (80 mg, 96%) as light brown solid. MS m/e: 193 ([M−H]$^-$)

4-Heteroaryl-cyclohexanecarboxylic acid Intermediate 12 cis-4-Pyrazol-1-yl-cyclohexanecarboxylic acid

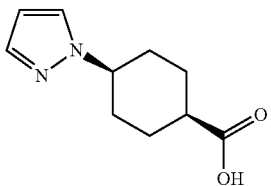 [SMILES: O=C(O)[C@H]1CC[C@@H](n2cccn2)CC1]

A solution of cis-4-pyrazol-1-yl-cyclohexanecarboxylic acid ethyl ester (95 mg, 0.427 mmol) in 1,4-dioxane (4.3 ml) and 2 M aqueous sodium hydroxide solution (2.2 ml, 4.4 mmol) was stirred at room temperature for 20 h. The pH was adjusted to 2 by addition of 2 M aqueous hydrochloric acid. The mixture was partitioned between ethyl acetate (25 ml) and water (25 ml). The layers were separated. The aqueous layer was extracted with two 25-ml portions of ethyl acetate. The combined organic layers were dried over anhydrous sodium sulfate and concentrated in vacuo to give the title compound (79 mg, 95%) as light brown solid. MS m/e: 193 ([M−H]$^-$)

4-Heteroaryl-cyclohexanecarboxylic acid Intermediate 13 trans-4-(3,5-Dimethyl-pyrazol-1-yl)-cyclohexanecarboxylic acid

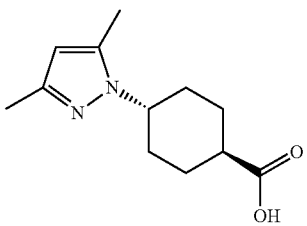 [SMILES: Cc1cc(C)n([C@H]2CC[C@H](C(=O)O)CC2)n1]

A solution of trans-4-(3,5-dimethyl-pyrazol-1-yl)-cyclohexanecarboxylic acid ethyl ester (162 mg, 0.647 mmol) in 1,4-dioxane (6.5 ml) and 2 M aqueous sodium hydroxide solution (3.2 ml, 6.4 mmol) was stirred at room temperature for 15 h. The pH was adjusted to 3 by addition of 2 M aqueous hydrochloric acid. The mixture was partitioned between ethyl acetate (25 ml) and water (25 ml). The layers were separated. The aqueous layer was extracted with two 25-ml portions of ethyl acetate. The combined organic layers were dried over 4-Heteroaryl-cyclohexanecarboxylic acid
Intermediate 14 trans-4-(3,4,5-Trimethyl-pyrazol-1-yl)-cyclohexanecarboxylic acid

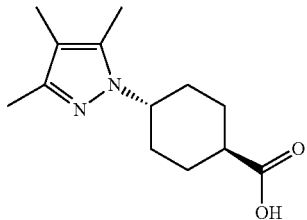 [SMILES: Cc1nn([C@H]2CC[C@H](C(=O)O)CC2)c(C)c1C]

A solution of trans-4-(3,4,5-trimethyl-pyrazol-1-yl)-cyclohexanecarboxylic acid ethyl ester (180 mg, 0.681 mmol) in 1,4-dioxane (6.8 ml) and 2 M aqueous sodium hydroxide solution (3.4 ml, 6.8 mmol) was stirred at room temperature for 3 days. The pH was adjusted to 3 by addition of 2 M aqueous hydrochloric acid. The mixture was partitioned between ethyl acetate (25 ml) and water (25 ml). The layers were separated. The aqueous layer was extracted with two 25-ml portions of ethyl acetate. The combined organic layers were dried over anhydrous sodium sulfate and concentrated in vacuo to give the title compound (141 mg, 88%) as light brown solid. MS m/e: 235 ([M−H]⁻)

Hydrazide Intermediates of Formula (II)

General Procedure (XIII): Hydrazide Formation from Acid

To a solution of a 4-heteroaryl-cyclohexanecarboxylic acid intermediate of formula (IX) (1 eq) and triethylamine (1.05 eq) in tetrahydrofuran (0.2 M) is added ethyl chloroformate (1.05 eq) at 0° C. The reaction mixture is stirred at 0° C. for 1 h. The ammonium salts are removed by filtration. The filtrate is added to a cold solution of hydrazine hydrate (2 eq) in methanol (0.2 M). The reaction mixture is stirred at room temperature for 2-16 h. The solvent is evaporated under reduced pressure, and the residue is partitioned between an organic solvent such as ethyl acetate or dichloromethane and water. The organic layer is separated. The aqueous layer is extracted with two or three portions of organic solvent. The combined organic layers are dried over anhydrous sodium sulfate and concentrated in vacuo to give a hydrazide intermediate of formula (II), which is usually used in the next step without further purification.

General Procedure (XIV): Hydrazide Formation from Ester

A mixture of a 4-heteroaryl-cyclohexanecarboxylic acid ester intermediate of formula (VIII) (1 eq) and hydrazine hydrate (2-6 eq) in n-butanol (0.2-1 M) is heated at reflux for 16-72 h. After cooling to room temperature the reaction mixture is partitioned between an organic solvent such as ethyl acetate or dichloromethane and water. The layers are separated and the aqueous layer is extracted with two portions of organic solvent. The combined organic layers are dried over anhydrous sodium sulfate and concentrated in vacuo to give a hydrazide intermediate of formula (II), which is usually used in the next step without further purification.

Hydrazide 1 trans-4-Oxazol-2-yl-cyclohexanecarboxylic acid hydrazide

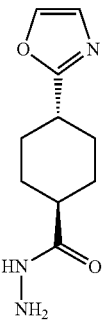

The title compound was obtained as white solid in 61% yield from trans-4-oxazol-2-yl-cyclohexanecarboxylic acid methyl ester according to general procedure (XIV). MS m/e: 210 ([M+H]⁺)

Hydrazide 2 trans-4-(4-Methyl-oxazol-2-yl)-cyclohexanecarboxylic acid hydrazide

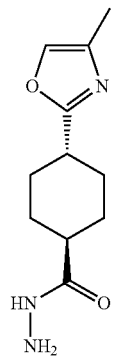

The title compound was obtained as white solid in 92% yield from trans-4-(4-methyl-oxazol-2-yl)-cyclohexanecarboxylic acid according to general procedure (XIII). MS m/e: 224 ([M+H]⁺)

Hydrazide 3 trans-4-(5-Methyl-oxazol-2-yl)-cyclohexanecarboxylic acid hydrazide

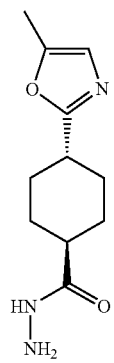

The title compound was obtained as off-white solid in 93% yield from trans-4-(5-methyl-oxazol-2-yl)-cyclohexanecarboxylic acid according to general procedure (XIII) MS m/e: 224 ([M+H]$^+$)

Hydrazide 4 trans-4-(4,5-Dimethyl-oxazol-2-yl)-cyclohexanecarboxylic acid hydrazide

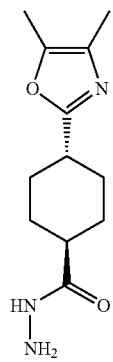

The title compound was obtained as white solid in 73% yield from trans-4-(4,5-dimethyl-oxazol-2-yl)-cyclohexanecarboxylic acid according to general procedure (XIII). MS m/e: 238 ([M+H]$^+$)

Hydrazide 5 trans-4-Thiazol-2-yl-cyclohexanecarboxylic acid hydrazide

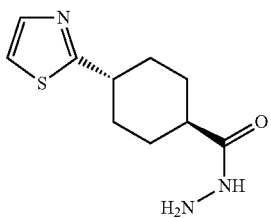 [SMILES: NNC(=O)[C@H]1CC[C@H](c2nccs2)CC1]

The title compound was obtained as light brown solid in 79% yield from trans-4-thiazol-2-yl-cyclohexanecarboxylic acid according to general procedure (XIII). MS m/e: 226 ([M+H]$^+$)

Hydrazide 6 trans-4-(4-Methyl-thiazol-2-yl)-cyclohexanecarboxylic acid hydrazide

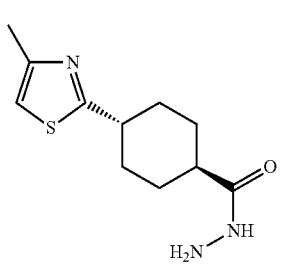 [SMILES: Cc1csc([C@H]2CC[C@H](C(=O)NN)CC2)n1]

The title compound was obtained as white solid in 59% yield from trans-4-(4-methyl-thiazol-2-yl)-cyclohexanecarboxylic acid according to general procedure (XIII). MS m/e: 240 ([M+H]$^+$)

Hydrazide 7 trans-4-(2-Methyl-thiazol-4-yl)-cyclohexanecarboxylic acid hydrazide

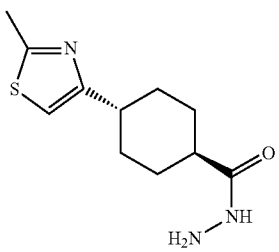 [SMILES: Cc1nc([C@H]2CC[C@H](C(=O)NN)CC2)cs1]

The title compound was obtained as off-white solid in 94% yield from 4-(2-methyl-thiazol-4-yl)-cyclohexanecarboxylic acid according to general procedure (XIII). MS m/e: 240 ([M+H]$^+$)

Hydrazide 8 trans-4-(5-Methyl-isoxazol-3-yl)-cyclohexanecarboxylic acid hydrazide

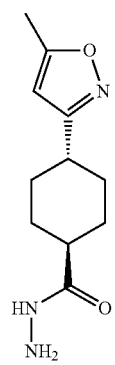

The title compound was obtained as white solid in 91% yield from trans-4-(5-methyl-isoxazol-3-yl)-cyclohexanecarboxylic acid methyl ester according to general procedure (XIV). MS m/e: 224 ([M+H]$^+$)

Hydrazide 9 trans-4-(4,5-Dimethyl-isoxazol-3-yl)-cyclohexanecarboxylic acid hydrazide

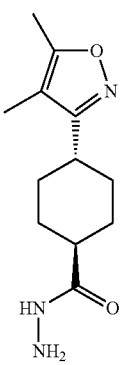 [SMILES: Cc1onc([C@H]2CC[C@H](C(=O)NN)CC2)c1C]

The title compound was obtained as white solid in quantitative yield from trans-4-(4,5-dimethyl-isoxazol-3-yl)-cyclohexanecarboxylic acid methyl ester according to general procedure (XIV). MS m/e: 238 ([M+H]$^+$)

Hydrazide 10 trans-4-(4-Chloro-5-methyl-isoxazol-3-yl)-cyclohexanecarboxylic acid hydrazide

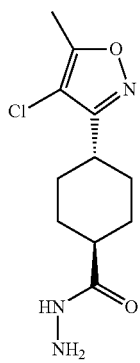

The title compound was obtained as white solid in 95% yield from trans-4-(4-chloro-5-methyl-isoxazol-3-yl)-cyclohexanecarboxylic acid methyl ester according to general procedure (XIV). MS m/e: 258 ([M+H]$^+$)

Hydrazide 11 trans-4-(4-Fluoro-5-methyl-isoxazol-3-yl)-cyclohexanecarboxylic acid hydrazide

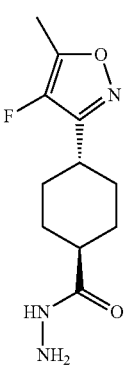

The title compound was obtained as off-white solid in 89% yield from trans-4-(4-fluoro-5-methyl-isoxazol-3-yl)-cyclohexanecarboxylic acid methyl ester according to general procedure (XIV). MS m/e: 242 ([M+H]$^+$)

Hydrazide 12 cis/trans-4-(5-Ethyl-isoxazol-3-yl)-cyclohexanecarboxylic acid hydrazide

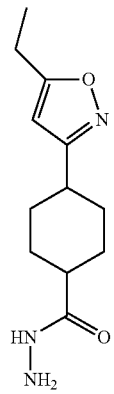

The title compound was obtained as white solid in quantitative yield from cis/trans-4-(5-ethyl-isoxazol-3-yl)-cyclohexanecarboxylic acid according to general procedure (XIII). MS m/e: 238 ([M+H]$^+$)

Hydrazide 13 trans-4-(4,5,6,7-Tetrahydro-benzo[d]isoxazol-3-yl)-cyclohexanecarboxylic acid hydrazide

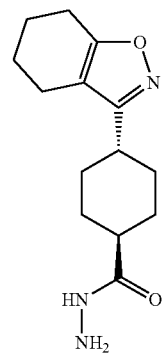 [SMILES: NNC(=O)[C@H]1CC[C@H](c2noc3c2CCCC3)CC1]

The title compound was obtained as white solid in 91% yield from trans-4-(4,5,6,7-tetrahydro-benzo[d]isoxazol-3-yl)-cyclohexanecarboxylic acid according to general procedure (XIII). MS m/e: 264 ([M+H]$^+$)

Hydrazide 14 cis-4-(4,5,6,7-Tetrahydro-benzo[d]isoxazol-3-yl)-cyclohexanecarboxylic acid hydrazide

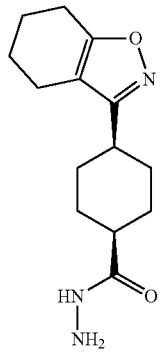 [SMILES: NNC(=O)[C@H]1CC[C@@H](c2noc3c2CCCC3)CC1]

The title compound was obtained as amorphous off-white solid in quantitative yield from cis-4-(4,5,6,7-tetrahydro-benzo[d]isoxazol-3-yl)-cyclohexanecarboxylic acid according to general procedure (XIII). MS m/e: 264 ([M+H]$^+$)

Hydrazide 15 trans-4-(4,5,6,7-Tetrahydro-benzo[c]isoxazol-3-yl)-cyclohexanecarboxylic acid hydrazide

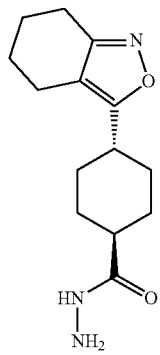 [SMILES: NNC(=O)[C@H]1CC[C@H](c2onc3c2CCCC3)CC1]

The title compound was obtained as white solid in 78% yield from trans-4-(4,5,6,7-tetrahydro-benzo[c]isoxazol-3-yl)-cyclohexanecarboxylic acid methyl ester according to general procedure (XIV). MS m/e: 264 ([M+H]$^+$)

Hydrazide 16 trans-4-(5-Methyl-[1,3,4]oxadiazol-2-yl)-cyclohexanecarboxylic acid hydrazide

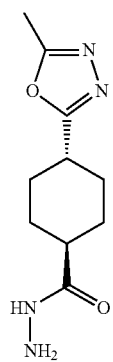

The crude title compound was obtained as pink liquid in 60% yield from trans-4-(5-methyl-[1,3,4]oxadiazol-2-yl)-cyclohexanecarboxylic acid methyl ester according to general procedure (XIV). MS m/e: 225 ([M+H]$^+$)

Hydrazide 17 trans-4-(3-Methyl-[1,2,4]oxadiazol-5-yl)-cyclohexanecarboxylic acid hydrazide

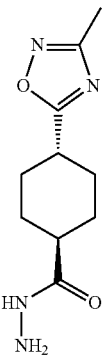

The title compound was obtained as white solid in 65% yield from trans-4-(3-methyl-[1,2,4]oxadiazol-5-yl)-cyclohexanecarboxylic acid methyl ester according to general procedure (XIV). MS m/e: 225 ([M+H]$^+$)

Hydrazide 18 trans-4-(3-Methyl-[1,2,4]thiadiazol-5-yl)-cyclohexanecarboxylic acid hydrazide

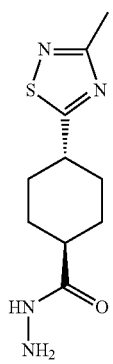

The title compound was obtained as white solid in 80% yield from trans-4-(3-methyl-[1,2,4]thiadiazol-5-yl)-cyclohexanecarboxylic acid methyl ester according to general procedure (XIV). MS m/e: 241 ([M+H]$^+$)

Hydrazide 19 trans-4-(5-Methyl-[1,2,4]oxadiazol-3-yl)-cyclohexanecarboxylic acid hydrazide

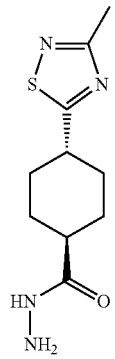

The title compound was obtained as white solid in 60% yield from trans-4-(5-methyl-[1,2,4]oxadiazol-3-yl)-cyclohexanecarboxylic acid methyl ester according to general procedure (XIV). MS m/e: 225 ([M+H]$^+$)

Hydrazide 20 cis-4-(5-Methyl-[1,2,4]oxadiazol-3-yl)-cyclohexanecarboxylic acid hydrazide

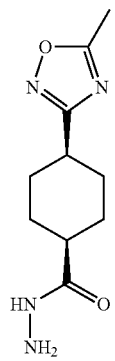

The title compound was obtained as off-white solid in 61% yield from cis-4-(5-methyl-[1,2,4]oxadiazol-3-yl)-cyclohexanecarboxylic acid ethyl ester according to general procedure (XIV). MS m/e: 225 ([M+H]$^+$)

Hydrazide 21 cis/trans-4-(5-Ethyl-[1,2,4]oxadiazol-3-yl)-cyclohexanecarboxylic acid hydrazide

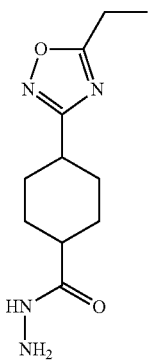

The title compound was obtained as yellow solid in 96% yield from cis/trans-4-(5-ethyl-[1,2,4]oxadiazol-3-yl)-cyclohexanecarboxylic acid ethyl ester according to general procedure (XIV). MS m/e: 239 ([M+H]$^+$)

Hydrazide 22 cis/trans-4-(5-Isopropyl-[1,2,4]oxadiazol-3-yl)-cyclohexanecarboxylic acid hydrazide

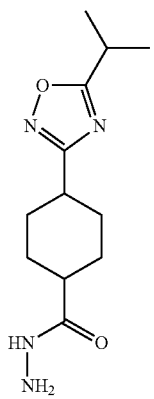 [SMILES: CC(C)c1nc(C2CCC(C(=O)NN)CC2)no1]

The title compound was obtained as light yellow oil in 68% yield from cis/trans-4-(5-isopropyl-[1,2,4]oxadiazol-3-yl)-cyclohexanecarboxylic acid ethyl ester according to general procedure (XIV). MS m/e: 253 ([M+H]$^+$)

Hydrazide 23 trans-4-(5-Methyl-[1,2,4]thiadiazol-3-yl)-cyclohexanecarboxylic acid hydrazide

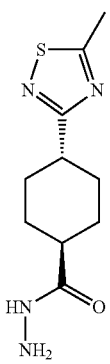

The title compound was obtained as off-white solid in 95% yield, which was contaminated with approximately 20% trans-4-(3-methyl-[1,2,4]thiadiazol-5-yl)-cyclohexanecarboxylic acid hydrazide, from trans-4-(5-methyl-[1,2,4]thiadiazol-3-yl)-cyclohexanecarboxylic acid methyl ester according to general procedure (XIV). MS m/e: 241 ([M+H]$^+$)

Hydrazide 24 trans-4-(5-Chloro-4-methyl-oxazol-2-yl)-cyclohexanecarboxylic acid hydrazide

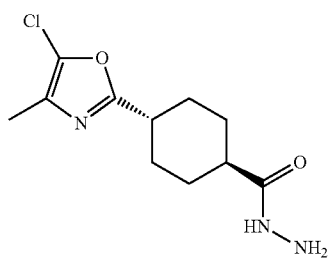 [SMILES: Cc1nc([C@H]2CC[C@H](C(=O)NN)CC2)oc1Cl]

The title compound was obtained as white solid in 72% yield from trans-4-(5-chloro-4-methyl-oxazol-2-yl)-cyclohexanecarboxylic acid according to general procedure (XIII). MS m/e: 258 ([M+H]$^+$)

Hydrazide 25 trans-4-(5-Chloro-4-methyl-thiazol-2-yl)-cyclohexanecarboxylic acid hydrazide

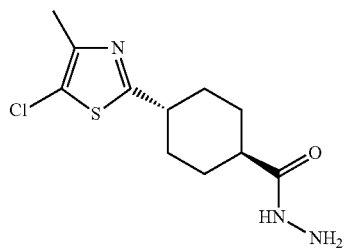 [SMILES: Cc1nc([C@H]2CC[C@H](C(=O)NN)CC2)sc1Cl]

The title compound was obtained as white solid in 30% yield from cis/trans-4-(5-chloro-4-methyl-thiazol-2-yl)-cyclohexanecarboxylic acid (1:5) according to general procedure (XIII). MS m/e: 274 ([M+H]$^+$)

Hydrazide 26 cis/trans-4-(4,5-Dimethyl-thiazol-2-yl)-cyclohexanecarboxylic acid hydrazide (1:7.5)

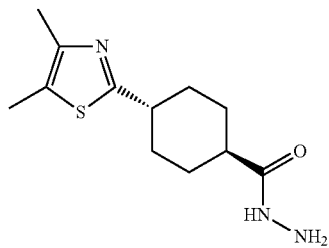 [SMILES: Cc1nc([C@H]2CC[C@H](C(=O)NN)CC2)sc1C]

The title compound was obtained as white solid in 75% yield from cis/trans-4-(4,5-dimethyl-thiazol-2-yl)-cyclohexanecarboxylic acid (1:5) according to general procedure (XIII). MS m/e: 254 ([M+H]$^+$)

Hydrazide 27 trans-4-(5,6-Dihydro-4H-cyclopenta[d]isoxazol-3-yl)-cyclohexanecarboxylic acid hydrazide

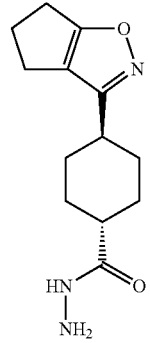

The title compound was obtained as off-white solid in 71% yield from trans-4-(5,6-dihydro-4H-cyclopenta[d]isoxazol-3-yl)-cyclohexanecarboxylic acid according to general procedure (XIII). MS m/e: 250 ([M+H]$^+$)

Hydrazide 28 trans-4-(4,5-Bis-hydroxymethyl-isoxazol-3-yl)-cyclohexanecarboxylic acid hydrazide

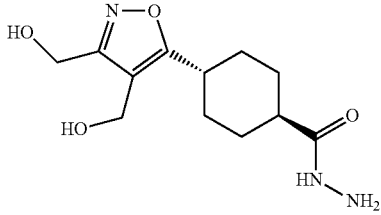 [SMILES: NNC(=O)[C@H]1CC[C@H](c2onc(CO)c2CO)CC1]

The title compound was obtained as light yellow solid in quantitative yield from trans-4-(4,5-bis-hydroxymethyl-isoxazol-3-yl)-cyclohexanecarboxylic acid methyl ester according to general procedure (XIV). MS m/e: 270 ([M+H]$^+$)

Hydrazide 29 trans-4-Pyrazol-1-yl-cyclohexanecarboxylic acid hydrazide

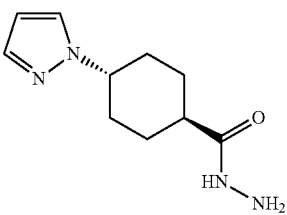 [SMILES: NNC(=O)[C@H]1CC[C@H](n2cccn2)CC1]

The title compound was obtained as off-white solid in 69% yield from trans-4-pyrazol-1-yl-cyclohexanecarboxylic acid according to general procedure (XIII). MS m/e: 209 ([M+H]⁺)

Hydrazide 30 cis-4-Pyrazol-1-yl-cyclohexanecarboxylic acid hydrazide

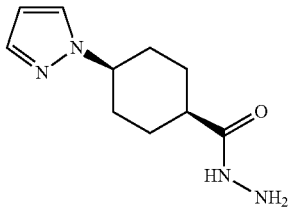 [SMILES: NNC(=O)[C@H]1CC[C@@H](n2cccn2)CC1]

The title compound was obtained as off-white solid in 72% yield from cis-4-pyrazol-1-yl-cyclohexanecarboxylic acid according to general procedure (XIII). MS m/e: 209 ([M+H]⁺)

Hydrazide 31 trans-4-(3,5-Dimethyl-pyrazol-1-yl)-cyclohexanecarboxylic acid hydrazide

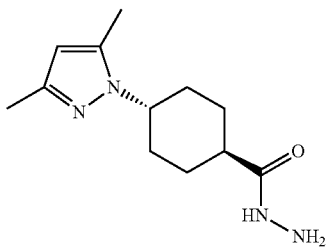 [SMILES: Cc1cc(C)n([C@H]2CC[C@H](C(=O)NN)CC2)n1]

The title compound was obtained as white solid in 88% yield from trans-4-(3,5-dimethyl-pyrazol-1-yl)-cyclohexanecarboxylic acid according to general procedure (XIII). MS m/e: 237 ([M+H]⁺)

Hydrazide 32 trans-4-(3,4,5-Trimethyl-pyrazol-1-yl)-cyclohexanecarboxylic acid hydrazide

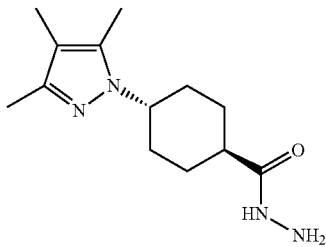 [SMILES: Cc1nn([C@H]2CC[C@H](C(=O)NN)CC2)c(C)c1C]

The title compound was obtained as off-white solid in 78% yield from trans-4-(3,4,5-trimethyl-pyrazol-1-yl)-cyclohexanecarboxylic acid according to general procedure (XIII). MS m/e: 251 ([M+H]⁺)

Thiolactam Intermediates of Formula III

7-Chloro-2-thioxo-1,2,3,5-tetrahydro-benzo[e][1,4]diazepine-4-carboxylic acid tert-butyl ester a) 4-Chloro-2-chloromethyl-1-nitro-benzene To a solution of 5-chloro-2-nitrobenzyl alcohol (80 g, 0.42 mol) and triethylamine (64 ml, 0.46 mol) in dichloromethane (840 ml) was added drop wise thionyl chloride (34 ml, 0.46 mol) during a period of 30 minutes while the internal temperature was kept below 32° C. by cooling with a water bath. The reaction mixture was stirred for 3 h. The solvent was evaporated and the residue was triturated in warm tert-butyl methyl ether (970 ml). The ammonium salts were removed by filtration and the filtrate was concentrated in vacuo to give the title compound (85 g, 99%) as brown oil which was used in the next step without purification. MS m/e: 205 (M⁺).

b) (5-Chloro-2-nitro-benzylamino)-acetic acid ethyl ester

A mixture of 4-chloro-2-chloromethyl-1-nitro-benzene (85 g, 0.41 mol), glycine ethyl ester hydrochloride (70 g, 0.50 mol) and triethylamine (121.4 ml, 0.8665 mol) in ethanol (1000 ml) was heated at reflux for 8 h. The solvent was evaporated and the residue was triturated in warm tert-butyl methyl ether. The ammonium salts were removed by filtration and the filtrate was concentrated in vacuo to give the title compound (111 g, 99%) as an amorphous brown solid which was used in the next step without purification. MS m/e: 273 (M+H⁺).

c) [tert-Butoxycarbonyl-(5-chloro-2-nitro-benzyl)-amino]-acetic acid ethyl ester A solution of (5-chloro-2-nitro-benzylamino)-acetic acid ethyl ester (110 g, 0.403 mol), di-tert-butyl dicarbonate (180 g, 0.807 mol) and 4-N,N-dimethylaminopyridine (2.51 g, 0.0202 mol) in dichloromethane (1200 ml) was stirred for 2 h at 0° C. and further 16 h at room temperature. The solvent was evaporated and the crude product was purified by flash chromatography with a cyclohexane/ethyl acetate mixture as eluent to give the title compound (76.4 g, 51%) as light yellow viscous oil. MS m/e: 373 (M+H⁺).

d) [(2-Amino-5-chloro-benzyl)-tert-butoxycarbonyl-amino]-acetic acid ethyl ester To a solution of [tert-butoxycarbonyl-(5-chloro-2-nitro-benzyl)-amino]-acetic acid ethyl ester (69.0 g, 0.186 mol) in ethyl acetate (1200 ml) was added zinc bromide (8.5 g, 0.037 mol). The reaction mixture was purged with argon after 15 minutes. After addition of the palladium catalyst (10% on activated charcoal, 7.9 g, 0.0074 mol) the mixture was hydrogenated at ambient pressure during a period of ca. 48 h until ca. 13 l of hydrogen gas had been consumed. The catalyst was removed by filtration and the filtrate was washed with two portions of saturated aqueous sodium bicarbonate solution and brine, each. The organic layer was dried over anhydrous sodium sulfate and concentrated in vacuo to give the title compound (60.6 g, 95.5%) as yellow waxy solid. MS m/e: 343 (M+H$^+$).

e) 7-Chloro-2-oxo-1,2,3,5-tetrahydro-benzo[1,4]diazepine-4-carboxylic acid tert-butyl ester To a solution of [(2-amino-5-chloro-benzyl)-tert-butoxycarbonyl-amino]-acetic acid ethyl ester (60 g, 0.18 mol) in tetrahydrofuran (600 ml) was added potassium tert-butoxide (22 g, 0.19 mol) in small portions at 5° C. under cooling on an ice-water batch. After completed addition the cooling bath was removed and reaction mixture was stirred for 3 h at room temperature followed by addition of water (400 ml), saturated aqueous ammonium chloride solution (280 ml) and ethyl acetate (800 ml). After 10 minutes the precipitate was collected by filtration. The layers were separated from the filtrate, dried over anhydrous sodium sulfate and concentrated in vacuo. The residue was combined with the precipitate, which had previously been collected by filtration, and crystallized from hot ethyl acetate to give the title compound (46 g, 88%) as white solid. MS m/e: 295 (M–H$^+$).

f) 7-Chloro-2-thioxo-1,2,3,5-tetrahydro-benzo[e][1,4]diazepine-4-carboxylic acid tert-butyl ester A mixture of 7-chloro-2-oxo-1,2,3,5-tetrahydro-benzo[1,4]diazepine-4-carboxylic acid tert-butyl ester (41.1 g, 0.139 mol) and 2,4-bis-(4-methoxyphenyl)-1,3,2,4-dithiadiphosphetane-2,4-disulfide (31.5 g, 0.0763 mol) in tetrahydrofuran (1100 ml) was heated at reflux for 3 h. The solvent was evaporated and the residue was triturated in tert-butyl methyl ether. The precipitate was removed by filtration and the filtrate was concentrated to dryness. The residue was crystallized from hot ethanol to give the title compound (37.5 g, 86.4%) as light yellow solid. MS m/e: 311 (M–H$^+$).

7-Fluoro-2-thioxo-1,2,3,5-tetrahydro-benzo[e][1,4]diazepine-4-carboxylic acid tert-butyl ester The title compound was obtained as light yellow solid in comparable yields according to the procedures described above for the synthesis of 7-chloro-2-thioxo-1,2,3,5-tetrahydro-benzo[e][1,4]diazepine-4-carboxylic acid tert-butyl ester using 5-fluoro-2-nitrobenzyl alcohol instead of 5-chloro-2-nitrobenzyl alcohol in step a). MS m/e: 297 (M–H$^+$).

General Procedure (XV): Condensation of Hydrazide and Thiolactam to Triazole

A mixture of a hydrazide of formula II (1-1.5 eq) and a thiolactam of formula III (1 eq) in n-butanol (0.1-0.2 M) is heated at reflux for 16-72 h. After cooling to room temperature the solvent is evaporated and the residue is purified by flash-chromatography to give a compound of formula I. When a thiolactam of formula III-1 (compounds of formula III in which R$^1$ is tert-butoxycarbonyl) is used the N-tert-butoxycarbonyl group of the resulting triazole product of formula I-1 can be partially or completely cleaved thermally, and a secondary amine of formula I-2 is obtained in addition or as the sole product.

General Procedure (XVI-a): Cleavage of N-tert-butoxycarbonyl (N-BOC) Group

A solution of an N-BOC derivative of formula I-1 (1 eq) in 1.25 M methanolic or 1.5 M ethanolic hydrogen chloride solution (10-20 eq HCl) is heated at 50° C. for 15-60 minutes. After cooling to room temperature the reaction mixture is concentrated in vacuo to give a secondary amine of formula I-2 as hydrochloride salt. Optionally the free base can be obtained by partitioning the hydrochloride salt between 1 M aqueous sodium hydroxide solution and an organic solvent, e.g. ethyl acetate or dichloromethane. The layers are separated and the aqueous layer is extracted with two portions of the organic solvent. The combined organic layers are dried over anhydrous sodium sulfate, filtered and concentrated in vacuo to give the free base of a compound of formula I-2.

General Procedure (XVI-b): Cleavage of N-tert-butoxycarbonyl (N-BOC) Group

A solution of an N-BOC derivative of general formula I-1 (1 eq) and trifluoroacetic acid (10-20 eq) in dichloromethane is stirred at room temperature for 6-24 h. The reaction mixture is partitioned between 1 M aqueous sodium hydroxide solution and an organic solvent such as ethyl acetate or dichloromethane. The layers are separated and the aqueous layer is extracted with two portions of the organic solvent. The combined organic layers are dried over anhydrous sodium sulfate, filtered and concentrated in vacuo to give the free base of a compound of formula I-2.

General Procedure (XVII-a): Reductive N-alkylation

A mixture of a compound of formula I-2 as free base or as hydrochloride salt (1 eq, 0.1-0.2 M), triethylamine (1 eq when the hydrochloride salt of a compound of formula I-2 is used) and an aldehyde or ketone (8 eq) in methanol is heated at reflux for 2-6 h. After cooling to 0° C. sodium cyanoborohydride (2-3 eq) is added. The reaction mixture is stirred for 3-16 h at room temperature and quenched with 1 M aqueous sodium hydroxide solution. The aqueous layer is extracted with ethyl acetate. The combined organic layers are dried over anhydrous sodium sulfate and concentrated in vacuo. Flash chromatography gives an N-alkyl compound of formula I.

General Procedure (XVII-b): Reductive N-alkylation

A mixture of a compound of formula I-2 as free base (1 eq, 0.1-0.2 M), an aldehyde or ketone (2 eq) and acetic acid (2 eq) in 1,2-dichloroethane is stirred for 5 h at room temperature. After addition of sodium triacetoxyborohydride (2.2 eq) the reaction mixture is stirred for 20 h. Quenching with methanol and N-ethyldiisopropylamine (2 eq) is followed by concentration of the mixture in vacuo. RP-HPLC with water (0.05% formic acid)/methanol as eluent gives an N-alkyl derivative of formula I.

General Procedure (XVIII): Reductive N-methylation

A mixture of a compound of formula I-2 as free base (1 eq, 0.1-0.2 M), sodium acetate (1.1 eq), acetic acid (1.1 eq) and an aqueous formaldehyde solution (36%, 1.4 eq) in dichloromethane is stirred at room temperature for 0.5-2 h. After cooling to 0° C. sodium triacetoxyborohydride (1.6 eq) is added. The cooling bath is removed and the mixture is stirred at room temperature for 2-16 h. The reaction is quenched by the addition of 1 M aqueous sodium hydroxide solution. The aqueous layer is extracted with ethyl acetate. The combined organic layers are dried over anhydrous sodium sulfate and concentrated in vacuo. Flash chromatography gives a compound of formula I-3, a compound of formula I in which R$^1$ is methyl.

EXAMPLE 1 trans-8-Chloro-1-(4-oxazol-2-yl-cyclohexyl)-4H,6H-2,3,5,10b-tetraaza-benzo[e]azulene-5-carboxylic acid tert-butyl ester The title compound was obtained as light yellow solid in 28% yield according to general procedure (XV).
Hydrazide: trans-4-Oxazol-2-yl-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 470 ([M+H]$^+$)

EXAMPLE 2 trans-8-Chloro-1-(4-oxazol-2-yl-cyclohexyl)-5,6-dihydro-4H-2,3,5,10b-tetraaza-benzo[e]azulene The title compound was obtained as yellow solid in quantitative yield from trans-8-chloro-1-(4-oxazol-2-yl-cyclohexyl)-4H,6H-2,3,5,10b-tetraaza-benzo[e]azulene-5-carboxylic acid tert-butyl ester according to general procedure (XVI-b). MS m/e: 370 ([M+H]$^+$).

EXAMPLE 3 trans-8-Chloro-5-methyl-1-(4-oxazol-2-yl-cyclohexyl)-5,6-dihydro-4H-2,3,5,10b-tetraaza-benzo[e]azulene The title compound was obtained as white solid in 63% yield from trans-8-chloro-1-(4-oxazol-2-yl-cyclohexyl)-5,6-dihydro-4H-2,3,5,10b-tetraaza-benzo[e]azulene and paraformaldehyde according to general procedure (XVII-a). MS m/e: 384 ([M+H]$^+$).

EXAMPLE 4 trans-8-Chloro-1-[4-(4-methyl-oxazol-2-yl)-cyclohexyl]-4H,6H-2,3,5,10b-tetraaza-benzo[e]azulene-5-carboxylic acid tert-butyl ester The title compound was obtained as white solid in 71% yield according to general procedure (XV).
Hydrazide: trans-4-(4-Methyl-oxazol-2-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 484 ([M+H]$^+$)

EXAMPLE 5 trans-8-Chloro-1-[4-(4-methyl-oxazol-2-yl)-cyclohexyl]-5,6-dihydro-4H-2,3,5,10b-tetraaza-benzo[e]azulene The title compound was obtained as white solid in quantitative yield from trans-8-chloro-1-[4-(4-methyl-oxazol-2-yl)-cyclohexyl]-4H,6H-2,3,5,10b-tetraaza-benzo[e]azulene-5-carboxylic acid tert-butyl ester according to general procedure (XVI-b). MS m/e: 384 ([M+H]$^+$).

EXAMPLE 6 trans-8-Chloro-5-methyl-1-[4-(4-methyl-oxazol-2-yl)-cyclohexyl]-5,6-dihydro-4H-2,3,5,10b-tetraaza-benzo[e]azulene The title compound was obtained as off-white solid in 67% yield from trans-8-chloro-1-[4-(4-methyl-oxazol-2-yl)-cyclohexyl]-5,6-dihydro-4H-2,3,5,10b-tetraaza-benzo[e]azulene and paraformaldehyde according to general procedure (XVII-a). MS m/e: 398 ([M+H]$^+$).

EXAMPLE 7 trans-8-Chloro-1-[4-(5-methyl-oxazol-2-yl)-cyclohexyl]-4H,6H-2,3,5,10b-tetraaza-benzo[e]azulene-5-carboxylic acid tert-butyl ester The title compound was obtained as white solid in 57% yield according to general procedure (XV).
Hydrazide: trans-4-(5-Methyl-oxazol-2-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 484 ([M+H]$^+$)

EXAMPLE 8 trans-8-Chloro-1-[4-(5-methyl-oxazol-2-yl)-cyclohexyl]-5,6-dihydro-4H-2,3,5,10b-tetraaza-benzo[e]azulene The title compound was obtained as off-white solid in quantitative yield from trans-8-chloro-1-[4-(5-methyl-oxazol-2-yl)-cyclohexyl]-4H,6H-2,3,5,10b-tetraaza-benzo[e]azulene-5-carboxylic acid tert-butyl ester according to general procedure (XVI-b). MS m/e: 384 ([M+H]$^+$).

EXAMPLE 9 trans-8-Chloro-5-methyl-1-[4-(5-methyl-oxazol-2-yl)-cyclohexyl]-5,6-dihydro-4H-2,3,5,10b-tetraaza-benzo[e]azulene The title compound was obtained as white solid in 75% yield from trans-8-chloro-1-[4-(5-methyl-oxazol-2-yl)-cyclohexyl]-5,6-dihydro-4H-2,3,5,10b-tetraaza-benzo[e]azulene and paraformaldehyde according to general procedure (XVII-a). MS m/e: 398 ([M+H]$^+$).

EXAMPLE 10 trans-8-Chloro-1-[4-(4,5-dimethyl-oxazol-2-yl)-cyclohexyl]-4H,6H-2,3,5,10b-tetraaza-benzo[e]azulene-5-carboxylic acid tert-butyl ester The title compound was obtained as white solid in 59% yield according to general procedure (XV).
Hydrazide: trans-4-(4,5-Dimethyl-oxazol-2-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 498 ([M+H]$^+$)

EXAMPLE 11 trans-8-Chloro-1-[4-(4,5-dimethyl-oxazol-2-yl)-cyclohexyl]-5,6-dihydro-4H-2,3,5,10b-tetraaza-benzo[e]azulene The title compound was obtained as white solid in 84% yield from trans-8-chloro-1-[4-(4,5-dimethyl-oxazol-2-yl)-cyclohexyl]-4H,6H-2,3,5,10b-tetraaza-benzo[e]azulene-5-carboxylic acid tert-butyl ester according to general procedure (XVI-b). MS m/e: 398 ([M+H]$^+$).

EXAMPLE 12 trans-8-Chloro-5-methyl-1-[4-(4,5-dimethyl-oxazol-2-yl)-cyclohexyl]-5,6-dihydro-4H-2,3,5,10b-tetraaza-benzo[e]azulene The title compound was obtained as white solid in 59% yield from trans-8-chloro-1-[4-(4,5-dimethyl-oxazol-2-yl)-cyclohexyl]-5,6-dihydro-4H-2,3,5,10b-tetraaza-benzo[e]azulene and paraformaldehyde according to general procedure (XVII-a). MS m/e: 412 ([M+H]$^+$).

EXAMPLE 13 trans-8-Chloro-1-(4-thiazol-2-yl-cyclohexyl)-4H,6H-2,3,5,10b-tetraaza-benzo[e]azulene-5-carboxylic acid tert-butyl ester The title compound was obtained as off-white solid in 57% yield according to general procedure (XV).
Hydrazide: trans-4-Thiazol-2-yl-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 486 ([M+H]$^+$)

EXAMPLE 14 trans-8-Chloro-1-(4-thiazol-2-yl-cyclohexyl)-5,6-dihydro-4H-2,3,5,10b-tetraaza-benzo[e]azulene The title compound was obtained as white solid in quantitative yield from trans-8-chloro-1-(4-thiazol-2-yl-cyclohexyl)-4H,6H-2,3,5,10b-tetraaza-benzo[e]azulene-5-carboxylic acid tert-butyl ester according to general procedure (XVI-b). MS m/e: 386 ([M+H]$^+$).

EXAMPLE 15 trans-8-Chloro-5-methyl-1-(4-thiazol-2-yl-cyclohexyl)-5,6-dihydro-4H-2,3,5,10b-tetraaza-benzo[e]azulene The title compound was obtained as white solid in 50% yield from trans-8-chloro-1-(4-thiazol-2-yl-cyclohexyl)-5,6-dihydro-4H-2,3,5,10b-tetraaza-benzo[e]azulene and paraformaldehyde according to general procedure (XVII-a). MS m/e: 400 ([M+H]$^+$).

EXAMPLE 16 trans-8-Chloro-1-[4-(4-methyl-thiazol-2-yl)-cyclohexyl]-4H,6H-2,3,5,10b-tetraaza-benzo[e]azulene-5-carboxylic acid tert-butyl ester The title compound was obtained as white solid in 52% yield according to general procedure (XV).
Hydrazide: trans-4-(4-Methyl-thiazol-2-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 500 ([M+H]$^+$)

EXAMPLE 17 trans-8-Chloro-1-[4-(4-methyl-thiazol-2-yl)-cyclohexyl]-5,6-dihydro-4H-2,3,5,10b-tetraaza-benzo[e]azulene The title compound was obtained as white solid in 91% yield from trans-8-chloro-1-[4-(4-methyl-thiazol-2-yl)-cyclohexyl]-4H,6H-2,3,5,10b-tetraaza-benzo[e]azulene-5-carboxylic acid tert-butyl ester according to general procedure (XVI-b). MS m/e: 400 ([M+H]$^+$).

EXAMPLE 18 trans-8-Chloro-5-methyl-1-[4-(4-methyl-thiazol-2-yl)-cyclohexyl]-5,6-dihydro-4H-2,3,5,10b-tetraaza-benzo[e]azulene The title compound was obtained as white solid in 55% yield from trans-8-chloro-1-[4-(4-methyl-thiazol-2-yl)-cyclohexyl]-5,6-dihydro-4H-2,3,5,10b-tetraaza-benzo[e]azulene and paraformaldehyde according to general procedure (XVII-a). MS m/e: 414 ([M+H]$^+$).

EXAMPLE 19 trans-8-Chloro-1-[4-(2-methyl-thiazol-4-yl)-cyclohexyl]-4H,6H-2,3,5,10b-tetraaza-benzo[e]azulene-5-carboxylic acid tert-butyl ester The title compound was obtained as white solid in 72% yield according to general procedure (XV).
Hydrazide: trans-4-(2-Methyl-thiazol-4-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 500 ([M+H]$^+$)

EXAMPLE 20 trans-8-Chloro-1-[4-(2-methyl-thiazol-4-yl)-cyclohexyl]-5,6-dihydro-4H-2,3,5,10b-tetraaza-benzo[e]azulene The title compound was obtained as white solid in 93% yield from trans-8-chloro-1-[4-(2-methyl-thiazol-4-yl)-cyclohexyl]-4H,6H-2,3,5,10b-tetraaza-benzo[e]azulene-5-carboxylic acid tert-butyl ester according to general procedure (XVI-b). MS m/e: 400 ([M+H]$^+$).

EXAMPLE 21 trans-8-Chloro-5-methyl-1-[4-(2-methyl-thiazol-4-yl)-cyclohexyl]-5,6-dihydro-4H-2,3,5,10b-tetraaza-benzo[e]azulene The title compound was obtained as white solid in 67% yield from trans-8-chloro-1-[4-(2-methyl-thiazol-4-yl)-cyclohexyl]-5,6-dihydro-4H-2,3,5,10b-tetraaza-benzo[e]azulene and paraformaldehyde according to general procedure (XVII-a). MS m/e: 414 ([M+H]$^+$).

EXAMPLE 22 trans-8-Chloro-1-[4-(5-methyl-isoxazol-3-yl)-cyclohexyl]-4H,6H-2,3,5,10b-tetraaza-benzo[e]azulene-5-carboxylic acid tert-butyl ester The title compound was obtained as white solid in 39% yield according to general procedure (XV).
Hydrazide: trans-4-(5-Methyl-isoxazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 484 ([M+H]$^+$)

EXAMPLE 23 trans-8-Chloro-1-[4-(5-methyl-isoxazol-3-yl)-cyclohexyl]-5,6-dihydro-4H-2,3,5,10b-tetraaza-benzo[e]azulene hydrochloride The title compound was obtained as white solid in quantitative yield from trans-8-chloro-1-[4-(5-methyl-isoxazol-3-yl)-cyclohexyl]-4H,6H-2,3,5,10b-tetraaza-benzo[e]azulene-5-carboxylic acid tert-butyl ester according to general procedure (XVI-a). MS m/e: 384 ([M+H]$^+$).

EXAMPLE 24 trans-8-Chloro-1-[4-(5-methyl-isoxazol-3-yl)-cyclohexyl]-5-methyl-5,6-dihydro-4H-2,3,5,10b-tetraaza-benzo[e]azulene The title compound was obtained as white solid in 54% yield from trans-8-chloro-1-[4-(5-methyl-isoxazol-3-yl)-cyclohexyl]-5,6-dihydro-4H-2,3,5,10b-tetraaza-benzo[e]azulene hydrochloride and paraformaldehyde according to general procedure (XVII-a). MS m/e: 398 ([M+H]$^+$).

EXAMPLE 25 trans-8-Chloro-5-ethyl-1-[4-(5-methyl-isoxazol-3-yl)-cyclohexyl]-5,6-dihydro-4H-2,3,5,10b-tetraaza-benzo[e]azulene The title compound was obtained as light brown solid in 11% yield from trans-8-chloro-1-[4-(5-methyl-isoxazol-3-yl)-cyclohexyl]-5,6-dihydro-4H-2,3,5,10b-tetraaza-benzo[e]azulene and acetaldehyde according to general procedure (XVII-b). MS m/e: 412 ([M+H]$^+$).

EXAMPLE 26 trans-8-Chloro-5-isoproyl-1-[4-(5-methyl-isoxazol-3-yl)-cyclohexyl]-5,6-dihydro-4H-2,3,5,10b-tetraaza-benzo[e]azulene The title compound was obtained as white solid in 69% yield from trans-8-chloro-1-[4-(5-methyl-isoxazol-3-yl)-cyclohexyl]-5,6-dihydro-4H-2,3,5,10b-tetraaza-benzo[e]azulene and acetone according to general procedure (XVII-b). MS m/e: 426 ([M+H]$^+$).

EXAMPLE 27 trans-8-Chloro-5-cyclobutyl-1-[4-(5-methyl-isoxazol-3-yl)-cyclohexyl]-5,6-dihydro-4H-2,3,5,10b-tetraaza-benzo[e]azulene The title compound was obtained as white solid in 40% yield from trans-8-chloro-1-[4-(5-methyl-isoxazol-3-yl)-cyclohexyl]-5,6-dihydro-4H-2,3,5,10b-tetraaza-benzo[e]azulene and cyclobutanone according to general procedure (XVII-b). MS m/e: 437 ([M+H]$^+$).

EXAMPLE 28 trans-8-Chloro-5-(2,2-difluoro-ethyl)-1-[4-(5-methyl-isoxazol-3-yl)-cyclohexyl]-5,6-dihydro-4H-2,3,5,10b-tetraaza-benzo[e]azulene A mixture of trans-8-chloro-1-[4-(5-methyl-isoxazol-3-yl)-cyclohexyl]-5,6-dihydro-4H-2,3,5,10b-tetraaza-benzo[e]azulene (50.0 mg, 0.130 mmol), cesium carbonate (84.9 mg, 0.261 mmol) and 2,2-difluoroethyl trifluoromethanesulfonate (41.8 mg, 0.195 mmol) in acetonitrile (1.3 ml) was heated at 70° C. for 20 h. After cooling to room temperature the reaction mixture was partitioned between 1 M aqueous sodium hydroxide solution (2 ml) and ethyl acetate (5 ml). The layers were separated. The aqueous layer was extracted with three 5-ml portions of ethyl acetate. The combined organic layers were concentrated in vacuo. Preparative RP-HPLC with water (0.05% formic acid)/methanol as eluent gave the title compound (13 mg, 21%) as off-white solid. MS m/e: 448 ([M+H]$^+$).

EXAMPLE 29 trans-8-Chloro-5-(2-methoxy-ethyl)-1-[4-(5-methyl-isoxazol-3-yl)-cyclohexyl]-5,6-dihydro-4H-2,3,5,10b-tetraaza-benzo[e]azulene A mixture of trans-8-chloro-1-[4-(5-methyl-isoxazol-3-yl)-cyclohexyl]-5,6-dihydro-4H-2,3,5,10b-tetraaza-benzo[e]azulene (50 mg, 0.13 mmol), cesium carbonate (85 mg, 0.26 mmol) and 2-bromoethyl methyl ether (0.025 ml, 0.26 mmol) in acetonitrile (1.3 ml) was heated at 70° C. for 20 h. After cooling to room temperature the reaction mixture was partitioned between 1 M aqueous sodium hydroxide solution (2 ml) and ethyl acetate (5 ml). The layers were separated. The aqueous layer was extracted with three 5-ml portions of ethyl acetate. The combined organic layers were concentrated in vacuo. Preparative RP-HPLC with water (0.05% formic acid)/methanol as eluent gave the title compound (17 mg, 29%) as off-white solid. MS m/e: 442 ([M+H]$^+$).

EXAMPLE 30 trans-(2-{8-Chloro-1-[4-(5-methyl-isoxazol-3-yl)-cyclohexyl]-4H,6H-2,3,5,10b-tetraaza-benzo[e]azulen-5-yl}-ethyl)-methyl-amine A mixture of trans-8-chloro-1-[4-(5-methyl-isoxazol-3-yl)-cyclohexyl]-5,6-dihydro-4H-2,3,5,10b-tetraaza-benzo[e]azulene (50.0 mg, 0.130 mmol), cesium carbonate (170 mg, 0.521 mmol) and 2-methylaminoethyl chloride hydrochloride (67.7 mg, 0.521 mmol) in acetonitrile (1.3 ml) was heated at 70° C. for 20 h. After cooling to room temperature the reaction mixture was partitioned between 1 M aqueous sodium hydroxide solution (2 ml) and ethyl acetate (5 ml). The layers were separated. The aqueous layer was extracted with three 5-ml portions of ethyl acetate. The combined organic layers were concentrated in vacuo. Preparative RP-HPLC with water (0.05% formic acid)/methanol as eluent gave the hydroformate salt of the title compound, which was liberated by filtration over aminopropyl modified silica gel (10 g) with methanol (20 ml) as eluent. The filtrate was concentrated to dryness. The residue was redissolved in ethyl acetate, filtrated over cotton wool and concentrated to dryness to give the title compound (38 mg, 66%) as off-white solid. MS m/e: 441 ([M+H]$^+$).

EXAMPLE 31 trans-1-{8-Chloro-1-[4-(5-methyl-isoxazol-3-yl)-cyclohexyl]-4H,6H-2,3,5,10b-tetraaza-benzo[e]azulen-5-yl}-ethanone To a solution of trans-8-chloro-1-[4-(5-methyl-isoxazol-3-yl)-cyclohexyl]-5,6-dihydro-4H-2,3,5,10b-tetraaza-benzo[e]azulene (50 mg, 0.13 mmol) and triethylamine (0.036 ml, 0.26 mmol) in dichloromethane (1.3 ml) was added acetyl chloride (0.019 ml, 0.26 mmol) at room temperature. Stirring for 45 minutes was followed by quenching with methanol (0.5 ml). The mixture was concentrated in vacuo. Preparative RP-HPLC with water (0.05% formic acid)/methanol as eluent gave the title compound (24 mg, 43%) as white solid. MS m/e: 426 ([M+H]$^+$).

EXAMPLE 32 trans-1-{8-Chloro-1-[4-(5-methyl-isoxazol-3-yl)-cyclohexyl]-4H,6H-2,3,5,10b-tetraaza-benzo[e]azulen-5-yl}-2-hydroxy-ethanone A solution of glycolic acid (11.9 mg, 0.156 mmol) and HATU (59.4 mg, 0.156 mmol) in N,N-dimethylformamide (1.0 ml) was stirred for 5 minutes at room temperature. trans-8-Chloro-1-[4-(5-methyl-isoxazol-3-yl)-cyclohexyl]-5,6-dihydro-4H-2,3,5,10b-tetraaza-benzo[e]azulene (50.0 mg, 0.130 mmol) and N-ethyldiisopropylamine (0.055 ml, 0.31 mmol) were added consecutively. The reaction mixture was stirred for 1 h. Preparative RP-HPLC with water (0.05% formic acid)/methanol as eluent gave the title compound (43 mg, 75%) as light yellow solid. MS m/e: 442 ([M+H]$^+$).

EXAMPLE 33 trans-1-{8-Chloro-1-[4-(5-methyl-isoxazol-3-yl)-cyclohexyl]-4H,6H-2,3,5,10b-tetraaza-benzo[e]azulen-5-yl}-2-dimethylamino-ethanone hydroformate A solution of N,N-dimethylglycine (16.1 mg, 0.156 mmol) and HATU (59.4 mg, 0.156 mmol) in N,N-dimethylformamide (1.0 ml) was stirred for 5 minutes at room temperature. trans-8-Chloro-1-[4-(5-methyl-isoxazol-3-yl)-cyclohexyl]-5,6-dihydro-4H-2,3,5,10b-tetraaza-benzo[e]azulene (50.0 mg, 0.130 mmol) and N-ethyl diisopropylamine (0.055 ml, 0.31 mmol) were added consecutively. The reaction mixture was stirred for 1 h. Preparative RP-HPLC with water (0.05% formic acid)/methanol as eluent gave the title compound (51 mg, 76%) as off-white solid. MS m/e: 469 ([M+H]$^+$).

EXAMPLE 34 trans-8-Chloro-5-methanesulfonyl-1-[4-(5-methyl-isoxazol-3-yl)-cyclohexyl]-5,6-dihydro-4H-2,3,5,10b-tetraaza-benzo[e]azulene To a solution of trans-8-chloro-1-[4-(5-methyl-isoxazol-3-yl)-cyclohexyl]-5,6-dihydro-4H-2,3,5,10b-tetraaza-benzo[e]azulene (50 mg, 0.13 mmol) and triethylamine (0.036 ml, 0.26 mmol) in dichloromethane (1.3 ml) was added methanesulfonyl chloride (0.020 ml, 0.26 mmol) at room temperature. Stirring for 45 minutes was followed by quenching with methanol (0.5 ml). The mixture was concentrated in vacuo. Preparative RP-HPLC with water (0.05% formic acid)/methanol as eluent gave the title compound (37 mg, 62%) as white solid. MS m/e: 462 ([M+H]$^+$).

EXAMPLE 35 trans-8-Chloro-1-[4-(5-methyl-isoxazol-3-yl)-cyclohexyl]-4H,6H-2,3,5,10b-tetraaza-benzo[e]azulene-5-sulfonic acid dimethylamide To a solution of trans-8-chloro-1-[4-(5-methyl-isoxazol-3-yl)-cyclohexyl]-5,6-dihydro-4H-2,3,5,10b-tetraaza-benzo[e]azulene (50 mg, 0.13 mmol) and triethylamine (0.036 ml, 0.26 mmol) in dichloromethane (1.3 ml) was added sulfamoyl chloride (0.028 ml, 0.26 mmol) at room temperature. Stirring for 20 h was followed by quenching with methanol (0.5 ml). The mixture was concentrated in vacuo. Preparative RP-HPLC with water (0.05% formic acid)/methanol as eluent gave the title compound (42 mg, 66%) as white solid. MS m/e: 491 ([M+H]$^+$).

EXAMPLE 36 trans-8-Fluoro-1-[4-(5-methyl-isoxazol-3-yl)-cyclohexyl]-4H,6H-2,3,5,10b-tetraaza-benzo[e]azulene-5-carboxylic acid tert-butyl ester The title compound was obtained as white solid in 73% yield according to general procedure (XV).
Hydrazide: trans-4-(5-Methyl-isoxazol-3-yl)-cyclohexanecarboxylic acid hydrazide
Thiolactam: 7-Fluoro-2-thioxo-1,2,3,5-tetrahydro-benzo[e][1,4]diazepine-4-carboxylic acid tert-butyl ester. MS m/e: 468 ([M+H]$^+$)

EXAMPLE 37 trans-8-Fluoro-1-[4-(5-methyl-isoxazol-3-yl)-cyclohexyl]-5,6-dihydro-4H-2,3,5,10b-tetraaza-benzo[e]azulene The title compound was obtained as off-white solid in 72% yield from trans-8-fluoro-1-[4-(5-methyl-isoxazol-3-yl)-cyclohexyl]-4H,6H-2,3,5,10b-tetraaza-benzo[e]azulene-5-carboxylic acid tert-butyl ester according to general procedure (XVI-b). MS m/e: 368 ([M+H]$^+$).

EXAMPLE 38 trans-8-Fluoro-1-[4-(5-methyl-isoxazol-3-yl)-cyclohexyl]-5-methyl-5,6-dihydro-4H-2,3,5,10b-tetraaza-benzo[e]azulene The title compound was obtained as white solid in 78% yield from trans-8-fluoro-1-[4-(5-methyl-isoxazol-3-yl)-cyclohexyl]-5,6-dihydro-4H-2,3,5,10b-tetraaza-benzo[e]azulene hydrochloride and paraformaldehyde according to general procedure (XVII-a). MS m/e: 382 ([M+H]$^+$).

EXAMPLE 39 trans-8-Chloro-1-[4-(4,5-dimethyl-isoxazol-3-yl)-cyclohexyl]-4H,6H-2,3,5,10b-tetraaza-benzo[e]azulene-5-carboxylic acid tert-butyl ester The title compound was obtained as white solid in 58% yield according to general procedure (XV).
Hydrazide: trans-4-(4,5-Dimethyl-isoxazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 498 ([M+H]$^+$)

EXAMPLE 40 trans-8-Chloro-1-[4-(4,5-dimethyl-isoxazol-3-yl)-cyclohexyl]-5,6-dihydro-4H-2,3,5,10b-tetraaza-benzo[e]azulene The title compound was obtained as off-white solid in 87% yield from trans-8-chloro-1-[4-(4,5-dimethyl-isoxazol-3-yl)- cyclohexyl]-4H,6H-2,3,5,10b-tetraaza-benzo[e]azulene-5-carboxylic acid tert-butyl ester according to general procedure (XVI-b). MS m/e: 398 ([M+H]+).

EXAMPLE 41 trans-8-Chloro-1-[4-(4,5-dimethyl-isoxazol-3-yl)-cyclohexyl]-5-methyl-5,6-dihydro-4H-2,3,5,10b-tetraaza-benzo[e]azulene The title compound was obtained as white solid in 88% yield from trans-8-chloro-1-[4-(4,5-dimethyl-isoxazol-3-yl)-cyclohexyl]-5,6-dihydro-4H-2,3,5,10b-tetraaza-benzo[e]azulene and paraformaldehyde according to general procedure (XVII-a). MS m/e: 412 ([M+H]+).

EXAMPLE 42 trans-8-Chloro-1-[4-(4-chloro-5-methyl-isoxazol-3-yl)-cyclohexyl]-4H,6H-2,3,5,10b-tetraaza-benzo[e]azulene-5-carboxylic acid tert-butyl ester The title compound was obtained as off-white solid in 75% yield according to general procedure (XV).
Hydrazide: trans-4-(4-Chloro-5-methyl-isoxazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 518 ([M+H]+)

EXAMPLE 43 trans-8-Chloro-1-[4-(4-chloro-5-methyl-isoxazol-3-yl)-cyclohexyl]-5,6-dihydro-4H-2,3,5,10b-tetraaza-benzo[e]azulene The title compound was obtained as off-white solid in quantitative yield from trans-8-chloro-1-[4-(4-chloro-5-methyl-isoxazol-3-yl)-cyclohexyl]-4H,6H-2,3,5,10b-tetraaza-benzo[e]azulene-5-carboxylic acid tert-butyl ester according to general procedure (XVI-b). MS m/e: 418 ([M+H]+).

EXAMPLE 44 trans-8-Chloro-1-[4-(4-chloro-5-methyl-isoxazol-3-yl)-cyclohexyl]-5-methyl-5,6-dihydro-4H-2,3,5,10b-tetraaza-benzo[e]azulene The title compound was obtained as white solid in 81% yield from trans-8-chloro-1-[4-(4-chloro-5-methyl-isoxazol-3-yl)-cyclohexyl]-5,6-dihydro-4H-2,3,5,10b-tetraaza-benzo[e]azulene and paraformaldehyde according to general procedure (XVII-a). MS m/e: 432 ([M+H]+).

EXAMPLE 45 trans-8-Chloro-1-[4-(4-fluoro-5-methyl-isoxazol-3-yl)-cyclohexyl]-4H,6H-2,3,5,10b-tetraaza-benzo[e]azulene-5-carboxylic acid tert-butyl ester The title compound was obtained as light yellow solid in 28% yield according to general procedure (XV).
Hydrazide: trans-4-(4-Fluoro-5-methyl-isoxazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 502 ([M+H]+)

EXAMPLE 46 trans-8-Chloro-1-[4-(4-fluoro-5-methyl-isoxazol-3-yl)-cyclohexyl]-5,6-dihydro-4H-2,3,5,10b-tetraaza-benzo[e]azulene The title compound was obtained as off-white solid in quantitative yield from trans-8-chloro-1-[4-(4-fluoro-5-methyl-isoxazol-3-yl)-cyclohexyl]-4H,6H-2,3,5,10b-tetraaza-benzo[e]azulene-5-carboxylic acid tert-butyl ester according to general procedure (XVI-b). MS m/e: 402 ([M+H]+).

EXAMPLE 47 trans-8-Chloro-1-[4-(4-fluoro-5-methyl-isoxazol-3-yl)-cyclohexyl]-5-methyl-5,6-dihydro-4H-2,3,5,10b-tetraaza-benzo[e]azulene The title compound was obtained as off-white solid in 60% yield from trans-8-chloro-1-[4-(4-fluoro-5-methyl-isoxazol-3-yl)-cyclohexyl]-5,6-dihydro-4H-2,3,5,10b-tetraaza-benzo[e]azulene and paraformaldehyde according to general procedure (XVII-a). MS m/e: 416 ([M+H]+).

EXAMPLE 48 cis-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester and

EXAMPLE 49 trans-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester cis-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester and trans-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester were obtained according to general procedure (XV) after chromatographic separation.
Hydrazide: cis/trans-4-(5-Ethyl-isoxazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester
cis-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester was obtained as white solid in 39% yield. MS m/e: 498 ([M+H]+)
trans-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester was obtained as white solid in 39% yield. MS m/e: 498 ([M+H]+)

EXAMPLE 50 cis-8-Chloro-1-[4-(5-ethyl-isoxazol-3-yl)-cyclohexyl]-5,6-dihydro-4H-2,3,5,10b-tetraaza-benzo[e]azulene hydrochloride The title compound was obtained as white solid in quantitative yield from cis-8-chloro-1-[4-(5-ethyl-isoxazol-3-yl)-cyclohexyl]-4H,6H-2,3,5,10b-tetraaza-benzo[e]azulene-5-carboxylic acid tert-butyl ester according to general procedure (XVI-a). MS m/e: 398 ([M+H]+).

EXAMPLE 51 cis-8-Chloro-1-[4-(5-ethyl-isoxazol-3-yl)-cyclohexyl]-5-methyl-5,6-dihydro-4H-2,3,5,10b-tetraaza-benzo[e]azulene The title compound was obtained as white solid in 34% yield from cis-8-chloro-1-[4-(5-ethyl-isoxazol-3-yl)-cyclohexyl]-5,6-dihydro-4H-2,3,5,10b-tetraaza-benzo[e]azulene hydrochloride and paraformaldehyde according to general procedure (XVII-a). MS m/e: 412 ([M+H]$^+$).

EXAMPLE 52 trans-8-Chloro-1-[4-(5-ethyl-isoxazol-3-yl)-cyclohexyl]-5,6-dihydro-4H-2,3,5,10b-tetraaza-benzo[e]azulene hydrochloride The title compound was obtained as white solid in quantitative yield from trans-8-chloro-1-[4-(5-ethyl-isoxazol-3-yl)-cyclohexyl]-4H,6H-2,3,5,10b-tetraaza-benzo[e]azulene-5-carboxylic acid tert-butyl ester according to general procedure (XVI-a). MS m/e: 398 ([M+H]$^+$).

EXAMPLE 53 trans-8-Chloro-1-[4-(5-ethyl-isoxazol-3-yl)-cyclohexyl]-5-methyl-5,6-dihydro-4H-2,3,5,10b-tetraaza-benzo[e]azulene The title compound was obtained as white solid in 68% yield from trans-8-chloro-1-[4-(5-ethyl-isoxazol-3-yl)-cyclohexyl]-5,6-dihydro-4H-2,3,5,10b-tetraaza-benzo[e]azulene hydrochloride and paraformaldehyde according to general procedure (XVII-a). MS m/e: 412 ([M+H]$^+$).

EXAMPLE 54 trans-8-Chloro-1-[4-(4,5,6,7-tetrahydro-benzo[d]isoxazol-3-yl)-cyclohexyl]-4H,6H-2,3,5,10b-tetraaza-benzo[e]azulene-5-carboxylic acid tert-butyl ester The title compound was obtained as light yellow solid in 77% yield according to general procedure (XV).
Hydrazide: trans-4-(4,5,6,7-Tetrahydro-benzo[d]isoxazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 524 ([M+H]$^+$)

EXAMPLE 55 trans-8-Chloro-1-[4-(4,5,6,7-tetrahydro-benzo[d]isoxazol-3-yl)-cyclohexyl]-5,6-dihydro-4H-2,3,5,10b-tetraaza-benzo[e]azulene The title compound was obtained as light yellow solid in 84% yield from trans-8-chloro-1-[4-(4,5,6,7-tetrahydro-benzo[d]isoxazol-3-yl)-cyclohexyl]-4H,6H-2,3,5,10b-tetraaza-benzo[e]azulene-5-carboxylic acid tert-butyl ester according to general procedure (XVI-a). MS m/e: 424 ([M+H]$^+$).

EXAMPLE 56 trans-8-Chloro-5-methyl-1-[4-(4,5,6,7-tetrahydro-benzo[d]isoxazol-3-yl)-cyclohexyl]-5,6-dihydro-4H-2,3,5,10b-tetraaza-benzo[e]azulene The title compound was obtained as white solid in 41% yield from trans-8-chloro-1-[4-(4,5,6,7-tetrahydro-benzo[d]isoxazol-3-yl)-cyclohexyl]-5,6-dihydro-4H-2,3,5,10b-tetraaza-benzo[e]azulene and paraformaldehyde according to general procedure (XVII-a). MS m/e: 438 ([M+H]$^+$).

EXAMPLE 57 cis-8-Chloro-1-[4-(4,5,6,7-tetrahydro-benzo[d]isoxazol-3-yl)-cyclohexyl]-4H,6H-2,3,5,10b-tetraaza-benzo[e]azulene-5-carboxylic acid tert-butyl ester The title compound was obtained as light yellow solid in 75% yield according to general procedure (XV).
Hydrazide: cis-4-(4,5,6,7-Tetrahydro-benzo[d]isoxazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 524 ([M+H]$^+$)

EXAMPLE 58 cis-8-Chloro-1-[4-(4,5,6,7-tetrahydro-benzo[d]isoxazol-3-yl)-cyclohexyl]-5,6-dihydro-4H-2,3,5,10b-tetraaza-benzo[e]azulene The title compound was obtained as off-white solid in quantitative yield from cis-8-chloro-1-[4-(4,5,6,7-tetrahydro-benzo[d]isoxazol-3-yl)-cyclohexyl]-4H,6H-2,3,5,10b-tetraaza-benzo[e]azulene-5-carboxylic acid tert-butyl ester according to general procedure (XVI-a). MS m/e: 424 ([M+H]$^+$).

EXAMPLE 59 cis-8-Chloro-5-methyl-1-[4-(4,5,6,7-tetrahydro-benzo[d]isoxazol-3-yl)-cyclohexyl]-5,6-dihydro-4H-2,3,5,10b-tetraaza-benzo[e]azulene The title compound was obtained as white solid in 57% yield from cis-8-chloro-1-[4-(4,5,6,7-tetrahydro-benzo[d]isoxazol-3-yl)-cyclohexyl]-5,6-dihydro-4H-2,3,5,10b-tetraaza-benzo[e]azulene and paraformaldehyde according to general procedure (XVII-a). MS m/e: 438 ([M+H]$^+$).

EXAMPLE 60 trans-8-Chloro-1-[4-(4,5,6,7-tetrahydro-benzo[c]isoxazol-3-yl)-cyclohexyl]-4H,6H-2,3,5,10b-tetraaza-benzo[e]azulene-5-carboxylic acid tert-butyl ester The title compound was obtained as white solid in 86% yield according to general procedure (XV).
Hydrazide: trans-4-(4,5,6,7-Tetrahydro-benzo[c]isoxazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 524 ([M+H]$^+$)

EXAMPLE 61 trans-8-Chloro-1-[4-(4,5,6,7-tetrahydro-benzo[c]
isoxazol-3-yl)-cyclohexyl]-5,6-dihydro-4H-2,3,5,
10b-tetraaza-benzo[e]azulene The title compound was obtained as white solid in 92% yield from trans-8-chloro-1-[4-(4,5,6,7-tetrahydro-benzo[c] isoxazol-3-yl)-cyclohexyl]-4H,6H-2,3,5,10b-tetraaza-benzo [e]azulene-5-carboxylic acid tert-butyl ester according to general procedure (XVI-a). MS m/e: 424 ([M+H]$^+$).

EXAMPLE 62 trans-8-Chloro-5-methyl-1-[4-(4,5,6,7-tetrahydro-
benzo[c]isoxazol-3-yl)-cyclohexyl]-5,6-dihydro-4H-
2,3,5,10b-tetraaza-benzo[e]azulene The title compound was obtained as white solid in 81% yield from trans-8-chloro-1-[4-(4,5,6,7-tetrahydro-benzo[c] isoxazol-3-yl)-cyclohexyl]-5,6-dihydro-4H-2,3,5,10b-tetraaza-benzo[e]azulene and paraformaldehyde according to general procedure (XVII-a). MS m/e: 438 ([M+H]$^+$).

EXAMPLE 63 trans-8-Chloro-1-[4-(5-methyl-[1,3,4]oxadiazol-2-
yl)-cyclohexyl]-4H,6H-2,3,5,10b-tetraaza-benzo[e]
azulene-5-carboxylic acid tert-butyl ester The title compound was obtained as off-white solid in 23% yield according to general procedure (XV).
Hydrazide: trans-4-(5-Methyl-[1,3,4]oxadiazol-2-yl)-cyclohexanecarboxylic acid hydrazide
Thiolactam: 7-Chloro-2-thioxo-1,2,3,5-tetrahydro-benzo[e] [1,4]diazepine-4-carboxylic acid tert-butyl ester. MS m/e: 485 ([M+H]$^+$)

EXAMPLE 64 trans-8-Chloro-1-[4-(5-methyl-[1,3,4]oxadiazol-2-
yl)-cyclohexyl]-5,6-dihydro-4H-2,3,5,10b-tetraaza-
benzo[e]azulene The title compound was obtained as white solid in quantitative yield from trans-8-chloro-1-[4-(5-methyl-[1,3,4]oxadiazol-2-yl)-cyclohexyl]-4H,6H-2,3,5,10b-tetraaza-benzo [e]azulene-5-carboxylic acid tert-butyl ester according to general procedure (XVI-b). MS m/e: 385 ([M+H]$^+$).

EXAMPLE 65 trans-8-Chloro-5-methyl-1-[4-(5-methyl-[1,3,4]oxa-
diazol-2-yl)-cyclohexyl]-5,6-dihydro-4H-2,3,5,10b-
tetraaza-benzo[e]azulene The title compound was obtained as white solid in 52% yield from trans-8-chloro-1-[4-(5-methyl-[1,3,4]oxadiazol-2-yl)-cyclohexyl]-5,6-dihydro-4H-2,3,5,10b-tetraaza-benzo [e]azulene and paraformaldehyde according to general procedure (XVII-a). MS m/e: 399 ([M+H]$^+$).

EXAMPLE 66 trans-8-Chloro-1-[4-(3-methyl-[1,2,4]oxadiazol-5-
yl)-cyclohexyl]-4H,6H-2,3,5,10b-tetraaza-benzo[e]
azulene-5-carboxylic acid tert-butyl ester The title compound was obtained as off-white solid in 79% yield according to general procedure (XV).
Hydrazide: trans-4-(3-Methyl-[1,2,4]oxadiazol-5-yl)-cyclohexanecarboxylic acid hydrazide
Thiolactam: 7-Chloro-2-thioxo-1,2,3,5-tetrahydro-benzo[e] [1,4]diazepine-4-carboxylic acid tert-butyl ester. MS m/e: 485 ([M+H]$^+$)

EXAMPLE 67 trans-8-Chloro-1-[4-(3-methyl-[1,2,4]oxadiazol-5-
yl)-cyclohexyl]-5,6-dihydro-4H-2,3,5,10b-tetraaza-
benzo[e]azulene hydrochloride The title compound was obtained as white solid in 93% yield from trans-8-chloro-1-[4-(3-methyl-[1,2,4]oxadiazol-5-yl)-cyclohexyl]-4H,6H-2,3,5,10b-tetraaza-benzo[e]azulene-5-carboxylic acid tert-butyl ester according to general procedure (XVI-a). MS m/e: 385 ([M+H]$^+$).

EXAMPLE 68 trans-8-Chloro-5-methyl-1-[4-(3-methyl-[1,2,4]oxa-
diazol-5-yl)-cyclohexyl]-5,6-dihydro-4H-2,3,5,10b-
tetraaza-benzo[e]azulene The title compound was obtained as white solid in 76% yield from trans-8-chloro-1-[4-(3-methyl-[1,2,4]oxadiazol-5-yl)-cyclohexyl]-5,6-dihydro-4H-2,3,5,10b-tetraaza-benzo [e]azulene hydrochloride and paraformaldehyde according to general procedure (XVII-a). MS m/e: 399 ([M+H]$^+$).

EXAMPLE 69 trans-8-Chloro-1-[4-(3-methyl-[1,2,4]thiadiazol-5-
yl)-cyclohexyl]-4H,6H-2,3,5,10b-tetraaza-benzo[e]
azulene-5-carboxylic acid tert-butyl ester The title compound was obtained as light yellow solid in 63% yield according to general procedure (XV).
Hydrazide: trans-4-(3-Methyl-[1,2,4]thiadiazol-5-yl)-cyclohexanecarboxylic acid hydrazide
Thiolactam: 7-Chloro-2-thioxo-1,2,3,5-tetrahydro-benzo[e] [1,4]diazepine-4-carboxylic acid tert-butyl ester. MS m/e: 501 ([M+H]$^+$)

EXAMPLE 70 trans-8-Chloro-1-[4-(3-methyl-[1,2,4]thiadiazol-5-
yl)-cyclohexyl]-5,6-dihydro-4H-2,3,5,10b-tetraaza-
benzo[e]azulene The title compound was obtained as white solid in quantitative yield from trans-8-chloro-1-[4-(3-methyl-[1,2,4]thiadiazol-5-yl)-cyclohexyl]-4H,6H-2,3,5,10b-tetraaza-benzo [e]azulene-5-carboxylic acid tert-butyl ester according to general procedure (XVI-a). MS m/e: 401 ([M+H]$^+$).

EXAMPLE 71 trans-8-Chloro-5-methyl-1-[4-(3-methyl-[1,2,4]thiadiazol-5-yl)-cyclohexyl]-5,6-dihydro-4H-2,3,5,10b-tetraaza-benzo[e]azulene The title compound was obtained as white solid in quantitative yield from trans-8-chloro-1-[4-(3-methyl-[1,2,4]thiadiazol-5-yl)-cyclohexyl]-5,6-dihydro-4H-2,3,5,10b-tetraaza-benzo[e]azulene and paraformaldehyde according to general procedure (XVII-a). MS m/e: 415 ([M+H]$^+$).

EXAMPLE 72 trans-8-Chloro-1-[4-(5-methyl-[1,2,4]oxadiazol-3-yl)-cyclohexyl]-4H,6H-2,3,5,10b-tetraaza-benzo[e]azulene-5-carboxylic acid tert-butyl ester The title compound was obtained as white solid in 87% yield according to general procedure (XV).
Hydrazide: trans-4-(5-Methyl-[1,2,4]oxadiazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 485 ([M+H]$^+$)

EXAMPLE 73 trans-8-Chloro-1-[4-(5-methyl-[1,2,4]oxadiazol-3-yl)-cyclohexyl]-5,6-dihydro-4H-2,3,5,10b-tetraaza-benzo[e]azulene hydrochloride The title compound was obtained as off-white solid in quantitative yield from trans-8-chloro-1-[4-(5-methyl-[1,2,4]oxadiazol-3-yl)-cyclohexyl]-4H,6H-2,3,5,10b-tetraaza-benzo[e]azulene-5-carboxylic acid tert-butyl ester according to general procedure (XVI-a). MS m/e: 385 ([M+H]$^+$).

EXAMPLE 74 trans-8-Chloro-5-methyl-1-[4-(5-methyl-[1,2,4]oxadiazol-3-yl)-cyclohexyl]-5,6-dihydro-4H-2,3,5,10b-tetraaza-benzo[e]azulene The title compound was obtained as white solid in 76% yield from trans-8-chloro-1-[4-(5-methyl-[1,2,4]oxadiazol-3-yl)-cyclohexyl]-5,6-dihydro-4H-2,3,5,10b-tetraaza-benzo[e]azulene hydrochloride and paraformaldehyde according to general procedure (XVII-a). MS m/e: 399 ([M+H]$^+$).

EXAMPLE 75 trans-8-Chloro-5-ethyl-1-[4-(5-methyl-[1,2,4]oxadiazol-3-yl)-cyclohexyl]-5,6-dihydro-4H-2,3,5,10b-tetraaza-benzo[e]azulene The title compound was obtained as white solid in 28% yield from trans-8-chloro-1-[4-(5-methyl-[1,2,4]oxadiazol-3-yl)-cyclohexyl]-5,6-dihydro-4H-2,3,5,10b-tetraaza-benzo[e]azulene hydrochloride and acetaldehyde according to general procedure (XVII-a). MS m/e: 413 ([M+H]$^+$).

EXAMPLE 76 trans-8-Chloro-5-isopropyl-1-[4-(5-methyl-[1,2,4]oxadiazol-3-yl)-cyclohexyl]-5,6-dihydro-4H-2,3,5,10b-tetraaza-benzo[e]azulene The title compound was obtained as white solid in 13% yield from trans-8-chloro-1-[4-(5-methyl-[1,2,4]oxadiazol-3-yl)-cyclohexyl]-5,6-dihydro-4H-2,3,5,10b-tetraaza-benzo[e]azulene hydrochloride and acetone according to general procedure (XVII-a). MS m/e: 427 ([M+H]$^+$).

EXAMPLE 77 trans-8-Chloro-5-cyclobutyl-1-[4-(5-methyl-[1,2,4]oxadiazol-3-yl)-cyclohexyl]-5,6-dihydro-4H-2,3,5,10b-tetraaza-benzo[e]azulene The title compound was obtained as white solid in 27% yield from trans-8-chloro-1-[4-(5-methyl-[1,2,4]oxadiazol-3-yl)-cyclohexyl]-5,6-dihydro-4H-2,3,5,10b-tetraaza-benzo[e]azulene hydrochloride and cyclobutanone according to general procedure (XVII-a). MS m/e: 439 ([M+H]$^+$)

EXAMPLE 78 trans-8-Chloro-5-cyclopentyl-1-[4-(5-methyl-[1,2,4]oxadiazol-3-yl)-cyclohexyl]-5,6-dihydro-4H-2,3,5,10b-tetraaza-benzo[e]azulene The title compound was obtained as white solid in 46% yield from trans-8-chloro-1-[4-(5-methyl-[1,2,4]oxadiazol-3-yl)-cyclohexyl]-5,6-dihydro-4H-2,3,5,10b-tetraaza-benzo[e]azulene hydrochloride and cyclopentanone according to general procedure (XVII-a). MS m/e: 453 ([M+H]$^+$).

EXAMPLE 79 trans-8-Chloro-5-(2,2-difluoro-ethyl)-1-[4-(5-methyl-[1,2,4]oxadiazol-3-yl)-cyclohexyl]-5,6-dihydro-4H-2,3,5,10b-tetraaza-benzo[e]azulene To a mixture of trans-8-chloro-1-[4-(5-methyl-[1,2,4]oxadiazol-3-yl)-cyclohexyl]-5,6-dihydro-4H-2,3,5,10b-tetraaza-benzo[e]azulene hydrochloride (0.100 g, 0.237 mmol) and N-ethyldiisopropylamine (0.122 ml, 0.712 mmol) in dichloromethane (2.4 ml) was added 2,2-difluoroethyl trifluoromethanesulfonate (0.061 g, 0.29 mmol). After stirring for 16 h the reaction mixture was partitioned between ethyl acetate (50 ml) and 0.5 M aqueous sodium hydroxide solution (50 ml). The layers were separated. The aqueous layer was extracted with one 50 ml-portion of ethyl acetate. The combined organic layers were dried over anhydrous sodium sulfate and concentrated in vacuo. Flash-chromatography with n-heptane/2-propanol as eluent gave the title compound (0.031 g, 33%) as colorless solid. MS m/e: 449 ([M+H]$^+$).

EXAMPLE 80 trans-1-{8-Chloro-1-[4-(5-methyl-[1,2,4]oxadiazol-3-yl)-cyclohexyl]-4H,6H-2,3,5,10b-tetraaza-benzo[e]azulen-5-yl}-ethanone To a solution of trans-8-chloro-1-[4-(5-methyl-[1,2,4]oxadiazol-3-yl)-cyclohexyl]-5,6-dihydro-4H-2,3,5,10b-tetraaza-benzo[e]azulene hydrochloride (0.10 g, 0.24 mmol) and triethylamine (0.70 ml, 0.50 mmol) in dichloromethane (4.8 ml) was added acetyl chloride (0.019 ml, 0.26 mmol) at room temperature. After stirring for 16 h the reaction mixture was concentrated in vacuo. Flash-chromatography with n-heptane/2-propanol as eluent gave the title compound (0.003 g, 3%) as white solid. MS m/e: 427 ([M+H]$^+$).

EXAMPLE 81 trans-8-Chloro-5-methanesulfonyl-1-[4-(5-methyl-[1,2,4]oxadiazol-3-yl)-cyclohexyl]-5,6-dihydro-4H-2,3,5,10b-tetraaza-benzo[e]azulene To a solution of trans-8-chloro-1-[4-(5-methyl-[1,2,4]oxadiazol-3-yl)-cyclohexyl]-5,6-dihydro-4H-2,3,5,10b-tetraaza-benzo[e]azulene hydrochloride (0.100 g, 0.24 mmol) and triethylamine (0.70 ml, 0.50 mmol) in dichloromethane (4.8 ml) was added methanesulfonyl chloride (0.020 ml, 0.26 mmol) at room temperature. After stirring for 16 h the reaction mixture was concentrated in vacuo. Flash-chromatography with n-heptane/2-propanol as eluent gave the title compound (0.053 g, 48%) as white solid. MS m/e: 463 ([M+H]$^+$).

EXAMPLE 82 cis-8-Chloro-1-[4-(5-methyl-[1,2,4]oxadiazol-3-yl)-cyclohexyl]-4H,6H-2,3,5,10b-tetraaza-benzo[e]azulene-5-carboxylic acid tert-butyl ester The title compound was obtained as white solid in 61% yield according to general procedure (XV).
Hydrazide: cis-4-(5-Methyl-[1,2,4]oxadiazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 485 ([M+H]$^+$)

EXAMPLE 83 cis-8-Chloro-1-[4-(5-methyl-[1,2,4]oxadiazol-3-yl)-cyclohexyl]-5,6-dihydro-4H-2,3,5,10b-tetraaza-benzo[e]azulene hydrochloride The title compound was obtained as white solid in 88% yield from cis-8-chloro-1-[4-(5-methyl-[1,2,4]oxadiazol-3-yl)-cyclohexyl]-4H,6H-2,3,5,10b-tetraaza-benzo[e]azulene-5-carboxylic acid tert-butyl ester according to general procedure (XVI-a). MS m/e: 385 ([M+H]$^+$).

EXAMPLE 84 cis-8-Chloro-5-methyl-1-[4-(5-methyl-[1,2,4]oxadiazol-3-yl)-cyclohexyl]-5,6-dihydro-4H-2,3,5,10b-tetraaza-benzo[e]azulene The title compound was obtained as white solid in 75% yield from cis-8-chloro-1-[4-(5-methyl-[1,2,4]oxadiazol-3-yl)-cyclohexyl]-5,6-dihydro-4H-2,3,5,10b-tetraaza-benzo[e]azulene hydrochloride and paraformaldehyde according to general procedure (XVII-a). MS m/e: 399 ([M+H]$^+$).

EXAMPLE 85 cis-8-Chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester and

EXAMPLE 86 trans-8-Chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester cis-8-Chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester and trans-8-chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester were obtained according to general procedure (XV) after chromatographic separation.
Hydrazide: cis/trans-4-(5-Ethyl-[1,2,4]oxadiazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester
cis-8-Chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester was obtained as yellow solid in 21% yield. MS m/e: 499 ([M+H]$^+$)
trans-8-Chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester was obtained as yellow solid in 28% yield. MS m/e: 499 ([M+H]$^+$)

EXAMPLE 87 trans-8-Chloro-1-[4-(5-ethyl-[1,2,4]oxadiazol-3-yl)-cyclohexyl]-5,6-dihydro-4H-2,3,5,10b-tetraaza-benzo[e]azulene hydrochloride The title compound was obtained as off-white solid in quantitative yield from trans-8-chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester according to general procedure (XVI-a). MS m/e: 399 ([M+H]$^+$).

EXAMPLE 88 trans-8-Chloro-5-ethyl-1-[4-(5-methyl-[1,2,4]oxadiazol-3-yl)-cyclohexyl]-5,6-dihydro-4H-2,3,5,10b-tetraaza-benzo[e]azulene The title compound was obtained as white solid in 84% yield from trans-8-chloro-1-[4-(5-ethyl-[1,2,4]oxadiazol-3-yl)-cyclohexyl]-5,6-dihydro-4H-2,3,5,10b-tetraaza-benzo[e]azulene hydrochloride and paraformaldehyde according to general procedure (XVII-a). MS m/e: 413 ([M+H]$^+$)

EXAMPLE 89 cis-8-Chloro-1-[4-(5-ethyl-[1,2,4]oxadiazol-3-yl)-cyclohexyl]-5,6-dihydro-4H-2,3,5,10b-tetraaza-benzo[e]azulene hydrochloride The title compound was obtained as off-white solid in quantitative yield from cis-8-chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester according to general procedure (XVI-a). MS m/e: 399 ([M+H]$^+$).

EXAMPLE 90 cis-8-Chloro-5-ethyl-1-[4-(5-methyl-[1,2,4]oxadia-zol-3-yl)-cyclohexyl]-5,6-dihydro-4H-2,3,5,10b-tetraaza-benzo[e]azulene The title compound was obtained as white solid in 82% yield from cis-8-chloro-1-[4-(5-ethyl-[1,2,4]oxadiazol-3-yl)-cyclohexyl]-5,6-dihydro-4H-2,3,5,10b-tetraaza-benzo[e]azulene hydrochloride and paraformaldehyde according to general procedure (XVII-a). MS m/e: 413 ([M+H]$^+$).

EXAMPLE 91 cis-8-Chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester and

EXAMPLE 92 trans-8-Chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester cis-8-Chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester and trans-8-chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester were obtained according to general procedure (XV) after chromatographic separation.

Hydrazide: cis/trans-4-(5-Isopropyl-[1,2,4]oxadiazol-3-yl)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester cis-8-Chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester was obtained as white solid in 16% yield. MS m/e: 499 ([M+H]$^+$)

trans-8-Chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester was obtained as white solid in 19% yield. MS m/e: 499 ([M+H]$^+$)

EXAMPLE 93 trans-8-Chloro-1-[4-(5-isopropyl-[1,2,4]oxadiazol-3-yl)-cyclohexyl]-5,6-dihydro-4H-2,3,5,10b-tetraaza-benzo[e]azulene hydrochloride The title compound was obtained as white solid in quantitative yield from trans-8-chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester according to general procedure (XVI-a). MS m/e: 413 ([M+H]$^+$).

EXAMPLE 94 trans-8-Chloro-5-isopropyl-1-[4-(5-methyl-[1,2,4]oxadiazol-3-yl)-cyclohexyl]-5,6-dihydro-4H-2,3,5,10b-tetraaza-benzo[e]azulene The title compound was obtained as white solid in 94% yield from trans-8-chloro-1-[4-(5-isopropyl-[1,2,4]oxadiazol-3-yl)-cyclohexyl]-5,6-dihydro-4H-2,3,5,10b-tetraaza-benzo[e]azulene hydrochloride and paraformaldehyde according to general procedure (XVII-a). MS m/e: 427 ([M+H]$^+$).

EXAMPLE 95 cis-8-Chloro-1-[4-(5-isopropyl-[1,2,4]oxadiazol-3-yl)-cyclohexyl]-5,6-dihydro-4H-2,3,5,10b-tetraaza-benzo[e]azulene hydrochloride The title compound was obtained as white solid in quantitative yield from cis-8-chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester according to general procedure (XVI-a). MS m/e: 413 ([M+H]$^+$)

EXAMPLE 96 cis-8-Chloro-5-isopropyl-1-[4-(5-methyl-[1,2,4]oxadiazol-3-yl)-cyclohexyl]-5,6-dihydro-4H-2,3,5,10b-tetraaza-benzo[e]azulene The title compound was obtained as white solid in 74% yield from cis-8-chloro-1-[4-(5-isopropyl-[1,2,4]oxadiazol-3-yl)-cyclohexyl]-5,6-dihydro-4H-2,3,5,10b-tetraaza-benzo[e]azulene hydrochloride and paraformaldehyde according to general procedure (XVII-a). MS m/e: 427 ([M+H]$^+$).

EXAMPLE 97 trans-8-Chloro-5-methyl-1-[4-(5-methyl-[1,2,4]thiadiazol-3-yl)-cyclohexyl]-5,6-dihydro-4H-2,3,5,10b-tetraaza-benzo[e]azulene a) trans-8-Chloro-1-[4-(5-methyl-[1,2,4]thiadiazol-3-yl)-cyclohexyl]-5,6-dihydro-4H-2,3,5,10b-tetraaza-benzo[e]azulene The title compound was obtained in 33% yield as off-white solid, which was contaminated with ca. 25% trans-8-chloro-1-[4-(3-methyl-[1,2,4]thiadiazol-5-yl)-cyclohexyl]-5,6-dihydro-4H-2,3,5,10b-tetraaza-benzo[e]azulene, by consecutively using general procedures (XV) and (XVI-a).

Hydrazide: trans-4-(5-Methyl-[1,2,4]thiadiazol-3-yl)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 401 ([M+H]$^+$)

b) trans-8-Chloro-5-methyl-1-[4-(5-methyl-[1,2,4]thiadiazol-3-yl)-cyclohexyl]-5,6-dihydro-4H-2,3,5,10b-tetraaza-benzo[e]azulene The title compound was obtained in 30% yield as white solid, which was contaminated with 25% trans-8-chloro-5-methyl-1-[4-(3-methyl-[1,2,4]thiadiazol-5-yl)-cyclohexyl]-5,6-dihydro-4H-2,3,5,10b-tetraaza-benzo[e]azulene, from trans-8-chloro-1-[4-(5-methyl-[1,2,4]thiadiazol-3-yl)-cyclohexyl]-5,6-dihydro-4H-2,3,5,10b-tetraaza-benzo[e]azulene and paraformaldehyde according to general procedure (XVII-a). MS m/e: 415 ([M+H]$^+$)

EXAMPLE 98 trans-8-Chloro-1-[4-(5-chloro-4-methyl-oxazol-2-yl)-cyclohexyl]-4H,6H-2,3,5,10b-tetraaza-benzo[e]azulene-5-carboxylic acid tert-butyl ester The title compound was obtained as white solid in 27% yield according to general procedure (XV).

Hydrazide: trans-4-(5-Chloro-4-methyl-oxazol-2-yl)-cyclohexanecarboxylic acid hydrazide Thiolactam: 7-Chloro-2-thioxo-1,2,3,5-tetrahydro-benzo[e][1,4]diazepine-4-carboxylic acid tert-butyl ester. MS m/e: 518 ([M+H]$^+$)

EXAMPLE 99 trans-8-Chloro-1-[4-(5-chloro-4-methyl-oxazol-2-yl)-cyclohexyl]-5,6-dihydro-4H-2,3,5,10b-tetraaza-benzo[e]azulene The title compound was obtained as white solid in 84% yield from trans-8-chloro-1-[4-(5-chloro-4-methyl-oxazol-2-yl)-cyclohexyl]-4H,6H-2,3,5,10b-tetraaza-benzo[e]azulene-5-carboxylic acid tert-butyl ester according to general procedure (XVI-b). MS m/e: 410 ([M+H]$^+$).

EXAMPLE 100 trans-8-Chloro-1-[4-(5-chloro-4-methyl-oxazol-2-yl)-cyclohexyl]-5-methyl-5,6-dihydro-4H-2,3,5,10b-tetraaza-benzo[e]azulene The title compound was obtained as white solid in 57% yield from trans-8-chloro-1-[4-(5-chloro-4-methyl-oxazol-2-yl)-cyclohexyl]-5,6-dihydro-4H-2,3,5,10b-tetraaza-benzo[e]azulene and paraformaldehyde according to general procedure (XVII-b). MS m/e: 432 ([M+H]$^+$).

EXAMPLE 101 trans-8-Chloro-1-[4-(5-chloro-4-methyl-thiazol-2-yl)-cyclohexyl]-4H,6H-2,3,5,10b-tetraaza-benzo[e]azulene-5-carboxylic acid tert-butyl ester The title compound was obtained as white solid in 58% yield according to general procedure (XV).
Hydrazide: trans-4-(5-Chloro-4-methyl-thiazol-2-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 534 ([M+H]$^+$)

EXAMPLE 102 trans-8-Chloro-1-[4-(5-chloro-4-methyl-thiazol-2-yl)-cyclohexyl]-5,6-dihydro-4H-2,3,5,10b-tetraaza-benzo[e]azulene The title compound was obtained as white solid in 86% yield from trans-8-chloro-1-[4-(5-chloro-4-methyl-thiazol-2-yl)-cyclohexyl]-4H,6H-2,3,5,10b-tetraaza-benzo[e]azulene-5-carboxylic acid tert-butyl ester according to general procedure (XVI-b). MS m/e: 434 ([M+H]$^+$).

EXAMPLE 103 trans-8-Chloro-1-[4-(5-chloro-4-methyl-thiazol-2-yl)-cyclohexyl]-5-methyl-5,6-dihydro-4H-2,3,5,10b-tetraaza-benzo[e]azulene The title compound was obtained as white solid in 46% yield from trans-8-chloro-1-[4-(5-chloro-4-methyl-thiazol-2-yl)-cyclohexyl]-5-methyl-5,6-dihydro-4H-2,3,5,10b-tetraaza-benzo[e]azulene and paraformaldehyde according to general procedure (XVII-b). MS m/e: 448 ([M+H]$^+$).

EXAMPLE 104 trans-8-Chloro-1-[4-(4,5-dimethyl-thiazol-2-yl)-cyclohexyl]-4H,6H-2,3,5,10b-tetraaza-benzo[e]azulene-5-carboxylic acid tert-butyl ester The title compound was obtained as white solid in 49% yield according to general procedure (XV).
Hydrazide: cis/trans-4-(4,5-Dimethyl-thiazol-2-yl)-cyclohexanecarboxylic acid hydrazide (1:7.5)
Thiolactam: 7-Chloro-2-thioxo-1,2,3,5-tetrahydro-benzo[e][1,4]diazepine-4-carboxylic acid tert-butyl ester. MS m/e: 514.5 ([M+H]$^+$)

EXAMPLE 105 trans-8-Chloro-1-[4-(4,5-dimethyl-thiazol-2-yl)-cyclohexyl]-5,6-dihydro-4H-2,3,5,10b-tetraaza-benzo[e]azulene The title compound was obtained as off-white solid in 93% yield from trans-8-chloro-1-[4-(4,5-dimethyl-thiazol-2-yl)-cyclohexyl]-4H,6H-2,3,5,10b-tetraaza-benzo[e]azulene-5-carboxylic acid tert-butyl ester according to general procedure (XVI-b). MS m/e: 414 ([M+H]$^+$).

EXAMPLE 106 trans-8-Chloro-1-[4-(4,5-dimethyl-thiazol-2-yl)-cyclohexyl]-5-methyl-5,6-dihydro-4H-2,3,5,10b-tetraaza-benzo[e]azulene The title compound was obtained as white solid in 45% yield from trans-8-chloro-1-[4-(4,5-dimethyl-thiazol-2-yl)-cyclohexyl]-5,6-dihydro-4H-2,3,5,10b-tetraaza-benzo[e]azulene according to general procedure (XVIII). MS m/e: 428 ([M+H]$^+$).

EXAMPLE 107 trans-8-Chloro-1-[4-(5,6-dihydro-4H-cyclopenta[d]isoxazol-3-yl)-cyclohexyl]-5-methyl-5,6-dihydro-4H-2,3,5,10b-tetraaza-benzo[e]azulene a) trans-8-Chloro-1-[4-(5,6-dihydro-4H-cyclopenta[d]isoxazol-3-yl)-cyclohexyl]-4H,6H-2,3,5,10b-tetraaza-benzo[e]azulene-5-carboxylic acid tert-butyl ester The title compound was obtained as brown solid with a purity of 85% in 13% yield according to general procedure (XV).
Hydrazide: trans-4-(5,6-Dihydro-4H-cyclopenta[d]isoxazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 510 ([M+H]$^+$)

b) trans-8-Chloro-1-[4-(5,6-dihydro-4H-cyclopenta[d]isoxazol-3-yl)-cyclohexyl]-5,6-dihydro-4H-2,3,5,10b-tetraaza-benzo[e]azulene The title compound was obtained as brown solid with a purity of 85% in 98% yield according to general procedure (XVI-b). MS m/e: 415 ([M+H]$^+$)

c) trans-8-Chloro-1-[4-(5,6-dihydro-4H-cyclopenta[d]isoxazol-3-yl)-cyclohexyl]-5-methyl-5,6-dihydro-4H-2,3,5,10b-tetraaza-benzo[e]azulene The title compound was obtained as light yellow solid with a purity of 90% in 76% yield from trans-8-chloro-1-[4-(5,6-dihydro-4H-cyclopenta[d]isoxazol-3-yl)-cyclohexyl]-5,6-dihydro-4H-2,3,5,10b-tetraaza-benzo[e]azulene according to general procedure (XVIII). MS m/e: 424 ([M+H]$^+$)

EXAMPLE 108 trans-1-[4-(4,5-Bis-hydroxymethyl-isoxazol-3-yl)-cyclohexyl]-8-chloro-4H,6H-2,3,5,10b-tetraaza-benzo[e]azulene-5-carboxylic acid tert-butyl ester The title compound was obtained in 11% yield as off-white solid according to general procedure (XV).
Hydrazide: trans-4-(4,5-Bis-hydroxymethyl-isoxazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 530 ([M+H]$^+$)

EXAMPLE 109 trans-8-Chloro-1-(4-pyrazol-1-yl-cyclohexyl)-4H,6H-2,3,5,10b-tetraaza-benzo[e]azulene-5-carboxylic acid tert-butyl ester The title compound was obtained as off-white solid in 47% yield according to general procedure (XV).
Hydrazide: trans-4-Pyrazol-1-yl-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 469 ([M+H]$^+$)

EXAMPLE 110 trans-8-Chloro-1-(4-pyrazol-1-yl-cyclohexyl)-5,6-dihydro-4H-2,3,5,10b-tetraaza-benzo[e]azulene The title compound was obtained as light yellow solid in 81% yield from trans-8-chloro-1-(4-pyrazol-1-yl-cyclohexyl)-4H,6H-2,3,5,10b-tetraaza-benzo[e]azulene-5-carboxylic acid tert-butyl ester according to general procedure (XVI-b). MS m/e: 369 ([M+H]$^+$)

EXAMPLE 111 trans-8-Chloro-5-methyl-1-(4-pyrazol-1-yl-cyclohexyl)-5,6-dihydro-4H-2,3,5,10b-tetraaza-benzo[e]azulene The title compound was obtained as white solid in 86% yield from trans-8-chloro-1-(4-pyrazol-1-yl-cyclohexyl)-5,6-dihydro-4H-2,3,5,10b-tetraaza-benzo[e]azulene according to general procedure (XVIII). MS m/e: 383 ([M+H]$^+$)

EXAMPLE 112 cis-8-Chloro-1-(4-pyrazol-1-yl-cyclohexyl)-4H,6H-2,3,5,10b-tetraaza-benzo[e]azulene-5-carboxylic acid tert-butyl ester The title compound was obtained as off-white solid in 67% yield according to general procedure (XV).
Hydrazide: cis-4-Pyrazol-1-yl-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 469 ([M+H]$^+$)

EXAMPLE 113 cis-8-Chloro-1-(4-pyrazol-1-yl-cyclohexyl)-5,6-dihydro-4H-2,3,5,10b-tetraaza-benzo[e]azulene The title compound was obtained as light yellow solid in 89% yield from cis-8-chloro-1-(4-pyrazol-1-yl-cyclohexyl)-4H,6H-2,3,5,10b-tetraaza-benzo[e]azulene-5-carboxylic acid tert-butyl ester according to general procedure (XVI-b). MS m/e: 369 ([M+H]$^+$)

EXAMPLE 114 cis-8-Chloro-5-methyl-1-(4-pyrazol-1-yl-cyclohexyl)-5,6-dihydro-4H-2,3,5,10b-tetraaza-benzo[e]azulene The title compound was obtained as white solid in 87% yield from cis-8-chloro-1-(4-pyrazol-1-yl-cyclohexyl)-5,6-dihydro-4H-2,3,5,10b-tetraaza-benzo[e]azulene according to general procedure (XVIII). MS m/e: 383 ([M+H]$^+$)

EXAMPLE 115 trans-8-Chloro-1-[4-(3,5-dimethyl-pyrazol-1-yl)-cyclohexyl]-4H,6H-2,3,5,10b-tetraaza-benzo[e]azulene-5-carboxylic acid tert-butyl ester The title compound was obtained as off-white solid in 52% yield according to general procedure (XV).
Hydrazide: trans-4-(3,5-Dimethyl-pyrazol-1-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 497 ([M+H]$^+$)

EXAMPLE 116 trans-8-Chloro-1-[4-(3,5-dimethyl-pyrazol-1-yl)-cyclohexyl]-5,6-dihydro-4H-2,3,5,10b-tetraaza-benzo[e]azulene The title compound was obtained as off-white solid in quantitative yield from trans-8-chloro-1-[4-(3,5-dimethyl-pyrazol-1-yl)-cyclohexyl]-4H,6H-2,3,5,10b-tetraaza-benzo[e]azulene-5-carboxylic acid tert-butyl ester according to general procedure (XVI-b). MS m/e: 397 ([M+H]$^+$)

EXAMPLE 117 trans-8-Chloro-1-[4-(3,5-dimethyl-pyrazol-1-yl)-cyclohexyl]-5-methyl-5,6-dihydro-4H-2,3,5,10b-tetraaza-benzo[e]azulene The title compound was obtained as white solid in 90% yield from trans-8-chloro-1-[4-(3,5-dimethyl-pyrazol-1-yl)- cyclohexyl]-5,6-dihydro-4H-2,3,5,10b-tetraaza-benzo[e] azulene according to general procedure (XVIII). MS m/e: 411 ([M+H]⁺)

EXAMPLE 118 trans-8-Chloro-1-[4-(3,4,5-trimethyl-pyrazol-1-yl)-cyclohexyl]-4H,6H-2,3,5,10b-tetraaza-benzo[e]azulene-5-carboxylic acid tert-butyl ester The title compound was obtained as white solid in 45% yield according to general procedure (XV).
Hydrazide: trans-4-(3,4,5-Trimethyl-pyrazol-1-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 511 ([M+H]⁺)

EXAMPLE 119 trans-8-Chloro-1-[4-(3,4,5-trimethyl-pyrazol-1-yl)-cyclohexyl]-5,6-dihydro-4H-2,3,5,10b-tetraaza-benzo[e]azulene The title compound was obtained as off-white solid in quantitative yield from trans-8-chloro-1-[4-(3,4,5-dimethyl-pyrazol-1-yl)-cyclohexyl]-4H,6H-2,3,5,10b-tetraaza-benzo[e]azulene-5-carboxylic acid tert-butyl ester according to general procedure (XVI-b). MS m/e: 411 ([M+H]⁺)

EXAMPLE 120 trans-8-Chloro-1-[4-(3,4,5-trimethyl-pyrazol-1-yl)-cyclohexyl]-5-methyl-5,6-dihydro-4H-2,3,5,10b-tetraaza-benzo[e]azulene The title compound was obtained as white solid in 84% yield from trans-8-chloro-1-[4-(3,4,5-trimethyl-pyrazol-1-yl)-cyclohexyl]-5,6-dihydro-4H-2,3,5,10b-tetraaza-benzo[e]azulene according to general procedure (XVIII). MS m/e: 425 ([M+H]⁺)

The invention claimed is:
1. A compound of the formula I

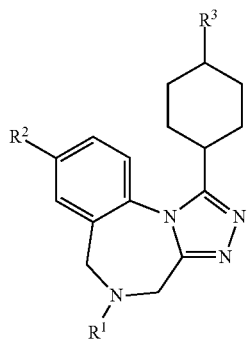

I wherein
R¹ is selected from the group consisting of
i) H,
ii) —$C_{1-6}$-alkyl, unsubstituted or substituted by 1 to 5 substituents individually selected from the group consisting of OH, halogen, cyano and $C_{1-6}$-alkoxy, iii) —$S(O)_2$—$C_{1-6}$-alkyl, whereby the $C_{1-6}$-alkyl is unsubstituted or substituted by 1 to 5 substituents individually selected from the group consisting of OH, halogen, cyano and $C_{1-6}$-alkoxy,
iv) —C(O)—$C_{1-6}$-alkyl, whereby the $C_{1-6}$-alkyl is unsubstituted or substituted by 1 to 5 substituents individually selected from the group consisting of OH, halogen, cyano and $C_{1-6}$-alkoxy,
v) —C(O)O—$C_{1-6}$-alkyl, whereby the $C_{1-6}$-alkyl is unsubstituted or substituted by 1 to 5 substituents individually selected from the group consisting of OH, halogen, cyano and $C_{1-6}$-alkoxy;
vi) cycloalkyl, unsubstituted or substituted by 1 to 5 substituents individually selected from the group consisting of OH, halogen, cyano, $C_{1-6}$-alkyl and $C_{1-6}$-alkoxy,
vii) —$S(O)_2$—$(CH_2)_q$—$NR^iR^{ii}$, wherein
q is 0 or 1,
$R^i$ and $R^{ii}$ is each individually selected from the group consisting of H and $C_{1-6}$-alkyl, or $R^i$ and $R^{ii}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy,
viii) —$(CH_2)_r$—$NR^{iii}R^{iv}$, wherein
r is 1, 2 or 3,
$R^{iii}$ and $R^{iv}$ is each individually selected from the group consisting of H and $C_{1-6}$-alkyl, or $R^{iii}$ and $R^{iv}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy, and
ix) —$C(O)(CH_2)_s$—$NR^vR^{vi}$, wherein
s is 1, 2 or 3,
$R^v$ and $R^{vi}$ is each individually selected from the group consisting of H and $C_{1-6}$-alkyl, or $R^v$ and $R^{vi}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy;
R² is halogen;
R³ is a 5-membered heteroaryl, unsubstituted or substituted by (R*)$_n$, each R* is individually selected from the group consisting of halogen, $C_{1-6}$-alkyl, halogen-$C_{1-6}$-alkyl and hydroxy-$C_{1-6}$-alkyl, wherein
n is 1, 2 or 3;
and two R* adjacent to each other can form a ring comprising 4, 5, 6 or 7 C;
or a pharmaceutically acceptable salt thereof.

2. The compound of claim 1,

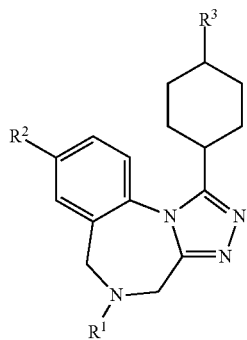

wherein
R¹ is selected from the group consisting of
i) H,
ii) —$C_{1-6}$-alkyl, unsubstituted or substituted by 1 to 5 substituents individually selected from the group consisting of OH, halogen, cyano and $C_{1-6}$-alkoxy,
iii) —$S(O)_2$—$C_{1-6}$-alkyl, whereby the $C_{1-6}$-alkyl is unsubstituted or substituted by 1 to 5 substituents individually selected from the group consisting of OH, halogen, cyano and $C_{1-6}$-alkoxy,
iv) —C(O)—$C_{1-6}$-alkyl, whereby the $C_{1-6}$-alkyl is unsubstituted or substituted by 1 to 5 substituents individually selected from the group consisting of OH, halogen, cyano and $C_{1-6}$-alkoxy,
v) —C(O)O—$C_{1-6}$-alkyl, whereby the $C_{1-6}$-alkyl is unsubstituted or substituted by 1 to 5 substituents individually selected from the group consisting of OH, halogen, cyano and $C_{1-6}$-alkoxy;
vi) cycloalkyl, unsubstituted or substituted by 1 to 5 substituents individually selected from the group consisting of OH, halogen, cyano, $C_{1-6}$-alkyl and $C_{1-6}$-alkoxy,
vii) —$S(O)_2$—$(CH_2)_q$—$NR^iR^{ii}$, wherein
q is 0 or 1,
$R^i$ and $R^{ii}$ is each individually selected from the group consisting of H and $C_{1-6}$-alkyl, or $R^i$ and $R^{ii}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy,
viii) —$(CH_2)_r$—$NR^{iii}R^{iv}$, wherein
r is 1, 2 or 3,
$R^{iii}$ and $R^{iv}$ is each individually selected from the group consisting of H and $C_{1-6}$-alkyl, or $R^{iii}$ and $R^{iv}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy, and
ix) —$C(O)(CH_2)_s$—$NR'R^{vi}$, wherein
s is 1, 2 or 3,
$R^v$ and $R^{vi}$ is each individually selected from the group consisting of H and $C_{1-6}$-alkyl, or $R^v$ and $R^{vi}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy;

R² is halogen;
R³ is a 5-membered heteroaryl, unsubstituted or substituted by $(R^*)_n$, each R* is individually selected from the group consisting of halogen, $C_{1-6}$-alkyl and halogen-$C_{1-6}$-alkyl, wherein
n is 1 or 2;
and two R* adjacent to each other can form a ring comprising 4, 5, 6 or 7 C;
or a pharmaceutically acceptable salt thereof.

3. The compound of claim 2, wherein R¹ is selected from the group consisting of
i) H,
ii) —$C_{1-6}$-alkyl, unsubstituted or substituted by 1 to 2 substituents individually selected from the group consisting of halogen and $C_{1-6}$-alkoxy,
iii) —$S(O)_2$—$C_{1-6}$-alkyl, whereby the $C_{1-6}$-alkyl is unsubstituted,
iv) —C(O)—$C_{1-6}$-alkyl, whereby the $C_{1-6}$-alkyl is unsubstituted or substituted by 1 to 2 OH,
v) —C(O)O—$C_{1-6}$-alkyl, whereby the $C_{1-6}$-alkyl is unsubstituted;
vi) unsubstituted cycloalkyl,
vii) —$S(O)_2$—$(CH_2)_q$—$NR^iR^{ii}$, wherein q is 0 and
$R^i$ and $R^{ii}$ is each individually selected from the group consisting of H and $C_{1-6}$-alkyl,
viii) —$(CH_2)_r$—$NR^{iii}R^{iv}$, wherein r is 2, and
$R^{iii}$ and $R^{iv}$ is each individually selected from the group consisting of H and $C_{1-6}$-alkyl, and
ix) —$C(O)(CH_2)_s$—$NR'R^{vi}$, wherein s is 1, and
$R^v$ and $R^{vi}$ is each individually selected from the group consisting of H and $C_{1-6}$-alkyl.

4. The compound of claim 3, wherein R¹ is selected from the group consisting of H, methyl, ethyl, isopropyl, 2,2-difluoro-ethyl, 2-methoxy-ethyl, 2-methylamino-ethyl, acetyl, 2-dimethylamino-acetyl, 2-hydroxy-acetyl, Boc, cyclobutyl, cyclopentyl, dimethylsulfonamidyl and methanesulfonyl.

5. The compound of claim 3, wherein R¹ is selected from the group consisting of
i) H,
ii) —$C_{1-6}$-alkyl, unsubstituted or substituted by 1 to 2 halogen,
iii) —$S(O)_2$—$C_{1-6}$-alkyl,
iv) —C(O)—$C_{1-6}$-alkyl, whereby the $C_{1-6}$-alkyl is unsubstituted or substituted by 1 to 2 OH, and
v) unsubstituted cycloalkyl.

6. The compound of claim 5, wherein R¹ is selected from the group consisting of H, methyl, 2,2-difluoro-ethyl, cyclobutyl, acetyl and methanesulfonyl.

7. The compound of claim 1, wherein R² is chloro.

8. The compound of claim 1, wherein R³ is selected from the group consisting of
i) [1,2,4]oxadiazolyl,
ii) [1,3,4]oxadiazolyl,
iii) oxazolyl,
iv) thiazolyl,
v) [1,2,4]thiadiazolyl,
vi) isoxazolyl, and
vii) 1H-pyrazolyl;
each unsubstituted or substituted by $(R^*)_n$, each R* is individually selected from the group consisting halogen and $C_{1-6}$-alkyl, wherein n=1, 2 or 3, or two R* adjacent to each other form with the atoms to which they are attached a ring comprising 6 C.

9. The compound of claim 8, wherein $R^3$ is selected from the group consisting of
i) [1,2,4]oxadiazolyl,
ii) [1,3,4]oxadiazolyl,
iii) oxazolyl,
iv) thiazolyl,
v) [1,2,4]thiadiazolyl, and
vi) isoxazolyl,
each unsubstituted or substituted by $(R^*)_n$, each $R^*$ is individually selected from the group consisting halogen and $C_{1-6}$-alkyl, wherein n=1-2 and two $R^*$ adjacent to each other form with the atoms to which they are attached a ring comprising 6 C.

10. The compound of claim 1, wherein $R^3$ is selected from the group consisting of oxazol-2-yl, 1H-pyrazol-1-yl, 2-methyl-thiazol-4-yl, 3,4,5-trimethyl-1H-pyrazol-1-yl, 3,5-dimethyl-1H-pyrazol-1-yl, 3-methyl-[1,2,4]thiadiazol-5-yl, 4,5,6,7-tetrahydro-benzo[c]isoxazol-3-yl, 4,5,6,7-tetrahydro-benzo[d]isoxazol-3-yl, 4,5-bis(hydroxymethyl)isoxazol-3-yl, 4,5-dimethyl-isoxazol-3-yl, 4,5-dimethyl-oxazol-2-yl, 4,5-dimethylthiazol-2-yl, 4-chloro-5-methyl-isoxazol-3-yl, 4-fluoro-5-methyl-isoxazol-3-yl, 4-methyl-oxazol-2-yl, 4-methyl-thiazol-2-yl, 5,6-dihydro-4H-cyclopenta[d]isoxazol, 5-chloro-4-methylthiazol-2-yl, 5-ethyl-[1,2,4]oxadiazol-3-yl, 5-ethyl-isoxazol-3-yl, 5-isopropyl-[1,2,4]oxadiazol-3-yl, 5-methyl-[1,2,4]oxadiazol-3-yl, 5-methyl-[1,2,4]thiadiazol-3-yl, 5-methyl-[1,3,4]oxadiazol-2-yl, 5-methyl-isoxazol-3-yl, 5-methyl-oxazol-2-yl, oxazol-2-yl and thiazol-2-yl.

11. The compound of claim 1, wherein $R^3$ is selected from the group consisting of 2-methyl-thiazol-4-yl, 3-methyl-[1,2,4]oxadiazol-5-yl, 3-methyl-[1,2,4]thiadiazol-5-yl, 4,5,6,7-tetrahydro-benzo[c]isoxazol-3-yl, 4,5,6,7-tetrahydro-benzo[d]isoxazol-3-yl, 4,5-dimethyl-isoxazol-3-yl, 4,5-dimethyl-oxazol-2-yl, 4-chloro-5-methyl-isoxazol-3-yl, 4-fluoro-5-methyl-isoxazol-3-yl, 4-methyl-oxazol-2-yl, 4-methyl-thiazol-2-yl, oxazol-2-yl, thiazol-2-yl, 5-ethyl-[1,2,4]oxadiazol-3-yl, 5-ethyl-isoxazol-3-yl, 5-isopropyl-[1,2,4]oxadiazol-3-yl, 5-methyl-[1,2,4]oxadiazol-3-yl, 5-methyl-[1,2,4]thiadiazol-3-yl, 5-methyl-[1,3,4]oxadiazol-2-yl, 5-methyl-isoxazol-3-yl and 5-methyl-oxazol-2-yl.

12. The compound of claim 1, wherein $R^3$ is selected from the group consisting of [1,2,4]oxadiazolyl, isoxazolyl, [1,2,4]thiadiazolyl, oxazolyl and thiazolyl, each unsubstituted or substituted by $(R^*)_n$, each $R^*$ is individually selected from the group consisting halogen and $C_{1-6}$-alkyl.

13. The compound of claim 1, wherein $R^3$ is selected from the group consisting of 5-ethyl-isoxazol-3-yl, 5-methyl-[1,2,4]oxadiazol-3-yl, 5-methyl-isoxazol-3-yl, 5-methyl-[1,2,4]thiadiazol-3-yl, 5-methyl-[1,2,4]oxadiazol-3-yl, 5-methyl-oxazol-2-yl, 4-methyl-thiazol-2-yl, 4-chloro-5-methyl-isoxazol-3-yl, 4,5-dimethyl-isoxazol-3-yl, 4,5-dimethyl-oxazol-2-yl and 4-fluoro-5-methyl-isoxazol-3-yl.

14. The compound of claim 1, selected from the group consisting of
cis-8-Chloro-1-(4-pyrazol-1-yl-cyclohexyl)-5,6-dihydro-4H-2,3,5,10b-tetraaza-benzo[e]azulene,
cis-8-Chloro-5-methyl-1-(4-pyrazol-1-yl-cyclohexyl)-5,6-dihydro-4H-2,3,5,10b-tetraaza-benzo[e]azulene,
cis-8-Chloro-5-methyl-1-(4-pyrazol-1-yl-cyclohexyl)-5,6-dihydro-4H-2,3,5,10b-tetraaza-benzo[e]azulene,
trans-1-[4-(4,5-Bis-hydroxymethyl-isoxazol-3-yl)-cyclohexyl]-8-chloro-4H,6H-2,3,5,10b-tetraaza-benzo[e]azulene-5-carboxylic acid tert-butyl ester,
trans-8-Chloro-1-(4-pyrazol-1-yl-cyclohexyl)-4H,6H-2,3,5,10b-tetraaza-benzo[e]azulene-5-carboxylic acid tert-butyl ester,
trans-8-Chloro-1-(4-pyrazol-1-yl-cyclohexyl)-5,6-dihydro-4H-2,3,5,10b-tetraaza-benzo[e]azulene,
trans-8-Chloro-1-[4-(3,4,5-trimethyl-pyrazol-1-yl)-cyclohexyl]-4H,6H-2,3,5,10b-tetraaza-benzo[e]azulene-5-carboxylic acid tert-butyl ester,
trans-8-Chloro-1-[4-(3,4,5-trimethyl-pyrazol-1-yl)-cyclohexyl]-5-methyl-5,6-dihydro-4H-2,3,5,10b-tetraaza-benzo[e]azulene,
trans-8-Chloro-1-[4-(3,4,5-trimethyl-pyrazol-1-yl)-cyclohexyl]-5,6-dihydro-4H-2,3,5,10b-tetraaza-benzo[e]azulene,
trans-8-Chloro-1-[4-(3,5-dimethyl-pyrazol-1-yl)-cyclohexyl]-4H,6H-2,3,5,10b-tetraaza-benzo[e]azulene-5-carboxylic acid tert-butyl ester,
trans-8-Chloro-1-[4-(3,5-dimethyl-pyrazol-1-yl)-cyclohexyl]-5,6-dihydro-4H-2,3,5,10b-tetraaza-benzo[e]azulene, and
trans-8-Chloro-1-[4-(3,5-dimethyl-pyrazol-1-yl)-cyclohexyl]-5-methyl-5,6-dihydro-4H-2,3,5,10b-tetraaza-benzo[e]azulene
or a pharmaceutically acceptable salt thereof.

15. The compound of claim 1, selected from the group consisting of
trans-8-Chloro-1-[4-(4,5-dimethyl-thiazol-2-yl)-cyclohexyl]-4H,6H-2,3,5,10b-tetraaza-benzo[e]azulene-5-carboxylic acid tert-butyl ester,
trans-8-Chloro-1-[4-(4,5-dimethyl-thiazol-2-yl)-cyclohexyl]-5,6-dihydro-4H-2,3,5,10b-tetraaza-benzo[e]azulene,
trans-8-Chloro-1-[4-(4,5-dimethyl-thiazol-2-yl)-cyclohexyl]-5-methyl-5,6-dihydro-4H-2,3,5,10b-tetraaza-benzo[e]azulene,
trans-8-Chloro-1-[4-(5,6-dihydro-4H-cyclopenta[d]isoxazol-3-yl)-cyclohexyl]-5-methyl-5,6-dihydro-4H-2,3,5,10b-tetraaza-benzo[e]azulene,
trans-8-Chloro-1-[4-(5-chloro-4-methyl-oxazol-2-yl)-cyclohexyl]-4H,6H-2,3,5,10b-tetraaza-benzo[e]azulene-5-carboxylic acid tert-butyl ester,
trans-8-Chloro-1-[4-(5-chloro-4-methyl-oxazol-2-yl)-cyclohexyl]-5,6-dihydro-4H-2,3,5,10b-tetraaza-benzo[e]azulene,
trans-8-Chloro-1-[4-(5-chloro-4-methyl-oxazol-2-yl)-cyclohexyl]-5-methyl-5,6-dihydro-4H-2,3,5,10b-tetraaza-benzo[e]azulene,
trans-8-Chloro-1-[4-(5-chloro-4-methyl-thiazol-2-yl)-cyclohexyl]-4H,6H-2,3,5,10b-tetraaza-benzo[e]azulene-5-carboxylic acid tert-butyl ester,
trans-8-Chloro-1-[4-(5-chloro-4-methyl-thiazol-2-yl)-cyclohexyl]-5,6-dihydro-4H-2,3,5,10b-tetraaza-benzo[e]azulene,
trans-8-Chloro-1-[4-(5-chloro-4-methyl-thiazol-2-yl)-cyclohexyl]-5-methyl-5,6-dihydro-4H-2,3,5,10b-tetraaza-benzo[e]azulene, and
trans-8-Chloro-5-methyl-1-(4-pyrazol-1-yl-cyclohexyl)-5,6-dihydro-4H-2,3,5,10b-tetraaza-benzo[e]azulene,
or a pharmaceutically acceptable salt thereof.

16. The compound of claim 1, selected from the group consisting of
trans-8-Chloro-1-(4-oxazol-2-yl-cyclohexyl)-4H,6H-2,3,5,10b-tetraaza-benzo[e]azulene-5-carboxylic acid tert-butyl ester,
trans-8-Chloro-1-(4-oxazol-2-yl-cyclohexyl)-5,6-dihydro-4H-2,3,5,10b-tetraaza-benzo[e]azulene, trans-8-Chloro-5-methyl-1-(4-oxazol-2-yl-cyclohexyl)-5,6-dihydro-4H-2,3,5,10b-tetraaza-benzo[e]azulene, trans-8-Chloro-1-[4-(4-methyl-oxazol-2-yl)-cyclohexyl]-4H,6H-2,3,5,10b-tetraaza-benzo[e]azulene-5-carboxylic acid tert-butyl ester, trans-8-Chloro-1-[4-(4-methyl-oxazol-2-yl)-cyclohexyl]-5,6-dihydro-4H-2,3,5,10b-tetraaza-benzo[e]azulene, trans-8-Chloro-1-[4-(5-methyl-oxazol-2-yl)-cyclohexyl]-4H,6H-2,3,5,10b-tetraaza-benzo[e]azulene-5-carboxylic acid tert-butyl ester, trans-8-Chloro-1-[4-(5-methyl-oxazol-2-yl)-cyclohexyl]-5,6-dihydro-4H-2,3,5,10b-tetraaza-benzo[e]azulene, trans-8-Chloro-1-[4-(4,5-dimethyl-oxazol-2-yl)-cyclohexyl]-4H,6H-2,3,5,10b-tetraaza-benzo[e]azulene-5-carboxylic acid tert-butyl ester, trans-8-Chloro-1-(4-thiazol-2-yl-cyclohexyl)-4H,6H-2,3,5,10b-tetraaza-benzo[e]azulene-5-carboxylic acid tert-butyl ester, and trans-8-Chloro-1-(4-thiazol-2-yl-cyclohexyl)-5,6-dihydro-4H-2,3,5,10b-tetraaza-benzo[e]azulene or a pharmaceutically acceptable salt thereof.

17. The compound of claim 1, selected from the group consisting of trans-8-Chloro-5-methyl-1-(4-thiazol-2-yl-cyclohexyl)-5,6-dihydro-4H-2,3,5,10b-tetraaza-benzo[e]azulene, trans-8-Chloro-1-[4-(4-methyl-thiazol-2-yl)-cyclohexyl]-4H,6H-2,3,5,10b-tetraaza-benzo[e]azulene-5-carboxylic acid tert-butyl ester, trans-8-Chloro-1-[4-(4-methyl-thiazol-2-yl)-cyclohexyl]-5,6-dihydro-4H-2,3,5,10b-tetraaza-benzo[e]azulene, trans-8-Chloro-1-[4-(2-methyl-thiazol-4-yl)-cyclohexyl]-4H,6H-2,3,5,10b-tetraaza-benzo[e]azulene-5-carboxylic acid tert-butyl ester, trans-Chloro-1-[4-(2-methyl-thiazol-4-yl)-cyclohexyl]-5,6-dihydro-4H-2,3,5,10b-tetraaza-benzo[e]azulene, trans-8-Chloro-5-methyl-1-[4-(2-methyl-thiazol-4-yl)-cyclohexyl]-5,6-dihydro-4H-2,3,5,10b-tetraaza-benzo[e]azulene, trans-8-Chloro-1-[4-(5-methyl-isoxazol-3-yl)-cyclohexyl]-4H,6H-2,3,5,10b-tetraaza-benzo[e]azulene-5-carboxylic acid tert-butyl ester, trans-8-Chloro-1-[4-(5-methyl-isoxazol-3-yl)-cyclohexyl]-5,6-dihydro-4H-2,3,5,10b-tetraaza-benzo[e]azulene, trans-8-Chloro-5-(2-methoxy-ethyl)-1-[4-(5-methyl-isoxazol-3-yl)-cyclohexyl]-5,6-dihydro-4H-2,3,5,10b-tetraaza-benzo[e]azulene, and trans-(2-{8-Chloro-1-[4-(5-methyl-isoxazol-3-yl)-cyclohexyl]-4H,6H-2,3,5,10b-tetraaza-benzo[e]azulen-5-yl}-ethyl)-methyl-amine or a pharmaceutically acceptable salt thereof.

18. The compound of claim 1, selected from the group consisting of trans-8-Chloro-5-ethyl-1-[4-(5-methyl-isoxazol-3-yl)-cyclohexyl]-5,6-dihydro-4H-2,3,5,10b-tetraaza-benzo[e]azulene, trans-1-{8-Chloro-1-[4-(5-methyl-isoxazol-3-yl)-cyclohexyl]-4H,6H-2,3,5,10b-tetraaza-benzo[e]azulen-5-yl}-2-hydroxy-ethanone, trans-1-{8-Chloro-1-[4-(5-methyl-isoxazol-3-yl)-cyclohexyl]-4H,6H-2,3,5,10b-tetraaza-benzo[e]azulen-5-yl}-2-dimethylamino-ethanone, trans-8-Chloro-5-isopropyl-1-[4-(5-methyl-isoxazol-3-yl)-cyclohexyl]-5,6-dihydro-4H-2,3,5,10b-tetraaza-benzo[e]azulene, trans-8-Chloro-1-[4-(5-methyl-isoxazol-3-yl)-cyclohexyl]-4H,6H-2,3,5,10b-tetraaza-benzo[e]azulene-5-sulfonic acid dimethylamide, trans-8-Fluoro-1-[4-(5-methyl-isoxazol-3-yl)-cyclohexyl]-4H,6H-2,3,5,10b-tetraaza-benzo[e]azulene-5-carboxylic acid tert-butyl ester, trans-8-Fluoro-1-[4-(5-methyl-isoxazol-3-yl)-cyclohexyl]-5,6-dihydro-4H-2,3,5,10b-tetraaza-benzo[e]azulene, trans-8-Fluoro-5-methyl-1-[4-(5-methyl-isoxazol-3-yl)-cyclohexyl]-5,6-dihydro-4H-2,3,5,10b-tetraaza-benzo[e]azulene, trans-8-Chloro-1-[4-(4,5-dimethyl-isoxazol-3-yl)-cyclohexyl]-4H,6H-2,3,5,10b-tetraaza-benzo[e]azulene-5-carboxylic acid tert-butyl ester, and trans-8-Chloro-1-[4-(4-chloro-5-methyl-isoxazol-3-yl)-cyclohexyl]-4H,6H-2,3,5,10b-tetraaza-benzo[e]azulene-5-carboxylic acid tert-butyl ester or a pharmaceutically acceptable salt thereof.

19. The compound of claim 1, selected from the group consisting of trans-8-Chloro-1-[4-(4-fluoro-5-methyl-isoxazol-3-yl)-cyclohexyl]-4H,6H-2,3,5,10b-tetraaza-benzo[e]azulene-5-carboxylic acid tert-butyl ester, cis-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester, trans-8-Chloro-1-[4-(5-ethyl-isoxazol-3-yl)-cyclohexyl]-4H,6H-2,3,5,10b-tetraaza-benzo[e]azulene-5-carboxylic acid tert-butyl ester, cis-8-Chloro-1-[4-(5-ethyl-isoxazol-3-yl)-cyclohexyl]-5,6-dihydro-4H-2,3,5,10b-tetraaza-benzo[e]azulene, cis-8-Chloro-1-[4-(5-ethyl-isoxazol-3-yl)-cyclohexyl]-5-methyl-5,6-dihydro-4H-2,3,5,10b-tetraaza-benzo[e]azulene, trans-8-Chloro-1-[4-(5-ethyl-isoxazol-3-yl)-cyclohexyl]-5,6-dihydro-4H-2,3,5,10b-tetraaza-benzo[e]azulene, trans-8-Chloro-1-[4-(4,5,6,7-tetrahydro-benzo[d]isoxazol-3-yl)-cyclohexyl]-4H,6H-2,3,5,10b-tetraaza-benzo[e]azulene-5-carboxylic acid tert-butyl ester, trans-8-Chloro-1-[4-(4,5,6,7-tetrahydro-benzo[d]isoxazol-3-yl)-cyclohexyl]-5,6-dihydro-4H-2,3,5,10b-tetraaza-benzo[e]azulene, trans-8-Chloro-5-methyl-1-[4-(4,5,6,7-tetrahydro-benzo[d]isoxazol-3-yl)-cyclohexyl]-5,6-dihydro-4H-2,3,5,10b-tetraaza-benzo[e]azulene, and cis-8-Chloro-1-[4-(4,5,6,7-tetrahydro-benzo[d]isoxazol-3-yl)-cyclohexyl]-4H,6H-2,3,5,10b-tetraaza-benzo[e]azulene-5-carboxylic acid tert-butyl ester or a pharmaceutically acceptable salt thereof.

20. The compound of claim 1, selected from the group consisting of cis-8-Chloro-1-[4-(4,5,6,7-tetrahydro-benzo[d]isoxazol-3-yl)-cyclohexyl]-5,6-dihydro-4H-2,3,5,10b-tetraaza-benzo[e]azulene, cis-8-Chloro-5-methyl-1-[4-(4,5,6,7-tetrahydro-benzo[d]isoxazol-3-yl)-cyclohexyl]-5,6-dihydro-4H-2,3,5,10b-tetraaza-benzo[e]azulene, trans-8-Chloro-1-[4-(4,5,6,7-tetrahydro-benzo[c]isoxazol-3-yl)-cyclohexyl]-4H,6H-2,3,5,10b-tetraaza-benzo[e]azulene-5-carboxylic acid tert-butyl ester, trans-8-Chloro-1-[4-(4,5,6,7-tetrahydro-benzo[c]isoxazol-3-yl)-cyclohexyl]-5,6-dihydro-4H-2,3,5,10b-tetraaza-benzo[e]azulene, trans-8-Chloro-5-methyl-1-[4-(4,5,6,7-tetrahydro-benzo[c]isoxazol-3-yl)-cyclohexyl]-5,6-dihydro-4H-2,3,5,10b-tetraaza-benzo[e]azulene, trans-8-Chloro-1-[4-(5-methyl-[1,3,4]oxadiazol-2-yl)-cyclohexyl]-4H,6H-2,3,5,10b-tetraaza-benzo[e]azulene-5-carboxylic acid tert-butyl ester, trans-8-Chloro-1-[4-(5-methyl-[1,3,4]oxadiazol-2-yl)-cyclohexyl]-5,6-dihydro-4H-2,3,5,10b-tetraaza-benzo[e]azulene, trans-8-Chloro-5-methyl-1-[4-(5-methyl-[1,3,4]oxadiazol-2-yl)-cyclohexyl]-5,6-dihydro-4H-2,3,5,10b-tetraaza-benzo[e]azulene, trans-8-Chloro-1-[4-(3-methyl-[1,2,4]oxadiazol-5-yl)-cyclohexyl]-4H,6H-2,3,5,10b-tetraaza-benzo[e]azulene-5-carboxylic acid tert-butyl ester, and trans-8-Chloro-1-[4-(3-methyl-[1,2,4]oxadiazol-5-yl)-cyclohexyl]-5,6-dihydro-4H-2,3,5,10b-tetraaza-benzo[e]azulene or a pharmaceutically acceptable salt thereof.

21. The compound of claim 1, selected from the group consisting of trans-8-Chloro-5-methyl-1-[4-(3-methyl-[1,2,4]oxadiazol-5-yl)-cyclohexyl]-5,6-dihydro-4H-2,3,5,10b-tetraaza-benzo[e]azulene, trans-8-Chloro-1-[4-(3-methyl-[1,2,4]thiadiazol-5-yl)-cyclohexyl]-4H,6H-2,3,5,10b-tetraaza-benzo[e]azulene-5-carboxylic acid tert-butyl ester, trans-8-Chloro-1-[4-(3-methyl-[1,2,4]thiadiazol-5-yl)-cyclohexyl]-5,6-dihydro-4H-2,3,5,10b-tetraaza-benzo[e]azulene, trans-8-Chloro-5-methyl-1-[4-(3-methyl-[1,2,4]thiadiazol-5-yl)-cyclohexyl]-5,6-dihydro-4H-2,3,5,10b-tetraaza-benzo[e]azulene, trans-8-Chloro-1-[4-(5-methyl-[1,2,4]oxadiazol-3-yl)-cyclohexyl]-4H,6H-2,3,5,10b -tetraaza-benzo[e]azulene-5-carboxylic acid tert-butyl ester, trans-8-Chloro-1-[4-(5-methyl-[1,2,4]oxadiazol-3-yl)-cyclohexyl]-5,6-dihydro-4H-2,3,5,10b-tetraaza-benzo[e]azulene, trans-8-Chloro-5-ethyl-1-[4-(5-methyl-[1,2,4]oxadiazol-3-yl)-cyclohexyl]-5,6-dihydro-4H-2,3,5,10b-tetraaza-benzo[e]azulene, trans-8-Chloro-5-isopropyl-1-[4-(5-methyl-[1,2,4]oxadiazol-3-yl)-cyclohexyl]-5,6-dihydro-4H-2,3,5,10b-tetraaza-benzo[e]azulene, trans-8-Chloro-5-cyclopentyl-1-[4-(5-methyl-[1,2,4]oxadiazol-3-yl)-cyclohexyl]-5,6-dihydro-4H-2,3,5,10b-tetraaza-benzo[e]azulene, and trans-8-Chloro-5-(2,2-difluoro-ethyl)-1-[4-(5-methyl-[1,2,4]oxadiazol-3-yl)-cyclohexyl]-5,6-dihydro-4H-2,3,5,10b-tetraaza-benzo[e]azulene or a pharmaceutically acceptable salt thereof.

22. The compound of claim 1, selected from the group consisting of trans-1-{8-Chloro-1-[4-(5-methyl-[1,2,4]oxadiazol-3-yl)-cyclohexyl]-4H,6H-2,3,5,10b-tetraaza-benzo[e]azulen-5-yl}-ethanone, trans-8-Chloro-5-methanesulfonyl-1-[4-(5-methyl-[1,2,4]oxadiazol-3-yl)-cyclohexyl]-5,6-dihydro-4H-2,3,5,10b-tetraaza-benzo[e]azulene, cis-8-Chloro-1-[4-(5-methyl-[1,2,4]oxadiazol-3-yl)-cyclohexyl]-4H,6H-2,3,5,10b-tetraaza-benzo[e]azulene-5-carboxylic acid tert-butyl ester, cis-8-Chloro-1-[4-(5-methyl-[1,2,4]oxadiazol-3-yl)-cyclohexyl]-5,6-dihydro-4H-2,3,5,10b-tetraaza-benzo[e]azulene, cis-8-Chloro-5-methyl-1-[4-(5-methyl-[1,2,4]oxadiazol-3-yl)-cyclohexyl]-5,6-dihydro-4H-2,3,5,10b-tetraaza-benzo[e]azulene, cis-8-Chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester, trans-8-Chloro-1-[4-(5-ethyl-[1,2,4]oxadiazol-3-yl)-cyclohexyl]-4H,6H-2,3,5,10b-tetraaza-benzo[e]azulene-5-carboxylic acid tert-butyl ester, trans-8-Chloro-1-[4-(5-ethyl-[1,2,4]oxadiazol-3-yl)-cyclohexyl]-5,6-dihydro-4H-2,3,5,10b-tetraaza-benzo[e]azulene, trans-8-Chloro-1-[4-(5-ethyl-[1,2,4]oxadiazol-3-yl)-cyclohexyl]-5-methyl-5,6-dihydro-4H-2,3,5,10b-tetraaza-benzo[e]azulene, and cis-8-Chloro-1-[4-(5-ethyl-[1,2,4]oxadiazol-3-yl)-cyclohexyl]-5,6-dihydro-4H-2,3,5,10b-tetraaza-benzo[e]azulene or a pharmaceutically acceptable salt thereof.

23. The compound of claim 1, selected from the group consisting of cis-8-Chloro-1-[4-(5-ethyl-[1,2,4]oxadiazol-3-yl)-cyclohexyl]-5-methyl-5,6-dihydro-4H-2,3,5,10b-tetraaza-benzo[e]azulene, cis-8-Chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester, trans-8-Chloro-1-[4-(5-isopropyl-[1,2,4]oxadiazol-3-yl)-cyclohexyl]-4H,6H-2,3,5,10b-tetraaza-benzo[e]azulene-5-carboxylic acid tert-butyl ester, trans-8-Chloro-1-[4-(5-isopropyl-[1,2,4]oxadiazol-3-yl)-cyclohexyl]-5,6-dihydro-4H-2,3,5,10b -tetraaza-benzo[e]azulene, trans-8-Chloro-1-[4-(5-isopropyl-[1,2,4]oxadiazol-3-yl)-cyclohexyl]-5-methyl-5,6-dihydro-4H-2,3,5,10b-tetraaza-benzo[e]azulene, cis-8-Chloro-1-[4-(5-isopropyl-[1,2,4]oxadiazol-3-yl)-cyclohexyl]-5,6-dihydro-4H-2,3,5,10b-tetraaza-benzo[e]azulene, and cis-8-Chloro-1-[4-(5-isopropyl-[1,2,4]oxadiazol-3-yl)-cyclohexyl]-5-methyl-5,6-dihydro-4H-2,3,5,10b-tetraaza-benzo[e]azulene or a pharmaceutically acceptable salt thereof.

24. The compound of claim 1, selected from the group consisting of trans-8-Chloro-1-[4-(5-ethyl-isoxazol-3-yl)-cyclohexyl]-5-methyl-5,6-dihydro-4H-2,3,5,10b-tetraaza-benzo[e]azulene, trans-8-Chloro-5-methyl-1-[4-(5-methyl[1,2,4]oxadiazol-3-yl)-cyclohexyl]-5,6-dihydro-4H-2,3,5,10b-tetraaza-benzo[e]azulene, trans-8-Chloro-5-methyl-1-[4-(5-methyl-isoxazol-3-yl)-cyclohexyl]-5,6-dihydro-4H-2,3,5,10b-tetraaza-benzo[e]azulene, trans-8-Chloro-5-methyl-1-[4-(5-methyl-[1,2,4]thiadiazol-3-yl)-cyclohexyl]-5,6-dihydro-4H-2,3,5,10b-tetraaza-benzo[e]azulene, trans-8-Chloro-5-cyclobutyl-1-[4-(5-methyl-[1,2,4]oxadiazol-3-yl)-cyclohexyl]-5,6-dihydro-4H-2,3,5,10b-tetraaza-benzo[e]azulene, trans-8-Chloro-5-methyl-1-[4-(4-methyl-oxazol-2-yl)-cyclohexyl]-5,6-dihydro-4H-2,3,5,10b-tetraaza-benzo[e]azulene, trans-8-Chloro-5-methyl-1-[4-(5-methyl-oxazol-2-yl)-cyclohexyl]-5,6-dihydro-4H-2,3,5,10b-tetraaza-benzo[e]azulene, trans-8-Chloro-5-methyl-1-[4-(4-methyl-thiazol-2-yl)-cyclohexyl]-5,6-dihydro-4H-2,3,5,10b-tetraaza-benzo[e]azulene, and trans-8-Chloro-1-[4-(4-chloro-5-methyl-isoxazol-3-yl)-cyclohexyl]-5,6-dihydro-4H-2,3,5,10b-tetraaza-benzo[e]azulene or a pharmaceutically acceptable salt thereof.

25. The compound of claim 1, selected from the group consisting of trans-8-Chloro-1-[4-(4,5-dimethyl-isoxazol-3-yl)-cyclohexyl]-5,6-dihydro-4H-2,3,5,10b-tetraaza-benzo[e]azulene, trans-8-Chloro-1-[4-(4-chloro-5-methyl-isoxazol-3-yl)-cyclohexyl]-5-methyl-5,6-dihydro-4H-2,3,5,10b-tetraaza-benzo[e]azulene, trans-8-Chloro-1-[4-(4,5-dimethyl-isoxazol-3-yl)-cyclohexyl]-5-methyl-5,6-dihydro-4H-2,3,5,10b-tetraaza-benzo[e]azulene, trans-8-Chloro-1-[4-(4,5-dimethyl-oxazol-2-yl)-cyclohexyl]-5,6-dihydro-4H-2,3,5,10b-tetraaza-benzo[e]azulene, trans-8-Chloro-1-[4-(4-fluoro-5-methyl-isoxazol-3-yl)-cyclohexyl]-5,6-dihydro-4H-2,3,5,10b-tetraaza-benzo[e]azulene, trans-8-Chloro-1-[4-(4,5-dimethyl-oxazol-2-yl)-cyclohexyl]-5-methyl-5,6-dihydro-4H-2,3,5,10b-tetraaza-benzo[e]azulene, trans-8-Chloro-1-[4-(4-fluoro-5-methyl-isoxazol-3-yl)-cyclohexyl]-5-methyl-5,6-dihydro-4H-2,3,5,10b-tetraaza-benzo[e]azulene, trans-1-{8-Chloro-1-[4-(5-methyl-isoxazol-3-yl)-cyclohexyl]-4H,6H-2,3,5,10b-tetraaza-benzo[e]azulen-5-yl}-ethanone, trans-8-Chloro-5-methanesulfonyl-1-[4-(5-methyl-isoxazol-3-yl)-cyclohexyl]-5,6-dihydro-4H-2,3,5,10b-tetraaza-benzo[e]azulene, trans-8-Chloro-5-cyclobutyl-1-[4-(5-methyl-isoxazol-3-yl)-cyclohexyl]-5,6-dihydro-4H-2,3,5,10b-tetraaza-benzo[e]azulene, and trans-8-Chloro-5-(2,2-difluoro-ethyl)-1-[4-(5-methyl-isoxazol-3-yl)-cyclohexyl]-5,6-dihydro-4H-2,3,5,10b-tetraaza-benzo[e]azulene or a pharmaceutically acceptable salt thereof.

26. The compound of claim 1, selected from the group consisting of trans-8-Chloro-1-[4-(5-ethyl-isoxazol-3-yl)-cyclohexyl]-5,6-dihydro-4H-2,3,5,10b-tetraaza-benzo[e]azulene*HCl, trans-8-Chloro-1-[4-(5-methyl-[1,2,4]oxadiazol-3-yl)-cyclohexyl]-5,6-dihydro-4H-2,3,5,10b-tetraaza-benzo[e]azulene*HCl, and trans-8-Chloro-1-[4-(5-methyl-isoxazol-3-yl)-cyclohexyl]-5,6-dihydro-4H-2,3,5,10b-tetraaza-benzo[e]azulene*HCl.

27. A pharmaceutical composition comprising a therapeutically effective amount of a compound of formula I

I wherein $R^1$ is selected from the group consisting of i) H, ii) —$C_{1-6}$-alkyl, unsubstituted or substituted by 1 to 5 substituents individually selected from the group consisting of OH, halogen, cyano and $C_{1-6}$-alkoxy, iii) —$S(O)_2$—$C_{1-6}$-alkyl, whereby the $C_{1-6}$-alkyl is unsubstituted or substituted by 1 to 5 substituents individually selected from the group consisting of OH, halogen, cyano and $C_{1-6}$-alkoxy, iv) —C(O)—$C_{1-6}$-alkyl, whereby the $C_{1-6}$-alkyl is unsubstituted or substituted by 1 to 5 substituents individually selected from the group consisting of OH, halogen, cyano and $C_{1-6}$-alkoxy, v) —C(O)O—$C_{1-6}$-alkyl, whereby the $C_{1-6}$-alkyl is unsubstituted or substituted by 1 to 5 substituents individually selected from the group consisting of OH, halogen, cyano and $C_{1-6}$-alkoxy;

vi) cycloalkyl, unsubstituted or substituted by 1 to 5 substituents individually selected from the group consisting of OH, halogen, cyano, $C_{1-6}$-alkyl and $C_{1-6}$-alkoxy, viii) —$S(O)_2$—$(CH_2)_q$—$NR^iR^{ii}$, wherein q is 0 or 1, $R^i$ and $R^{ii}$ is each individually selected from the group consisting of H and $C_{1-6}$-alkyl, or $R^i$ or $R^{ii}$ and form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy, viii) —$(CH_2)_r$—$NR^{iii}R^{iv}$, wherein r is 1, 2 or 3, $R^{iii}$ and $R^{iv}$ is each individually selected from the group consisting of H and $C_{1-6}$-alkyl, or $R^{iii}$ and $R^{iv}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy, and ix) —$C(O)(CH_2)_s$—$NR^vR^{vi}$, wherein s is 1, 2 or 3, $R^v$ and $R^{vi}$ is each individually selected from the group consisting of H and $C_{1-6}$-alkyl, or $R^v$ and $R^{vi}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy;

$R^2$ is halogen;

$R^3$ is a 5-membered heteroaryl, unsubstituted or substituted by $(R^*)_n$, each $R^*$ is individually selected from the group consisting of halogen, $C_{1-6}$-alkyl, halogen-$C_{1-6}$alkyl and hydroxy-$C_{1-6}$-alkyl, wherein n is 1, 2 or 3;

and two $R^*$ adjacent to each other can form a ring comprising 4, 5, 6 or 7 C;

or a pharmaceutically acceptable salt thereof and a pharmaceutically acceptable carrier.

* * * * *